United States Patent
Voskoboynikov et al.

(10) Patent No.: US 7,910,783 B2
(45) Date of Patent: Mar. 22, 2011

(54) PREPARATION OF SUBSTITUTED BRIDGED INDENYL AND RELATED LIGANDS

(75) Inventors: Alexander Z. Voskoboynikov, Moscow (RU); Mikhail V. Nikulin, Moscow (RU); Alexey N. Ryabov, Moscow (RU); Alexander V. Lygin, Moscow (RU); Catalina L. Coker, Baytown, TX (US); Jo Ann M. Canich, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 1165 days.

(21) Appl. No.: 11/302,846

(22) Filed: Dec. 14, 2005

(65) Prior Publication Data

US 2007/0135596 A1 Jun. 14, 2007

(51) Int. Cl.
C07C 13/28 (2006.01)
C07C 13/32 (2006.01)
C07C 13/465 (2006.01)
C07C 13/567 (2006.01)

(52) U.S. Cl. ........... 585/27; 585/457; 585/462; 585/471
(58) Field of Classification Search ............ 585/27, 585/457, 462, 471
See application file for complete search history.

(56) References Cited

U.S. PATENT DOCUMENTS

| | | | |
|---|---|---|---|
| 4,794,096 A | 12/1988 | Ewen | |
| 5,789,634 A | 8/1998 | Sullivan et al. | |

FOREIGN PATENT DOCUMENTS

| | | |
|---|---|---|
| DE | 3443087 A1 | 5/1986 |
| EP | 0567970 | 3/1993 |
| EP | 0629632 | 4/2000 |
| EP | 1640377 | 3/2006 |
| WO | 98/40331 | 9/1998 |
| WO | 01/14388 | 3/2001 |
| WO | 03/084904 | 10/2003 |

OTHER PUBLICATIONS

U.S. Appl. No. 11/300,002, filed Dec. 14, 2005, Voskoboynikov et al.
U.S. Appl. No. 11/300,032, filed Dec. 14, 2005, Voskoboynikov et al.
U.S. Appl. No. 11/300,054, filed Dec. 14, 2005, Voskoboynikov et al.
U.S. Appl. No. 11/300,240, filed Dec. 14, 2005, Voskoboynikov et al.
U.S. Appl. No. 11/302,798, filed Dec. 14, 2005, Voskoboynikov et al.
U.S. Appl. No. 11/302,821, filed Dec. 14, 2005, Voskoboynikov et al.
U.S. Appl. No. 11/302,997, filed Dec. 14, 2005, Voskoboynikov et al.
U.S. Appl. No. 11/302,998, filed Dec. 14, 2005, Voskoboynikov et al.
Wild et al., "Synthesis and Molecular Structures of Chiral ansa-Titanocene Derivatives with Bridged Tetrahydroindenyl Ligands," J. Organomet. Chem. 1982, 232, 233-47.
"Selectivity in Propene Polymerization with Metallocene Catalysts", Chem. Rev. 2000, vol. 100, No. 4, 1253-4345.
Panarello et al., "Use of Oxirane Ring-Opening Reactions for Synthesis of Ethylene-Bis (Indenyl) Ligands Containing Alkene Tethers," Synlett 2005, 5, 797-800.
Panarello et al., "Selective Alkylation and Suzuki Coupling as an Efficient Strategy for Introducing Functional Anchors to the Ethylene-Bis (Indenyl) Ligand," Tetrahedron Letters 2005, 46, 1353-1356.
Ishihara et al., "Design of Bronsted Acid Assisted Chiral Lewis Acid (BLA) Catalysts for Highly Enantioselective Diels-Alder Reactions," Journal of the American Chemical Society 1998, 120, 6920-6930.
Suzuki, "Recent Advances in the Cross-Coupling Reactions of Organoboron Derivatives with Organic Electrophiles, 1995-1998," Journal of Organometallic Chemistry 1999, 576, 147-168.
Bailey et al., Effect of Solvent on the Lithium-Bromine Exchange of Aryl Bromides: Reactions of n-Butyllithium and tert-Butyllithium with 1-Bromo-4-tert-butylbenzene at 0° C., J. Org. Chem., 2006, vol. 71, No. 7, pp. 2825-2828.
Parham et al., Preparation of Aroylbenzoic Acid. Reaction of Aryllithium Reagents with Phthalic Anhydride[1], J. Org. Chem., vol. 41, No. 7, pp. 1268-1269, 1976.
Jones et al., Methods of Preparation of Organometallic Compounds, Chemical Review, 1954, vol. 54, No. 5, pp. 835-890.

*Primary Examiner* — Caixia Lu

(57) ABSTRACT

A process for preparing a chelating ligand of the formula (II) from a chelating ligand of the formula (I) via an $sp^2$-$sp^2$ or $sp^2$-$sp^3$ coupling reaction with an organometallic compound of the formula (III).

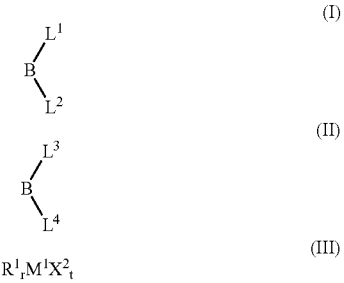

wherein B is a bridging group that is bonded to $L^1$ and $L^2$ in formula (I) and to $L^3$ and $L^4$ in formula (II); $L^1$ is a substituted monocyclic or polycyclic ligand that comprises at least one chlorine, bromine, iodine, or sulfonate substituent, directly bonded to an $sp^2$ carbon atom of the ring structure of the ligand; $L^2$ is a monoanionic ligand; or $L^2$ may, independently, be defined as $L^1$; $L^3$ is the same group as $L^1$, but said at least one chlorine, bromine, iodine, or sulfonate substituent is replaced with a hydrocarbyl, substituted hydrocarbyl, halocarbyl, or substituted halocarbyl fragment; $L^4$ is the same group as $L^2$, though, when $L^2$ is defined as $L^1$, $L^4$ may be the same as $L^3$ or $L^1$; $R^1$ is a hydrocarbyl, substituted hydrocarbyl, halocarbyl, or substituted halocarbyl; $M^1$ is an element of group 1, 2, 12, 13 or 14 of the Periodic Table of the Elements; each $X^2$, if present, is selected independently from the group consisting of halogen atoms, the hydroxyl group, alkoxy groups, aryloxy groups, mesylate, tosylate and triflate; r is 1, 2 or 3, and t is 0, 1 or 2, where r+t corresponds to the oxidation number of $M^1$.

95 Claims, No Drawings

PREPARATION OF SUBSTITUTED BRIDGED INDENYL AND RELATED LIGANDS

FIELD

The present invention relates to a process for preparing substituted bridged indenyl and related ligands, to the substituted ligands prepared in this way and to their use in preparing metallocenes for olefin polymerization catalysts.

BACKGROUND

Various processes and catalysts exist for the homopolymerization or copolymerization of olefins. For many applications, it is desirable for a polyolefin to have a high weight average molecular weight while having a relatively narrow molecular weight distribution. A high weight average molecular weight, when accompanied by a narrow molecular weight distribution, provides a polyolefin with high strength properties.

Traditional Ziegler-Natta catalysts systems—a transition metal compound co-catalyzed by an aluminum alkyl—are typically capable of producing polyolefins having a high molecular weight, but with a broad molecular weight distribution.

More recently a catalyst system has been developed wherein the transition metal compound has one or more cyclopentadienyl ring ligands (typically two)—such transition metal compound being referred to herein as a "metallocene"—which catalyzes the production of olefin monomers to polyolefins. Accordingly, titanocenes, zirconocenes and hafnocenes, have been utilized as the transition metal component in such "metallocene" containing catalyst system for the production of polyolefins and ethylene-alpha-olefin copolymers.

Catalysts that produce isotactic polyolefins are disclosed in U.S. Pat. No. 4,794,096. This patent discloses a chiral, stereorigid metallocene catalyst which is activated by an alumoxane cocatalyst and which is reported to polymerize olefins to isotactic polyolefin forms. Alumoxane co-catalyzed metallocene structures which have been reported to polymerize alpha-olefins stereoregularly include the ethylene bridged bis-indenyl and bis-tetrahydroindenyl titanium and zirconium (IV) catalysts. Such catalyst systems were synthesized and studied in Wild et al., *J. Organomet. Chem.* 232, 233-47 (1982), and were later reported in Ewen and Kaminsky et al., mentioned above, to polymerize alpha-olefins stereoregularly. Further reported in West German Off. DE 3443087A1 (1986), but without giving experimental verification, is that the bridge length of such stereorigid metallocenes can vary from a $C_1$ to $C_4$ hydrocarbon and the metallocene rings can be simple or bi-cyclic but must be asymmetric. When substituted or unsubstituted indenyl or tetrahydroindenyl based, these metallocenes are bridged in the "1-position" of the (hydro) indenyl ring, and are of C2 symmetry. Generally speaking, it is the C2 symmetric structure (also referred to as the d/l-enantiomers or racemic complexes) that produces isotactic poly-alpha-olefins. An alternate form is the Cs symmetric or meso form that produces atactic poly-alpha-olefins.

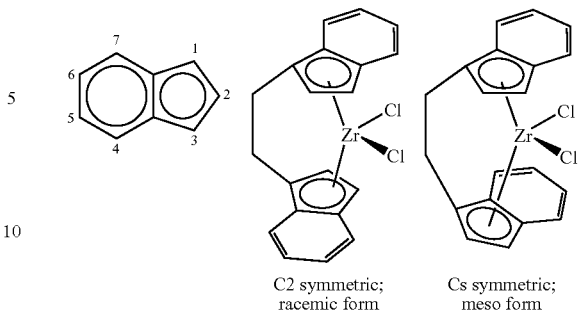

C2 symmetric; racemic form    Cs symmetric; meso form

Thus, use of substituted bridged bis-indenyl and related ligands as starting materials makes it possible to obtain chiral ansa-metallocenes which are of great importance as transition metal components of active catalysts in the stereospecific polymerization of olefins. Variation of the ligand system, for example by means of substitution, enables the catalyst properties to be influenced in a targeted manner. This makes it possible to alter the polymer yield, the molecular weight distribution, the tacticity and the melting point of the polymers to the desired degree (*Chem. Rev.* 2000, vol. 100, no. 4; *Metallocenes: Synthesis, Reactivity, Applications* Ed. by A. Togni, R. L. Halterman.—Wiley-VCH, 1998). Bridged zirconocenes containing, as π ligands, indenyl radicals, which bear the bridge in position 1 and which preferably bear a hydrocarbon radical in position 2 and a hydrocarbon radical in position 4, have been found to be particularly highly active and stereoselective catalyst systems (European Patent Publication No. 0567970 A1; European Patent Publication No 0629632 A2). The ligand systems used for these highly active metallocenes are prepared from the corresponding indenes.

A number of processes comprising an inexpensive coupling reaction have been described for the preparation of certain aryl- and alkyl-substituted indenes and indanones (International Patent Publication No. WO 98/40331; U.S. Pat. No. 5,789,634; International Patent Publication No. WO 03/084904 A1). However, the synthesis of aryl-, alkyl-, and alkenyl-substituted bridged indenyl and related ligands has not been studied so far, though this methodology could provide an attractive route for obtaining libraries of the substituted metal complexes. Also, in the case of bridged indenyl and related ligands with an $SiR_2$ bridge, Suzuki coupling reactions in protic medium will result in cleavage of such allylic silicon bridging group [*Metal-catalyzed cross coupling reactions* by Diederich, F.; Stang, P. J., Eds.; Wiley-VCH, 1998].

There is therefore a need for a simple and flexible process for preparing aryl-, alkyl-, and alkenyl-substituted bridged indenyl and related chelating ligands which are important intermediates for the preparation of active compounds and metallocene complexes.

According to the invention, it has now been found that substituted bridged indenyl and related chelating ligands containing halogen and/or sulfonate as leaving groups can be converted in a simple manner into substituted bridged indenyl and related chelating ligands which contain hydrocarbyl, substituted hydrocarbyl, halocarbyl, or substituted halocarbyl substituents bound via $sp^2$ or $sp^3$ center and which can be further used for the preparation of active compounds and metallocene complexes.

SUMMARY

In one aspect, the present invention resides in a process for preparing a chelating ligand of the formula (II) from a chelating ligand of the formula (I) via an sp²-sp² or sp²-sp³ coupling reaction with an organometallic compound of formula (III):

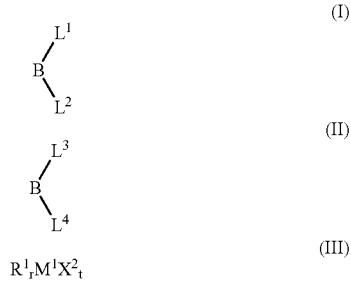

$$R^1{}_rM^1X^2{}_t \quad (III)$$

wherein

B is a bridging group that is bonded to $L^1$ and $L^2$ in formula (I) and to $L^3$ and $L^4$ in formula (II);

$L^1$ is a substituted monocyclic or polycyclic ligand that comprises at least one chlorine, bromine, iodine, or sulfonate substituent, directly bonded to an sp² carbon atom of the ring structure of the ligand;

$L^2$ is a monoanionic ligand; or $L^2$ may, independently, be defined as $L^1$;

$L^3$ is the same group as $L^1$, but said at least one chlorine, bromine, iodine, or sulfonate substituent is replaced with a hydrocarbyl, substituted hydrocarbyl, halocarbyl, or substituted halocarbyl fragment;

$L^4$ is the same group as $L^2$, though, when $L^2$ is defined as $L^1$, $L^4$ may be the same as $L^3$ or $L^1$;

$R^1$ is a hydrocarbyl, substituted hydrocarbyl, halocarbyl, or substituted halocarbyl;

$M^1$ is an element of Group 1, 2, 12, 13 or 14 of the Periodic Table of the Elements, preferably Li, Na, K, Rb, Cs, Be, Mg, Ca, Sr, Ba, B, Si, Sn, Zn, Cd or Hg, more preferably B, Si, Sn, Zn, Cd or Hg, and most preferably B, Sn or Zn;

each $X^2$, if present, is selected independently from the group consisting of halogen atoms, the hydroxyl group, alkoxy groups, aryloxy groups, mesylate, tosylate and triflate, preferably from the group consisting of halogen atoms, the hydroxyl group, alkoxy and aryloxy;

r is 1, 2 or 3, and t is 0, 1 or 2, where r+t corresponds to the oxidation number of $M^1$.

Conveniently, $L^1$ is a substituted indenyl, a substituted heteroindenyl, a substituted fluorenyl, or a substituted heterofluorenyl ligand.

Conveniently, $L^2$ is a substituted or unsubstituted monocyclic or polycyclic ligand, preferably a substituted or unsubstituted cyclopentadienyl ligand, a substituted or unsubstituted heterocyclopentadienyl ligand, a substituted or unsubstituted indenyl ligand, a substituted or unsubstituted heteroindenyl ligand, a substituted or unsubstituted fluorenyl ligand, a substituted or unsubstituted heterofluorenyl ligand.

Preferably, $L^1$ comprises at least one chlorine, bromine, or triflate directly bonded to an sp² carbon atom of the ring structure of the ligand, and most preferably $L^1$ comprises at least one bromine or triflate directly bonded to an sp² carbon atom of the ring structure of the ligand.

Ligands of formula (II) have been further used to obtain the respective metallocenes. The latter compounds, when combined with activators, readily polymerize various unsaturated monomers.

Definitions

As used herein, the numbering scheme for the Periodic Table Groups is the new notation as set out in CHEMICAL AND ENGINEERING NEWS, 63(5), 27 (1985). Note however that in some of the formulae herein the capital letter "B" is used to indicate a bridge. It is not intended that such bridges be limited to boron, even if boron is one of the possible substituents.

As used herein, Me is methyl, t-Bu and $^tBu$ are tertiary butyl, iPr and $^iPr$ are isopropyl, Cy is cyclohexyl, and Ph is phenyl.

The terms "hydrocarbyl radical," "hydrocarbyl" and "hydrocarbyl group" are used interchangeably throughout this document. Likewise the terms "group", "radical", and "substituent" are also used interchangeably in this document. For purposes of this disclosure, "hydrocarbyl radical" is defined to be $C_1$-$C_{100}$ radicals, that may be linear, branched, or cyclic, and when cyclic, aromatic or non-aromatic, and include substituted hydrocarbyl radicals, halocarbyl radicals, and substituted halocarbyl radicals, silylcarbyl radicals, and germylcarbyl radicals as these terms are defined below.

Substituted hydrocarbyl radicals are radicals in which at least one hydrogen atom has been substituted with at least one functional group such as NR*₂, OR*, SeR*, TeR*, PR*₂, AsR*₂, SbR*₂, SR*, BR*₂, SiR*₃, GeR*₃, SnR*₃, PbR*₃ and the like or where at least one non-hydrocarbon atom or group has been inserted within the hydrocarbyl radical, such as —O—, —S—, —Se—, —Te—, —N(R*)—, =N—, —P(R*)—, =P—, —As(R*)—, =As—, —Sb(R*)—, =Sb—, —B(R*)—, =B—, —Si(R*)₂—, —Ge(R*)₂—, —Sn(R*)₂—, —Pb(R*)₂— and the like, where R* is independently a hydrocarbyl or halocarbyl radical, and two or more R* may join together to form a substituted or unsubstituted saturated, partially unsaturated or aromatic cyclic or polycyclic ring structure.

Halocarbyl radicals are radicals in which one or more hydrocarbyl hydrogen atoms have been substituted with at least one halogen (e.g. F, Cl, Br, I) or halogen-containing group (e.g. $CF_3$).

Substituted halocarbyl radicals are radicals in which at least one halocarbyl hydrogen or halogen atom has been substituted with at least one functional group such as NR*2, OR*, SeR*, TeR*, PR*₂, AsR*₂, SbR*₂, SR*, BR*₂, SiR*3, GeR*₃, SnR*3, PbR*₃ and the like or where at least one non-carbon atom or group has been inserted within the halocarbyl radical such as —O—, —S—, —Se—, —Te—, —N(R*)—, =N—, —P(R*)—, =P—, —As(R*)—, =As—, —Sb(R*)—, =Sb—, —B(R*)—, =B—, —Si(R*)₂—, —Ge(R*)₂—, —Sn(R*)₂—, —Pb(R*)₂— and the like, where R* is independently a hydrocarbyl or halocarbyl radical provided that at least one halogen atom remains on the original halocarbyl radical. Additionally, two or more R* may join together to form a substituted or unsubstituted saturated, partially unsaturated or aromatic cyclic or polycyclic ring structure.

Silylcarbyl radicals (also called silylcarbyls) are groups in which the silyl functionality is bonded directly to the indicated atom or atoms. Examples include $SiH_3$, $SiH_2R*$, SiHR*₂, SiR*₃, SiH₂(OR*), SiH(OR*)₂, Si(OR*)₃, SiH₂(NR*₂), SiH(NR*₂)₂, Si(NR*₂)₃, and the like where R* is independently a hydrocarbyl or halocarbyl radical and two or more R* may join together to form a substituted or unsubstituted saturated, partially unsaturated or aromatic cyclic or polycyclic ring structure.

Germylcarbyl radicals (also called germylcarbyls) are groups in which the germyl functionality is bonded directly to the indicated atom or atoms. Examples include $GeH_3$, GeH₂R*, GeHR*₂, GeR⁵₃, GeH₂(OR*), GeH(OR*)₂, Ge(OR*)₃, GeH₂(NR*₂), GeH(NR*₂)₂, Ge(NR*₂)₃, and the like where R* is independently a hydrocarbyl or halocarbyl radical and two or more R* may join together to form a substituted or unsubstituted saturated, partially unsaturated or aromatic cyclic or polycyclic ring structure.

Polar radicals, functional groups, or polar groups are groups in which the heteroatom functionality is bonded directly to the indicated atom or atoms. They include heteroatoms of groups 1-17 of the periodic table either alone or connected to other elements by covalent or other interactions such as ionic, van der Waals forces, or hydrogen bonding. Examples of functional groups include carboxylic acid, acid halide, carboxylic ester, carboxylic salt, carboxylic anhydride, aldehyde and their chalcogen (Group 14) analogues, alcohol and phenol, ether, peroxide and hydroperoxide, carboxylic amide, hydrazide and imide, amidine and other nitrogen analogues of amides, nitrile, amine and imine, azo, nitro, other nitrogen compounds, sulfur acids, selenium acids, thiols, sulfides, sulfoxides, sulfones, phosphines, phosphates, other phosphorus compounds, silanes, boranes, borates, alanes, aluminates. Functional groups may also be taken broadly to include organic polymer supports or inorganic support material such as alumina, and silica. Preferred examples of polar groups include $NR*_2$, $OR*$, $SeR*$, $TeR*$, $PR*_2$, $AsR*_2$, $SbR*_2$, $SR*$, $BR*_2$, $SnR*_3$, $PbR*_3$ and the like where R* is independently a hydrocarbyl, substituted hydrocarbyl, halocarbyl or substituted halocarbyl radical as defined above and two R* may join together to form a substituted or unsubstituted saturated, partially unsaturated or aromatic cyclic or polycyclic ring structure.

Sulfonate radical is a group in which hydrocarbyl, substituted hydrocarbyl, halocarbyl, or substituted halocarbyl is bonded to sulfur in —O—S(=O)$_2$ group. Examples include $SO_3Me$ (mesylate), $SO_3$(4-tosyl) (tosylate), $SO_3CF_3$ (triflate), $SO_3$(n-$C_4F_9$) (nonaflate) and the like.

In using the terms "substituted or unsubstituted monocyclic or polycyclic ligand", "substituted or unsubstituted cyclopentadienyl ligand", "substituted or unsubstituted heterocyclopentadienyl ligand", "substituted or unsubstituted indenyl ligand", "substituted or unsubstituted heteroindenyl ligand", "substituted or unsubstituted fluorenyl ligand", "substituted or unsubstituted heterofluorenyl ligand", "substituted or unsubstituted pentadienyl ligand", "substituted or unsubstituted allyl ligand", and "substituted or unsubstituted boratabenzene ligand", the substitution to the aforementioned ligand may be hydrocarbyl, substituted hydrocarbyl, halocarbyl, substituted halocarbyl, silylcarbyl, or germylcarbyl.

In some embodiments, the hydrocarbyl radical is independently selected from methyl, ethyl, ethenyl and isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, triacontynyl, butadienyl, pentadienyl, hexadienyl, heptadienyl, octadienyl, nonadienyl, and decadienyl. Also included are isomers of saturated, partially unsaturated and aromatic cyclic and polycyclic structures wherein the radical may additionally be subjected to the types of substitutions described above. Examples include phenyl, methylphenyl, dimethylphenyl, ethylphenyl, diethylphenyl, propylphenyl, dipropylphenyl, benzyl, methylbenzyl, naphthyl, anthracenyl, cyclopentyl, cyclopentenyl, cyclohexyl, cyclohexenyl, methylcyclohexyl, cycloheptyl, cycloheptenyl, norbornyl, norbornenyl, adamantyl and the like. For this disclosure, when a radical is listed, it indicates that radical type and all other radicals formed when that radical type is subjected to the substitutions defined above. Alkyl, alkenyl and alkynyl radicals listed include all isomers including where appropriate cyclic isomers, for example, butyl includes n-butyl, 2-methylpropyl, 1-methylpropyl, tert-butyl, and cyclobutyl (and analogous substituted cyclopropyls); pentyl includes n-pentyl, cyclopentyl, 1-methylbutyl, 2-methylbutyl, 3-methylbutyl, 1-ethylpropyl, and neopentyl (and analogous substituted cyclobutyls and cyclopropyls); butenyl includes E and Z forms of 1-butenyl, 2-butenyl, 3-butenyl, 1-methyl-1-propenyl, 1-methyl-2-propenyl, 2-methyl-1-propenyl and 2-methyl-2-propenyl (and cyclobutenyls and cyclopropenyls). Cyclic compound having substitutions include all isomer forms, for example, methylphenyl would include ortho-methylphenyl, meta-methylphenyl and para-methylphenyl; dimethylphenyl would include 2,3-dimethylphenyl, 2,4-dimethylphenyl, 2,5-dimethylphenyl, 2,6-diphenylmethyl, 3,4-dimethylphenyl, and 3,5-dimethylphenyl.

For nomenclature purposes, the following numbering schemes are used for cyclopentadienyl, indenyl, fluorenyl, and cyclopentanaphthyl (also termed benzindenyl). It should be noted that indenyl can be considered ascyclopentadienyl fused with a benzene ring. Analogously, fluorenyl can be considered a cyclopentadienyl with two phenyl rings fused onto the cyclopentadienyl ring. Each structure below is drawn and named as an anion.

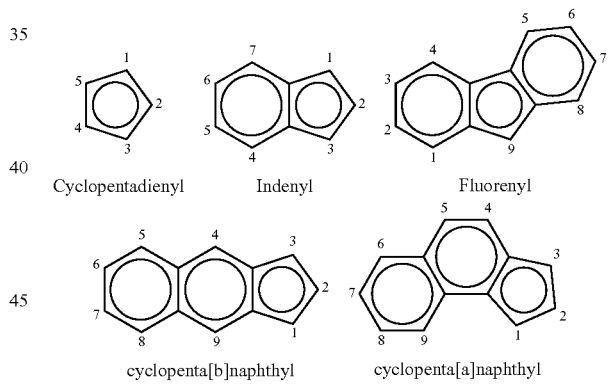

Cyclopentadienyl  Indenyl  Fluorenyl cyclopenta[b]naphthyl  cyclopenta[a]naphthyl A similar numbering and nomenclature scheme is used for heterocyclopentadienyls, heterophenyls, heteropentalenyls, heterocyclopentapentalenyls, heteroindenyls, heterofluorenyls, heterocyclopentanaphthyls, heterocyclopentaindenyls, heterobenzocyclopentaindenyls, and the like, as illustrated below. Each structure is drawn and named as an anion.

Non-limiting examples of heterocyclopentadienyls include:

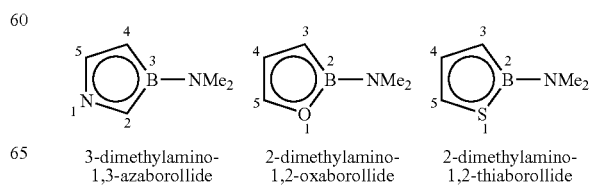

3-dimethylamino-1,3-azaborollide  2-dimethylamino-1,2-oxaborollide  2-dimethylamino-1,2-thiaborollide -continued

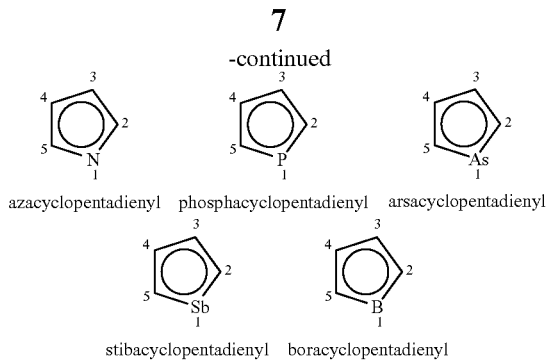

azacyclopentadienyl  phosphacyclopentadienyl  arsacyclopentadienyl stibacyclopentadienyl  boracyclopentadienyl Further non-limiting examples of heterocyclopentadienyls include 1,3-diazacyclopentadienyl, 1,3-diphosphacyclopentadienyl, 1,3-diarsacyclopentadienyl, 1,3-distibacyclopentadienyl, 1,3-diboracyclopentadienyl, 1,3-azaphosphacyclopentadienyl, 1,3-azaarsacylcopentadienyl, 1,3-azastibacyclopentadienyl, 1,3-azaboracyclopentadienyl, 1,3-arsaphosphacyclopentadienyl, 1,3-arsastibacyclopentadienyl, 1,3-arsaboracyclopentadienyl, 1,3-boraphosphacyclopentadienyl, 1,3-borastibacylcopentadienyl, 1,3-phosphastibacyclopentadienyl, 1,2-diazacyclopentadienyl, 1,2-diphosphacyclopentadienyl, 1,2-diarsacyclopentadienyl, 1,2-distibacyclopentadienyl, 1,2-diboracyclopentadienyl, 1,2-azaphosphacyclopentadienyl, 1,2-azaarsacylcopentadienyl, 1,2-azastibacyclopentadienyl, 1,2-azaboracyclopentadienyl, 1,2-arsaphosphacyclopentadienyl, 1,2-arsastibacyclopentadienyl, 1,2-arsaboracyclopentadienyl, 1,2-boraphosphacyclopentadienyl, 1,2-borastibacylcopentadienyl, 1,2-phosphastibacyclopentadienyl, 3-dihydrocarbylamino-1,3-azaborollide, 2-dihydrocarbylamino-1,2-oxaborollide, 2-dihydrocarbylamino-1,2-thiaborollide, 3-hydrocarbyloxy-1,3-azaborollide, 2-hydrocarbyloxy-1,2-oxaborollide, 2-hydrocarbyloxy-1,2-thiaborollide, 3-hydrocarbyl-1,3-azaborollide, 2-hydrocarbyl-1,2-oxaborollide, and 2-hydrocarbyl-1,2-thiaborollide, where hydrocarbyl is a "hydrocarbyl radical" as previously defined.

Non-limiting examples of heterophenyls include:

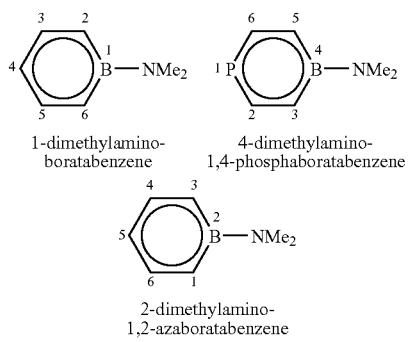

1-dimethylamino-  4-dimethylamino-
boratabenzene  1,4-phosphaboratabenzene 2-dimethylamino-
1,2-azaboratabenzene Further non-limiting examples of heterophenyls include 1-dihydrocarbylaminoboratabenzene, 4-dihydrocarbylamino-1,4-phosphaboratabenzene, 2-dihydrocarbylamino-1,2-azaboratabenzene, 1-hydrocarbyloxyboratabenzene, 4-hydrocarbyloxy-1,4-phosphaboratabenzene, 2-hydrocarbyloxy-1,2-azaboratabenzene, 1-hydrocarbylboratabenzene, 4-hydrocarbyl-1,4-phosphaboratabenzene, and 2-hydrocarbyl-1,2-azaboratabenzene, where hydrocarbyl is a "hydrocarbyl radical" as previously defined.

Non-limiting examples of heteropentalenyls include:

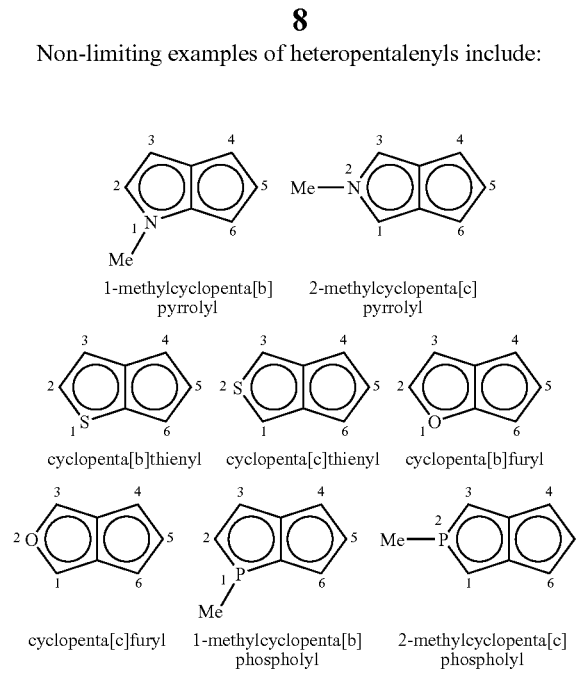

1-methylcyclopenta[b]  2-methylcyclopenta[c]
pyrrolyl  pyrrolyl cyclopenta[b]thienyl  cyclopenta[c]thienyl  cyclopenta[b]furyl cyclopenta[c]furyl  1-methylcyclopenta[b]  2-methylcyclopenta[c]
pholyl  pholyl Further non-limiting examples of heteropentalenyls include cyclopenta[b]selenophenyl, cyclopenta[c]selenophenyl, cyclopenta[b]tellurophenyl, cyclopenta[c]tellurophenyl, 1-hydrocarbylcyclopenta[b]arsolyl, 2-hydrocarbylcyclopenta[c]arsolyl, 1-hydrocarbylcyclopenta[b]stibolyl, 2-hydrocarbylcyclopenta[c]stibolyl, 1-hydrocarbylcyclopenta[b]pyrrolyl, 2-hydrocarbylcyclopenta[c]pyrrolyl, 1-hydrocarbylcyclopenta[b]phospholyl, and 2-hydrocarbylcyclopenta[c]phospholyl, where hydrocarbyl is a "hydrocarbyl radical" as previously defined.

Non-limiting examples of heterocylopentapentalenyls include the following, where Z and Q independently represent the heteroatoms O, S, Se, or Te, or heteroatom groups, NR, PR, AsR, or SbR where R** is hydrogen, or a hydrocarbyl, substituted hydrocarbyl, halocarbyl, substituted halocarbyl, silylcarbyl, or germylcarbyl substituent.

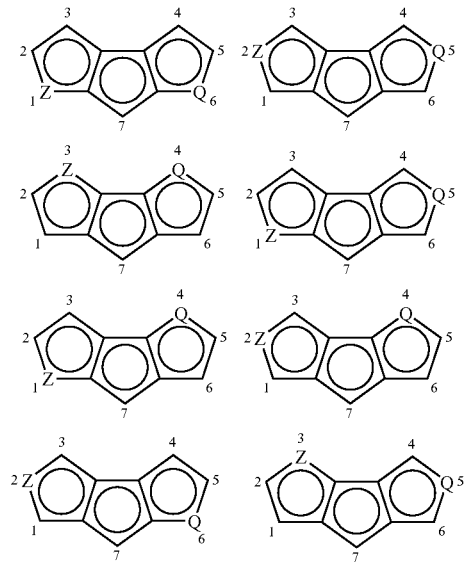

-continued

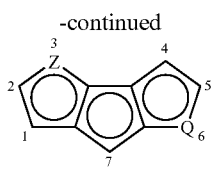

Non-limiting examples of heteroindenyls include:

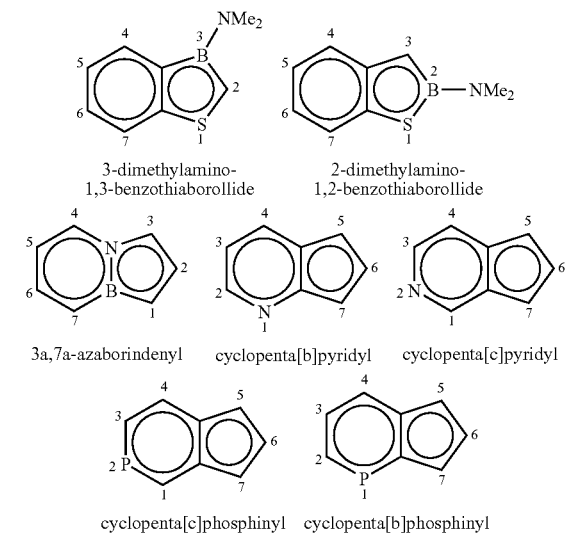

3-dimethylamino-1,3-benzothiaborollide  2-dimethylamino-1,2-benzothiaborollide 3a,7a-azaborindenyl   cyclopenta[b]pyridyl   cyclopenta[c]pyridyl cyclopenta[c]phosphinyl   cyclopenta[b]phosphinyl Further non-limiting examples of heteroindenyls include cyclopenta[b]arsinyl, cyclopenta[c]arsinyl, cyclopenta[b]stibinyl, cyclopenta[c]stibinyl, 3-dihydrocarbylamino-1,3-benzothiaborollide, 2-dihydrocarbylamino-1,2-benzothiaborollide, 3-hydrocarbyloxy-1,3-benzothiaborollide, 2-hydrocarbyloxy-1,2-benzothiaborollide, 3-hydrocarbyl-1,3-benzothiaborollide, and 2-hydrocarbyl-1,2-benzothiaborollide, where hydrocarbyl is a "hydrocarbyl radical" as previously defined.

Non-limiting examples of heterofluorenyls include:

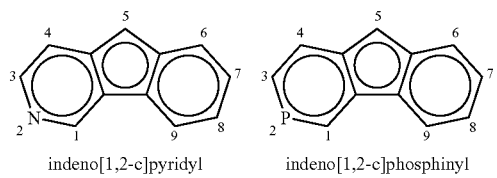

indeno[1,2-c]pyridyl   indeno[1,2-c]phosphinyl

Non-limiting examples of heterocyclopentanaphthyls include:

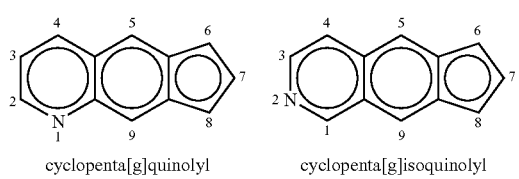

cyclopenta[g]quinolyl   cyclopenta[g]isoquinolyl

Further non-limiting examples of heterocyclopentanaphthyls include cyclopenta[g]phosphinolyl, cyclopenta[g]isophosphinolyl, cyclopenta[g]arsinolyl, and cyclopenta[g]isoarsinolyl.

Non-limiting examples of heterocyclopentaindenyls include:

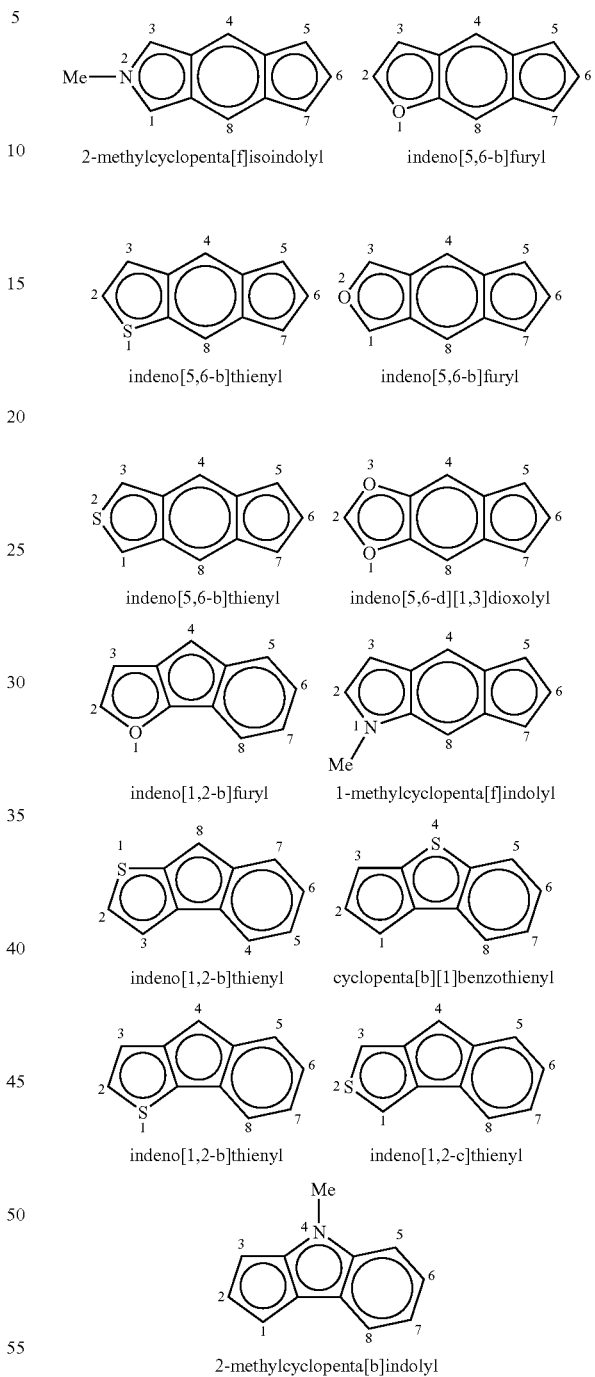

2-methylcyclopenta[f]isoindolyl   indeno[5,6-b]furyl indeno[5,6-b]thienyl   indeno[5,6-b]furyl indeno[5,6-b]thienyl   indeno[5,6-d][1,3]dioxolyl indeno[1,2-b]furyl   1-methylcyclopenta[f]indolyl indeno[1,2-b]thienyl   cyclopenta[b][1]benzothienyl indeno[1,2-b]thienyl   indeno[1,2-c]thienyl 2-methylcyclopenta[b]indolyl Further non-limiting examples of heterocyclopentaindenyls include 1-hydrocarboncylcyclopenta[f]phosphindolyl, 2-hydrocarboncylcyclopenta[f]isophosphindolyl, 1-hydrocarbylcyclopenta[f]arsindolyl, 2-hydrocarbylcyclopenta[f]isoarsindolyl, indeno[5,6-b]selenophenyl, indeno[5,6-b]tellurophenyl, indeno[5,6-c]selenophenyl, indeno[5,6-c]tellurophenyl, 2-hydrocarbylcylcyclopenta[f]isoindolyl, and 1-hydrocarbylcyclopenta[f]indolyl, where hydrocarbyl is a "hydrocarbyl radical" as previously defined.

Non-limiting examples of heterobenzocyclopentaindenyls include:

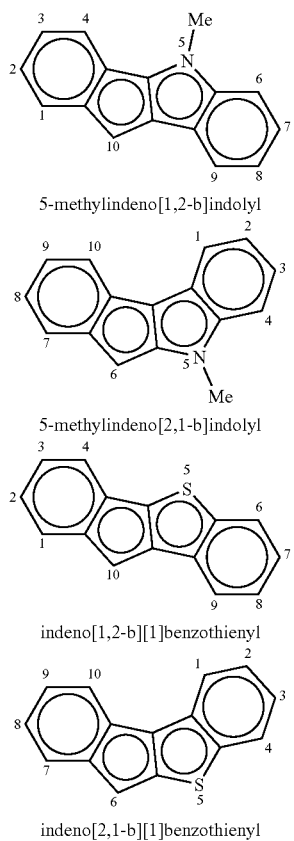

5-methylindeno[1,2-b]indolyl 5-methylindeno[2,1-b]indolyl indeno[1,2-b][1]benzothienyl indeno[2,1-b][1]benzothienyl Further non-limiting examples of heterobenzocyclopentaindenyls include 5-hydrocarbylindeno[1,2-b]indolyl and 5-hydrocarbylindeno[2,1-b]indolyl, where hydrocarbyl is a "hydrocarbyl radical" as previously defined.

The term "arene" ligand is used herein to mean an unsaturated cyclic hydrocarbyl ligand that can consist of one ring, or two or more fused or catenated rings.

As used herein, the term "monocyclic ligand" is intended to mean any substituted or unsubstituted $C_5$ to $C_{100}$ monoanionic aromatic five-membered or six-membered single ring structure composed of ring carbon atoms, either alone or in combination with one or more ring heteroatoms. In contrast, the term "monocyclic arene ligand" is used herein to mean a substituted or unsubstituted monoanionic $C_5$ to $C_{100}$ hydrocarbyl ligand that contains an aromatic five-membered single hydrocarbyl ring structure (also referred to as a cyclopentadienyl ring).

As used herein, the term "polycyclic ligand" is intended to mean any substituted or unsubstituted $C_5$ to $C_{103}$ monoanionic partially unsaturated or aromatic multiple fused ring structure containing at least one aromatic five-membered ring structure, said ligand composed of ring carbon atoms, either alone or in combination with one or more ring heteroatoms. In contrast, the term "polycyclic arenyl ligand" is used herein to mean a substituted or unsubstituted monoanionic $C_8$ to $C_{103}$ hydrocarbyl ligand that contains an aromatic five-membered hydrocarbyl ring (also referred to as a cyclopentadienyl ring) that is fused to one or two partially unsaturated, or aromatic hydrocarbyl ring structures which may be fused to additional saturated, partially unsaturated, or aromatic hydrocarbyl rings.

Monocyclic ligands include substituted or unsubstituted heterocyclopentadienyls and heterophenyls. Monocyclic arenyl ligands include substituted or unsubstituted cyclopentadienyls. Polycyclic ligands include substituted or unsubstituted, partially unsaturated or aromatic heteroindenyls, heteropentalenyls, heterocyclopentapentalenyls, heterofluorenyls, heterocyclopentanaphthyls, heterocyclopentaindenyls, and heterobenzocyclopentaindenyls. Polycyclic arenyl ligands include substituted or unsubstituted, partially unsaturated or aromatic indenyls, fluorenyls, and cyclopentanaphthyls.

Non-limiting examples of polycyclic arene ligands, named also as monoanionic ligands, include indenyl, 4,5-dihydroindenyl, 4,7-dihydroindenyl, 4,5,6,7-tetrahydroindenyl, fluorenyl, 1,2-dihydrotetrahydrofluorenyl, 1,4-dihydrotetrahydrofluorenyl, 3,4-dihydrotetrahydrofluorenyl, 1,2,3,4-tetrahydrofluorenyl, 1,2,5,6-tetrahydrofluorenyl, 1,2,7,8-tetrahydrofluorenyl, 3,4,5,6-tetrahydrofluorenyl, 1,4,5,8-tetrahydrofluorenyl, 1,2,3,4,5,6,7,8-octahydrofluorenyl, cyclopenta[b]naphthyl, 4,4a-dihydrocyclopenta[b]naphthyl, 5,6-dihydrocyclopenta[b]naphthyl, 5,8-dihydrocyclopenta[b]naphthyl, 4,9-dihydrocyclopenta[b]naphthyl, 4,4a,5,6-tetrahydrocyclopenta[b]naphthyl, 4,5,8,9-tetrahydrocyclopenta[b]naphthyl, 4,4a,7,8-tetrahydrocyclopenta[b]naphthyl, 4,4a,8a,9-tetrahydrocyclopenta[b]naphthyl, 5,6,7,8-tetrahydrocyclopenta[b]naphthyl, 4,4a,5,8-tetrahydrocyclopenta[b]naphthyl, 4,5,6,9-tetrahydrocyclopenta[b]naphthyl, 4,6,7,8-tetrahydrocyclopenta[b]naphthyl, 4,6,7,9-tetrahydrocyclopenta[b]naphthyl, 4,4a,5,9-tetrahydrocyclopenta[b]naphthyl, 4,4a,5,6,7,8-hexahydrocyclopenta[b]naphthyl, 4,4a,5,6,8a,9-hexahydrocyclopenta[b]naphthyl, 4,4a,5,8,8a,9-hexahydrocyclopenta[b]naphthyl, 4,5,6,7,8,9-hexahydrocyclopenta[b]naphthyl, 4,4a,5,6,7,9-hexahydrocyclopenta[b]naphthyl, 4,4a,5,6,7,8,8a,9-octahydrocyclopenta[b]naphthyl, cyclopenta[a]naphthyl, 4,5-dihydrocyclopenta[a]naphthyl, 6,7-dihydrocyclopenta[a]naphthyl, 8,9-dihydrocyclopenta[a]naphthyl, 5a,9a-dihydrocyclopenta[a]naphthyl, 6,9-dihydrocyclopenta[a]naphthyl, 7,9a-dihydrocyclopenta[a]naphthyl, 4,9a-dihydrocyclopenta[a]naphthyl, 5a,8-dihydrocyclopenta[a]naphthyl, 4,5,5a,9a-tetrahydrocyclopenta[a]naphthyl, 4,5,6,7-tetrahydrocyclopenta[a]naphthyl, 4,5,8,9-tetrahydrocyclopenta[a]naphthyl, 5a,6,7,9a-tetrahydrocyclopenta[a]naphthyl, 6,7,8,9-tetrahydrocyclopenta[a]naphthyl, 5a,8,9,9a-tetrahydrocyclopenta[a]naphthyl, 4,5,7,9a-tetrahydrocyclopenta[a]naphthyl, 5a,6,7,9a-tetrahydrocyclopenta[a]naphthyl, 7,8,9,9a-tetrahydrocyclopenta[a]naphthyl, 4,6,7,9a-tetrahydrocyclopenta[a]naphthyl, 4,8,9,9a-tetrahydrocyclopenta[a]naphthyl, 4,5,6,9-tetrahydrocyclopenta[a]naphthyl, 4,5,5a,8-tetrahydrocyclopenta[a]naphthyl, 5a,6,7,8-tetrahydrocyclopenta[a]naphthyl, 5a,6,9,9a-tetrahydrocyclopenta[a]naphthyl, 5a,6,7,8,9,9a-hexahydrocyclopenta[a]naphthyl, 4,6,7,8,9,9a-hexahydrocyclopenta[a]naphthyl, 4,5,7,8,9,9a-hexahydrocyclopenta[a]naphthyl, 4,5,5a,8,9,9a-hexahydrocyclopenta[a]naphthyl, 4,5,5a,6,9,9a-hexahydrocyclopenta[a]naphthyl, 4,5,5a,6,7,9a-hexahydrocyclopenta[a]naphthyl, 4,5,5a,6,7,8-hexahydrocyclopenta[a]naphthyl, 4,5,6,7,8,9-hexahydrocyclopenta[a]naphthyl, 4,5,5a,6,7,8,9,9a-hexahydrocyclopenta[a]naphthyl, 4,5,5a,6,7,8,9,9a-octahydrocyclopenta[a]naphthyl, 5,6-trimethyleneindenyl, 4,5-trimethyleneindenyl, 5,6-pentamethyleneindenyl, 4,5- pentamethyleneindenyl, 5,6-hexamethyleneindenyl, 4,5-hexamethyleneindenyl, 5,6-heptamethyleneindenyl, 4,5-heptamethyleneindenyl, 5,6-octamethyleneindenyl, 4,5-octamethyleneindenyl, 5,6-nonamethyleneindenyl, 4,5-nonamethyleneindenyl, 5,6-decamethyleneindenyl, 4,5-decamethyleneindenyl, 5,6-undecamethyleneindenyl, 4,5-undecamethyleneindenyl, 5,6-dodecamethyleneindenyl, 4,5-dodecamethyleneindenyl, 5,6-tridecamethyleneindenyl, 4,5-tridecamethyleneindenyl, 5,6-tetradecamethyleneindenyl, 4,5-tetradecamethyleneindenyl, 5,6-pentadecamethyleneindenyl, 4,5-pentadecamethyleneindenyl, 5,6-hexadecamethyleneindenyl, 4,5-hexadecamethyleneindenyl, 5,6-heptadecamethyleneindenyl, 4,5-heptadecamethyleneindenyl, 5,6-octadecamethyleneindenyl, 4,5-octadecamethyleneindenyl, 5,6-nonadecamethyleneindenyl, 4,5-nonadecamethyleneindenyl, 5,6-eicosamethyleneindenyl, 4,5-eicosamethyleneindenyl, (6Z,8Z,10Z)-cycloocta[e]indenyl, (5Z,7Z,9Z)-cycloocta[f]indenyl, (5E,7Z,9E,11Z,13E)-cyclododeca[f]indenyl, (6E,8Z,10E,12Z,14E)-cyclododeca[e]indenyl, benz[a]fluorenyl, benz[b]fluorenyl, benz[c]fluorenyl, naphth[2,3-a]fluorenyl, naphth[2,3-b]fluorenyl, naphth[2,3-c]fluorenyl, naphth[1,2-a]fluorenyl, naphth[1,2-b]fluorenyl, naphth[1,2-c]fluorenyl, 2,3-tetramethylenefluorenyl, 1,2-tetramethylenefluorenyl, 3,4-tetramethylenefluorenyl, 2,3-trimethylenefluorenyl, 1,2-trimethylenefluorenyl, 3,4-trimethylenefluorenyl, 2,3-pentamethylenefluorenyl, 1,2-pentamethylenefluorenyl, 3,4-pentamethylenefluorenyl, 2,3-hexamethylenefluorenyl, 1,2-hexamethylenefluorenyl, 3,4-hexamethylenefluorenyl, 2,3-heptamethylenefluorenyl, 1,2-heptamethylenefluorenyl, 3,4-heptamethylenefluorenyl, 2,3-octamethylenefluorenyl, 1,2-octamethylenefluorenyl, 3,4-octamethylenefluorenyl, 2,3-nonamethylenefluorenyl, 1,2-nonamethylenefluorenyl, 3,4-nonamethylenefluorenyl, 2,3-decamethylenefluorenyl, 1,2-decamethylenefluorenyl, 3,4-decamethylenefluorenyl, 2,3-undecamethylenefluorenyl, 1,2-undecamethylenefluorenyl, 3,4-undecamethylenefluorenyl, 2,3-dodecamethylenefluorenyl, 1,2-dodecamethylenefluorenyl, 3,4-dodecamethylenefluorenyl, 2,3-tetramethylene-6,7-tetramethylenefluorenyl, 1,2-tetramethylene-7,8-tetramethylenefluorenyl, 3,4-tetramethylene-5,6-tetramethylenefluorenyl, bis-benz[2,3;6,7]fluorenyl, bis-benz[2,3;5,6]fluorenyl, bis-benz[1,2;7,8]fluorenyl, bis-benz[1,2;5,6]fluorenyl, bis-benz[1,2;6,7]fluorenyl, bis-benz[1,2;7,8]fluorenyl, and bis-benz[3,4;5,6]fluorenyl.

Partially hydrogenated polycyclic arene ligands retain the numbering scheme of the parent polycyclic arene ligand, namely the numbering schemes defined for indenyl, fluorenyl, cyclopenta[b]naphthyl, and cyclopenta[a]naphthyl ligands.

A "ring heteroatom" is a heteroatom that is within a cyclic ring structure. A "heteroatom substituent" is a heteroatom containing group that is directly bonded to a ring structure through the heteroatom. The terms "ring heteroatom" and "heteroatom substituent" are illustrated below where Z is a heteroatom group preferably S, O, Se, Te, N—R', P—R', As—R', Sb—R' or B—R' and each $R^1$ is independently a hydrocarbyl, substituted hydrocarbyl, halocarbyl or substituted halocarbyl radical as defined above and two $R^1$ may join together to form a substituted or unsubstituted saturated, partially unsaturated or aromatic cyclic or polycyclic ring structure. If R' is bonded to boron, $R^1$ can additionally be a Group 15 or Group 16 group where the heteroatom is directly bonded to boron and $R^1$ is then preferably an O—R" group or an N—$R_{12}$ group, where each R" is independently a hydrocarbyl, substituted hydrocarbyl, halocarbyl or substituted halocarbyl radical as defined above and two R" may join together to form a substituted or unsubstituted saturated, partially unsaturated or aromatic cyclic or polycyclic ring structure.

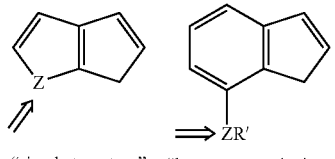

"ring heteroatom"  "heteroatom substituent"

A "ring carbon atom" is a carbon atom that is part of a cyclic ring structure. By this definition, an indenyl fragment has nine ring carbon atoms.

A "bondable ring position" is a ring position that is capable of bearing a substituent or bridging substituent. For example, cyclopenta[b]thienyl has five bondable ring positions (at the carbon atoms) and one non-bondable ring position (the sulfur atom); cyclopenta[b]pyrrolyl has six bondable ring positions (at the carbon atoms and at the nitrogen atom).

In the context of this document, "homopolymerization" would produce a polymer made from one monomer. For example, homopolymerization of propylene would produce homopolypropylene. Homopolymerization of ethylene would produce homopolyethylene. Likewise, "copolymerization" would produce polymers with more than one monomer type. For example, ethylene copolymers include polymers of ethylene with α-olefins, cyclic olefins and diolefins, vinylaromatic olefins, α-olefinic diolefins, substituted α-olefins, and/or acetylenically unsaturated monomers. Non-limiting examples of α-olefins include ethylene, propylene, 1-butene, 1-pentene, 1-hexene, 1-heptene, 1-octene, 1-nonene, 1-decene, 1-undecene 1-dodecene, 1-tridecene, 1-tetradecene, 1-pentadecene, 1-hexadecene, 1-heptadecene, 1-octadecene, 1-nonadecene, 1-eicosene, 1-heneicosene, 1-docosene, 1-tricosene, 1-tetracosene, 1-pentacosene, 1-hexacosene, 1-heptacosene, 1-octacosene, 1-nonacosene, 1-triacontene, 4-methyl-1-pentene, 3-methyl-1-pentene, 5-methyl-1-nonene, 3,5,5-trimethyl-1-hexene, vinylcyclohexane, and vinylnorbornane. Non-limiting examples of cyclic olefins and diolefins include cyclobutene, cyclopentene, cyclohexene, cycloheptene, cyclooctene, cyclononene, cyclodecene, norbornene, 4-methylnorbornene, 2-methylcyclopentene, 4-methylcyclopentene, vinylcyclohexane, norbornadiene, dicyclopentadiene, 5-ethylidene-2-norbornene, vinylcyclohexene, 5-vinyl-2-norbornene, 1,3-divinylcyclopentane, 1,2-divinylcyclohexane, 1,3-divinylcyclohexane, 1,4-divinylcyclohexane, 1,5-divinylcyclooctane, 1-allyl-4-vinylcyclohexane, 1,4-diallylcyclohexane, 1-allyl-5-vinylcyclooctane, and 1,5-diallylcyclooctane. Non-limiting examples of vinylaromatic olefins include styrene, para-methylstyrene, para-t-butylstyrene, vinylnaphthylene, vinyltoluene, and divinylbenzene. Non-limiting examples of α-olefinic dienes include 1,4-hexadiene, 1,5-hexadiene, 1,5-heptadiene, 1,6-heptadiene, 6-methyl-1,6-heptadiene, 1,7-octadiene, 7-methyl-1,7-octadiene, 1,9-decadiene, 1,11-dodecene, 1,13-tetradecene and 9-methyl-1,9-decadiene. Substituted α-olefins (also called functional group containing α-olefins) include those containing at least one non-carbon Group 13 to 17 atom bound to a carbon atom of the substituted α-olefin where such substitution if silicon may be adjacent to the double bond or terminal to the double bond, or anywhere in between, and where inclusion of non-carbon and non-silicon atoms such as for example B, O, S, Se, Te, N, P, Ge, Sn, Pb, As, F, Cl, Br, or I, are contemplated, where such non-carbon or non-silicon moieties are sufficiently far removed from the double bond so as not to interfere with the coordination polymerization reaction with the catalyst and so to retain the generally hydrocarbyl characteristic. By sufficiently far removed from the double bond we intend that the number of carbon atoms, or the number of carbon and silicon atoms, separating the double bond and the non-carbon or non-silicon moiety is preferably 6 or greater, e.g. 7, or 8, or 9, or 10, or 11, or 12, or 13, or 14 or more. The number of such carbon atoms, or carbon and silicon atoms, is counted from immediately adjacent to the double bond to immediately adjacent to the non-carbon or non-silicon moiety. Examples include 8,8,8-trifluoro-1-octene, 8-methoxyoct-1-ene, 8-methylsulfanyloct-1-ene, 8-dimethylaminooct-1-ene, or combinations thereof. The use of functional group-containing α-olefins where the functional group is closer to the double bond is also within the scope of embodiments of the invention when such olefins may be incorporated in the same manner as are their α-olefin analogs. See, "Metallocene Catalysts and Borane Reagents in The Block/Graft Reactions of Polyolefins", T. C. Chung, et al, *Polym. Mater. Sci. Eng.*, v. 73, p. 463 (1995), and the masked α-olefin monomers of U.S. Pat. No. 5,153,282. Such monomers permit the preparation of both functional-group containing copolymers capable of subsequent derivatization, and of functional macromers which may be used as graft and block type polymeric segments. Copolymerization can also incorporate α-olefinic macromonomers of up to 2000 mer units.

For purposes of this disclosure, the term oligomer refers to compositions having 2-75 mer units and the term polymer refers to compositions having 76 or more mer units. A mer is defined as a unit of an oligomer or polymer that originally corresponded to the monomer(s) used in the oligomerization or polymerization reaction. For example, the mer of polyethylene would be ethylene.

The term "catalyst system" is defined to mean a catalyst precursor/activator pair. When "catalyst system" is used to describe such a pair before activation, it means the unactivated catalyst (precatalyst) together with an activator and, optionally, a co-activator. When it is used to describe such a pair after activation, it means the activated catalyst and the activator or other charge-balancing moiety.

The transition metal compound may be neutral as in a precatalyst, or a charged species with a counter ion as in an activated catalyst system.

Catalyst precursor is also often referred to as precatalyst, catalyst, catalyst compound, catalyst precursor, transition metal compound or transition metal complex. These words are used interchangeably. Activator and cocatalyst are also used interchangeably. A scavenger is a compound that is typically added to facilitate oligomerization or polymerization by scavenging impurities. Some scavengers may also act as activators and may be referred to as co-activators. A co-activator, that is not a scavenger, may also be used in conjunction with an activator in order to form an active catalyst. In some embodiments a co-activator can be pre-mixed with the transition metal compound to form an alkylated transition metal compound, also referred to as an alkylated invention compound.

Noncoordinating anion (NCA) is defined to mean an anion either that does not coordinate to the catalyst metal cation or that does coordinate to the metal cation, but only weakly. An NCA coordinates weakly enough that a neutral Lewis base, such as an olefinically or acetylenically unsaturated monomer can displace it from the catalyst center. Any metal or metalloid that can form a compatible, weakly coordinating complex may be used or contained in the noncoordinating anion. Suitable metals include, but are not limited to, aluminum, gold, and platinum. Suitable metalloids include, but are not limited to, boron, aluminum, phosphorus, and silicon.

A stoichiometric activator can be either neutral or ionic. The terms ionic activator, and stoichiometric ionic activator can be used interchangeably. Likewise, the terms neutral stoichiometric activator, and Lewis acid activator can be used interchangeably.

DETAILED DESCRIPTION

The chelating ligands according to the invention can be used to synthesize the respective transition metal derivatives of importance as catalyst components for the production of polymers or oligomers, including homopolymers, such as homopolyethylene or homopolypropylene, copolymers of ethylene with other olefins including alpha-olefins, and copolymers of propylene with other olefins including alpha-olefins.

In a first embodiment, the invention provides a process for preparing a chelating ligand of the formula (II) from a chelating ligand of the formula (I) via an sp$^2$-sp$^2$ or sp$^2$-sp$^3$ coupling reaction with an organometallic compound of formula (III):

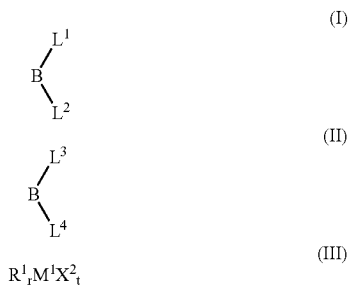

wherein
B is a bridging group that is bonded to L$^1$ and L$^2$ in formula (I) and to L$^3$ and L$^4$ in formula (II);
L$^1$ is a substituted monocyclic or polycyclic ligand that comprises at least one chlorine, bromine, iodine, or sulfonate substituent, directly bonded to an sp$^2$ carbon atom of the ring structure of the ligand;
L$^2$ is a monoanionic ligand; or L$^2$ may, independently, be defined as L$^1$;
L$^3$ is the same group as L$^1$, but said at least one chlorine, bromine, iodine, or sulfonate substituent is replaced with a hydrocarbyl, substituted hydrocarbyl, halocarbyl, or substituted halocarbyl fragment;
L$^4$ is the same group as L$^2$, though, when L$^2$ is defined as L$^1$, L$^4$ may be the same as L$^3$ or L$^1$;
R$^1$ is a hydrocarbyl, substituted hydrocarbyl, halocarbyl, or substituted halocarbyl;
M$^1$ is an element of group 1, 2, 12, 13 or 14 of the Periodic Table of the Elements, preferably Li, Na, K, Rb, Cs, Be, Mg, Ca, Sr, Ba, B, Si, Sn, Zn, Cd or Hg, more preferably B, Si, Sn, Zn, Cd or Hg, and most preferably B, Sn or Zn;
each X$^2$, if present, is selected independently from the group consisting of halogen atoms, the hydroxyl group, alkoxy groups, aryloxy groups, mesylate, tosylate and triflate, preferably from the group consisting of halogen atoms, the hydroxyl group, alkoxy and aryloxy;
r is 1, 2 or 3, and
t is 0, 1 or 2, where r+t corresponds to the oxidation number of M$^1$.

Conveniently, $L^1$ is a substituted indenyl, a substituted heteroindenyl, a substituted fluorenyl, or a substituted heterofluorenyl ligand.

Conveniently, $L^2$ is a substituted or unsubstituted monocyclic or polycyclic ligand, preferably a substituted or unsubstituted cyclopentadienyl ligand, a substituted or unsubstituted heterocyclopentadienyl ligand, a substituted or unsubstituted indenyl ligand, a substituted or unsubstituted heteroindenyl ligand, a substituted or unsubstituted fluorenyl ligand, a substituted or unsubstituted heterofluorenyl ligand.

Preferably, $L^1$ comprises at least one chlorine, bromine, or triflate directly bonded to an $sp^2$ carbon atom of the ring structure of the ligand, and most preferably $L^1$ comprises at least one bromine or triflate directly bonded to an $sp^2$ carbon atom of the ring structure of the ligand.

In a second embodiment, the invention provides a process for preparing a chelating ligand of the formula (IIa), (IIb), or (IIc) from a chelating ligand of the formula (Ia), (Ib), or (Ic), respectively:

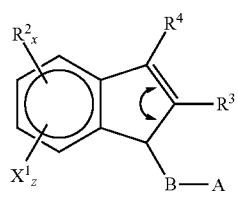
(Ia)

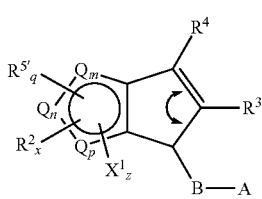
(Ib)

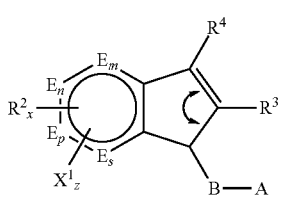
(Ic)

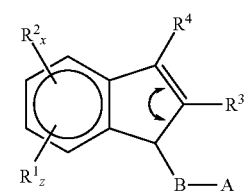
(IIa)

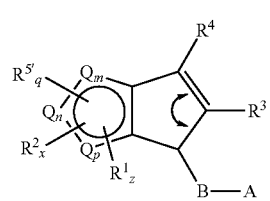
(IIb)

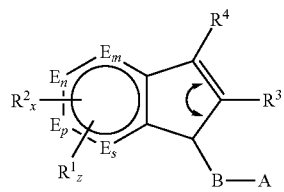
(IIc)

and a coupling component of the formula (III)

$$R^1_r M^1 X^2_t \quad \text{(III)}$$

wherein $M^1$ is an element of group 1, 2, 12, 13 or 14 of the Periodic Table of the Elements, preferably Li, Na, K, Rb, Cs, Be, Mg, Ca, Sr, Ba, B, Si, Sn, Zn, Cd or Hg, more preferably B, Si, Sn, Zn, Cd or Hg, and most preferably B, Sn or Zn;

the or each $X^1$ is a chlorine, bromine, iodine, triflate, or sulfonate group, preferably chlorine, bromine, or triflate, and more preferably bromine or triflate, and the or each $X^1$ is directly bonded to an $sp^2$ carbon atom of the ring structure of the ligand;

each $X^2$, if present, is selected independently from the group consisting of halogen atoms, hydroxyl groups, alkoxy groups and aryloxy groups;

$R^1$ is a hydrocarbyl, substituted hydrocarbyl, halocarbyl, or substituted halocarbyl;

$R^2$, $R^3$, $R^4$, and $R^5$ are, independently selected from hydrogen, hydrocarbyl, substituted hydrocarbyl, halocarbyl, substituted halocarbyl, silylcarbyl, germylcarbyl radicals and polar groups as defined above; provided that all $R^2$ groups may be different and, optionally, adjacent $R^2$, $R^3$, $R^4$, and $R^5$ groups may also together form a cyclic aliphatic or aromatic ring system which may in turn be substituted and may contain heteroatoms; for example, the $R^3$ and $R^4$ groups together may form a cyclic aromatic or heteroaromatic ring, i.e. form fluorenyl or heterofluorenyl fragment in the formulas (Ia), (Ib), (Ic), (IIa), (IIb), and (IIc); and provided further that $R^2$, $R^3$, and $R^4$ groups are attached to ring carbons; $R^{5'}$ groups are attached to heteroatoms;

each Q, if present, is, independently, a Group 16 atom, a Group 15 atom, or boron, and preferably S, O, N, or P; when a Q is a Group 15 atom or boron, "q" is one, indicating the presence of one $R^{5'}$ bonded to Q, and when a Q is a Group 16 atom, "q" is zero, indicating the absence of $R^{5'}$; m, n, and p are independently zero or one, and m+n+p=1; when m or n or p is one, Q is present in the ring as a Group 16 or Group 15 atom or as boron; when m or n or p is zero, Q is absent and is replaced by a ring carbon atom having either a substituent $R^2$ or a substituent $X^1$;

each E, if present, is, independently, a Group 15 atom, preferably N or P; when E is present, it does not have any substituents; m, n, p, and s are independently zero or one, and m+n+p+s=1; when m or n or p or s is one, E is present in the ring as a Group 15 atom; when m or n or p or s is zero, E is absent and is replaced by a ring carbon atom having either a substituent $R^2$ or a substituent $X^1$;

B is a bridging group that contains a Group 13, 14, 15, or 16 element;

A is a substituted or unsubstituted monocyclic or polycyclic ligand, preferably a substituted or unsubstituted cyclopentadienyl, a substituted or unsubstituted heterocyclopentadienyl, a substituted or unsubstituted indenyl, a substituted or unsubstituted heteroindenyl, a substituted or unsubstituted fluorenyl, or a substituted or unsubstituted heterofluorenyl;

x represents the number of $R^2$ substituents bonded to the aryl fused to the cyclopentadienyl in structures (Ia) and (IIa), the number of $R^2$ substituents bonded to the 5-member heterocyclic fragment in the structures (Ib) and (IIb), or the number of $R^2$ substituents bonded to the 6-member heterocyclic fragment in the structures (Ic) and (IIc);

x is 0, 1, 2, or 3 in structures (Ia) and (IIa);
x is 0 or 1 in structures (Ib) and (IIb);
x is 0, 1, or 2 in structures (Ic and IIc);
z represents the number of $X^1$ substituents converted to $R^1$ substituents and is 1, 2, 3, or 4 in structures (Ia) and (IIa); 1 or 2 in structures (Ib) and (IIb); and 1, 2, or 3 in structures (Ic) and (IIc);
x+z is 4 in structures (Ia) and (IIa);
x+z is 2 in structures (Ib) and (IIb);
x+z is 3 in structures (Ic) and (IIc);
r is 1, 2 or 3, and
t is 0, 1 or 2, where r+t corresponds to the oxidation number of $M^1$.

In a third embodiment, the invention provides a process for preparing a chelating ligand of the formula (Va), (Vb), (Vc), (Vd), (Ve), (Vf), (Vg), (Vh), (Vi), (Vk), (Vm), (Vn), (Vo), (Vp), (Vq), (Vr), (Vs), (Vt), (Vu), (Vv), (Vw), (Vx), or (Vy) from a chelating ligand of the formula (IVa), (IVb), (IVc), (IVd), (IVe), (IVf), (IVg), (IVh), (IVi), (IVk), (UVm), (IVn), (IVo), (IVp), (IVq), (IVr), (IVs), (IVt), (IVu), (IVv), (IVw), (IVx), or (IVy), respectively, and a coupling component of the formula (III):

$$R^1{}_r M^1 X^2{}_t \quad (III)$$

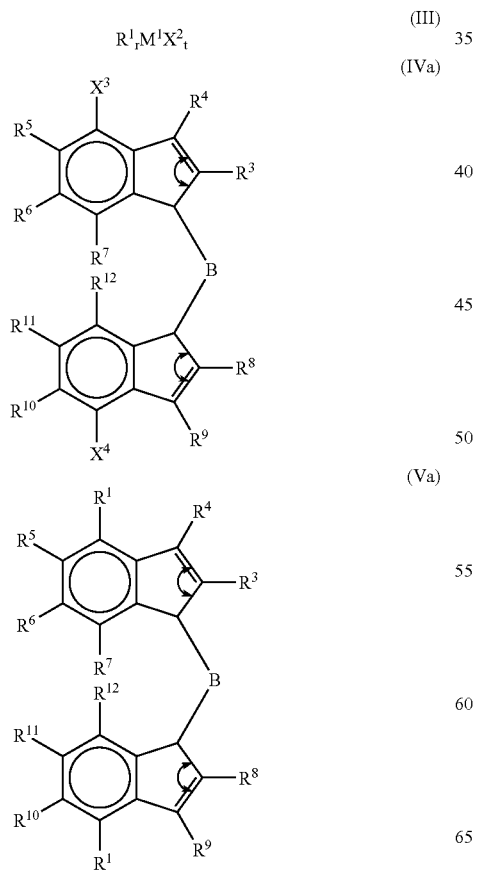

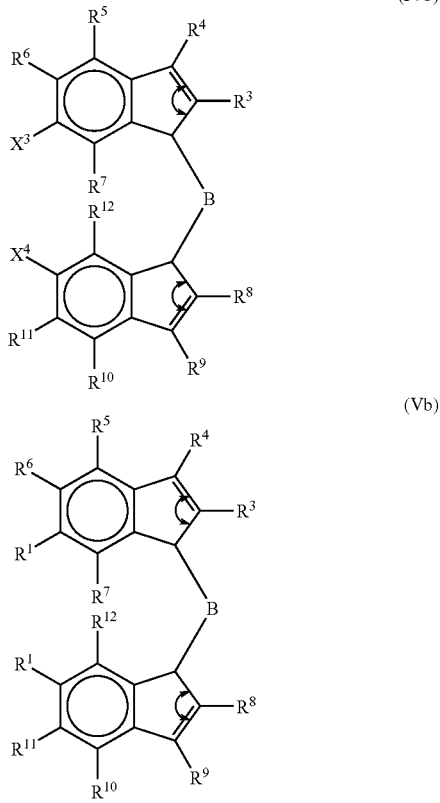

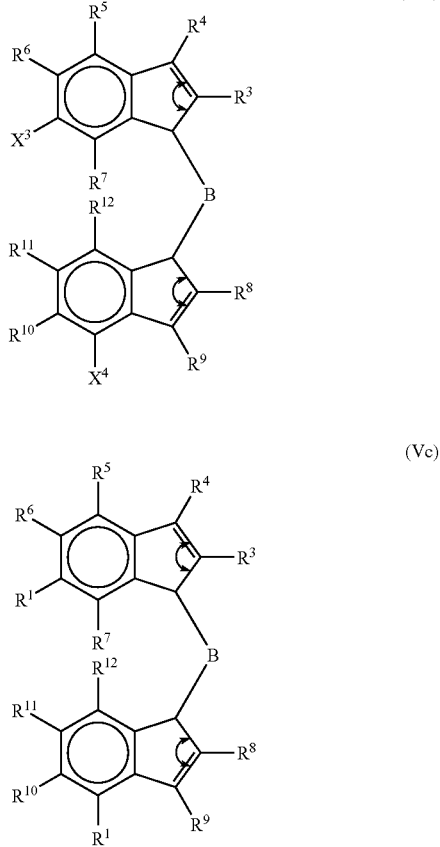

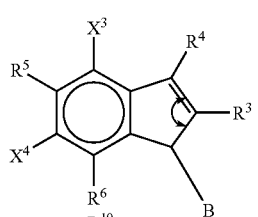
(IVd)
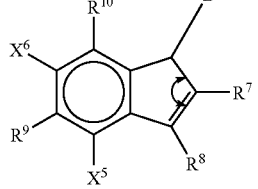
(Vd)
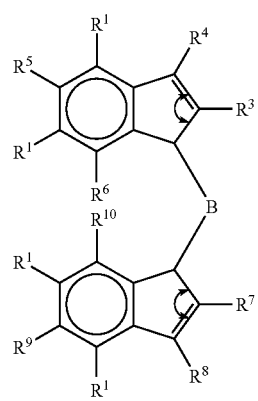
(IVe)
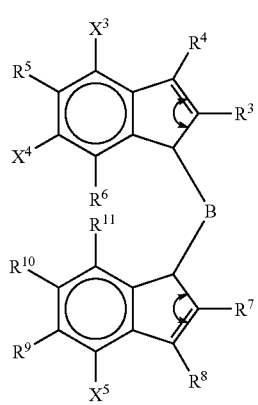
(Ve)
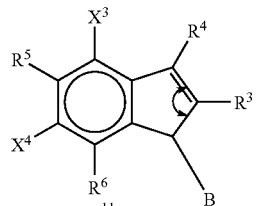
(IVf)
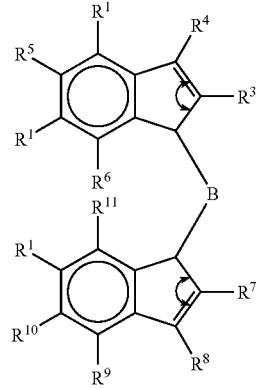
(Vf)
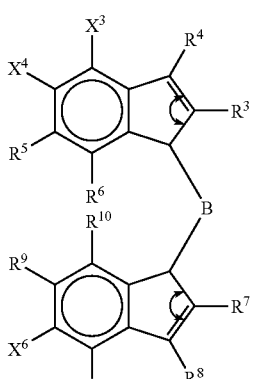
(IVg)
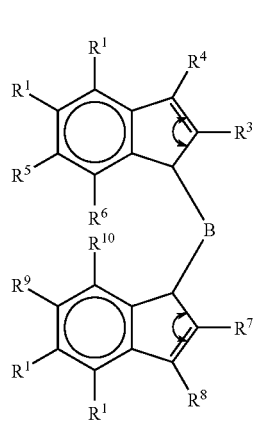
(Vg)

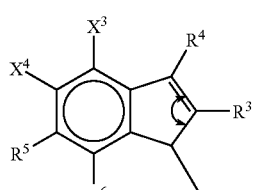
(IVh)
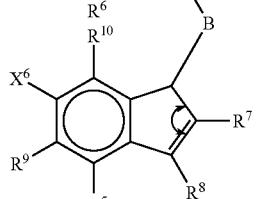
(Vh)
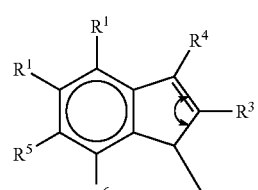
(IVi)
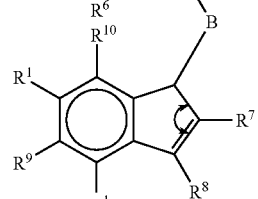
(Vi)
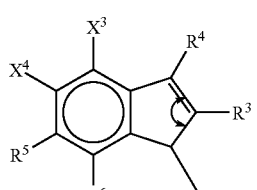
(IVk)
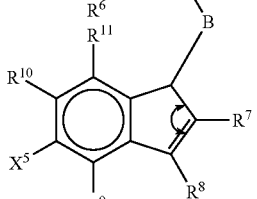
(Vk)
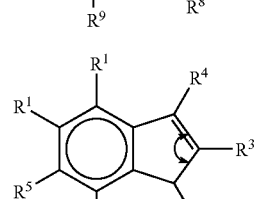
(IVm)
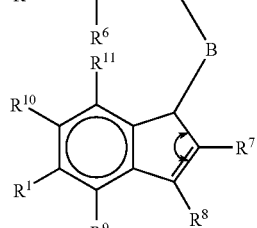
(Vm)

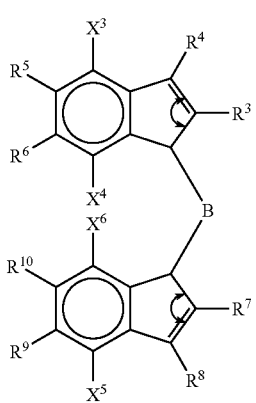 (IVn)
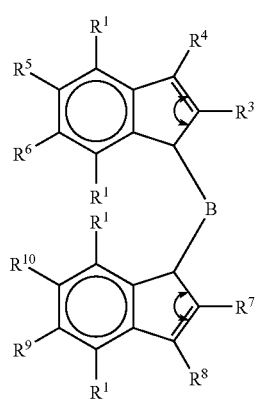 (Vn)
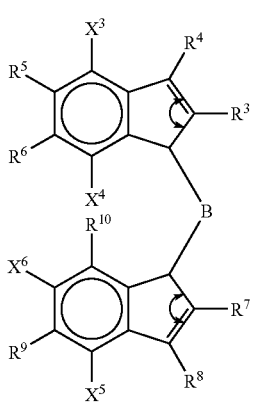 (IVo)
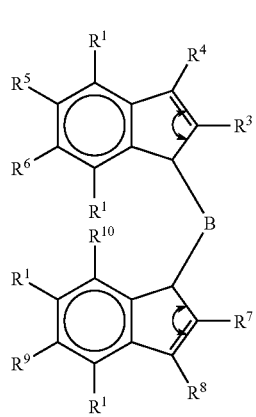 (Vo)
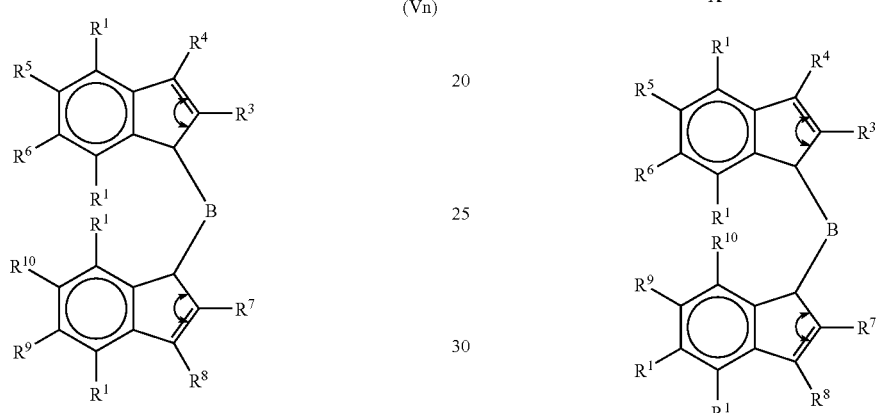 (IVp)
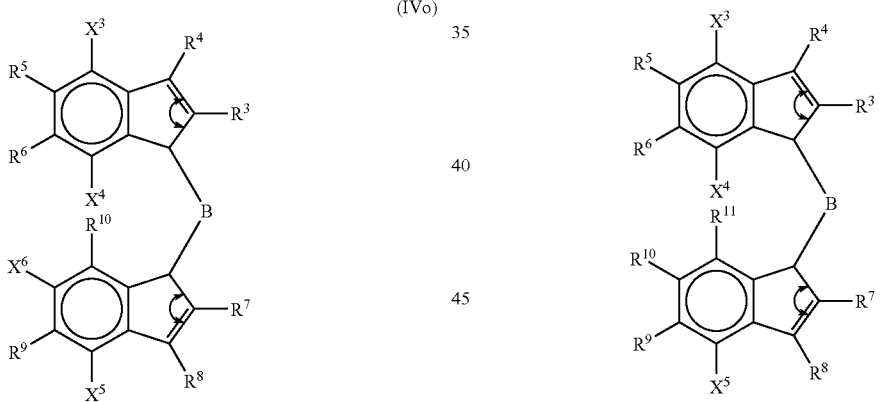 (Vp)
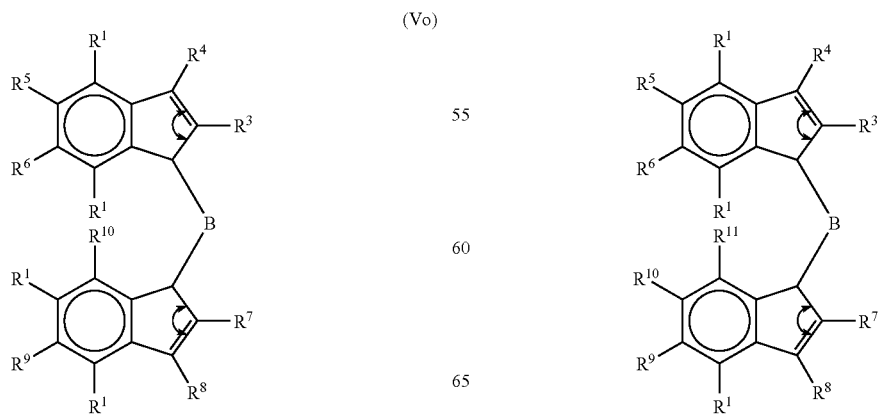 (IVq)
(Vq)

(IVr)
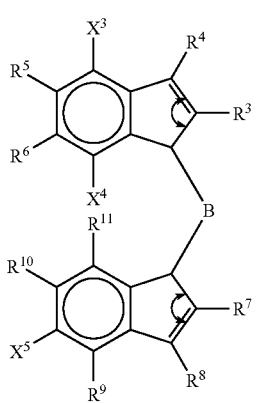
(Vr)
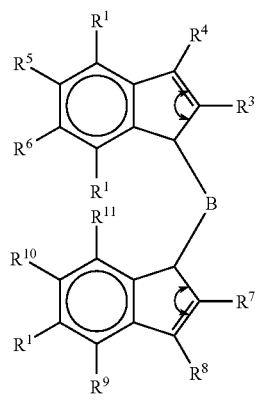
(IVs)
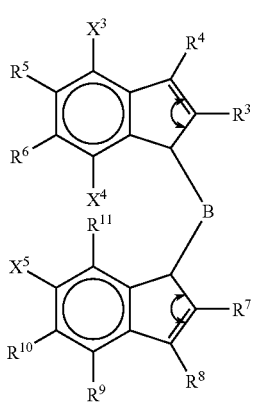
(Vs)
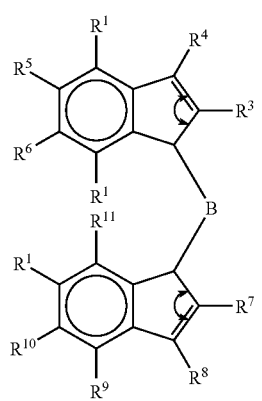
(IVt)
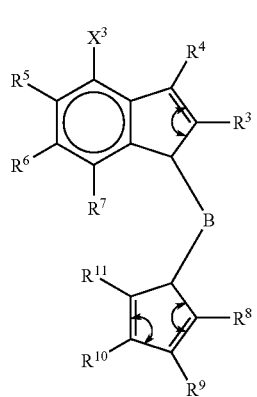
(Vt)
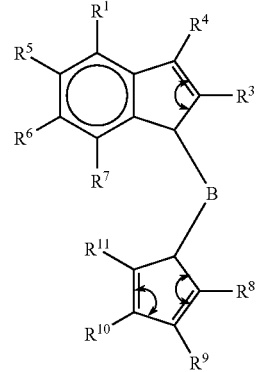
(IVu)
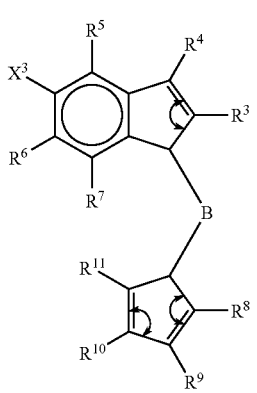
(Vu)
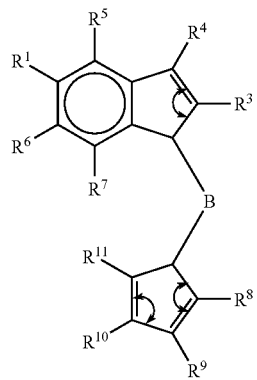

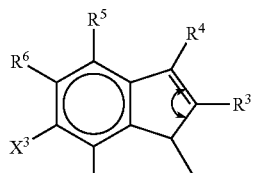
(IVv)
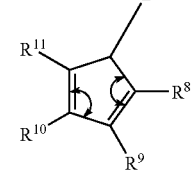
(Vv)
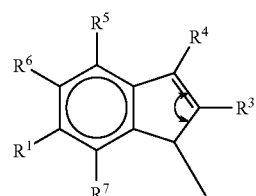
(IVw)
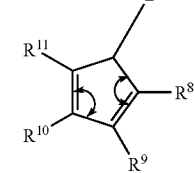
(Vw)
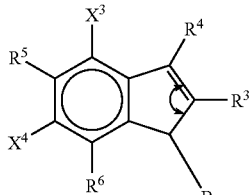
(IVx)
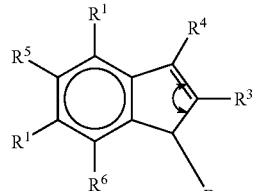
(Vx)
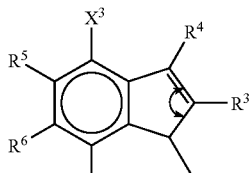
(IVy)
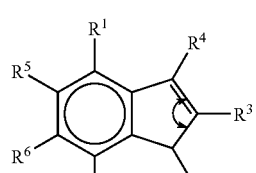
(Vy)
wherein:
$M^1$ is an element of group 1, 2, 12, 13 or 14 of the Periodic Table of the Elements, preferably Li, Na, K, Rb, Cs, Be, Mg, Ca, Sr, Ba, B, Si, Sn, Zn, Cd or Hg, more preferably B, Si, Sn, Zn, Cd or Hg, and most preferably B, Sn or Zn;

$X^3$, $X^4$, $X^5$, $X^6$ are, independently, chlorine, bromine, iodine, triflate, or sulfonate groups, preferably chlorine, bromine, or triflate, and more preferably bromine or triflate;

each $X^2$, if present, is selected independently from the group consisting of halogen atoms, the hydroxyl groups, alkoxy groups and aryloxy groups;

$R^1$ is a hydrocarbyl, substituted hydrocarbyl, halocarbyl, or substituted halocarbyl;

$R^3$, $R^4$, $R^5$, $R^6$, $R^7$, $R^8$, $R^9$, $R^{10}$, $R^{11}$, $R^{12}$ are, independently, hydrogen, hydrocarbyl, substituted hydrocarbyl, halocarbyl, substituted halocarbyl, silylcarbyl, germylcarbyl radical or polar group as defined above, where, optionally, adjacent $R^3$, $R^4$, $R^5$, $R^6$, $R^7$, $R^8$, $R^9$, $R^{10}$, $R^{11}$, $R^{12}$ groups may also together form a cyclic aliphatic or aromatic ring system which may in turn be substituted and may contain heteroatoms;

B is a bridging group that contains a Group 13, 14, 15, or 16 element;

r is 1, 2 or 3, and t is 0, 1 or 2, where r+t corresponds to the oxidation number of $M^1$.

In a fourth embodiment, the invention provides a process for preparing a chelating ligand of the formula (VIIa), (VIb), (VIc), (VIId), (VIIe), (VIIf), (VIIg), (VIIh), (VIIi), (VIIk), (VIIm), (VIIn), (VIIo), (VIIp), (VIIq), (VIIr), or (VIs) from a chelating ligand of the formula (VIa), (VIb), (VIc), (VId), (VIe), (VIf), (VIg), (VIh), (VIi), (VIk), (VIm), (VIn), (VIo), (VIp), (VIq), (VIr), or (VIs), respectively, and a coupling component of the formula (III):

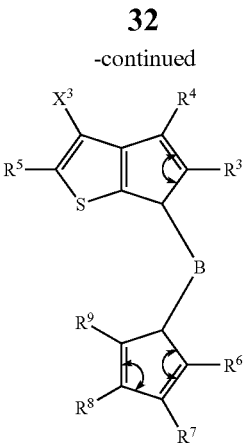

(III)

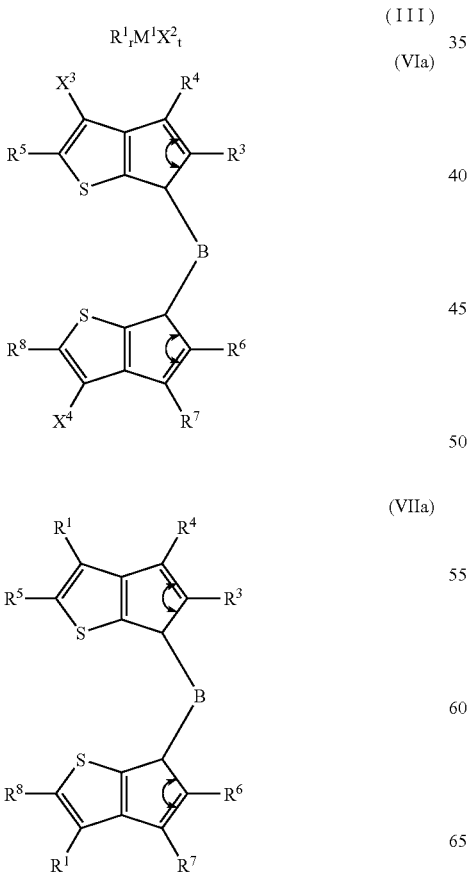

(VIa)

(VIIa)

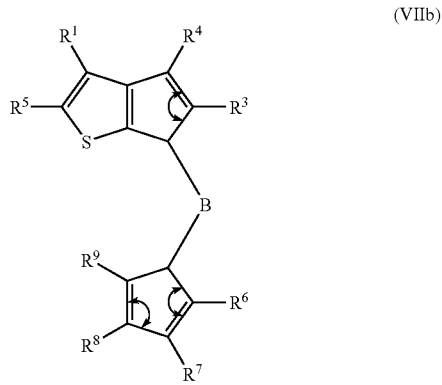

(VIb)

(VIIb)

(VIc)

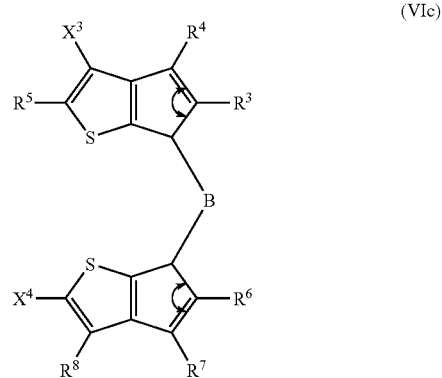

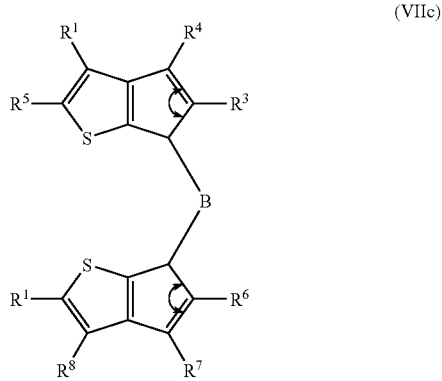

(VIIc)

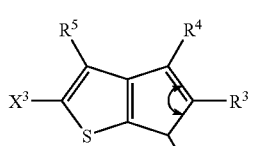
(VId)
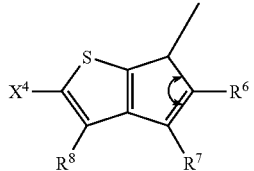
(VIId)
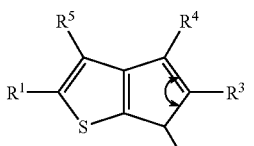
(VIe)
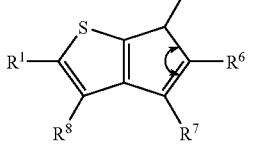
(VIIe)
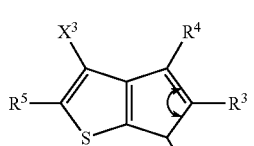
(VIf)
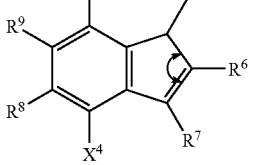
(VIIf)
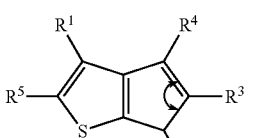
(VIg)
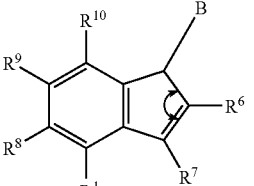
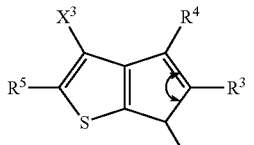
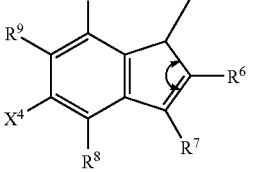
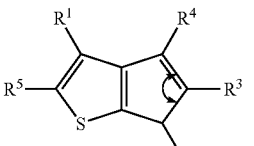
(VIIg)
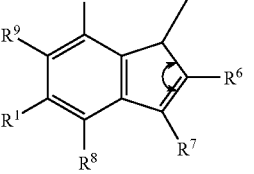

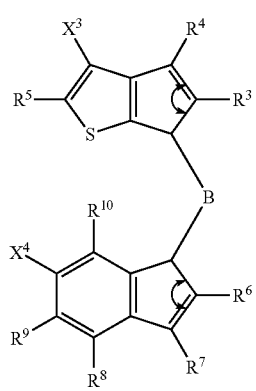 (VIh)
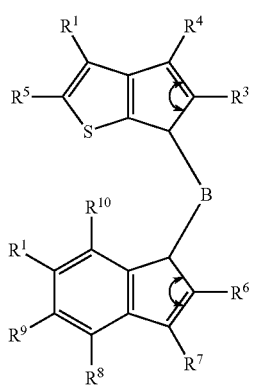 (VIIh)
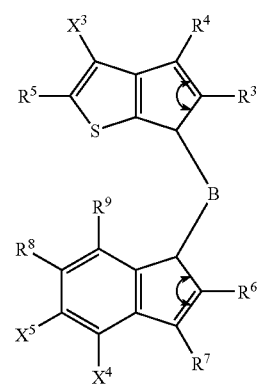 (VIi)
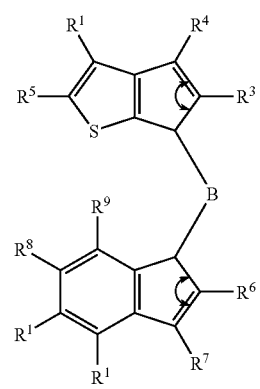 (VIIi)
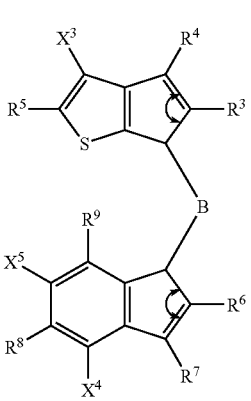 (VIk)
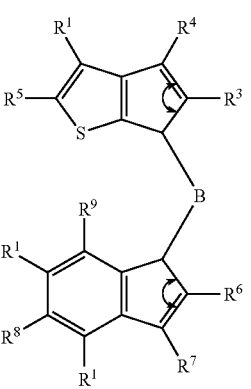 (VIIk)
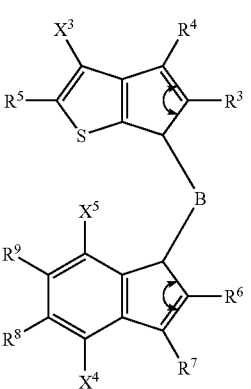 (VIm)
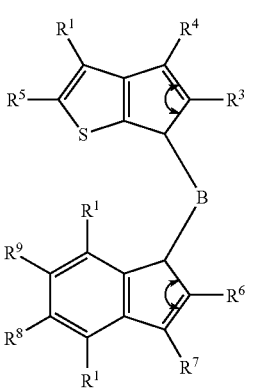 (VIIm)

(VIn)
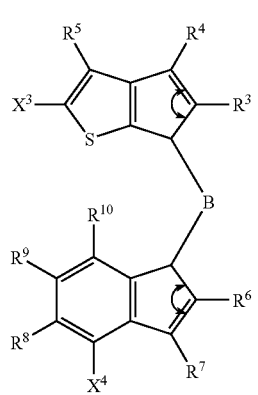
(VIIn)
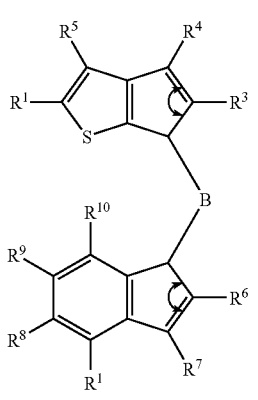
(VIo)
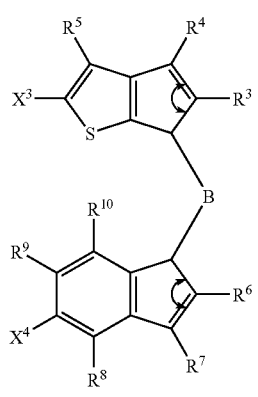
(VIIo)
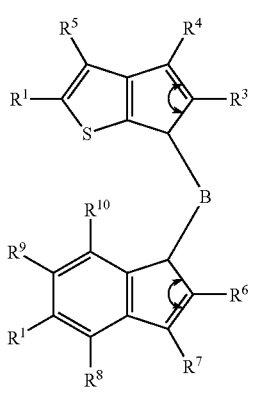
(VIp)
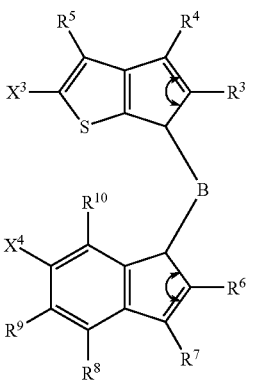
(VIIp)
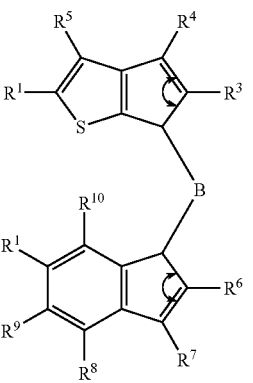
(VIq)
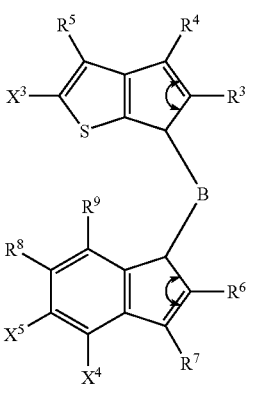
(VIIq)
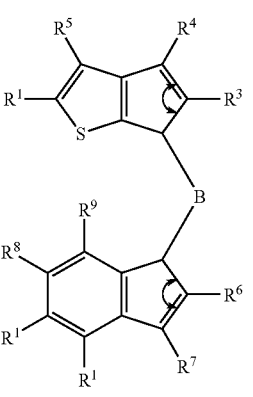

-continued

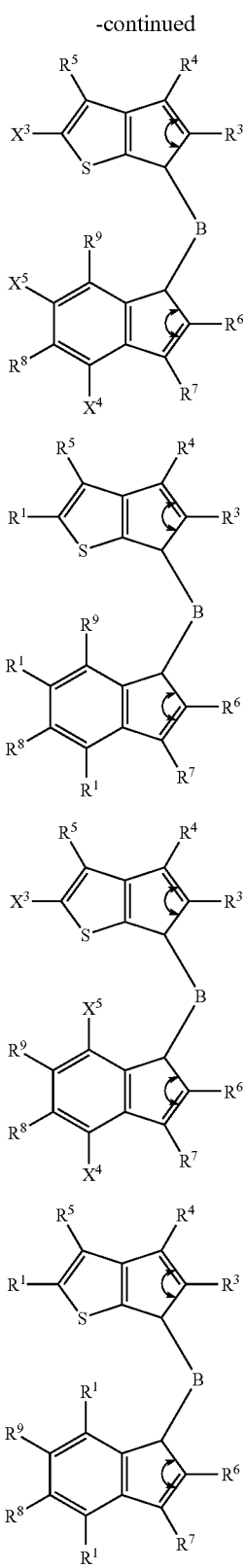

(VIr)

(VIIr)

(VIs)

(VIIs)

wherein:
$M^1$ is an element of group 1, 2, 12, 13 or 14 of the Periodic Table of the Elements, preferably Li, Na, K, Rb, Cs, Be, Mg, Ca, Sr, Ba, B, Si, Sn, Zn, Cd or Hg, more preferably B, Si, Sn, Zn, Cd or Hg, and most preferably B, Sn or Zn;

$X^3$, $X^4$, $X^5$, $X^6$ are, independently, chlorine, bromine, iodine, triflate, or sulfonate groups, preferably chlorine, bromine, or triflate, and more preferably, bromine or triflate;

each $X^2$, if present, is selected independently from the group consisting of halogen atoms, the hydroxyl groups, alkoxy groups and aryloxy groups;

$R^1$ is a hydrocarbyl, substituted hydrocarbyl, halocarbyl, or substituted halocarbyl;

$R^3$, $R^4$, $R^5$, $R^6$, $R^7$, $R^8$, $R^9$, $R^{10}$ are, independently, hydrogen, hydrocarbyl, substituted hydrocarbyl, halocarbyl, substituted halocarbyl, silylcarbyl, germylcarbyl radical or polar group as defined above, where, optionally, adjacent $R^3$, $R^4$, $R^5$, $R^6$, $R^7$, $R^8$, $R^9$, and $R^{10}$ groups may also together form a cyclic aliphatic or aromatic ring system which may in turn be substituted and may contain heteroatoms;

B is a bridging group that contains a Group 13, 14, 15, or 16 element;

r is 1, 2 or 3; and t is 0, 1 or 2, where r+t corresponds to the oxidation number of $M^1$.

In a fifth embodiment, the invention provides a process for preparing a chelating ligand of the formula (IId), (IId), or (IIf) from a chelating ligand of the formula (Id), (Ie), or (If), respectively, and a coupling component of the formula (III):

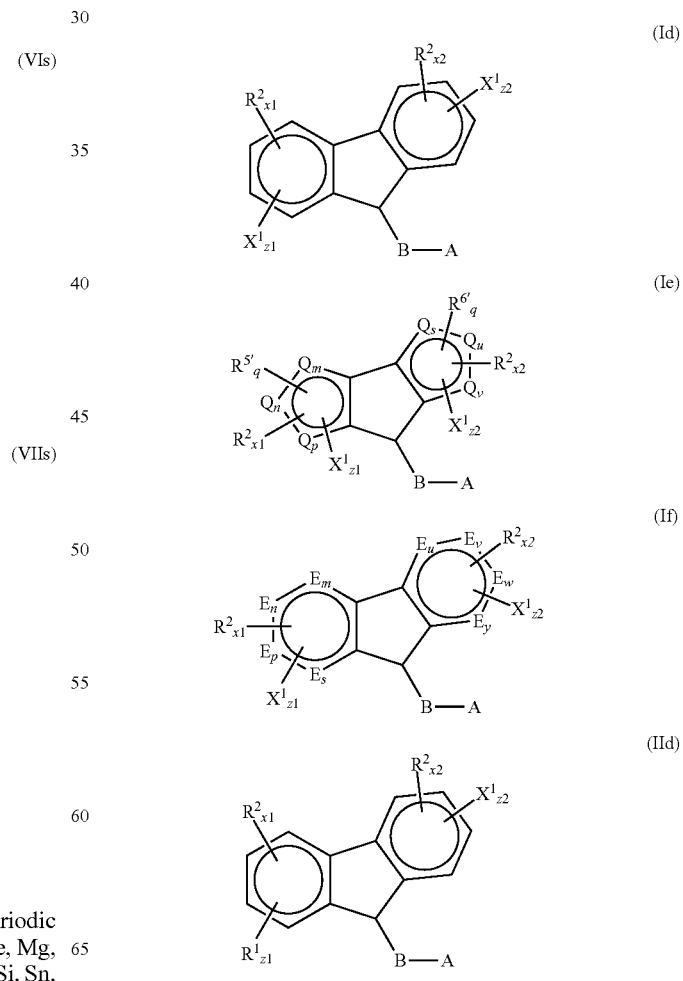

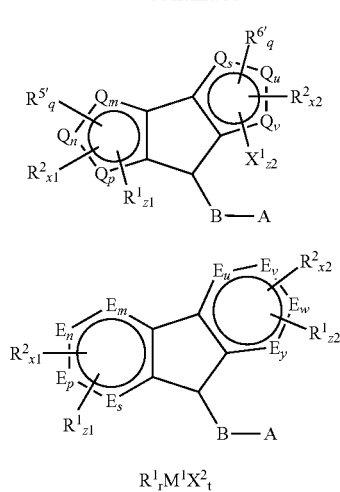

(III)

$R^1_r M^1 X^2_t$ wherein:

$M^1$ is an element of group 1, 2, 12, 13 or 14 of the Periodic Table of the Elements, preferably Li, Na, K, Rb, Cs, Be, Mg, Ca, Sr, Ba, B, Si, Sn, Zn, Cd or Hg, more preferably B, Si, Sn, Zn, Cd or Hg, and most preferably B, Sn or Zn;

each $X^1$ is independently a chlorine, bromine, iodine, triflate, or sulfonate group, preferably chlorine, bromine, or triflate, and more preferably, bromine or triflate, and each $X^1$ is directly bonded to an $sp^2$ carbon atom of the ring structure of the ligand;

each $X^2$, if present, is selected independently from the group consisting of halogen atoms, the hydroxyl groups, alkoxy groups and aryloxy groups;

$R^1$ is a hydrocarbyl, substituted hydrocarbyl, halocarbyl, or substituted halocarbyl;

$R^2$, R5', and R6' are, independently, hydrogen, hydrocarbyl, substituted hydrocarbyl, halocarbyl, substituted halocarbyl, silylcarbyl, germylcarbyl radical or polar group as defined above; provided that all $R^2$ groups may be different and, optionally, adjacent $R^2$, $R^{5'}$, and $R^{6'}$ groups may also together to form a cyclic aliphatic or aromatic ring system which may in turn be substituted and may contain heteroatoms; and provided further that $R^2$ groups are attached to ring carbons; $R^{5'}$ and $R^{6'}$ groups are attached to heteroatoms;

B is a bridging group that contains a Group 13, 14, 15, or 16 element;

A is a substituted or unsubstituted monocyclic or polycyclic ligand, preferably a substituted or unsubstituted cyclopentadienyl, a substituted or unsubstituted heterocyclopentadienyl, a substituted or unsubstituted indenyl, a substituted or unsubstituted heteroindenyl, a substituted or unsubstituted fluorenyl, or a substituted or unsubstituted heterofluorenyl;

each Q, if present, is independently, a Group 16 atom, a Group 15 atom, or boron, and preferably S, O, N, or P; when a Q is a Group 15 atom or boron, "q" is one, indicating the presence of one $R^5$ or $R^6$, as the case may be, bonded to Q, and when a Q is a Group 16 atom, "q" is zero, indicating the absence of $R^5$ or $R^6$, as the case may be; m, n, p, s, u, and v are independently zero or one, m+n+p=1, and s+u+v=1; when m or n or p or s or u or v is one, Q is present as a Group 16 or a Group 15 atom or as boron; when m or n or p or s or u or v is zero, Q is absent and is replaced by a ring carbon atom having either a substituent $R^2$ or a substituent $X^1$;

each E if present, is, independently, a Group 15 atom, preferably N or P; when E is present it does not have any substituents; m, n, p, s, u, v, w, and y are independently zero or one, m+n+p+s=1, and u+v+w+y=0 or 1; when m or n or p or s or u or v or w or y is present, E is present in the ring as a Group 15 atom; when m or n or p or s or u or v or w or y is zero, E is absent and is replaced by a ring carbon having either a substituent $R^2$ or a substituent $X^1$;

x1+x2 represents the total number of $R^2$ substituents bonded to the fluorenyl ligand instructures (Id) and (IId) or the total number of $R^2$ substituents bonded to the heterofluorenyl ligands in structures (Ie), (If), (IIe) and (IIf);

x1+x2 is 0, 1, 2, 3, 4, 5, 6, or 7 in structures (Id) and (IId);
x1+x2 is 0, 1, 2, or 3 in structures (Ie) and (IIe);
x1+x2 is 0, 1, 2, 3, 4, or 5 in structures (If) and (IIf); z1+z2 represents the total number of $X^1$ substituents converted to $R^1$ substituents and bonded to the fluorenyl ligand in structures (Id) and (IId), or the number of $X^1$ substituents converted to $R^1$ substituents and bonded to the heterofluorenyl ligand in structures (Ie), (If), (IIe), and (IIf);

z1+z2 is 1, 2, 3, 4, 5, 6, 7, or 8 in structures (Id) and (IId);
z1+z2 is 1, 2, 3 or 4 in structures (Ie) and (IIe);
z1+z2 is 1, 2, 3, 4, 5, 6, or 7 in structures (If) and (IIf);
x1+x2+z1+z2 is 8 in structures (Id) and (IId);
x1+x2+z1+z2 is 4 in structures (Ie) and (IIe);
x1+x2+z1+z2 is 6 in structures (If) and (IIf) when u+v+w+y=1;
x1+x2+z1+z2 is 7 in structures (If) and (IIf) when u+v+w+y=0;
r is 1, 2 or 3, and
t is 0, 1 or 2, where r+t corresponds to the oxidation number of $M^1$.

In a fifth embodiment, the invention provides a process for preparing a chelating ligand of the formula (IXa), (IXb), (IXc), (IXd), (IXe), (IXf), (IXg), (IXh), (IXi), or (IXk) from a chelating ligand of the formula (VIIIa), (VIIIb), (VIIIc), (VIIId), (VIIIe), (VIIIf), (VIIIg), (VIIIh), (VIIIi), or (VIIIk), respectively, and a coupling component of the formula (III):

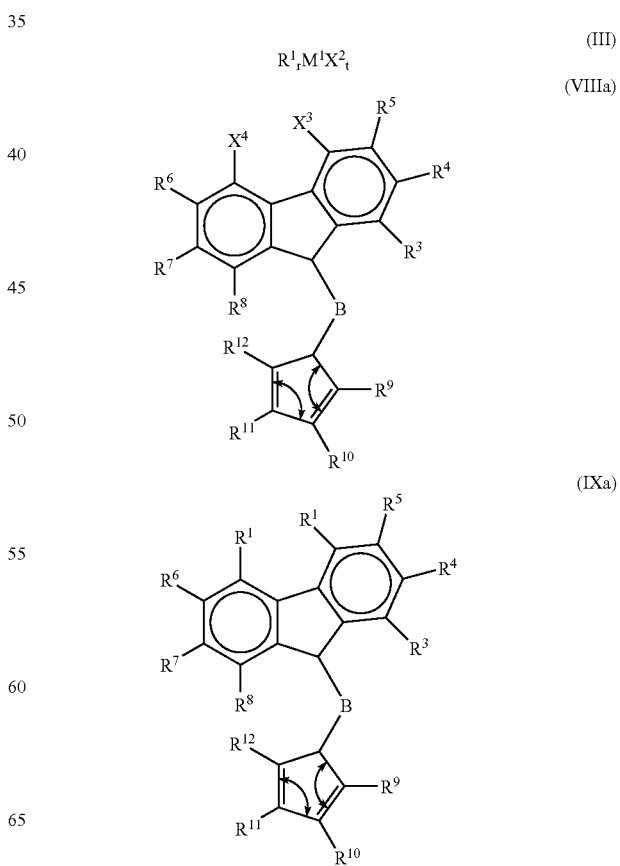

-continued
(VIIIb)
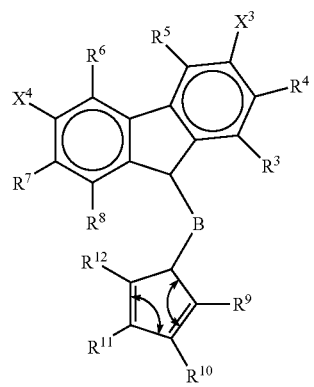
(IXb)
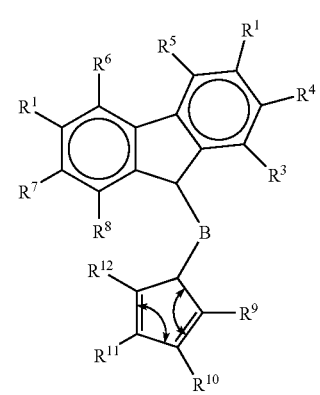
(VIIIc)
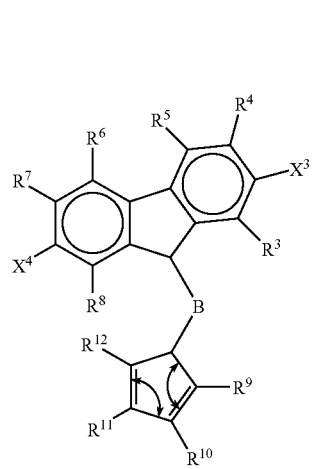
(IXc)
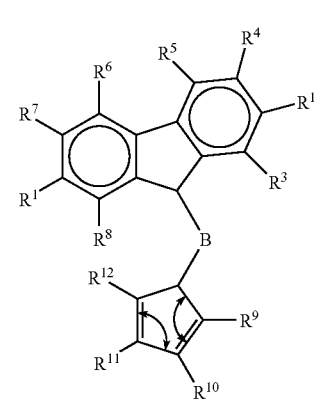
(VIIId)
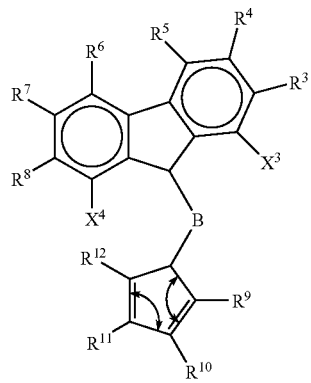
(IXd)
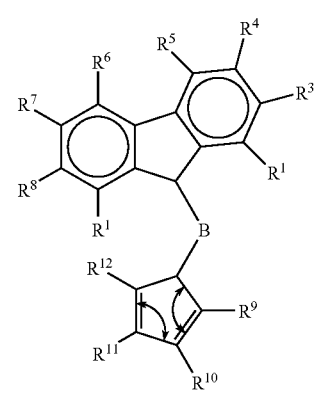
(VIIIe)
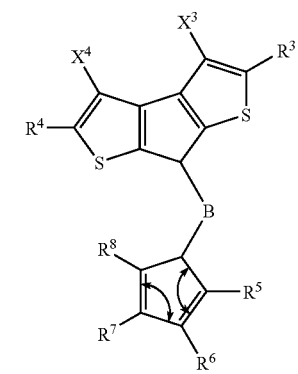
(IXe)
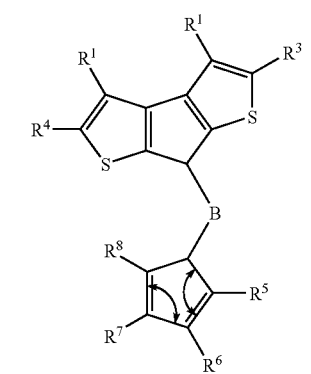

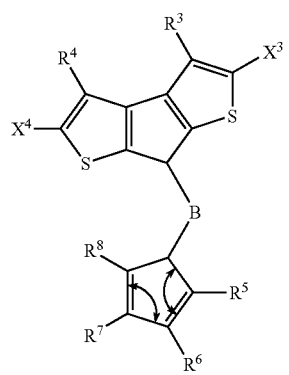 (VIIIf)
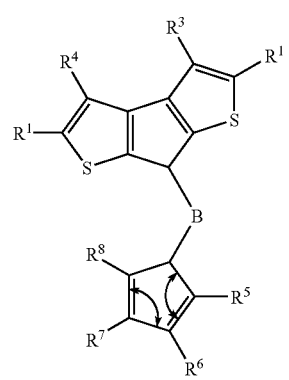 (IXf)
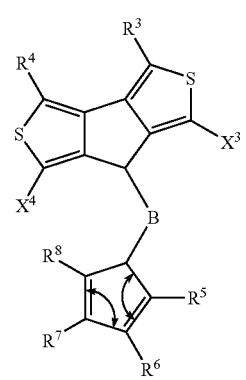 (VIIIg)
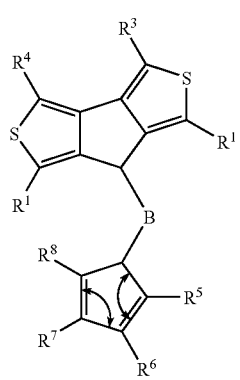 (IXg)
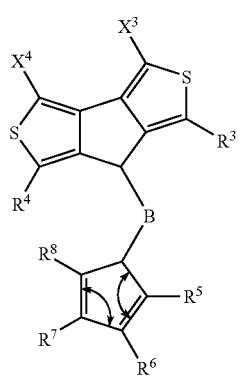 (VIIIh)
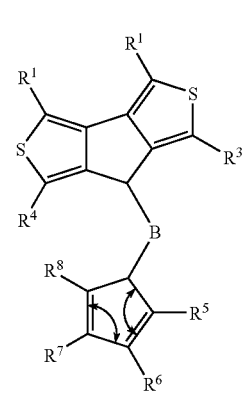 (IXh)
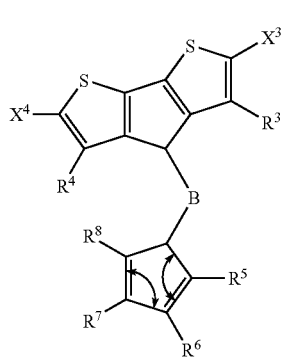 (VIIIi)
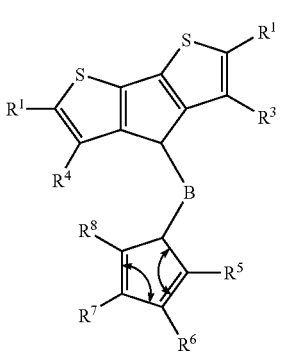 (IXi)

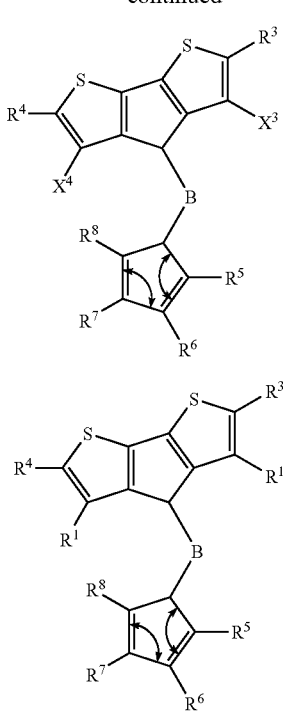

wherein:

M¹ is an element of group 1, 2, 12, 13 or 14 of the Periodic Table of the Elements, preferably Li, Na, K, Rb, Cs, Be, Mg, Ca, Sr, Ba, B, Si, Sn, Zn, Cd or Hg, more preferably B, Si, Sn, Zn, Cd or Hg, and most preferably B, Sn or Zn;

$X^3$, $X^4$ are, independently, a chlorine, bromine, iodine, triflate, or sulfonate group, preferably chlorine, bromine, or triflate, and more preferably, bromine or triflate;

each $X^2$, if present, is selected independently from the group consisting of halogen atoms, the hydroxyl groups, alkoxy groups and aryloxy groups;

$R^1$ is a hydrocarbyl, substituted hydrocarbyl, halocarbyl, or substituted halocarbyl;

$R^3$, $R^4$, $R^5$, $R^6$, $R^7$, $R^8$, $R^9$, $R^{10}$, $R^{11}$, $R^{12}$ are, independently, hydrogen, hydrocarbyl, substituted hydrocarbyl, halocarbyl, substituted halocarbyl, silylcarbyl, germylcarbyl radical or polar group as defined above, where, optionally, adjacent $R^3$, $R^4$, $R^5$, $R^6$, $R^7$, $R^8$, $R^9$, $R^{10}$, $R^{11}$, $R^{12}$ groups may also together form a cyclic aliphatic or aromatic ring system which may in turn be substituted and may contain heteroatoms;

B is a bridging group that contains a Group 13, 14, 15, or 16 element;

r is 1, 2 or 3, and t is 0, 1 or 2, where r+t corresponds to the oxidation number of $M^1$.

Conveniently, B in each of formulae given in all the embodiments of this invention is a bridging group containing boron or a Group 14, 15 or 16 element. Examples of suitable bridging groups include R'$_2$C, R'$_2$Si, R'$_2$Ge, R'$_2$CCR'$_2$, R'$_2$CCR'$_2$CR'$_2$, R'$_2$CCR'$_2$CR'$_2$CR'$_2$, R' C═CR', R' C═CR'CR'$_2$, R'$_2$CCR'═CR'CR'$_2$, R' C═CR'CR'═CR', R' C═CR'CR'$_2$CR'$_2$, R'$_2$CSiR'$_2$, R'$_2$SiSiR'$_2$, R'$_2$CSiR'$_2$CR'$_2$, R'$_2$SiCR'$_2$SiR'$_2$, R'C═CR'SiR'$_2$, R'$_2$CGeR'$_2$, R'$_2$GeGeR'$_2$, R'$_2$CGeR'$_2$CR'$_2$, R'$_2$GeCR'$_2$GeR'$_2$, R'$_2$SiGeR'$_2$, R'C═CR'GeR'$_2$, R'B, R'$_2$C—BR', R'$_2$C—BR'—CR'$_2$, R'$_2$C—O—CR'$_2$, R'$_2$CR'$_2$C—O—CR'$_2$CR'$_2$, R'$_2$C—O—CR'$_2$CR'$_2$, R'$_2$C—O—CR'═CR', R'$_2$C—S—CR'$_2$, R'$_2$CR'$_2$C—S—CR'$_2$CR'$_2$, R'$_2$C—S—CR'$_2$CR'$_2$, R'$_2$C—S—CR'═CR', R'$_2$C—Se—CR'$_2$, R'$_2$CR'$_2$C—Se—CR'$_2$CR'$_2$, R'$_2$C—Se—CR'$_2$CR'$_2$, R'$_2$C—Se—CR'═CR', R'$_2$C—N═CR', R'$_2$C—NR'—CR'$_2$, R'$_2$C—NR'—CR'$_2$CR'$_2$, R'$_2$C—NR'—CR'═CR', R'$_2$CR'$_2$C—NR'—CR'$_2$CR'$_2$, R'$_2$C—P═CR', and R'$_2$C—PR'—CR'$_2$ where R' is hydrogen or a $C_1$-$C_{20}$ containing hydrocarbyl, substituted hydrocarbyl, halocarbyl, substituted halocarbyl, silylcarbyl or germylcarbyl substituent and optionally two or more adjacent R' may join to form a substituted or unsubstituted, saturated, partially unsaturated or aromatic, cyclic or polycyclic substituent. Preferred examples for the bridging group B include $CH_2$, $CH_2CH_2$, $CH(CH_3)_2$, $SiMe_2$, $SiPh_2$, $SiMePh$, $Si(CH_2)_3$, and $Si(CH_2)_4$.

Non-limiting examples of chelating ligands of the formula (I) include:

bis(4-bromo-2-methylinden-1-yl)dimethylsilane,
bis(4-bromoinden-1-yl)dimethylsilane,
bis(4-bromoinden-2-yl)dimethylsilane,
(4-bromoinden-1-yl)(4-bromoinden-2-yl)dimethylsilane,
bis(4-chloro-2-methylinden-1-yl)dimethylsilane,
bis(4-iodo-2-methylinden-1-yl)dimethylsilane,
bis(4-bromo-2-methylinden-1-yl)diethylsilane,
bis(4-bromo-2-methylinden-1-yl)methylphenylsilane,
bis(4-bromo-2-methylinden-1-yl)diphenylsilane,
bis(4-bromo-2-methylinden-1-yl)dimethylgermane,
bis(4-bromo-2-methylinden-1-yl)phenylphosphine,
bis(4-bromo-2-methylinden-1-yl)methylphosphine,
bis(4-bromo-2-methylinden-1-yl)isopropylphosphine,
1,2-bis(4-bromo-2-methylinden-1-yl)-1', 1'',2',2''-tetramethyldisilane,
1,2-bis(4-bromo-2-methylinden-1-yl)ethane,
cis-1,2-bis(4-bromo-2-methylinden-1-yl)ethylene,
bis(4-bromo-2-methylinden-1-yl)methane,
2,2'-bis(4-bromo-2-methylinden-1-yl)propane,
bis(4-bromo-2-methylinden-1-yl)diphenylmethane,
bis(4,6-dibromo-2-methylinden-1-yl)dimethylsilane,
bis(4-bromo-6-chloro-2-methylinden-1-yl)dimethylsilane,
bis(4-bromo-2,6-dimethylinden-1-yl)dimethylsilane,
bis(4-bromo-2-methyl-6-isopropylinden-1-yl)dimethylsilane,
bis(4-bromo-2-methyl-6-fluoroinden-1-yl)dimethylsilane,
bis(4-bromo-2-methyl-6-methoxyinden-1-yl)dimethylsilane,
bis(4-bromo-2-methyl-6-dimethylaminoinden-1-yl)dimethylsilane,
bis(4-bromo-2-methyl-6-diphenylphosphinoinden-1-yl)dimethylsilane,
bis(4-bromo-2-methyl-6-methylsulfoinden-1-yl)dimethylsilane,
bis(4-bromo-2-methyl-6-trimethylsilylinden-1-yl)dimethylsilane,
bis(4-bromo-2-methyl-6-phenylinden-1-yl)dimethylsilane,
bis(4-bromo-2-methyl-6-naphthylinden-1-yl)dimethylsilane,
bis(4-bromo-2-methyl-6-N-indolylinden-1-yl)dimethylsilane,
bis(4-bromo-2-methyl-6-trifluoromethylinden-1-yl)dimethylsilane,
bis[4-bromo-2-methyl-6-(2-thienyl)inden-1-yl]dimethylsilane,
bis[4-bromo-2-methyl-6-(4-pyridyl)inden-1-yl]dimethylsilane,
bis(4-bromo-2-ethylinden-1-yl)dimethylsilane,
bis(4-bromo-2-isopropylinden-1-yl)dimethylsilane,
bis(4-bromo-2-phenylinden-1-yl)dimethylsilane, (4-bromo-2-methylinden-1-yl)(4-chloro-2-methylinden-1-yl)dimethylsilane,
(4-bromo-2-methylinden-1-yl)(4-fluoro-2-methylinden-1-yl)dimethylsilane,
(4-bromo-2-methylinden-1-yl)(4-iodo-2-methylinden-1-yl)dimethylsilane,
(4-bromo-2-methylinden-1-yl)(2-methylinden-1-yl)dimethylsilane,
(4-bromo-2-methylinden-1-yl)(2-isopropylinden-1-yl)dimethylsilane,
(4-bromo-2-methylinden-1-yl)(inden-1-yl)dimethylsilane,
(4-bromo-2-methylinden-1-yl)(inden-2-yl)dimethylsilane,
(4-bromo-2-methylinden-1-yl)(2,4,6-trimethylinden-1-yl)dimethylsilane,
(4-bromo-2-methylinden-1-yl)(4-phenyl-2-methylinden-1-yl)dimethylsilane,
(4-bromo-2-methylinden-1-yl)(4-naphthyl-2-methylinden-1-yl)dimethylsilane,
(4-bromo-2-methylinden-1-yl)[4-(2,5-dimethylphenyl)-2-methylinden-1-yl]dimethylsilane,
(4-bromo-2-methylinden-1-yl)[4-(3,5-dimethylphenyl)-2-methylinden-1-yl]dimethylsilane,
(4-bromo-2-methylinden-1-yl)[4-(3,5-diisopropylphenyl)-2-methylinden-1-yl]dimethylsilane,
(4-bromo-2-methylinden-1-yl)[4-(3,5-di-tert-butylphenyl)-2-methylinden-1-yl]dimethylsilane,
(4-bromo-2-methylinden-1-yl)[4-(2-thienyl)-2-methylinden-1-yl]dimethylsilane,
(4-bromo-2-methylinden-1-yl)[4-(4-pyridyl)-2-methylinden-1-yl]dimethylsilane,
(4-bromo-2-methylinden-1-yl)(4-tert-butyl-2-methylinden-1-yl)dimethylsilane,
(4-bromo-2-methylinden-1-yl)(4-cyclohexyl-2-methylinden-1-yl)dimethylsilane,
(4-bromo-2-methylinden-1-yl)(4-isopropyl-2-methylinden-1-yl)dimethylsilane,
(4-bromo-2-methylinden-1-yl)(4-trimethysilyl-2-methylinden-1-yl)dimethylsilane,
(4-bromo-2-methylinden-1-yl)(4-trimethylgermyl-2-methylinden-1-yl)dimethylsilane,
(4-bromo-2-methylinden-1-yl)(4-methylthio-2-methylinden-1-yl)dimethylsilane,
(4-bromo-2-methylinden-1-yl)(4-diphenylphosphino-2-methylinden-1-yl)dimethylsilane,
(4-bromo-2-methylinden-1-yl)(4-trifluoromethyl-2-methylinden-1-yl)dimethylsilane,
(4-bromo-2-methylinden-1-yl)(cyclopentadienyl)dimethylsilane,
(4-bromo-2-methylinden-1-yl)(3-methylcyclopentadien-1-yl)dimethylsilane,
(4-bromo-2-methylinden-1-yl)(3-tert-butylcyclopentadien-1-yl)dimethylsilane,
(4-bromo-2-methylinden-1-yl)(3-trimethylsilylcyclopentadien-1-yl)dimethylsilane,
(4-bromo-2-methylinden-1-yl)(3-phenylcyclopentadien-1-yl)dimethylsilane,
(4-bromo-2-methylinden-1-yl)[3-(2-thienyl)cyclopentadien-1-yl]dimethylsilane,
(4-bromo-2-methylinden-1-yl)(3-diphenylphosphinocyclopentadien-1-yl)dimethylsilane,
(4-bromo-2-methylinden-1-yl)(2,3,4,5-tetramethylcyclopentadien-1-yl)dimethylsilane,
(4-bromo-2-methylinden-1-yl)(fluoren-9-yl)dimethylsilane,
(4-bromo-2-methylinden-1-yl)(3,6-dimethylfluoren-9-yl)dimethylsilane,
(4-bromo-2-methylinden-1-yl)(3,6-di-tert-butylfluoren-9-yl)dimethylsilane,
(4-bromo-2-methylinden-1-yl)(2,7-dibromofluoren-9-yl)dimethylsilane,
(2-methylinden-1-yl)(2,7-dibromofluoren-9-yl)dimethylsilane,
(2-methylinden-1-yl)(2,7-dichlorofluoren-9-yl)dimethylsilane,
(2-methylinden-1-yl)(2,7-diiodofluoren-9-yl)dimethylsilane,
(2-methyl-4-phenylinden-1-yl)(2,7-dibromofluoren-9-yl)dimethylsilane,
(2,4-dimethylinden-1-yl)(2,7-dibromofluoren-9-yl)dimethylsilane,
(2-methyl-4-trimethylsilylinden-1-yl)(2,7-dibromofluoren-9-yl)dimethylsilane,
(2-methyl-4-tert-butylinden-1-yl)(2,7-dibromofluoren-9-yl)dimethylsilane,
(2-methyl-4-methoxyinden-1-yl)(2,7-dibromofluoren-9-yl)dimethylsilane,
(2-methyl-4-dimethylaminoinden-1-yl)(2,7-dibromofluoren-9-yl)dimethylsilane,
(2-methyl-4-trifluoromethylinden-1-yl)(2,7-dibromofluoren-9-yl)dimethylsilane,
(cyclopentadienyl)(2,7-dibromofluoren-9-yl)dimethylsilane,
(3-methylcyclopentadien-1-yl)(2,7-dibromofluoren-9-yl)dimethylsilane,
(3-tert-butylcyclopentadien-1-yl)(2,7-dibromofluoren-9-yl)dimethylsilane,
(3-phenylcyclopentadien-1-yl)(2,7-dibromofluoren-9-yl)dimethylsilane,
(3-trimethylsilylcyclopentadien-1-yl)(2,7-dibromofluoren-9-yl)dimethylsilane,
(3,4-dimethylcyclopentadien-1-yl)(2,7-dibromofluoren-9-yl)dimethylsilane,
[3-(2-thienyl)cyclopentadien-1-yl](2,7-dibromofluoren-9-yl)dimethylsilane,
(fluoren-9-yl)(2,7-dibromofluoren-9-yl)dimethylsilane,
(3,6-dimethylfluoren-9-yl)(2,7-dibromofluoren-9-yl)dimethylsilane,
(3,6-ditertbutylfluoren-9-yl)(2,7-dibromofluoren-9-yl)dimethylsilane,
(3,6-diphenylfluoren-9-yl)(2,7-dibromofluoren-9-yl)dimethylsilane,
bis(4-bromo-2-methyl-5,6,7,8-tetrahydrocyclopenta[b]naphth-1-yl)dimethylsilane,
bis(5-bromo-2-methyl-6,7,8,9-tetrahydrocyclopenta[a]naphth-3-yl)dimethylsilane,
bis(4-bromo-2-methylcyclopenta[b]naphth-1-yl)dimethylsilane,
bis(7-bromo-2,4-dimethylcyclopenta[b]naphth-1-yl)dimethylsilane,
bis(8-bromo-6-methylindeno[5,6-d][1,3]dioxol-5-yl)dimethylsilane,
bis(4-bromo-2,3,6-trimethylindeno[5,6-b]thien-7-yl)dimethylsilane,
bis(2-bromo-4,6-dimethylindeno[5,6-b]thien-7-yl)dimethylsilane,
bis(4-bromo-1,2,3,6-tetramethylcyclopenta[f]indol-7-yl)dimethylsilane,
bis(4-bromo-1-phenyl-2,3,6-trimethylcyclopenta[f]indol-7-yl)dimethylsilane,
bis(5-bromo-7-methylcyclopenta[g]quinol-8-yl)dimethylsilane,
bis(2-bromo-5,7-dimethylcyclopenta[g]quinol-8-yl)dimethylsilane,
(cyclopentadienyl)(4-bromo-2-methyl-5,6,7,8-tetrahydrocyclopenta[b]naphth-1-yl)dimethylsilane, (cyclopentadienyl)(5-bromo-2-methyl-6,7,8,9-tetrahydrocyclopenta[a]naphth-3-yl)dimethylsilane,
(cyclopentadienyl)(4-bromo-2-methylcyclopenta[b]naphth-1-yl)dimethylsilane,
(cyclopentadienyl)(7-bromo-2,4-dimethylcyclopenta[b]naphth-1-yl)dimethylsilane,
(cyclopentadienyl)(8-bromo-6-methylindeno[5,6-d][1,3]dioxol-5-yl)dimethylsilane,
(cyclopentadienyl)(4-bromo-2,3,6-trimethylindeno[5,6-b]thien-7-yl)dimethylsilane,
(cyclopentadienyl)(2-bromo-4,6-dimethylindeno[5,6-b]thien-7-yl)dimethylsilane,
(cyclopentadienyl)(4-bromo-1,2,3,6-tetramethylcyclopenta[/]indol-7-yl)dimethylsilane,
(cyclopentadienyl)(4-bromo-1-phenyl-2,3,6-trimethylcyclopenta[f]indol-7-yl)dimethylsilane,
(cyclopentadienyl)(5-bromo-7-methylcyclopenta[g]quinol-8-yl)dimethylsilane,
(cyclopentadienyl)(2-bromo-5,7-dimethylcyclopenta[g]quinol-8-yl)dimethylsilane,
(inden-1-yl)(4-bromo-2-methyl-5,6,7,8-tetrahydrocyclopenta[b]naphth-1-yl)dimethylsilane,
(inden-1-yl)(5-bromo-2-methyl-6,7,8,9-tetrahydrocyclopenta[a]naphth-3-yl)dimethylsilane,
(inden-1-yl)(4-bromo-2-methylcyclopenta[b]naphth-1-yl)dimethylsilane,
(inden-1-yl)(7-bromo-2,4-dimethylcyclopenta[b]naphth-1-yl)dimethylsilane,
(inden-1-yl)(8-bromo-6-methylindeno[5,6-d][1,3]dioxol-5-yl)dimethylsilane,
(inden-1-yl)(4-bromo-2,3,6-trimethylindeno[5,6-b]thien-7-yl)dimethylsilane,
(inden-1-yl)(2-bromo-4,6-dimethylindeno[5,6-b]thien-7-yl)dimethylsilane,
(inden-1-yl)(4-bromo-1,2,3,6-tetramethylcyclopenta[f]indol-7-yl)dimethylsilane,
(inden-1-yl)(4-bromo-1-phenyl-2,3,6-trimethylcyclopenta[f]indol-7-yl)dimethylsilane,
(inden-1-yl)(5-bromo-7-methylcyclopenta[g]quinol-8-yl)dimethylsilane,
(inden-1-yl)(2-bromo-5,7-dimethylcyclopenta[g]quinol-8-yl)dimethylsilane,
(inden-2-yl)(4-bromo-2-methyl-5,6,7,8-tetrahydrocyclopenta[b]naphth-1-yl)dimethylsilane,
(inden-2-yl)(5-bromo-2-methyl-6,7,8,9-tetrahydrocyclopenta[a]naphth-3-yl)dimethylsilane,
(inden-2-yl)(4-bromo-2-methylcyclopenta[b]naphth-1-yl)dimethylsilane,
(inden-2-yl)(7-bromo-2,4-dimethylcyclopenta[b]naphth-1-yl)dimethylsilane,
(inden-2-yl)(8-bromo-6-methylindeno[5,6-d][1,3]dioxol-5-yl)dimethylsilane,
(inden-2-yl)(4-bromo-2,3,6-trimethylindeno[5,6-b]thien-7-yl)dimethylsilane,
(inden-2-yl)(2-bromo-4,6-dimethylindeno[5,6-b]thien-7-yl)dimethylsilane,
(inden-2-yl)(4-bromo-1,2,3,6-tetramethylcyclopenta[/]indol-7-yl)dimethylsilane,
(inden-2-yl)(4-bromo-1-phenyl-2,3,6-trimethylcyclopenta[/]indol-7-yl)dimethylsilane,
(inden-2-yl)(5-bromo-7-methylcyclopenta[g]quinol-8-yl)dimethylsilane,
(inden-2-yl)(2-bromo-5,7-dimethylcyclopenta[g]quinol-8-yl)dimethylsilane,
(4-bromo-2-methylinden-1-yl)(4-bromo-2-methyl-5,6,7,8-tetrahydrocyclopenta[b]naphth-1-yl)dimethylsilane,
(4-bromo-2-methylinden-1-yl)(5-bromo-2-methyl-6,7,8,9-tetrahydrocyclopenta[a]naphth-3-yl)dimethylsilane,
(4-bromo-2-methylinden-1-yl)(4-bromo-2-methylcyclopenta[b]naphth-1-yl)dimethylsilane,
(4-bromo-2-methylinden-1-yl)(7-bromo-2,4-dimethylcyclopenta[b]naphth-1-yl)dimethylsilane,
(4-bromo-2-methylinden-1-yl)(8-bromo-6-methylindeno[5,6-d][1,3]dioxol-5-yl)dimethylsilane,
(4-bromo-2-methylinden-1-yl)(4-bromo-2,3,6-trimethylindeno[5,6-b]thien-7-yl)dimethylsilane,
(4-bromo-2-methylinden-1-yl)(2-bromo-4,6-dimethylindeno[5,6-b]thien-7-yl)dimethylsilane,
(4-bromo-2-methylinden-1-yl)(4-bromo-1,2,3,6-tetramethylcyclopenta[/]indol-7-yl)dimethylsilane,
(4-bromo-2-methylinden-1-yl)(4-bromo-1-phenyl-2,3,6-trimethylcyclopenta[f]indol-7-yl)dimethylsilane,
(4-bromo-2-methylinden-1-yl)(5-bromo-7-methylcyclopenta[g]quinol-8-yl)dimethylsilane,
(4-bromo-2-methylinden-1-yl)(2-bromo-5,7-dimethylcyclopenta[g]quinol-8-yl)dimethylsilane,
(fluoren-9-yl)(4-bromo-2-methyl-5,6,7,8-tetrahydrocyclopenta[b]naphth-1-yl)dimethylsilane,
(fluoren-9-yl)(5-bromo-2-methyl-6,7,8,9-tetrahydrocyclopenta[a]naphth-3-yl)dimethylsilane,
(fluoren-9-yl)(4-bromo-2-methylcyclopenta[b]naphth-1-yl)dimethylsilane,
(fluoren-9-yl)(7-bromo-2,4-dimethylcyclopenta[b]naphth-1-yl)dimethylsilane,
(fluoren-9-yl)(8-bromo-6-methylindeno[5,6-d][1,3]dioxol-5-yl)dimethylsilane,
(fluoren-9-yl)(4-bromo-2,3,6-trimethylindeno[5,6-b]thien-7-yl)dimethylsilane,
(fluoren-9-yl)(2-bromo-4,6-dimethylindeno[5,6-b]thien-7-yl)dimethylsilane,
(fluoren-9-yl)(4-bromo-1,2,3,6-tetramethylcyclopenta[f]indol-7-yl)dimethylsilane,
(fluoren-9-yl)(4-bromo-1-phenyl-2,3,6-trimethylcyclopenta[/]indol-7-yl)dimethylsilane,
(fluoren-9-yl)(5-bromo-7-methylcyclopenta[g]quinol-8-yl)dimethylsilane,
(fluoren-9-yl)(2-bromo-5,7-dimethylcyclopenta[g]quinol-8-yl)dimethylsilane,
2,2'-bis(4-bromo-3-dimethylamino-1,3-benzothiaborollide)dimethylsilane,
bis(4-bromo-3a,7a-azaborollide)dimethylsilane,
3,3'-bis(7-bromo-2-dimethylamino-1,2-benzothiaborollide)dimethylsilane,
5,5'-bis(3-bromo-2-dimethylamino-1,2-thiaborollide)dimethylsilane,
2,2'-(cyclopentadienyl)(4-bromo-3-dimethylamino-1,3-benzothiaborollide)dimethylsilane,
(cyclopentadienyl)(4-bromo-3a,7a-azaborinden-1-yl)dimethylsilane,
1,3'-(cyclopentadienyl)(7-bromo-2-dimethylamino-1,2-benzothiaborollide)dimethylsilane,
1,5'-(cyclopentadienyl)(3-bromo-2-dimethylamino-1,2-thiaborollide)dimethylsilane,
1,2'-(indenyl)(4-bromo-3-dimethylamino-1,3-benzothiaborollide)dimethylsilane,
(inden-1-yl)(4-bromo-3a,7a-azaborinden-1-yl)dimethylsilane,
1,3'-(indenyl)(7-bromo-2-dimethylamino-1,2-benzothiaborollide)dimethylsilane,
1,5'-(indenyl)(3-bromo-2-dimethylamino-1,2-thiaborollide)dimethylsilane,
2,2'-(indenyl)(4-bromo-3-dimethylamino-1,3-benzothiaborollide)dimethylsilane, (inden-2-yl)(4-bromo-3a,7a-azaborinden-1-yl)dimethylsilane,
2,3'-(indenyl)(7-bromo-2-dimethylamino-1,2-benzothiaborollide)dimethylsilane,
2,5'-(indenyl)(3-bromo-2-dimethylamino-1,2-thiaborollide)dimethylsilane,
9,2'-(fluorenyl)(4-bromo-3-dimethylamino-1,3-benzothiaborollide)dimethylsilane,
(fluoren-9-yl)(4-bromo-3a,7a-azaborinden-1-yl)dimethylsilane,
9,3'-(fluorenyl)(7-bromo-2-dimethylamino-1,2-benzothiaborollide)dimethylsilane,
9,5'-(fluorenyl)(3-bromo-2-dimethylamino-1,2-thiaborollide)dimethylsilane,
bis(4-bromoinden-1-yl)methane,
bis(4-bromoinden-2-yl)methane,
(4-bromoinden-1-yl)(4-bromoinden-2-yl)methane,
bis(4-chloro-2-methylinden-1-yl)methane,
bis(4-iodo-2-methylinden-1-yl)methane,
bis(4,6-dibromo-2-methylinden-1-yl)methane,
bis(4-bromo-6-chloro-2-methylinden-1-yl)methane,
bis(4-bromo-2,6-dimethylinden-1-yl)methane,
bis(4-bromo-2-methyl-6-isopropylinden-1-yl)methane,
bis(4-bromo-2-methyl-6-fluoroinden-1-yl)methane,
bis(4-bromo-2-methyl-6-methoxyinden-1-yl)methane,
bis(4-bromo-2-methyl-6-dimethylaminoinden-1-yl)methane,
bis(4-bromo-2-methyl-6-diphenylphosphinoinden-1-yl)methane,
bis(4-bromo-2-methyl-6-methylsulfoinden-1-yl)methane,
bis(4-bromo-2-methyl-6-trimethylsilylinden-1-yl)methane,
bis(4-bromo-2-methyl-6-phenylinden-1-yl)methane,
bis(4-bromo-2-methyl-6-naphthylinden-1-yl)methane,
bis(4-bromo-2-methyl-6-N-indolylinden-1-yl)methane,
bis(4-bromo-2-methyl-6-trifluoromethylinden-1-yl)methane,
bis[4-bromo-2-methyl-6-(2-thienyl)inden-1-yl]methane,
bis[4-bromo-2-methyl-6-(4-pyridyl)inden-1-yl]methane,
bis(4-bromo-2-ethylinden-1-yl)methane,
bis(4-bromo-2-isopropylinden-1-yl)methane,
bis(4-bromo-2-phenylinden-1-yl)methane,
(4-bromo-2-methylinden-1-yl)(4-chloro-2-methylinden-1-yl)methane,
(4-bromo-2-methylinden-1-yl)(4-fluoro-2-methylinden-1-yl)methane,
(4-bromo-2-methylinden-1-yl)(4-iodo-2-methylinden-1-yl)methane,
(4-bromo-2-methylinden-1-yl)(2-methylinden-1-yl)methane,
(4-bromo-2-methylinden-1-yl)(2-isopropylinden-1-yl)methane,
(4-bromo-2-methylinden-1-yl)(inden-1-yl)methane,
(4-bromo-2-methylinden-1-yl)(inden-2-yl)methane,
(4-bromo-2-methylinden-1-yl)(2,4,6-trimethylinden-1-yl)methane,
(4-bromo-2-methylinden-1-yl)(4-phenyl-2-methylinden-1-yl)methane,
(4-bromo-2-methylinden-1-yl)(4-naphthyl-2-methylinden-1-yl)methane,
(4-bromo-2-methylinden-1-yl)[4-(2,5-dimethylphenyl)-2-methylinden-1-yl]methane,
(4-bromo-2-methylinden-1-yl)[4-(3,5-dimethylphenyl)-2-methylinden-1-yl]methane,
(4-bromo-2-methylinden-1-yl)[4-(3,5-diisopropylphenyl)-2-methylinden-1-yl]methane,
(4-bromo-2-methylinden-1-yl)[4-(3,5-di-tert-butylphenyl)-2-methylinden-1-yl]methane,
(4-bromo-2-methylinden-1-yl)[4-(2-thienyl)-2-methylinden-1-yl]methane,
(4-bromo-2-methylinden-1-yl)[4-(4-pyridyl)-2-methylinden-1-yl]methane,
(4-bromo-2-methylinden-1-yl)(4-tert-butyl-2-methylinden-1-yl)methane,
(4-bromo-2-methylinden-1-yl)(4-cyclohexyl-2-methylinden-1-yl)methane,
(4-bromo-2-methylinden-1-yl)(4-isopropyl-2-methylinden-1-yl)methane,
(4-bromo-2-methylinden-1-yl)(4-trimethysilyl-2-methylinden-1-yl)methane,
(4-bromo-2-methylinden-1-yl)(4-trimethylgermyl-2-methylinden-1-yl)methane,
(4-bromo-2-methylinden-1-yl)(4-methylthio-2-methylinden-1-yl)methane,
(4-bromo-2-methylinden-1-yl)(4-diphenylphosphino-2-methylinden-1-yl)methane,
(4-bromo-2-methylinden-1-yl)(4-trifluoromethyl-2-methylinden-1-yl)methane,
(4-bromo-2-methylinden-1-yl)(cyclopentadienyl)methane,
(4-bromo-2-methylinden-1-yl)(3-methylcyclopentadien-1-yl)methane,
(4-bromo-2-methylinden-1-yl)(3-tert-butylcyclopentadien-1-yl)methane,
(4-bromo-2-methylinden-1-yl)(3-trimethylsilylcyclopentadien-1-yl)methane,
(4-bromo-2-methylinden-1-yl)(3-phenylcyclopentadien-1-yl)methane,
(4-bromo-2-methylinden-1-yl)[3-(2-thienyl)cyclopentadien-1-yl]methane,
(4-bromo-2-methylinden-1-yl)(3-diphenylphosphinocyclopentadien-1-yl)methane,
(4-bromo-2-methylinden-1-yl)(2,3,4,5-tetramethylcyclopentadien-1-yl)methane,
(4-bromo-2-methylinden-1-yl)(fluoren-9-yl)methane,
(4-bromo-2-methylinden-1-yl)(3,6-dimethylfluoren-9-yl)methane,
(4-bromo-2-methylinden-1-yl)(3,6-di-tert-butylfluoren-9-yl)methane,
(4-bromo-2-methylinden-1-yl)(2,7-dibromofluoren-9-yl)methane,
(2-methylinden-1-yl)(2,7-dibromofluoren-9-yl)methane,
(2-methylinden-1-yl)(2,7-dichlorofluoren-9-yl)methane,
(2-methylinden-1-yl)(2,7-diiodofluoren-9-yl)methane,
(2-methyl-4-phenylinden-1-yl)(2,7-dibromofluoren-9-yl)methane,
(2,4-dimethylinden-1-yl)(2,7-dibromofluoren-9-yl)methane,
(2-methyl-4-trimethylsilylinden-1-yl)(2,7-dibromofluoren-9-yl)methane,
(2-methyl-4-tert-butylinden-1-yl)(2,7-dibromofluoren-9-yl)methane,
(2-methyl-4-methoxyinden-1-yl)(2,7-dibromofluoren-9-yl)methane,
(2-methyl-4-dimethylaminoinden-1-yl)(2,7-dibromofluoren-9-yl)methane,
(2-methyl-4-trifluoromethylinden-1-yl)(2,7-dibromofluoren-9-yl)methane,
(cyclopentadienyl)(2,7-dibromofluoren-9-yl)methane,
(3-methylcyclopentadien-1-yl)(2,7-dibromofluoren-9-yl)methane,
(3-tert-butylcyclopentadien-1-yl)(2,7-dibromofluoren-9-yl)methane,
(3-phenylcyclopentadien-1-yl)(2,7-dibromofluoren-9-yl)methane, (3-trimethylsilylcyclopentadien-1-yl)(2,7-dibromofluoren-9-yl)methane,
(3,4-dimethylcyclopentadien-1-yl)(2,7-dibromofluoren-9-yl)methane,
[3-(2-thienyl)cyclopentadien-1-yl](2,7-dibromofluoren-9-yl)methane,
(fluoren-9-yl)(2,7-dibromofluoren-9-yl)methane,
(3,6-dimethylfluoren-9-yl)(2,7-dibromofluoren-9-yl)methane,
(3,6-ditertbutylfluoren-9-yl)(2,7-dibromofluoren-9-yl)methane,
(3,6-diphenylfluoren-9-yl)(2,7-dibromofluoren-9-yl)methane,
bis(4-bromo-2-methyl-5,6,7,8-tetrahydrocyclopenta[b]naphth-1-yl)methane,
bis(5-bromo-2-methyl-6,7,8,9-tetrahydrocyclopenta[a]naphth-3-yl)methane,
bis(4-bromo-2-methylcyclopenta[b]naphth-1-yl)methane,
bis(7-bromo-2,4-dimethylcyclopenta[b]naphth-1-yl)methane,
bis(8-bromo-6-methylindeno[5,6-d][1,3]dioxol-5-yl)methane,
bis(4-bromo-2,3,6-trimethylindeno[5,6-b]thien-7-yl)methane,
bis(2-bromo-4,6-dimethylindeno[5,6-b]thien-7-yl)methane,
bis(4-bromo-1,2,3,6-tetramethylcyclopenta[f]indol-7-yl)methane,
bis(4-bromo-1-phenyl-2,3,6-trimethylcyclopenta[f]indol-7-yl)methane,
bis(5-bromo-7-methylcyclopenta[g]quinol-8-yl)methane,
bis(2-bromo-5,7-dimethylcyclopenta[g]quinol-8-yl)methane,
(cyclopentadienyl)(4-bromo-2-methyl-5,6,7,8-tetrahydrocyclopenta[b]naphth-1-yl)methane,
(cyclopentadienyl)(5-bromo-2-methyl-6,7,8,9-tetrahydrocyclopenta[a]naphth-3-yl)methane,
(cyclopentadienyl)(4-bromo-2-methylcyclopenta[b]naphth-1-yl)methane,
(cyclopentadienyl)(7-bromo-2,4-dimethylcyclopenta[b]naphth-1-yl)methane,
(cyclopentadienyl)(8-bromo-6-methylindeno[5,6-d][1,3]dioxol-5-yl)methane,
(cyclopentadienyl)(4-bromo-2,3,6-trimethylindeno[5,6-b]thien-7-yl)methane,
(cyclopentadienyl)(2-bromo-4,6-dimethylindeno[5,6-b]thien-7-yl)methane,
(cyclopentadienyl)(4-bromo-1,2,3,6-tetramethylcyclopenta[f]indol-7-yl)methane,
(cyclopentadienyl)(4-bromo-1-phenyl-2,3,6-trimethylcyclopenta[/]indol-7-yl)methane,
(cyclopentadienyl)(5-bromo-7-methylcyclopenta[g]quinol-8-yl)methane,
(cyclopentadienyl)(2-bromo-5,7-dimethylcyclopenta[g]quinol-8-yl)methane,
(inden-1-yl)(4-bromo-2-methyl-5,6,7,8-tetrahydrocyclopenta[b]naphth-1-yl)methane,
(inden-1-yl)(5-bromo-2-methyl-6,7,8,9-tetrahydrocyclopenta[a]naphth-3-yl)methane,
(inden-1-yl)(4-bromo-2-methylcyclopenta[b]naphth-1-yl)methane,
(inden-1-yl)(7-bromo-2,4-dimethylcyclopenta[b]naphth-1-yl)methane,
(inden-1-yl)(8-bromo-6-methylindeno[5,6-d][1,3]dioxol-5-yl)methane,
(inden-1-yl)(4-bromo-2,3,6-trimethylindeno[5,6-b]thien-7-yl)methane,
(inden-1-yl)(2-bromo-4,6-dimethylindeno[5,6-b]thien-7-yl)methane,
(inden-1-yl)(4-bromo-1,2,3,6-tetramethylcyclopenta[f]indol-7-yl)methane,
(inden-1-yl)(4-bromo-1-phenyl-2,3,6-trimethylcyclopenta[/]indol-7-yl)methane,
(inden-1-yl)(5-bromo-7-methylcyclopenta[g]quinol-8-yl)methane,
(inden-1-yl)(2-bromo-5,7-dimethylcyclopenta[g]quinol-8-yl)methane,
(inden-2-yl)(4-bromo-2-methyl-5,6,7,8-tetrahydrocyclopenta[b]naphth-1-yl)methane,
(inden-2-yl)(5-bromo-2-methyl-6,7,8,9-tetrahydrocyclopenta[a]naphth-3-yl)methane,
(inden-2-yl)(4-bromo-2-methylcyclopenta[b]naphth-1-yl)methane,
(inden-2-yl)(7-bromo-2,4-dimethylcyclopenta[b]naphth-1-yl)methane,
(inden-2-yl)(8-bromo-6-methylindeno[5,6-d][1,3]dioxol-5-yl)methane,
(inden-2-yl)(4-bromo-2,3,6-trimethylindeno[5,6-b]thien-7-yl)methane,
(inden-2-yl)(2-bromo-4,6-dimethylindeno[5,6-b]thien-7-yl)methane,
(inden-2-yl)(4-bromo-1,2,3,6-tetramethylcyclopenta[f]indol-7-yl)methane,
(inden-2-yl)(4-bromo-1-phenyl-2,3,6-trimethylcyclopenta[f]indol-7-yl)methane,
(inden-2-yl)(4-bromocyclopenta[b]pyrid-7-yl)methane,
(inden-2-yl)(5-bromo-7-methylcyclopenta[g]quinol-8-yl)methane,
(inden-2-yl)(2-bromo-5,7-dimethylcyclopenta[g]quinol-8-yl)methane,
(4-bromo-2-methylinden-1-yl)(4-bromo-2-methyl-5,6,7,8-tetrahydrocyclopenta[b]naphth-1-yl)methane,
(4-bromo-2-methylinden-1-yl)(5-bromo-2-methyl-6,7,8,9-tetrahydrocyclopenta[a]naphth-3-yl)methane,
(4-bromo-2-methylinden-1-yl)(4-bromo-2-methylcyclopenta[b]naphth-1-yl)methane,
(4-bromo-2-methylinden-1-yl)(7-bromo-2,4-dimethylcyclopenta[b]naphth-1-yl)methane,
(4-bromo-2-methylinden-1-yl)(8-bromo-6-methylindeno[5,6-d][1,3]dioxol-5-yl)methane,
(4-bromo-2-methylinden-1-yl)(4-bromo-2,3,6-trimethylindeno[5,6-b]thien-7-yl)methane,
(4-bromo-2-methylinden-1-yl)(2-bromo-4,6-dimethylindeno[5,6-b]thien-7-yl)methane,
(4-bromo-2-methylinden-1-yl)(4-bromo-1,2,3,6-tetramethylcyclopenta[f]indol-7-yl)methane,
(4-bromo-2-methylinden-1-yl)(4-bromo-1-phenyl-2,3,6-trimethylcyclopenta[/]indol-7-yl)methane,
(4-bromo-2-methylinden-1-yl)(5-bromo-7-methylcyclopenta[g]quinol-8-yl)methane,
(4-bromo-2-methylinden-1-yl)(2-bromo-5,7-dimethylcyclopenta[g]quinol-8-yl)methane,
(fluoren-9-yl)(4-bromo-2-methyl-5,6,7,8-tetrahydrocyclopenta[b]naphth-1-yl)methane,
(fluoren-9-yl)(5-bromo-2-methyl-6,7,8,9-tetrahydrocyclopenta[a]naphth-3-yl)methane,
(fluoren-9-yl)(4-bromo-2-methylcyclopenta[b]naphth-1-yl)methane,
(fluoren-9-yl)(7-bromo-2,4-dimethylcyclopenta[b]naphth-1-yl)methane,
(fluoren-9-yl)(8-bromo-6-methylindeno[5,6-d][1,3]dioxol-5-yl)methane,
(fluoren-9-yl)(4-bromo-2,3,6-trimethylindeno[5,6-b]thien-7-yl)methane, (fluoren-9-yl)(2-bromo-4,6-dimethylindeno[5,6-b]thien-7-yl)methane,
(fluoren-9-yl)(4-bromo-1,2,3,6-tetramethylcyclopenta[f]indol-7-yl)methane,
(fluoren-9-yl)(4-bromo-1-phenyl-2,3,6-trimethylcyclopenta[f]indol-7-yl)methane,
(fluoren-9-yl)(5-bromo-7-methylcyclopenta[g]quinol-8-yl)methane,
(fluoren-9-yl)(4-bromocyclopenta[b]pyrid-7-yl)methane,
(fluoren-9-yl)(2-bromo-5,7-dimethylcyclopenta[g]quinol-8-yl)methane,
2,2'-bis(4-bromo-3-dimethylamino-1,3-benzothiaborollide)methane,
bis(4-bromo-3a,7a-azaborinden-1-yl)methane,
3,3'-bis(7-bromo-2-dimethylamino-1,2-benzothiaborollide)methane,
5,5'-bis(3-bromo-2-dimethylamino-1,2-thiaborollide)methane,
1,2'-(cyclopentadienyl)(4-bromo-3-dimethylamino-1,3-benzothiaborollide)methane,
(cyclopentadienyl)(4-bromo-3a,7a-azaborinden-1-yl)methane,
1,3'-(cyclopentadienyl)(7-bromo-2-dimethylamino-1,2-benzothiaborollide)methane,
1,5'-(cyclopentadienyl)(3-bromo-2-dimethylamino-1,2-thiaborollide)methane,
1,2'-(inden-1-yl)(4-bromo-3-dimethylamino-1,3-benzothiaborollide)methane,
(inden-1-yl)(4-bromo-3a,7a-azaborinden-1-yl)methane,
1,3'-(inden-1-yl)(7-bromo-2-dimethylamino-1,2-benzothiaborollide)methane,
1,5'-(inden-1-yl)(3-bromo-2-dimethylamino-1,2-thiaborollide)methane,
2,2'-(inden-2-yl)(4-bromo-3-dimethylamino-1,3-benzothiaborollide)methane,
(inden-2-yl)(4-bromo-3a,7a-azaborinden-1-yl)methane,
2,3'-(inden-2-yl)(7-bromo-2-dimethylamino-1,2-benzothiaborollide)methane,
2,5'-(inden-2-yl)(3-bromo-2-dimethylamino-1,2-thiaborollide)methane,
9,2'-(fluoren-9-yl)(4-bromo-3-dimethylamino-1,3-benzothiaborollide)methane,
(fluoren-9-yl)(4-bromo-3a,7a-azaborinden-1-yl)methane,
9,3'-(fluoren-9-yl)(7-bromo-2-dimethylamino-1,2-benzothiaborolidei)methane,
9,5'-(fluoren-9-yl)(3-bromo-2-dimethylamino-1,2-thiaborollide)methane,
2,2-bis(4-bromoinden-1-yl)propane,
2,2-bis(4-bromoinden-2-yl)propane,
2-(4-bromoinden-1-yl)-2-(4-bromoinden-2-yl)propane,
2,2-bis(4-chloro-2-methylinden-1-yl)propane,
2,2-bis(4-iodo-2-methylinden-1-yl)propane,
2,2-bis(4,6-dibromo-2-methylinden-1-yl)propane,
2,2-bis(4-bromo-6-chloro-2-methylinden-1-yl)propane,
2,2-bis(4-bromo-2,6-dimethylinden-1-yl)propane,
2,2-bis(4-bromo-2-methyl-6-isopropylinden-1-yl)propane,
2,2-bis(4-bromo-2-methyl-6-fluoroinden-1-yl)propane,
2,2-bis(4-bromo-2-methyl-6-methoxyinden-1-yl)propane,
2,2-bis(4-bromo-2-methyl-6-dimethylaminoinden-1-yl)propane,
2,2-bis(4-bromo-2-methyl-6-diphenylphosphinoinden-1-yl)propane,
2,2-bis(4-bromo-2-methyl-6-methylsulfoinden-1-yl)propane,
2,2-bis(4-bromo-2-methyl-6-trimethylsilylinden-1-yl)propane,
2,2-bis(4-bromo-2-methyl-6-phenylinden-1-yl)propane,
2,2-bis(4-bromo-2-methyl-6-naphthylinden-1-yl)propane,
2,2-bis(4-bromo-2-methyl-6-N-indolylinden-1-yl)propane,
2,2-bis(4-bromo-2-methyl-6-trifluoromethylinden-1-yl)propane,
2,2-bis[4-bromo-2-methyl-6-(2-thienyl)inden-1-yl]propane,
2,2-bis[4-bromo-2-methyl-6-(4-pyridyl)inden-1-yl]propane,
2,2-bis(4-bromo-2-ethylinden-1-yl)propane,
2,2-bis(4-bromo-2-isopropylinden-1-yl)propane,
2,2-bis(4-bromo-2-phenylinden-1-yl)propane,
2-(4-bromo-2-methylinden-1-yl)-2-(4-chloro-2-methylinden-1-yl)propane,
2-(4-bromo-2-methylinden-1-yl)-2-(4-fluoro-2-methylinden-1-yl)propane,
2-(4-bromo-2-methylinden-1-yl)-2-(4-iodo-2-methylinden-1-yl)propane,
2-(4-bromo-2-methylinden-1-yl)-2-(2-methylinden-1-yl)propane,
2-(4-bromo-2-methylinden-1-yl)-2-(2-isopropylinden-1-yl)propane,
2-(4-bromo-2-methylinden-1-yl)-2-(inden-1-yl)propane,
2-(4-bromo-2-methylinden-1-yl)-2-(inden-2-yl)propane,
2-(4-bromo-2-methylinden-1-yl)-2-(2,4,6-trimethylinden-1-yl)propane,
2-(4-bromo-2-methylinden-1-yl)-2-(4-phenyl-2-methylinden-1-yl)propane,
2-(4-bromo-2-methylinden-1-yl)-2-(4-naphthyl-2-methylinden-1-yl)propane,
2-(4-bromo-2-methylinden-1-yl)-2-[4-(2,5-dimethylphenyl)-2-methylinden-1-yl]propane,
2-(4-bromo-2-methylinden-1-yl)-2-[4-(3,5-dimethylphenyl)-2-methylinden-1-yl]propane,
2-(4-bromo-2-methylinden-1-yl)-2-[4-(3,5-diisopropylphenyl)-2-methylinden-1-yl]propane,
2-(4-bromo-2-methylinden-1-yl)-2-[4-(3,5-di-tert-butylphenyl)-2-methylinden-1-yl]propane,
2-(4-bromo-2-methylinden-1-yl)-2-[4-(2-thienyl)-2-methylinden-1-yl]propane,
2-(4-bromo-2-methylinden-1-yl)-2-[4-(4-pyridyl)-2-methylinden-1-yl]propane,
2-(4-bromo-2-methylinden-1-yl)-2-(4-tert-butyl-2-methylinden-1-yl)propane,
2-(4-bromo-2-methylinden-1-yl)-2-(4-cyclohexyl-2-methylinden-1-yl)propane,
2-(4-bromo-2-methylinden-1-yl)-2-(4-isopropyl-2-methylinden-1-yl)propane,
2-(4-bromo-2-methylinden-1-yl)-2-(4-trimethysilyl-2-methylinden-1-yl)propane,
2-(4-bromo-2-methylinden-1-yl)-2-(4-trimethylgermyl-2-methylinden-1-yl)propane,
2-(4-bromo-2-methylinden-1-yl)-2-(4-methylthio-2-methylinden-1-yl)propane,
2-(4-bromo-2-methylinden-1-yl)-2-(4-diphenylphosphino-2-methylinden-1-yl)propane,
2-(4-bromo-2-methylinden-1-yl)-2-(4-trifluoromethyl-2-methylinden-1-yl)propane,
2-(4-bromo-2-methylinden-1-yl)-2-(cyclopentadienyl)propane,
2-(4-bromo-2-methylinden-1-yl)-2-(3-methylcyclopentadien-1-yl)propane,
2-(4-bromo-2-methylinden-1-yl)-2-(3-tert-butylcyclopentadien-1-yl)propane,
2-(4-bromo-2-methylinden-1-yl)-2-(3-trimethylsilylcyclopentadien-1-yl)propane,
2-(4-bromo-2-methylinden-1-yl)-2-(3-phenylcyclopentadien-1-yl)propane,
2-(4-bromo-2-methylinden-1-yl)-2-[3-(2-thienyl)cyclopentadien-1-yl]propane, 2-(4-bromo-2-methylinden-1-yl)-2-(3-diphenylphosphinocyclopentadien-1-yl)propane,
2-(4-bromo-2-methylinden-1-yl)-2-(2,3,4,5-tetramethylcyclopentadien-1-yl)propane,
2-(4-bromo-2-methylinden-1-yl)-2-(fluoren-9-yl)propane,
2-(4-bromo-2-methylinden-1-yl)-2-(3,6-dimethylfluoren-9-yl)propane,
2-(4-bromo-2-methylinden-1-yl)-2-(3,6-di-tert-butylfluoren-9-yl)propane,
2-(4-bromo-2-methylinden-1-yl)-2-(2,7-dibromofluoren-9-yl)propane,
2-(2-methylinden-1-yl)-2-(2,7-dibromofluoren-9-yl)propane,
2-(2-methylinden-1-yl)-2-(2,7-dichlorofluoren-9-yl)propane,
2-(2-methylinden-1-yl)-2-(2,7-diiodofluoren-9-yl)propane,
2-(2-methyl-4-phenylinden-1-yl)-2-(2,7-dibromofluoren-9-yl)propane,
2-(2,4-dimethylinden-1-yl)-2-(2,7-dibromofluoren-9-yl)propane,
2-(2-methyl-4-trimethylsilylinden-1-yl)-2-(2,7-dibromofluoren-9-yl)propane,
2-(2-methyl-4-tert-butylinden-1-yl)-2-(2,7-dibromofluoren-9-yl)propane,
2-(2-methyl-4-methoxyinden-1-yl)-2-(2,7-dibromofluoren-9-yl)propane,
2-(2-methyl-4-dimethylaminoinden-1-yl)-2-(2,7-dibromofluoren-9-yl)propane,
2-(2-methyl-4-trifluoromethylinden-1-yl)-2-(2,7-dibromofluoren-9-yl)propane,
2-(cyclopentadienyl)-2-(2,7-dibromofluoren-9-yl)propane,
2-(3-methylcyclopentadien-1-yl)-2-(2,7-dibromofluoren-9-yl)propane,
2-(3-tert-butylcyclopentadien-1-yl)-2-(2,7-dibromofluoren-9-yl)propane,
2-(3-phenylcyclopentadien-1-yl)-2-(2,7-dibromofluoren-9-yl)propane,
2-(3-trimethylsilylcyclopentadien-1-yl)-2-(2,7-dibromofluoren-9-yl)propane,
2-(3,4-dimethylcyclopentadien-1-yl)-2-(2,7-dibromofluoren-9-yl)propane,
2-[3-(2-thienyl)cyclopentadien-1-yl]-2-(2,7-dibromofluoren-9-yl)propane,
2-(fluoren-9-yl)-2-(2,7-dibromofluoren-9-yl)propane,
2-(3,6-dimethylfluoren-9-yl)-2-(2,7-dibromofluoren-9-yl)propane,
2-(3,6-ditertbutylfluoren-9-yl)-2-(2,7-dibromofluoren-9-yl)propane,
2-(3,6-diphenylfluoren-9-yl)-2-(2,7-dibromofluoren-9-yl)propane,
2,2-bis(4-bromo-2-methyl-5,6,7,8-tetrahydrocyclopenta[b]naphth-1-yl)propane,
2,2-bis(5-bromo-2-methyl-6,7,8,9-tetrahydrocyclopenta[a]naphth-3-yl)propane,
2,2-bis(4-bromo-2-methylcyclopenta[b]naphth-1-yl)propane,
2,2-bis(7-bromo-2,4-dimethylcyclopenta[b]naphth-1-yl)propane,
2,2-bis(8-bromo-6-methylindeno[5,6-d][1,3]dioxol-5-yl)propane,
2,2-bis(4-bromo-2,3,6-trimethylindeno[5,6-b]thien-7-yl)propane,
2,2-bis(2-bromo-4,6-dimethylindeno[5,6-b]thien-7-yl)propane,
2,2-bis(4-bromo-1,2,3,6-tetramethylcyclopenta[/]indol-7-yl)propane,
2,2-bis(4-bromo-1-phenyl-2,3,6-trimethylcyclopenta[f]indol-7-yl)propane,
2,2-bis(5-bromo-7-methylcyclopenta[g]quinol-8-yl)propane,
2,2-bis(2-bromo-5,7-dimethylcyclopenta[g]quinol-8-yl)propane,
2-(cyclopentadienyl)-2-(4-bromo-2-methyl-5,6,7,8-tetrahydrocyclopenta[b]naphth-1-yl)propane,
2-(cyclopentadienyl)-2-(5-bromo-2-methyl-6,7,8,9-tetrahydrocyclopenta[a]naphth-3-yl)propane,
2-(cyclopentadienyl)-2-(4-bromo-2-methylcyclopenta[b]naphth-1-yl)propane,
2-(cyclopentadienyl)-2-(7-bromo-2,4-dimethylcyclopenta[b]naphth-1-yl)propane,
2-(cyclopentadienyl)-2-(8-bromo-6-methylindeno[5,6-d][1,3]dioxol-5-yl)propane,
2-(cyclopentadienyl)-2-(4-bromo-2,3,6-trimethylindeno[5,6-b]thien-7-yl)propane,
2-(cyclopentadienyl)-2-(2-bromo-4,6-dimethylindeno[5,6-b]thien-7-yl)propane,
2-(cyclopentadienyl)-2-(4-bromo-1,2,3,6-tetramethylcyclopenta[f]indol-7-yl)propane,
2-(cyclopentadienyl)-2-(4-bromo-1-phenyl-2,3,6-trimethylcyclopenta[f]indol-7-yl)propane,
2-(cyclopentadienyl)-2-(4-bromocyclopenta[b]pyrid-7-yl)propane,
2-(cyclopentadienyl)-2-(5-bromo-7-methylcyclopenta[g]quinol-8-yl)propane,
2-(cyclopentadienyl)-2-(2-bromo-5,7-dimethylcyclopenta[g]quinol-8-yl)propane,
2-(inden-1-yl)-2-(4-bromo-2-methyl-5,6,7,8-tetrahydrocyclopenta[b]naphth-1-yl)propane,
2-(inden-1-yl)-2-(5-bromo-2-methyl-6,7,8,9-tetrahydrocyclopenta[a]naphth-3-yl)propane,
2-(inden-1-yl)-2-(4-bromo-2-methylcyclopenta[b]naphth-1-yl)propane,
2-(inden-1-yl)-2-(7-bromo-2,4-dimethylcyclopenta[b]naphth-1-yl)propane,
2-(inden-1-yl)-2-(8-bromo-6-methylindeno[5,6-d][1,3]dioxol-5-yl)propane,
2-(inden-1-yl)-2-(4-bromo-2,3,6-trimethylindeno[5,6-b]thien-7-yl)propane,
2-(inden-1-yl)-2-(2-bromo-4,6-dimethylindeno[5,6-b]thien-7-yl)propane,
2-(inden-1-yl)-2-(4-bromo-1,2,3,6-tetramethylcyclopenta[f]indol-7-yl)propane,
2-(inden-1-yl)-2-(4-bromo-1-phenyl-2,3,6-trimethylcyclopenta[/]indol-7-yl)propane,
2-(inden-1-yl)-2-(5-bromo-7-methylcyclopenta[g]quinol-8-yl)propane,
2-(inden-1-yl)-2-(2-bromo-5,7-dimethylcyclopenta[g]quinol-8-yl)propane,
2-(inden-2-yl)-2-(4-bromo-2-methyl-5,6,7,8-tetrahydrocyclopenta[b]naphth-1-yl)propane,
2-(inden-2-yl)-2-(5-bromo-2-methyl-6,7,8,9-tetrahydrocyclopenta[a]naphth-3-yl)propane,
2-(inden-2-yl)-2-(4-bromo-2-methylcyclopenta[b]naphth-1-yl)propane,
2-(inden-2-yl)-2-(7-bromo-2,4-dimethylcyclopenta[b]naphth-1-yl)propane,
2-(inden-2-yl)-2-(8-bromo-6-methylindeno[5,6-d][1,3]dioxol-5-yl)propane,
2-(inden-2-yl)-2-(4-bromo-2,3,6-trimethylindeno[5,6-b]thien-7-yl)propane,
2-(inden-2-yl)-2-(2-bromo-4,6-dimethylindeno[5,6-b]thien-7-yl)propane, 2-(inden-2-yl)-2-(4-bromo-1,2,3,6-tetramethylcyclopenta[f]indol-7-yl)propane,
2-(inden-2-yl)-2-(4-bromo-1-phenyl-2,3,6-trimethylcyclopenta[f]indol-7-yl)propane,
2-(inden-2-yl)-2-(5-bromo-7-methylcyclopenta[g]quinol-8-yl)propane,
2-(inden-2-yl)-2-(2-bromo-5,7-dimethylcyclopenta[g]quinol-8-yl)propane,
2-(4-bromo-2-methylinden-1-yl)-2-(4-bromo-2-methyl-5,6,7,8-tetrahydrocyclopenta[b]naphth-1-yl)propane,
2-(4-bromo-2-methylinden-1-yl)-2-(5-bromo-2-methyl-6,7,8,9-tetrahydrocyclopenta[a]naphth-3-yl)propane,
2-(4-bromo-2-methylinden-1-yl)-2-(4-bromo-2-methylcyclopenta[b]naphth-1-yl)propane,
2-(4-bromo-2-methylinden-1-yl)-2-(7-bromo-2,4-dimethylcyclopenta[b]naphth-1-yl)propane,
2-(4-bromo-2-methylinden-1-yl)-2-(8-bromo-6-methylindeno[5,6-d][1,3]dioxol-5-yl)propane,
2-(4-bromo-2-methylinden-1-yl)-2-(4-bromo-2,3,6-trimethylindeno[5,6-b]thien-7-yl)propane,
2-(4-bromo-2-methylinden-1-yl)-2-(2-bromo-4,6-dimethylindeno[5,6-b]thien-7-yl)propane,
2-(4-bromo-2-methylinden-1-yl)-2-(4-bromo-1,2,3,6-tetramethylcyclopenta[f]indol-7-yl)propane,
2-(4-bromo-2-methylinden-1-yl)-2-(4-bromo-1-phenyl-2,3,6-trimethylcyclopenta[f]indol-7-yl)propane,
2-(4-bromo-2-methylinden-1-yl)-2-(5-bromo-7-methylcyclopenta[g]quinol-8-yl)propane,
2-(4-bromo-2-methylinden-1-yl)-2-(4-bromocyclopenta[b]pyrid-7-yl)propane,
2-(4-bromo-2-methylinden-1-yl)-2-(2-bromo-5,7-dimethylcyclopenta[g]quinol-8-yl)propane,
2-(fluoren-9-yl)-2-(4-bromo-2-methyl-5,6,7,8-tetrahydrocyclopenta[b]naphth-1-yl)propane,
2-(fluoren-9-yl)-2-(5-bromo-2-methyl-6,7,8,9-tetrahydrocyclopenta[a]naphth-3-yl)propane,
2-(fluoren-9-yl)-2-(4-bromo-2-methylcyclopenta[b]naphth-1-yl)propane,
2-(fluoren-9-yl)-2-(7-bromo-2,4-dimethylcyclopenta[b]naphth-1-yl)propane,
2-(fluoren-9-yl)-2-(8-bromo-6-methylindeno[5,6-d][1,3]dioxol-5-yl)propane,
2-(fluoren-9-yl)-2-(4-bromo-2,3,6-trimethylindeno[5,6-b]thien-7-yl)propane,
2-(fluoren-9-yl)-2-(2-bromo-4,6-dimethylindeno[5,6-b]thien-7-yl)propane,
2-(fluoren-9-yl)-2-(4-bromo-1,2,3,6-tetramethylcyclopenta[/]indol-7-yl)propane,
2-(fluoren-9-yl)-2-(4-bromo-1-phenyl-2,3,6-trimethylcyclopenta[/]indol-7-yl)propane,
2-(fluoren-9-yl)-2-(5-bromo-7-methylcyclopenta[g]quinol-8-yl)propane,
2-(fluoren-9-yl)-2-(2-bromo-5,7-dimethylcyclopenta[g]quinol-8-yl)propane,
1,2-bis(4-bromoinden-1-yl)ethane,
1,2-bis(4-bromoinden-2-yl)ethane,
1,2-(4-bromoinden-1-yl)(4-bromoinden-2-yl)ethane,
1,2-bis(4-chloro-2-methylinden-1-yl)ethane,
1,2-bis(4-iodo-2-methylinden-1-yl)ethane,
1,2-bis(4,6-dibromo-2-methylinden-1-yl)ethane,
1,2-bis(4-bromo-6-chloro-2-methylinden-1-yl)ethane,
1,2-bis(4-bromo-2,6-dimethylinden-1-yl)ethane,
1,2-bis(4-bromo-2-methyl-6-isopropylinden-1-yl)ethane,
1,2-bis(4-bromo-2-methyl-6-fluoroinden-1-yl)ethane,
1,2-bis(4-bromo-2-methyl-6-methoxyinden-1-yl)ethane,
1,2-bis(4-bromo-2-methyl-6-dimethylaminoinden-1-yl)ethane,
1,2-bis(4-bromo-2-methyl-6-diphenylphosphinoinden-1-yl)ethane,
1,2-bis(4-bromo-2-methyl-6-methylsulfoinden-1-yl)ethane,
1,2-bis(4-bromo-2-methyl-6-trimethylsilylinden-1-yl)ethane,
1,2-bis(4-bromo-2-methyl-6-phenylinden-1-yl)ethane,
1,2-bis(4-bromo-2-methyl-6-naphthylinden-1-yl)ethane,
1,2-bis(4-bromo-2-methyl-6-N-indolylinden-1-yl)ethane,
1,2-bis(4-bromo-2-methyl-6-trifluoromethylinden-1-yl)ethane,
1,2-bis[4-bromo-2-methyl-6-(2-thienyl)inden-1-yl]ethane,
1,2-bis[4-bromo-2-methyl-6-(4-pyridyl)inden-1-yl]ethane,
1,2-bis(4-bromo-2-ethylinden-1-yl)ethane,
1,2-bis(4-bromo-2-isopropylinden-1-yl)ethane,
1,2-bis(4-bromo-2-phenylinden-1-yl)ethane,
1-(4-bromo-2-methylinden-1-yl)-2-(4-chloro-2-methylinden-1-yl)ethane,
1-(4-bromo-2-methylinden-1-yl)-2-(4-fluoro-2-methylinden-1-yl)ethane,
1-(4-bromo-2-methylinden-1-yl)-2-(4-iodo-2-methylinden-1-yl)ethane,
1-(4-bromo-2-methylinden-1-yl)-2-(2-methylinden-1-yl)ethane,
1-(4-bromo-2-methylinden-1-yl)-2-(2-isopropylinden-1-yl)ethane,
1-(4-bromo-2-methylinden-1-yl)-2-(inden-1-yl)ethane,
1-(4-bromo-2-methylinden-1-yl)-2-(inden-2-yl)ethane,
1-(4-bromo-2-methylinden-1-yl)-2-(2,4,6-trimethylinden-1-yl)ethane,
1-(4-bromo-2-methylinden-1-yl)-2-(4-phenyl-2-methylinden-1-yl)ethane,
1-(4-bromo-2-methylinden-1-yl)-2-(4-naphthyl-2-methylinden-1-yl)ethane,
1-(4-bromo-2-methylinden-1-yl)-2-[4-(2,5-dimethylphenyl)-2-methylinden-1-yl]ethane,
1-(4-bromo-2-methylinden-1-yl)-2-[4-(3,5-dimethylphenyl)-2-methylinden-1-yl]ethane,
1-(4-bromo-2-methylinden-1-yl)-2-[4-(3,5-diisopropylphenyl)-2-methylinden-1-yl]ethane,
1-(4-bromo-2-methylinden-1-yl)-2-[4-(3,5-di-tert-butylphenyl)-2-methylinden-1-yl]ethane,
1-(4-bromo-2-methylinden-1-yl)-2-[4-(2-thienyl)-2-methylinden-1-yl]ethane,
1-(4-bromo-2-methylinden-1-yl)-2-[4-(4-pyridyl)-2-methylinden-1-yl]ethane,
1-(4-bromo-2-methylinden-1-yl)-2-(4-tert-butyl-2-methylinden-1-yl)ethane,
1-(4-bromo-2-methylinden-1-yl)-2-(4-cyclohexyl-2-methylinden-1-yl)ethane,
1-(4-bromo-2-methylinden-1-yl)-2-(4-isopropyl-2-methylinden-1-yl)ethane,
1-(4-bromo-2-methylinden-1-yl)-2-(4-trimethysilyl-2-methylinden-1-yl)ethane,
1-(4-bromo-2-methylinden-1-yl)-2-(4-trimethylgermyl-2-methylinden-1-yl)ethane,
1-(4-bromo-2-methylinden-1-yl)-2-(4-methylthio-2-methylinden-1-yl)ethane,
1-(4-bromo-2-methylinden-1-yl)-2-(4-diphenylphosphino-2-methylinden-1-yl)ethane,
1-(4-bromo-2-methylinden-1-yl)-2-(4-trifluoromethyl-2-methylinden-1-yl)ethane,
1-(4-bromo-2-methylinden-1-yl)-2-(cyclopentadienyl)ethane,
1-(4-bromo-2-methylinden-1-yl)-2-(3-methylcyclopentadien-1-yl)ethane,
1-(4-bromo-2-methylinden-1-yl)-2-(3-tert-butylcyclopentadien-1-yl)ethane, 1-(4-bromo-2-methylinden-1-yl)-2-(3-trimethylsilylcyclopentadien-1-yl)ethane,
1-(4-bromo-2-methylinden-1-yl)-2-(3-phenylcyclopentadien-1-yl)ethane,
1-(4-bromo-2-methylinden-1-yl)-2-[3-(2-thienyl)cyclopentadien-1-yl]ethane,
1-(4-bromo-2-methylinden-1-yl)-2-(3-diphenylphosphinocyclopentadien-1-yl)ethane,
1-(4-bromo-2-methylinden-1-yl)-2-(2,3,4,5-tetramethylcyclopentadien-1-yl)ethane,
1-(4-bromo-2-methylinden-1-yl)-2-(fluoren-9-yl)ethane,
1-(4-bromo-2-methylinden-1-yl)-2-(3,6-dimethylfluoren-9-yl)ethane,
1-(4-bromo-2-methylinden-1-yl)-2-(3,6-di-tert-butylfluoren-9-yl)ethane,
1-(4-bromo-2-methylinden-1-yl)-2-(2,7-dibromofluoren-9-yl)ethane,
1-(2-methylinden-1-yl)-2-(2,7-dibromofluoren-9-yl)ethane,
1-(2-methylinden-1-yl)-2-(2,7-dichlorofluoren-9-yl)ethane,
1-(2-methylinden-1-yl)-2-(2,7-diiodofluoren-9-yl)ethane,
1-(2-methyl-4-phenylinden-1-yl)-2-(2,7-dibromofluoren-9-yl)ethane,
1-(2,4-dimethylinden-1-yl)-2-(2,7-dibromofluoren-9-yl)ethane,
1-(2-methyl-4-trimethylsilylinden-1-yl)-2-(2,7-dibromofluoren-9-yl)ethane,
1-(2-methyl-4-tert-butylinden-1-yl)-2-(2,7-dibromofluoren-9-yl)ethane,
1-(2-methyl-4-methoxyinden-1-yl)-2-(2,7-dibromofluoren-9-yl)ethane,
1-(2-methyl-4-dimethylaminoinden-1-yl)-2-(2,7-dibromofluoren-9-yl)ethane,
1-(2-methyl-4-trifluoromethylinden-1-yl)-2-(2,7-dibromofluoren-9-yl)ethane,
1-(cyclopentadienyl)-2-(2,7-dibromofluoren-9-yl)ethane,
1-(3-methylcyclopentadien-1-yl)-2-(2,7-dibromofluoren-9-yl)ethane,
1-(3-tert-butylcyclopentadien-1-yl)-2-(2,7-dibromofluoren-9-yl)ethane,
1-(3-phenylcyclopentadien-1-yl)-2-(2,7-dibromofluoren-9-yl)ethane,
1-(3-trimethylsilylcyclopentadien-1-yl)-2-(2,7-dibromofluoren-9-yl)ethane,
1-(3,4-dimethylcyclopentadien-1-yl)-2-(2,7-dibromofluoren-9-yl)ethane,
1-[3-(2-thienyl)cyclopentadien-1-yl]-2-(2,7-dibromofluoren-9-yl)ethane,
1-(fluoren-9-yl)-2-(2,7-dibromofluoren-9-yl)ethane,
1-(3,6-dimethylfluoren-9-yl)-2-(2,7-dibromofluoren-9-yl)ethane,
1-(3,6-ditertbutylfluoren-9-yl)-2-(2,7-dibromofluoren-9-yl)ethane,
1-(3,6-diphenylfluoren-9-yl)-2-(2,7-dibromofluoren-9-yl)ethane,
1,2-bis(4-bromo-2-methyl-5,6,7,8-tetrahydrocyclopenta[b]naphth-1-yl)ethane,
1,2-bis(5-bromo-2-methyl-6,7,8,9-tetrahydrocyclopenta[a]naphth-3-yl)ethane,
1,2-bis(4-bromo-2-methylcyclopenta[b]naphth-1-yl)ethane,
1,2-bis(7-bromo-2,4-dimethylcyclopenta[b]naphth-1-yl)ethane,
1,2-bis(8-bromo-6-methylindeno[5,6-d][1,3]dioxol-5-yl)ethane,
1,2-bis(4-bromo-2,3,6-trimethylindeno[5,6-b]thien-7-yl)ethane,
1,2-bis(2-bromo-4,6-dimethylindeno[5,6-b]thien-7-yl)ethane,
1,2-bis(4-bromo-1,2,3,6-tetramethylcyclopenta[f]indol-7-yl)ethane,
1,2-bis(4-bromo-1-phenyl-2,3,6-trimethylcyclopenta[/]indol-7-yl)ethane,
1,2-bis(5-bromo-7-methylcyclopenta[g]quinol-8-yl)ethane,
1,2-bis(2-bromo-5,7-dimethylcyclopenta[g]quinol-8-yl)ethane,
1-(cyclopentadienyl)-2-(4-bromo-2-methyl-5,6,7,8-tetrahydrocyclopenta[b]naphth-1-yl)ethane,
1-(cyclopentadienyl)-2-(5-bromo-2-methyl-6,7,8,9-tetrahydrocyclopenta[a]naphth-3-yl)ethane,
1-(cyclopentadienyl)-2-(4-bromo-2-methylcyclopenta[b]naphth-1-yl)ethane,
1-(cyclopentadienyl)-2-(7-bromo-2,4-dimethylcyclopenta[b]naphth-1-yl)ethane,
1-(cyclopentadienyl)-2-(8-bromo-6-methylindeno[5,6-d][1,3]dioxol-5-yl)ethane,
1-(cyclopentadienyl)-2-(4-bromo-2,3,6-trimethylindeno[5,6-b]thien-7-yl)ethane,
1-(cyclopentadienyl)-2-(2-bromo-4,6-dimethylindeno[5,6-b]thien-7-yl)ethane,
1-(cyclopentadienyl)-2-(4-bromo-1,2,3,6-tetramethylcyclopenta[/]indol-7-yl)ethane,
1-(cyclopentadienyl)-2-(4-bromo-1-phenyl-2,3,6-trimethylcyclopenta[/]indol-7-yl)ethane,
1-(cyclopentadienyl)-2-(5-bromo-7-methylcyclopenta[g]quinol-8-yl)ethane,
1-(cyclopentadienyl)-2-(2-bromo-5,7-dimethylcyclopenta[g]quinol-8-yl)ethane,
1-(inden-1-yl)-2-(4-bromo-2-methyl-5,6,7,8-tetrahydrocyclopenta[b]naphth-1-yl)ethane,
1-(inden-1-yl)-2-(5-bromo-2-methyl-6,7,8,9-tetrahydrocyclopenta[a]naphth-3-yl)ethane,
1-(inden-1-yl)-2-(4-bromo-2-methylcyclopenta[b]naphth-1-yl)ethane,
1-(inden-1-yl)-2-(7-bromo-2,4-dimethylcyclopenta[b]naphth-1-yl)ethane,
1-(inden-1-yl)-2-(8-bromo-6-methylindeno[5,6-d][1,3]dioxol-5-yl)ethane,
1-(inden-1-yl)-2-(4-bromo-2,3,6-trimethylindeno[5,6-b]thien-7-yl)ethane,
1-(inden-1-yl)-2-(2-bromo-4,6-dimethylindeno[5,6-b]thien-7-yl)ethane,
1-(inden-1-yl)-2-(4-bromo-1,2,3,6-tetramethylcyclopenta[f]indol-7-yl)ethane,
1-(inden-1-yl)-2-(4-bromo-1-phenyl-2,3,6-trimethylcyclopenta[f]indol-7-yl)ethane,
1-(inden-1-yl)-2-(5-bromo-7-methylcyclopenta[g]quinol-8-yl)ethane,
1-(inden-1-yl)-2-(2-bromo-5,7-dimethylcyclopenta[g]quinol-8-yl)ethane,
1-(inden-2-yl)-2-(4-bromo-2-methyl-5,6,7,8-tetrahydrocyclopenta[b]naphth-1-yl)ethane,
1-(inden-2-yl)-2-(5-bromo-2-methyl-6,7,8,9-tetrahydrocyclopenta[a]naphth-3-yl)ethane,
1-(inden-2-yl)-2-(4-bromo-2-methylcyclopenta[b]naphth-1-yl)ethane,
1-(inden-2-yl)-2-(7-bromo-2,4-dimethylcyclopenta[b]naphth-1-yl)ethane,
1-(inden-2-yl)-2-(8-bromo-6-methylindeno[5,6-d][1,3]dioxol-5-yl)ethane,
1-(inden-2-yl)-2-(4-bromo-2,3,6-trimethylindeno[5,6-b]thien-7-yl)ethane,
1-(inden-2-yl)-2-(2-bromo-4,6-dimethylindeno[5,6-b]thien-7-yl)ethane,
1-(inden-2-yl)-2-(4-bromo-1,2,3,6-tetramethylcyclopenta[f]indol-7-yl)ethane, 1-(inden-2-yl)-2-(4-bromo-1-phenyl-2,3,6-trimethylcyclopenta[f]indol-7-yl)ethane,
1-(inden-2-yl)-2-(5-bromo-7-methylcyclopenta[g]quinol-8-yl)ethane,
1-(inden-2-yl)-2-(2-bromo-5,7-dimethylcyclopenta[g]quinol-8-yl)ethane,
1-(4-bromo-2-methylinden-1-yl)-2-(4-bromo-2-methyl-5,6,7,8-tetrahydrocyclopenta[b]naphth-1-yl)ethane,
1-(4-bromo-2-methylinden-1-yl)-2-(5-bromo-2-methyl-6,7,8,9-tetrahydrocyclopenta[a]naphth-3-yl)ethane,
1-(4-bromo-2-methylinden-1-yl)-2-(4-bromo-2-methylcyclopenta[b]naphth-1-yl)ethane,
1-(4-bromo-2-methylinden-1-yl)-2-(7-bromo-2,4-dimethylcyclopenta[b]naphth-1-yl)ethane,
1-(4-bromo-2-methylinden-1-yl)-2-(8-bromo-6-methylindeno[5,6-d][1,3]dioxol-5-yl)ethane,
1-(4-bromo-2-methylinden-1-yl)-2-(4-bromo-2,3,6-trimethylindeno[5,6-b]thien-7-yl)ethane,
1-(4-bromo-2-methylinden-1-yl)-2-(2-bromo-4,6-dimethylindeno[5,6-b]thien-7-yl)ethane,
1-(4-bromo-2-methylinden-1-yl)-2-(4-bromo-1,2,3,6-tetramethylcyclopenta[/]indol-7-yl)ethane,
1-(4-bromo-2-methylinden-1-yl)-2-(4-bromo-1-phenyl-2,3,6-trimethylcyclopenta[f]indol-7-yl)ethane,
1-(4-bromo-2-methylinden-1-yl)-2-(5-bromo-7-methylcyclopenta[g]quinol-8-yl)ethane,
1-(4-bromo-2-methylinden-1-yl)-2-(2-bromo-5,7-dimethylcyclopenta[g]quinol-8-yl)ethane,
1-(fluoren-9-yl)-2-(4-bromo-2-methyl-5,6,7,8-tetrahydrocyclopenta[b]naphth-1-yl)ethane,
1-(fluoren-9-yl)-2-(5-bromo-2-methyl-6,7,8,9-tetrahydrocyclopenta[a]naphth-3-yl)ethane,
1-(fluoren-9-yl)-2-(4-bromo-2-methylcyclopenta[b]naphth-1-yl)ethane,
1-(fluoren-9-yl)-2-(7-bromo-2,4-dimethylcyclopenta[b]naphth-1-yl)ethane,
1-(fluoren-9-yl)-2-(8-bromo-6-methylindeno[5,6-d][1,3]dioxol-5-yl)ethane,
1-(fluoren-9-yl)-2-(4-bromo-2,3,6-trimethylindeno[5,6-b]thien-7-yl)ethane,
1-(fluoren-9-yl)-2-(2-bromo-4,6-dimethylindeno[5,6-b]thien-7-yl)ethane,
1-(fluoren-9-yl)-2-(4-bromo-1,2,3,6-tetramethylcyclopenta[f]indol-7-yl)ethane,
1-(fluoren-9-yl)-2-(4-bromo-1-phenyl-2,3,6-trimethylcyclopenta[/]indol-7-yl)ethane,
1-(fluoren-9-yl)-2-(4-bromocyclopenta[b]pyrid-7-yl)ethane,
1-(fluoren-9-yl)-2-(5-bromo-7-methylcyclopenta[g]quinol-8-yl)ethane,
1-(fluoren-9-yl)-2-(2-bromo-5,7-dimethylcyclopenta[g]quinol-8-yl)ethane,
1,2-bis[2-(4-bromo-3-dimethylamino-1,3-benzothiaborollide)]ethane,
1,2-bis(4-bromo-3a,7a-azaborinden-1-yl)ethane,
1,2-bis[3-(7-bromo-2-dimethylamino-1,2-benzothiaborolide)]ethane,
1,2-bis[5-(3-bromo-2-dimethylamino-1,2-thiaborollide)]ethane,
1-(cyclopentadienyl)-2-[2-(4-bromo-3-dimethylamino-1,3-benzothiaborollide)]ethane,
1-(cyclopentadienyl)-2-(4-bromo-3a,7a-azaborinden-1-yl)ethane,
1-(cyclopentadienyl)-2-[3-(7-bromo-2-dimethylamino-1,2-benzothiaborollide)]ethane,
1-(cyclopentadienyl)-2-[5-(3-bromo-2-dimethylamino-1,2-thiaborollide)]ethane,
1-(inden-1-yl)-2-[2-(4-bromo-3-dimethylamino-1,3-benzothiaborollide)]ethane,
1-(inden-1-yl)-2-(4-bromo-3a,7a-azaborinden-1-yl)ethane,
1-(inden-1-yl)-2-[3-(7-bromo-2-dimethylamino-1,2-benzothiaboralide-3)]ethane,
1-(inden-1-yl)-2-[5-(3-bromo-2-dimethylamino-1,2-thiaborollide)]ethane,
1-(inden-2-yl)-2-[2-(4-bromo-3-dimethylamino-1,3-benzothiaborollide)]ethane,
1-(inden-2-yl)-2-(4-bromo-3a,7a-azaborinden-1-yl)ethane,
1-(inden-2-yl)-2-[3-(7-bromo-2-dimethylamino-1,2-benzothiaborollide)]ethane,
1-(inden-2-yl)-2-[5-(3-bromo-2-dimethylamino-1,2-thiaborollide)]ethane,
1-(fluoren-9-yl)-2-[2-(4-bromo-3-dimethylamino-1,3-benzothiaborollide)]ethane,
1-(fluoren-9-yl)-2-(4-bromo-3a,7a-azaborinden-1-yl)ethane,
1-(fluoren-9-yl)-2-[3-(7-bromo-2-dimethylamino-1,2-benzothiaborolide)]ethane, and
1-(fluoren-9-yl)-2-[5-(3-bromo-2-dimethylamino-1,2-thiaborollide]ethane.

Starting materials of the formula (I) used in the synthetic process of the present invention can be synthesized in a simple manner by customary methods of the prior art (*Metallocenes: Synthesis, Reactivity, Applications*, Ed. by A. Togni, R. L. Halterman.—Wiley-VCH, 1998). For instance, deprotonation of halo-substituted indene followed by treatment with $R_2SiCl_2$ gives bis-indenyl ligands with $R_2Si$ bridge in position 1 of indenyls (WO 9840331). The respective compounds with $CR_2$ bridge can be readily prepared, for example, by the nucleophilic addition of the haloindenyl anion to fulvenes (WO 2004087775).

Aliphatic, heteroaliphatic, aromatic, heteroaromatic, alkenyl, and heteroalkenyl organometallic compounds of the formula (III) are likewise obtainable in a simple manner by standard methods of the prior art or can be purchased commercially. The synthesis of organozinc reagents, of importance in Negishi reactions, is described, for example, in *Organozinc Reagents*, Ed. by P. Knochel, P. Jones, Oxford U Press, 1999. The synthesis of boronic acids, of importance in Suzuki-Miyaura reactions, is described, for example, in *Organic Synthesis, Collective Volume IV*, Wiley, 1963. The synthesis of organotin reagents, of importance in Stille reactions, is described, for example, in V. Farina, V. Krishnamurthy, W. J. Scott, *The Stille Reaction*, Wiley, 1998 and the references cited therein. The synthesis of other organometallic reagents of the formula (III) involves standard methods of organometallic chemistry and is described, for example, in *Organometallics in Synthesis*, Ed. By M. Schlosser, and in J. March, Advanced Organic Chemistry, $4^{th}$ Edition, 1992 and the references cited therein.

The synthesis of chelating ligands of the formula (II) which are substituted by hydrocarbyl groups in the six-membered ring of indenes and heteroindenes or in the five-membered heterocyclic ring of cyclopentathiophenes and related fragments is carried out by means of a transition metal-catalyzed $sp^2$-$sp^3$ and $sp^2$-$sp^2$ coupling reaction of halo-substituted chelating ligands of the formula (I) with organometallic reagents of the formula (III). These reactions are carried out in suitable solvents, such as diethyl ether, tetrahydrofuran, toluene, etc., under an inert gas atmosphere. In principle, it is possible to use transition metal complexes of Groups 8 to 10 of the Periodic Table of the Elements, preferably Group 10. Particularly useful complexes are complexes of nickel and palladium. Non-limiting examples of transition metal catalysts include: palladium chloride, palladium bromide, palladium iodide, palladium dibenzylidenacetone, palladium acetate, dichlorobis(triphenylphosphine)palladium, bis(tri-tert-butylphosphine)palladium, dichlorobis(triphenylphosphine)palladium(II), polymer-bound catalysts such as dichlorobis(triphenylphosphine)palladium(II) polymer bound or tetrakis(triphenylphosphine)palladium(0) polymer bound (both are available from Aldrich Chemical Company where the polymer is a divinylbenzene crosslinked polystyrene), nickel chloride, nickel bromide, nickel iodide, nickel acetylacetonate, dichlorobis(triphenylphosphine)nickel, bis(1,5-cyclooctadienyl)nickel, bis(cyclopentadienyl)nickel.

Alternatively, the catalyst can be a mixture of one or more of the above mentioned salts and a suitable ligand. This combination can considerably increase the yield of the target products of the cross-coupling reactions. Non-limiting examples of such ligands (which may be polymer-supported) include: trimethylphosphine, triethylphosphine, triisopropylphosphine, tri(tert-butyl)phosphine, tricyclohexylphosphine, triphenylphosphine, tri(o-tolyl)phosphine, (2-biphenyl)di(tert-butyl)phosphine, (2'-dimethylaminobiphenyl-2)di(tert-butyl)phosphine, (9-phenanthrenyl)dicyclohexylphosphine, 1,1'-bis(di-tert-butylphosphino)ferrocene, XANTPHOS, DPEPHOS, 2,2'-bipyridyl, o-phenanthroline, 1,1'-bis(diphenylphosphino)ferrocene, mtrimethylphosphite, triethylphosphite, triisopropylphosphite, triphenylphosphite, tricyclohexylphosphite, tribenzylphosphite as well as carbine ligand of the following formula:

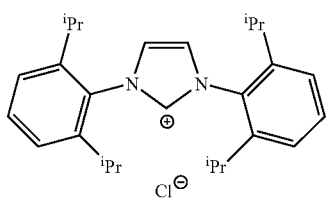

Examples of commercially available polymeric bound phosphines include poly(ethylene glycol)triphenylphosphine; and dicyclohexylphenylphosphine, polymer-bound; (4-hydroxyphenyl)diphenylphosphine, polymer-bound; triphenylphosphine, polymer-supported; R-(+)-2,2'-bis(diphenylphosphino)-1,1'-binaphthalene, polymer-bound; S-(−)-2,2'-bis(diphenylphosphino)-1,1'-binaphthalene, polymer-bound (all available from Aldrich Chemical Company where the polymer-bound or polymer-supported is a divinylbenzene crosslinked polystyrene).

The most preferred ligands for nickel catalyst are: triphenylphosphine, triethylphosphite; 2,2'-bipyridyl and o-phenanthroline. The most preferred ligands for palladium catalyst are: tri(tert-butyl)phosphine, (2-biphenyl)di(tert-butyl)phosphine, (2'-dimethylaminobiphenyl-2)di(tert-butyl)phosphine, (9-phenanthrenyl)dicyclohexylphosphine, 1,1'-bis(di-tert-butylphosphino)ferrocene, XANTPHOS, and the carbene ligand shown above.

Different cross-coupling reactions can be used to functionalize the starting chelating ligands of the formula (I) to obtain the cross-coupling products of the formula (II). The general protocols for the Kumada reaction using Grignard reagents, the Suzuki reaction using organoboron compounds, particularly NaBPh$_4$, boronic acids and their ethers, the Negishi reaction using organozinc compounds, the Stille reaction using organotin derivatives, and other cross-coupling reactions are described in *Metal-Catalyzed Cross-Coupling Reactions*, Ed. by F. Diederich, P. J. Stang, Wiley, 1998 and the references cited therein.

Non-limiting examples of Grignard reagents of the formula (III) which are preferred in the process of the present invention include: methylmagnesium chloride, methylmagnesium bromide, methylmagnesium iodide, dimethylmagnesium, ethylmagnesium bromide, n-propylmagnesium chloride, isopropylmagnesium chloride, n-butylmagnesium chloride, sec-butylmagnesium chloride, isobutylmagnesium chloride, tert-butylmagnesium chloride, cyclopentylmagnesium chloride, cyclohexylmagnesium chloride, benzylmagnesium chloride, 4-methylbenzylmagnesium chloride, 4-methoxybenzylmagnesium chloride, 4-trifluoromethyhnagnesium chloride, diphenylmethylmagnesium bromide, adamantylmagnesum bromide, cyclohexenylmagnesium chloride, isopropenylmagnesium chloride, 2-phenylethenylmagnesium bromide, trimethylsilylmethylmagnesium chloride, neopentylmagnesium chloride, methoxymethylmagnesium chloride, 3-methoxypropylmagnesium chloride, dimethylaminomethylmagnesium chloride, diphenylphosphinomethylmagnesium chloride, 2-pyridylmagnesium bromide, 4-pyridylmagnesium chloride, 2-thienylmagnesium bromide, 2-benzothienylmagnesium bromide, 2-benzofurylmagnesium chloride, 3-(N-methylindolyl)magnesium bromide, phenylmagnesium bromide, 2-methylphenylmagnesium bromide, 3-methylphenylmagnesium bromide, 4-methylphenylmagnesium bromide, 4-tert-butylphenylmagnesium bromide, 2,6-dimethylphenylmagnesium bromide, 2,6-diisopropylphenylmagnesium bromide, 3,5-dimethylphenylmagnesium chloride, 2,5-dimethylphenylmagnesium chloride, 3,5-diisopropylphenylmagnesium chloride, 3,5-tert-butylphenylmagnesium chloride, 2-isopropylphenylmagnesium chloride, 3-trifluoromethylphenylmagnesium chloride, 4-fluorophenylmagnesium chloride, 4-methoxyphenylmagnesium chloride, 2-methoxyphenylmagnesium chloride, 4-dimethylaminophenylmagnesium chloride, 1-naphthylmagnesium chloride, 2-naphthylmagnesium chloride, and pentafluorophenylmagnesium bromide.

The most preferred Grignard reagents are: cyclopentylmagnesium chloride, cyclohexylmagnesium chloride, 2-thienylmagnesium bromide, 3,5-dimethylphenylmagnesium chloride, 2,5-dimethylphenylmagnesium chloride, 3,5-diisopropylphenylmagnesium chloride, 3,5-tert-butylphenylmagnesium chloride, 1-naphthylmagnesium chloride.

Non-limiting examples of organozinc reagents of the formula (III) which are preferred in the process of the present invention include: methylzinc chloride, methylzinc bromide, methylzinc iodide, dimethylzinc, ethylzinc bromide, n-propylzinc chloride, isopropylzinc chloride, n-butylzinc chloride, sec-butylzinc chloride, isobutylzinc chloride, tert-butylzinc chloride, cyclopentylzinc chloride, cyclohexylzinc chloride, benzylzinc chloride, 4-methylbenzylzinc chloride, 4-methoxybenzylzinc chloride, 4-trifluoromethylzinc chloride, diphenylmethylzinc bromide, adamantylmagnesum bromide, cyclohexenylzinc chloride, isopropenylzinc chloride, 2-phenylethenylzinc bromide, trimethylsilylmethylzinc chloride, neopentylzinc chloride, methoxymethylzinc chloride, 3-methoxypropylzinc chloride, dimethylaminomethylzinc chloride, diphenylphosphinomethylzinc chloride, 2-pyridylzinc bromide, 4-pyridylzinc chloride, 2-thienylzinc bromide, 2-benzothienylzinc bromide, 2-benzofurylzinc chloride, 3-(N-methylindolyl)zinc bromide, phenylzinc bromide, 2-methylphenylzinc bromide, 3-methylphenylzinc bromide, 4-methylphenylzinc bromide, 4-tert-butylphenylzinc bromide, 2,6-dimethylphenylzinc bromide, 2,6-diisopropylphenylzinc bromide, 3,5-dimethylphenylzinc chloride, 2,5-dimethylphenylzinc chloride, 3,5-diisopropylphenylzinc chloride, 3,5-tert-butylphenylzinc chloride, 2-isopropylphenylzinc chloride, 3-trifluoromethylphenylzinc chloride, 4-fluorophenylzinc chloride, 4-methoxyphenylzinc chloride, 2-methoxyphenylzinc chloride, 4-dimethylaminophenylzinc chloride, 1-naphthylzinc chloride, 2-naphthylzinc chloride, 4-cyanophenylzinc bromide, 4-carboethoxyphenylzinc iodide, pentafluorophenylzinc bromide.

The most preferred organozinc reagents are: cyclopentylzinc chloride, cyclohexylzinc chloride, 2-thienylzinc bromide, 3,5-dimethylphenylzinc chloride, 2,5-dimethylphenylzinc chloride, 3,5-diisopropylphenylzinc chloride, 3,5-tert-butylphenylzinc chloride, 1-naphthylzinc chloride.

Non-limiting examples of organoboron reagents of the formula (III) which are preferred in the process of the present invention are: methylboronic acid, ethylboronic acid, n-propylboronic acid, isopropylboronic acid, n-butylboronic acid, sec-butylboronic acid, isobutylboronic acid, tert-butylboronic acid, cyclopentylboronic acid, cyclohexylboronic acid, benzylboronic acid, 4-methylbenzylboronic acid, 4-methoxybenzylboronic acid, 4-trifluoromethylboronic acid, diphenylmethylboronic acid, adamantylboronic acid, cyclohexenylboronic acid, isopropenylboronic acid, 2-phenylethenylboronic acid, trimethylsilylmethylboronic acid, neopentylboronic acid, methoxymethylboronic acid, 3-methoxypropylboronic acid, dimethylaminomethylboronic acid, diphenylphosphinomethylboronic acid, 2-pyridylboronic acid, 4-pyridylboronic acid, 2-thienylboronic acid, 2-benzothienylboronic acid, 2-benzofurylboronic acid, 3-(N-methylindolyl)boronic acid, phenylboronic acid, sodium tetraphenylborate, 4,4,5,5-tetramethyl-2-phenyl-1,3,2-dioxaborolane, 2-phenyl-1,3,2-benzodioxaborole, triphenylboron, 2-methylphenylboronic acid, 3-methylphenylboronic acid, 4-methylphenylboronic acid, 4-tert-butylphenylboronic acid, 2,6-dimethylphenylboronic acid, 2,6-diisopropylphenylboronic acid, 3,5-dimethylphenylboronic acid, 2,5-dimethylphenylboronic acid, 3,5-diisopropylphenylboronic acid, 3,5-tert-butylphenylboronic acid, 2-isopropylphenylboronic acid, 3-trifluoromethylphenylboronic acid, 4-fluorophenylboronic acid, 4-methoxyphenylboronic acid, 2-methoxyphenylboronic acid, 4-dimethylaminophenylboronic acid, 1-naphthylboronic acid, 2-naphthylboronic acid, 4-cyanophenylboronic acid, 4-carboethoxyphenylboronic acid, pentafluorophenylboronic acid.

The most preferred organoboron reagents are: 2-thienylboronic acid, 3,5-dimethylphenylboronic acid, 2,5-dimethylphenylboronic acid, 3,5-diisopropylphenylboronic acid, 3,5-tert-butylphenylboronic acid, 1-naphthylboronic acid.

The cross-coupling reactions using organoboron reagents (Suzuki reaction) require a base in addition to $NaBPh_4$. Non-limiting examples of bases to be used include: potassium carbonate, sodium carbonate, lithium carbonate, cesium carbonate, rubidium carbonate, lithium hydroxide, sodium hydroxide, potassium hydroxide, sodium triphosphate, potassium triphosphate, sodium hydrocarbonate, calcium carbonate, calcium oxide, barium carbonate, barium oxide, aluminium carbonate, aluminium oxide, yttrium carbonate, yttrium oxide, cerium carbonate, cerium oxide, barium hydroxide, calcium hydroxide, yttrium hydroxide, cerium hydroxide, aluminium hydroxide, sodium methylate, sodium ethylate, sodium isopropylate, sodium n-butoxide, sodium tert-butoxide, lithium ethylate, potassium ethylate.

Non-limiting examples of organotin reagents of the formula (III) which are preferred in the process of the present invention include: tetramethyltin, teraethyltin, tetracyclohexyltin, 2-pyridyl-tri-n-butyltin, 4-pyridyl-tri-n-butyltin, 2-thienyl-tri-n-butyltin, 2-benzothienyl-tri-n-butyltin, 2-benzofuryl-tri-n-butyltin, 3-(N-methylindolyl)-tri-n-butyltin, phenyl-tri-n-butyltin, phenyltrimethyltin, phenyltriethyltin, phenyltriisopropyltin, phenyltriisobutyltin, phenyltricyclohexyltin, tetraphenyltin, 2-methylphenyl-tri-n-butyltin, 3-methylphenyl-tri-n-butyltin, 4-methylphenyl-tri-n-butyltin, 4-tert-butylphenyl-tri-n-butyltin, 2,6-dimethylphenyl-tri-n-butyltin, 2,6-diisopropylphenyl-tri-n-butyltin, 3,5-dimethylphenyl-tri-n-butyltin, 2,5-dimethylphenyl-tri-n-butyltin, 3,5-diisopropylphenyl-tri-n-butyltin, 3,5-tert-butylphenyl-tri-n-butyltin, 2-isopropylphenyl-tri-n-butyltin, 3-trifluoromethylphenyl-tri-n-butyltin, 4-fluorophenyl-tri-n-butyltin, 4-methoxyphenyl-tri-n-butyltin, 2-methoxyphenyl-tri-n-butyltin, 4-dimethylaminophenyl-tri-n-butyltin, 1-naphthyl-tri-n-butyltin, 2-naphthyl-tri-n-butyltin, 4-cyanophenyl-tri-n-butyltin, 4-carboethoxyphenyl-tri-n-butyltin, pentafluorophenyl-tri-n-butyltin, phenyltin trichloride, phenyltin tribromide, phenyltin triiodide, phenyltin trifluoride, phenyltin triethoxyde.

The most preferred organotin reagents are: 2-thienyl-tri-n-butyltin, 3,5-dimethylphenyl-tri-n-butyltin, 2,5-dimethylphenyl-tri-n-butyltin, 3,5-diisopropylphenyl-tri-n-butyltin, 3,5-tert-butylphenyl-tri-n-butyltin, 1-naphthyl-tri-n-butyltin.

The cross-coupling reactions using organotin reagents (Stille reaction) require the use of a nucleophilic aid agent. Non-limiting examples of such aiding agents to be used include: lithium fluoride, sodium fluoride, potassium fluoride, rubidium fluoride, cesium fluoride, tetramethylammonium fluoride, tetraethylammonium fluoride, tetra-n-butylammonium fluoride, magnesium fluoride, calcium fluoride, barium fluoride, aluminium fluoride, tetramethylphosphonium fluoride, lithium chloride, sodium bromide, potassium chloride, rubidium chloride, cesium chloride, tetramethylammonium chloride, tetraethylammonium chloride, tetra-n-butylammonium chloride, magnesium chloride, calcium chloride, barium chloride, aluminium chloride, tetramethylphosphonium chloride, lithium hydroxide, sodium hydroxide, potassium hydroxide, rubidium hydroxide, cesium hydroxide, tetramethylammonium hydroxide, tetraethylammonium hydroxide, tetra-n-butylammonium hydroxide, magnesium hydroxide, calcium hydroxide, barium hydroxide, aluminium hydroxide, tetramethylphosphonium hydroxide, lithium methoxide, sodium methoxide, potassium methoxide, rubidium methoxide, cesium methoxide, magnesium methoxide, calcium methoxide, barium methoxide, aluminium methoxide, sodium ethoxide, sodium n-propoxide, sodium isopropoxide, sodium n-butoxide, sodium isobutoxide, sodium sec-butoxide, sodium phenoxide.

Non-limiting examples of organometallic compounds of the formula (III), other than Grignard, organozinc, organoboron, and organotin reagents, include: dimethylcadmium, diphenylcadmium, trimethylindium, tripenylindium, phenylindium dichloride, trimethylgallium, triphenylgallium, phenylgallium dichloride, tetraphenylsilane, phenyltrichlorosilane, phenyltrimethoxysilane, tetraphenylgermane, phenyltrichlorogermane, phenyltrimethoxygermane, triphenylbismuth, phenylbismuth dichloride, phenylbismuth diethoxide.

In most cases it is sufficient to use the particularly preferred catalyst $NiCl_2(dppp)_2$ or $NiCl_2(PPh_3)_2$ in an amount of 0.01 to 5 mol %, preferably 1 to 3 mol % and most preferably about 2 mol %, in each case relative to the chelating ligand of the formula (I) used. Analogously, in most cases it is sufficient to use the particularly preferred catalyst $Pd(OAc)_2$ in combination with a phosphine or phosphine ligand such as ligands A through N, or Pd(P'Bu₃)₂ in an amount of 0.000001 to 5 mol %, preferably 0.01 to 2 mol % and most preferably about 1 mol %, in each case based on the chelating ligand of the formula (I) used. OAc is O₂CCH₃.

Suitable solvents for the metal-catalyzed cross-coupling of chelating ligands of the formula (I) with organometallic reagents of the formula (III) are, for example, aliphatic ethers such as diethyl ether, dibutyl ether, methyl tert-butyl ether, tetrahydrofuran, dioxane and dimethoxyethane, aliphatic hydrocarbons such as pentane, hexane and the like, aromatic hydrocarbons such as benzene, toluene, xylenes and the like. In many cases, other solvents can be used, such as dimethylformamide, water, acetone and the like. Mixtures of various solvents in various mixing ratios can also be used according to the present invention to match the solubility of the starting materials and end products to the reaction conditions in an optimal fashion. It should be noted that protic solvents such as water, alcohols and their mixtures with aprotic solvents can be also be used, but only in the case of Suzuki reactions involving starting materials (I) where the bridging group B is not SiR₂, GeR₂, SiR₂—SiR₂, GeR₂—GeR₂, BR, BR—BR and the like, since these groups are labile in the presence of the transition-metal catalyst in protic solvents.

A person skilled in the art will choose solvents or solvent mixtures appropriate to the specific substitution pattern of the starting compounds and the catalysts and reagents used by means of simple tests or on the basis of known solubilities and solvent properties.

In preferred embodiments of the process of the present invention, the chelating ligand of the formula (I) together with a sufficient amount of solvent are placed in the reaction vessel under an inert atmosphere. The catalyst, an optional ligand and an optional base or nucleophilic aid agent are subsequently added followed by the addition of a solution of the organometallic compound of the formula (III) in a suitable solvent at room or lower (−78° C. to +10° C.) temperatures. The cross-coupling reaction can be carried out by vigorous stirring at room or elevated temperatures depending on the reaction under study, the reagents and the catalyst used. Addition of the reagents, catalyst and other additives can be performed in different orders. A person skilled in the art will choose an appropriate procedure depending on the reactivity and substitution of the individual reagents.

Non-limiting preferred examples of the chelating ligands of the formula (II), where R is hydrocarbyl, substituted hydrocarbyl, halocarbyl, or substituted halocarbyl, which can be prepared according to the present invention include:
bis(4-R-2-methylinden-1-yl)dimethylsilane,
bis(4-R-2-inden-1-yl)dimethylsilane,
(4-R-inden-1-yl)(4-chloroinden-1-yl)dimethylsilane,
(4-R-inden-1-yl)(4-bromoinden-1-yl)dimethylsilane,
(4-R-inden-1-yl)(4-iodoinden-1-yl)dimethylsilane,
bis(4-R-inden-1-yl)dimethylsilane,
bis(4-R-inden-2-yl)dimethylsilane,
(4-R-inden-1-yl)(4-R-inden-2-yl)dimethylsilane,
bis(4-R-2-methylinden-1-yl)diethylsilane,
bis(4-R-2-methylinden-1-yl)methylphenylsilane,
bis(4-R-2-methylinden-1-yl)diphenylsilane,
bis(4-R-2-methylinden-1-yl)dimethylgermane,
bis(4-R-2-methylinden-1-yl)phenylphosphine,
bis(4-R-2-methylinden-1-yl)methylphosphine,
bis(4-R-2-methylinden-1-yl)isopropylphosphine,
1,2-bis(4-R-2-methylinden-1-yl)-1',1'',2',2''-tetramethyldisilane,
1,2-bis(4-R-2-methylinden-1-yl)ethane,
cis-1,2-bis(4-R-2-methylinden-1-yl)ethylene,
bis(4-R-2-methylinden-1-yl)methane,
2,2'-bis(4-R-2-methylinden-1-yl)propane,
bis(4-R-2-methylinden-1-yl)diphenylmethane,
bis(4,6-di-2-methylinden-1-yl)dimethylsilane,
bis(4-R-2,6-dimethylinden-1-yl)dimethylsilane,
bis(4-R-2-methyl-6-isopropylinden-1-yl)dimethylsilane,
bis(4-R-2-methyl-6-methoxyinden-1-yl)dimethylsilane,
bis(4-R-2-methyl-6-dimethylaminoinden-1-yl)dimethylsilane,
bis(4-R-2-methyl-6-diphenylphosphinoinden-1-yl)dimethylsilane,
bis(4-R-2-methyl-6-methylsulfoinden-1-yl)dimethylsilane,
bis(4-R-2-methyl-6-trimethylsilylinden-1-yl)dimethylsilane,
bis(4-R-2-methyl-6-phenylinden-1-yl)dimethylsilane,
bis(4-R-2-methyl-6-naphthylinden-1-yl)dimethylsilane,
bis(4-R-2-methyl-6-N-indolylinden-1-yl)dimethylsilane,
bis(4-R-2-methyl-6-trifluoromethylinden-1-yl)dimethylsilane,
bis[4-R-2-methyl-6-(2-thienyl)inden-1-yl]dimethylsilane,
bis[4-R-2-methyl-6-(4-pyridyl)inden-1-yl]dimethylsilane,
bis(4-R-2-ethylinden-1-yl)dimethylsilane,
bis(4-R-2-isopropylinden-1-yl)dimethylsilane,
bis(4-R-2-phenylinden-1-yl)dimethylsilane,
(4-R-2-methylinden-1-yl)(4-fluoro-2-methylinden-1-yl)dimethylsilane,
(4-R-2-methylinden-1-yl)(2-methylinden-1-yl)dimethylsilane,
(4-R-2-methylinden-1-yl)(2-isopropylinden-1-yl)dimethylsilane,
(4-R-2-methylinden-1-yl)(inden-1-yl)dimethylsilane,
(4-R-2-methylinden-1-yl)(inden-2-yl)dimethylsilane,
(4-R-2-methylinden-1-yl)(2,4,6-trimethylinden-1-yl)dimethylsilane,
(4-R-2-methylinden-1-yl)(4-phenyl-2-methylinden-1-yl)dimethylsilane,
(4-R-2-methylinden-1-yl)(4-naphthyl-2-methylinden-1-yl)dimethylsilane,
(4-R-2-methylinden-1-yl)[4-(2,5-dimethylphenyl)-2-methylinden-1-yl]dimethylsilane,
(4-R-2-methylinden-1-yl)[4-(3,5-dimethylphenyl)-2-methylinden-1-yl]dimethylsilane,
(4-R-2-methylinden-1-yl)[4-(3,5-diisopropylphenyl)-2-methylinden-1-yl]dimethylsilane,
(4-R-2-methylinden-1-yl)[4-(3,5-di-tert-butylphenyl)-2-methylinden-1-yl]dimethylsilane,
(4-R-2-methylinden-1-yl)[4-(2-thienyl)-2-methylinden-1-yl]dimethylsilane,
(4-R-2-methylinden-1-yl)[4-(4-pyridyl)-2-methylinden-1-yl]dimethylsilane,
(4-R-2-methylinden-1-yl)(4-tert-butyl-2-methylinden-1-yl)dimethylsilane,
(4-R-2-methylinden-1-yl)(4-cyclohexyl-2-methylinden-1-yl)dimethylsilane,
(4-R-2-methylinden-1-yl)(4-isopropyl-2-methylinden-1-yl)dimethylsilane,
(4-R-2-methylinden-1-yl)(4-trimethysilyl-2-methylinden-1-yl)dimethylsilane,
(4-R-2-methylinden-1-yl)(4-trimethylgermyl-2-methylinden-1-yl)dimethylsilane,
(4-R-2-methylinden-1-yl)(4-methylthio-2-methylinden-1-yl)dimethylsilane,
(4-R-2-methylinden-1-yl)(4-diphenylphosphino-2-methylinden-1-yl)dimethylsilane,
(4-R-2-methylinden-1-yl)(4-trifluoromethyl-2-methylinden-1-yl)dimethylsilane,
(4-R-2-methylinden-1-yl)(cyclopentadienyl)dimethylsilane, (4-R-2-methylinden-1-yl)(3-methylcyclopentadien-1-yl)dimethylsilane,
(4-R-2-methylinden-1-yl)(3-tert-butylcyclopentadien-1-yl)dimethylsilane,
(4-R-2-methylinden-1-yl)(3-trimethylsilylcyclopentadien-1-yl)dimethylsilane,
(4-R-2-methylinden-1-yl)(3-phenylcyclopentadien-1-yl)dimethylsilane,
(4-R-2-methylinden-1-yl) [3-(2-thienyl)cyclopentadien-1-yl]dimethylsilane,
(4-R-2-methylinden-1-yl)(3-diphenylphosphinocyclopentadien-1-yl)dimethylsilane,
(4-R-2-methylinden-1-yl)(2,3,4,5-tetramethylcyclopentadien-1-yl)dimethylsilane,
(4-R-2-methylinden-1-yl)(fluoren-9-yl)dimethylsilane,
(4-R-2-methylinden-1-yl)(3,6-dimethylfluoren-9-yl)dimethylsilane,
(4-R-2-methylinden-1-yl)(3,6-di-tert-butylfluoren-9-yl)dimethylsilane,
(4-R-2-methylinden-1-yl)(2,7-di-fluoren-9-yl)dimethylsilane,
(2-methylinden-1-yl)(2,7-di-R-fluoren-9-yl)dimethylsilane,
(2-methyl-4-phenylinden-1-yl)(2,7-di-R-fluoren-9-yl)dimethylsilane,
(2,4-dimethylinden-1-yl)(2,7-di-R-fluoren-9-yl)dimethylsilane,
(2-methyl-4-trimethylsilylinden-1-yl)(2,7-di-R-fluoren-9-yl)dimethylsilane,
(2-methyl-4-tert-butylinden-1-yl)(2,7-di-R-fluoren-9-yl)dimethylsilane,
(2-methyl-4-methoxyinden-1-yl)(2,7-di-R-fluoren-9-yl)dimethylsilane,
(2-methyl-4-dimethylaminoinden-1-yl)(2,7-di-R-fluoren-9-yl)dimethylsilane,
(2-methyl-4-trifluoromethylinden-1-yl)(2,7-di-R-fluoren-9-yl)dimethylsilane,
(cyclopentadienyl)(2,7-di-R-fluoren-9-yl)dimethylsilane,
(3-methylcyclopentadien-1-yl)(2,7-di-R-fluoren-9-yl)dimethylsilane,
(3-tert-butylcyclopentadien-1-yl)(2,7-di-R-fluoren-9-yl)dimethylsilane,
(3-phenylcyclopentadien-1-yl)(2,7-di-R-fluoren-9-yl)dimethylsilane,
(3-trimethylsilylcyclopentadien-1-yl)(2,7-di-R-fluoren-9-yl)dimethylsilane,
(3,4-dimethylcyclopentadien-1-yl)(2,7-di-R-fluoren-9-yl)dimethylsilane,
[3-(2-thienyl)cyclopentadien-1-yl](2,7-di-R-fluoren-9-yl)dimethylsilane,
(fluoren-9-yl)(2,7-di-R-fluoren-9-yl)dimethylsilane,
(3,6-dimethylfluoren-9-yl)(2,7-di-R-fluoren-9-yl)dimethylsilane,
(3,6-ditertbutylfluoren-9-yl)(2,7-di-R-fluoren-9-yl)dimethylsilane,
(3,6-diphenylfluoren-9-yl)(2,7-di-R-fluoren-9-yl)dimethylsilane,
bis(4-R-2-methyl-5,6,7,8-tetrahydrocyclopenta[b]naphth-1-yl)dimethylsilane,
bis(5-R-2-methyl-6,7,8,9-tetrahydrocyclopenta[a]naphth-3-yl)dimethylsilane,
bis(4-R-2-methylcyclopenta[b]naphth-1-yl)dimethylsilane,
bis(7-R-2,4-dimethylcyclopenta[b]naphth-1-yl)dimethylsilane,
bis(8-R-6-methylindeno[5,6-d][1,3]dioxol-5-yl)dimethylsilane,
bis(4-R-2,3,6-trimethylindeno[5,6-b]thien-7-yl)dimethylsilane,
bis(2-R-4,6-dimethylindeno[5,6-b]thien-7-yl)dimethylsilane,
bis(4-R-1,2,3,6-tetramethylcyclopenta[f]indol-7-yl)dimethylsilane,
bis(4-R-1-phenyl-2,3,6-trimethylcyclopenta[/]indol-7-yl)dimethylsilane,
bis(5-R-7-methylcyclopenta[g]quinol-8-yl)dimethylsilane,
bis(2-R-5,7-dimethylcyclopenta[g]quinol-8-yl)dimethylsilane,
(cyclopentadienyl)(4-R-2-methyl-5,6,7,8-tetrahydrocyclopenta[b]naphth-1-yl)dimethylsilane,
(cyclopentadienyl)(5-R-2-methyl-6,7,8,9-tetrahydrocyclopenta[a]naphth-3-yl)dimethylsilane,
(cyclopentadienyl)(4-R-2-methylcyclopenta[b]naphth-1-yl)dimethylsilane,
(cyclopentadienyl)(7-R-2,4-dimethylcyclopenta[b]naphth-1-yl)dimethylsilane,
(cyclopentadienyl)(8-R-6-methylindeno[5,6-d][1,3]dioxol-5-yl)dimethylsilane,
(cyclopentadienyl)(4-R-2,3,6-trimethylindeno[5,6-b]thien-7-yl)dimethylsilane,
(cyclopentadienyl)(2-R-4,6-dimethylindeno[5,6-b]thien-7-yl)dimethylsilane,
(cyclopentadienyl)(4-R-1,2,3,6-tetramethylcyclopenta[/]indol-7-yl)dimethylsilane,
(cyclopentadienyl)(4-R-1-phenyl-2,3,6-trimethylcyclopenta[f]indol-7-yl)dimethylsilane,
(cyclopentadienyl)(5-R-7-methylcyclopenta[g]quinol-8-yl)dimethylsilane,
(cyclopentadienyl)(2-R-5,7-dimethylcyclopenta[g]quinol-8-yl)dimethylsilane,
(inden-1-yl)(4-R-2-methyl-5,6,7,8-tetrahydrocyclopenta[b]naphth-1-yl)dimethylsilane,
(inden-1-yl)(5-R-2-methyl-6,7,8,9-tetrahydrocyclopenta[a]naphth-3-yl)dimethylsilane,
(inden-1-yl)(4-R-2-methylcyclopenta[b]naphth-1-yl)dimethylsilane,
(inden-1-yl)(7-R-2,4-dimethylcyclopenta[b]naphth-1-yl)dimethylsilane,
(inden-1-yl)(8-R-6-methylindeno[5,6-d][1,3]dioxol-5-yl)dimethylsilane,
(inden-1-yl)(4-R-2,3,6-trimethylindeno[5,6-b]thien-7-yl)dimethylsilane,
(inden-1-yl)(2-R-4,6-dimethylindeno[5,6-b]thien-7-yl)dimethylsilane,
(inden-1-yl)(4-R-1,2,3,6-tetramethylcyclopenta[f]indol-7-yl)dimethylsilane,
(inden-1-yl)(4-R-1-phenyl-2,3,6-trimethylcyclopenta[f]indol-7-yl)dimethylsilane,
(inden-1-yl)(5-R-7-methylcyclopenta[g]quinol-8-yl)dimethylsilane,
(inden-1-yl)(2-R-5,7-dimethylcyclopenta[g]quinol-8-yl)dimethylsilane,
(inden-2-yl)(4-R-2-methyl-5,6,7,8-tetrahydrocyclopenta[b]naphth-1-yl)dimethylsilane,
(inden-2-yl)(5-R-2-methyl-6,7,8,9-tetrahydrocyclopenta[a]naphth-3-yl)dimethylsilane,
(inden-2-yl)(4-R-2-methylcyclopenta[b]naphth-1-yl)dimethylsilane,
(inden-2-yl)(7-R-2,4-dimethylcyclopenta[b]naphth-1-yl)dimethylsilane,
(inden-2-yl)(8-R-6-methylindeno[5,6-d][1,3]dioxol-5-yl)dimethylsilane,
(inden-2-yl)(4-R-2,3,6-trimethylindeno[5,6-b]thien-7-yl)dimethylsilane,
(inden-2-yl)(2-R-4,6-dimethylindeno[5,6-b]thien-7-yl)dimethylsilane, (inden-2-yl)(4-R-1,2,3,6-tetramethylcyclopenta[/]indol-7-yl)dimethylsilane,
(inden-2-yl)(4-R-1-phenyl-2,3,6-trimethylcyclopenta[f]indol-7-yl)dimethylsilane,
(inden-2-yl)(5-R-7-methylcyclopenta[g]quinol-8-yl)dimethylsilane,
(inden-2-yl)(2-R-5,7-dimethylcyclopenta[g]quinol-8-yl)dimethylsilane,
(4-R-2-methylinden-1-yl)(4-R-2-methyl-5,6,7,8-tetrahydrocyclopenta[b]naphth-1-yl)dimethylsilane,
(4-R-2-methylinden-1-yl)(5-R-2-methyl-6,7,8,9-tetrahydrocyclopenta[a]naphth-3-yl)dimethylsilane,
(4-R-2-methylinden-1-yl)(4-R-2-methylcyclopenta[b]naphth-1-yl)dimethylsilane,
(4-R-2-methylinden-1-yl)(7-R-2,4-dimethylcyclopenta[b]naphth-1-yl)dimethylsilane,
(4-R-2-methylinden-1-yl)(8-R-6-methylindeno[5,6-d][1,3]dioxol-5-yl)dimethylsilane,
(4-R-2-methylinden-1-yl)(4-R-2,3,6-trimethylindeno[5,6-b]thien-7-yl)dimethylsilane,
(4-R-2-methylinden-1-yl)(2-R-4,6-dimethylindeno[5,6-b]thien-7-yl)dimethylsilane,
(4-R-2-methylinden-1-yl)(4-R-1,2,3,6-tetramethylcyclopenta[f]indol-7-yl)dimethylsilane,
(4-R-2-methylinden-1-yl)(4-R-1-phenyl-2,3,6-trimethylcyclopenta[/]indol-7-yl)dimethylsilane,
(4-R-2-methylinden-1-yl)(5-R-7-methylcyclopenta[g]quinol-8-yl)dimethylsilane,
(4-R-2-methylinden-1-yl)(2-R-5,7-dimethylcyclopenta[g]quinol-8-yl)dimethylsilane,
(fluoren-9-yl)(4-R-2-methyl-5,6,7,8-tetrahydrocyclopenta[b]naphth-1-yl)dimethylsilane,
(fluoren-9-yl)(5-R-2-methyl-6,7,8,9-tetrahydrocyclopenta[a]naphth-3-yl)dimethylsilane,
(fluoren-9-yl)(4-R-2-methylcyclopenta[b]naphth-1-yl)dimethylsilane,
(fluoren-9-yl)(7-R-2,4-dimethylcyclopenta[b]naphth-1-yl)dimethylsilane,
(fluoren-9-yl)(8-R-6-methylindeno[5,6-d][1,3]dioxol-5-yl)dimethylsilane,
(fluoren-9-yl)(4-R-2,3,6-trimethylindeno[5,6-b]thien-7-yl)dimethylsilane,
(fluoren-9-yl)(2-R-4,6-dimethylindeno[5,6-b]thien-7-yl)dimethylsilane,
(fluoren-9-yl)(4-R-1,2,3,6-tetramethylcyclopenta[/]indol-7-yl)dimethylsilane,
(fluoren-9-yl)(4-R-1-phenyl-2,3,6-trimethylcyclopenta[f]indol-7-yl)dimethylsilane,
(fluoren-9-yl)(5-R-7-methylcyclopenta[g]quinol-8-yl)dimethylsilane,
(fluoren-9-yl)(2-R-5,7-dimethylcyclopenta[g]quinol-8-yl)dimethylsilane,
2,2'-bis(4-R-3-dimethylamino-1,3-benzothiaborollideyl)dimethylsilane,
bis(4-R-3a,7a-azaborinden-1-yl)dimethylsilane,
3,3'-bis(7-R-2-dimethylamino-1,2-benzothiaborollide)dimethylsilane,
5,5'-bis(3-R-2-dimethylamino-1,2-thiaborollide)dimethylsilane,
1,2'-(cyclopentadienyl)(4-R-3-dimethylamino-1,3-benzothiaborollide) dimethylsilane,
(cyclopentadienyl)(4-R-3a,7a-azaborinden-1-yl)dimethylsilane,
1,3'-(cyclopentadienyl)(7-R-2-dimethylamino-1,2-benzothiaborollide) dimethylsilane,
1,5'-(cyclopentadienyl)(3-R-2-dimethylamino-1,2-thiaborollide)dimethylsilane,
1,2'-(indenyl)(4-R-3-dimethylamino-1,3-benzothiaborollide)dimethylsilane,
(inden-1-yl)(4-R-3a,7a-azaborinden-1-yl)dimethylsilane,
1,3'-(indenyl)(7-R-2-dimethylamino-1,2-benzothiaborollide)dimethylsilane,
1,5'-(indenyl)(3-R-2-dimethylamino-1,2-thiaborollide)dimethylsilane,
2,2'-(indenyl)(4-R-3-dimethylamino-1,3-benzothiaborollide)dimethylsilane,
(inden-2-yl)(4-R-3a,7a-azaborinden-1-yl)dimethylsilane,
2,3'-(indenyl)(7-R-2-dimethylamino-1,2-benzothiaborollide)dimethylsilane,
2,5'-(indenyl)(3-R-2-dimethylamino-1,2-thiaborollide)dimethylsilane,
9,2'-(fluorenyl)(4-R-3-dimethylamino-1,3-benzothiaborollide)dimethylsilane,
(fluoren-9-yl)(4-R-3a,7a-azaborinden-1-yl)dimethylsilane,
9,3'-(fluorenyl)(7-R-2-dimethylamino-1,2-benzothiaborollide)dimethylsilane,
9,5'-(fluorenyl)(3-R-2-dimethylamino-1,2-thiaborollide) dimethylsilane,
bis(4-R-inden-1-yl)methane,
bis(4-R-inden-2-yl)methane,
(4-R-inden-1-yl)(4-R-inden-2-yl)methane,
bis(4,6-di-R-2-methylinden-1-yl)methane,
bis(4-R-2,6-dimethylinden-1-yl)methane,
bis(4-R-2-methyl-6-isopropylinden-1-yl)methane,
bis(4-R-2-methyl-6-fluoroinden-1-yl)methane,
bis(4-R-2-methyl-6-methoxyinden-1-yl)methane,
bis(4-R-2-methyl-6-dimethylaminoinden-1-yl)methane,
bis(4-R-2-methyl-6-diphenylphosphinoinden-1-yl)methane,
bis(4-R-2-methyl-6-methylsulfoinden-1-yl)methane,
bis(4-R-2-methyl-6-trimethylsilylinden-1-yl)methane,
bis(4-R-2-methyl-6-phenylinden-1-yl)methane,
bis(4-R-2-methyl-6-naphthylinden-1-yl)methane,
bis(4-R-2-methyl-6-N-indolylinden-1-yl)methane,
bis(4-R-2-methyl-6-trifluoromethylinden-1-yl)methane,
bis[4-R-2-methyl-6-(2-thienyl)inden-1-yl]methane,
bis[4-R-2-methyl-6-(4-pyridyl)inden-1-yl]methane,
bis(4-R-2-ethylinden-1-yl)methane,
bis(4-R-2-isopropylinden-1-yl)methane,
bis(4-R-2-phenylinden-1-yl)methane,
(4-R-2-methylinden-1-yl)(4-fluoro-2-methylinden-1-yl)methane,
(4-R-2-methylinden-1-yl)(2-methylinden-1-yl)methane,
(4-R-2-methylinden-1-yl)(2-isopropylinden-1-yl)methane,
(4-R-2-methylinden-1-yl)(inden-1-yl)methane,
(4-R-2-methylinden-1-yl)(inden-2-yl)methane,
(4-R-2-methylinden-1-yl)(2,4,6-trimethylinden-1-yl)methane,
(4-R-2-methylinden-1-yl)(4-phenyl-2-methylinden-1-yl)methane,
(4-R-2-methylinden-1-yl)(4-naphthyl-2-methylinden-1-yl)methane,
(4-R-2-methylinden-1-yl)[4-(2,5-dimethylphenyl)-2-methylinden-1-yl]methane,
(4-R-2-methylinden-1-yl)[4-(3,5-dimethylphenyl)-2-methylinden-1-yl]methane,
(4-R-2-methylinden-1-yl)[4-(3,5-diisopropylphenyl)-2-methylinden-1-yl]methane,
(4-R-2-methylinden-1-yl)[4-(3,5-di-tert-butylphenyl)-2-methylinden-1-yl]methane,
(4-R-2-methylinden-1-yl)[4-(2-thienyl)-2-methylinden-1-yl]methane,
(4-R-2-methylinden-1-yl) [4-(4-pyridyl)-2-methylinden-1-yl]methane, (4-R-2-methylinden-1-yl)(4-tert-butyl-2-methylinden-1-yl)methane,
(4-R-2-methylinden-1-yl)(4-cyclohexyl-2-methylinden-1-yl)methane,
(4-R-2-methylinden-1-yl)(4-isopropyl-2-methylinden-1-yl)methane,
(4-R-2-methylinden-1-yl)(4-trimethysilyl-2-methylinden-1-yl)methane,
(4-R-2-methylinden-1-yl)(4-trimethylgermyl-2-methylinden-1-yl)methane,
(4-R-2-methylinden-1-yl)(4-methylthio-2-methylinden-1-yl)methane,
(4-R-2-methylinden-1-yl)(4-diphenylphosphino-2-methylinden-1-yl)methane,
(4-R-2-methylinden-1-yl)(4-trifluoromethyl-2-methylinden-1-yl)methane,
(4-R-2-methylinden-1-yl)(cyclopentadienyl)methane,
(4-R-2-methylinden-1-yl)(3-methylcyclopentadien-1-yl)methane,
(4-R-2-methylinden-1-yl)(3-tert-butylcyclopentadien-1-yl)methane,
(4-R-2-methylinden-1-yl)(3-trimethylsilylcyclopentadien-1-yl)methane,
(4-R-2-methylinden-1-yl)(3-phenylcyclopentadien-1-yl)methane,
(4-R-2-methylinden-1-yl)[3-(2-thienyl)cyclopentadien-1-yl]methane,
(4-R-2-methylinden-1-yl)(3-diphenylphosphinocyclopentadien-1-yl)methane,
(4-R-2-methylinden-1-yl)(2,3,4,5-tetramethylcyclopentadien-1-yl)methane,
(4-R-2-methylinden-1-yl)(fluoren-9-yl)methane,
(4-R-2-methylinden-1-yl)(3,6-dimethylfluoren-9-yl)methane,
(4-R-2-methylinden-1-yl)(3,6-di-tert-butylfluoren-9-yl)methane,
(4-R-2-methylinden-1-yl)(2,7-di-R-fluoren-9-yl)methane,
(2-methylinden-1-yl)(2,7-di-R-fluoren-9-yl)methane,
(2-methyl-4-phenylinden-1-yl)(2,7-di-R-fluoren-9-yl)methane,
(2,4-dimethylinden-1-yl)(2,7-di-R-fluoren-9-yl)methane,
(2-methyl-4-trimethylsilylinden-1-yl)(2,7-di-R-fluoren-9-yl)methane,
(2-methyl-4-tert-butylinden-1-yl)(2,7-di-R-fluoren-9-yl)methane,
(2-methyl-4-methoxyinden-1-yl)(2,7-di-R-fluoren-9-yl)methane,
(2-methyl-4-dimethylaminoinden-1-yl)(2,7-di-R-fluoren-9-yl)methane,
(2-methyl-4-trifluoromethylinden-1-yl)(2,7-di-R-fluoren-9-yl)methane,
(cyclopentadienyl)(2,7-di-R-fluoren-9-yl)methane,
(3-methylcyclopentadien-1-yl)(2,7-di-R-fluoren-9-yl)methane,
(3-tert-butylcyclopentadien-1-yl)(2,7-di-R-fluoren-9-yl)methane,
(3-phenylcyclopentadien-1-yl)(2,7-di-R-fluoren-9-yl)methane,
(3-trimethylsilylcyclopentadien-1-yl)(2,7-di-R-fluoren-9-yl)methane,
(3,4-dimethylcyclopentadien-1-yl)(2,7-di-R-fluoren-9-yl)methane,
[3-(2-thienyl)cyclopentadien-1-yl] (2,7-di-R-fluoren-9-yl)methane,
(fluoren-9-yl)(2,7-di-R-fluoren-9-yl)methane,
(3,6-dimethylfluoren-9-yl)(2,7-di-R-fluoren-9-yl)methane,
(3,6-ditertbutylfluoren-9-yl)(2,7-di-R-fluoren-9-yl)methane,
(3,6-diphenylfluoren-9-yl)(2,7-di-R-fluoren-9-yl)methane,
bis(4-R-2-methyl-5,6,7,8-tetrahydrocyclopenta[b]naphth-1-yl)methane,
bis(5-R-2-methyl-6,7,8,9-tetrahydrocyclopenta[a]naphth-3-yl)methane,
bis(4-R-2-methylcyclopenta[b]naphth-1-yl)methane,
bis(7-R-2,4-dimethylcyclopenta[b]naphth-1-yl)methane,
bis(8-R-6-methylindeno[5,6-d][1,3]dioxol-5-yl)methane,
bis(4-R-2,3,6-trimethylindeno[5,6-b]thien-7-yl)methane,
bis(2-R-4,6-dimethylindeno[5,6-b]thien-7-yl)methane,
bis(4-R-1,2,3,6-tetramethylcyclopenta[/]indol-7-yl)methane,
bis(4-R-1-phenyl-2,3,6-trimethylcyclopenta[/]indol-7-yl)methane,
bis(5-R-7-methylcyclopenta[g]quinol-8-yl)methane,
bis(2-R-5,7-dimethylcyclopenta[g]quinol-8-yl)methane,
(cyclopentadienyl)(4-R-2-methyl-5,6,7,8-tetrahydrocyclopenta[b]naphth-1-yl)methane,
(cyclopentadienyl)(5-R-2-methyl-6,7,8,9-tetrahydrocyclopenta[a]naphth-3-yl)methane,
(cyclopentadienyl)(4-R-2-methylcyclopenta[b]naphth-1-yl)methane,
(cyclopentadienyl)(7-R-2,4-dimethylcyclopenta[b]naphth-1-yl)methane,
(cyclopentadienyl)(8-R-6-methylindeno[5,6-d][1,3]dioxol-5-yl)methane,
(cyclopentadienyl)(4-R-2,3,6-trimethylindeno[5,6-b]thien-7-yl)methane,
(cyclopentadienyl)(2-R-4,6-dimethylindeno[5,6-b]thien-7-yl)methane,
(cyclopentadienyl)(4-R-1,2,3,6-tetramethylcyclopenta[f])indol-7-yl)methane,
(cyclopentadienyl)(4-R-1-phenyl-2,3,6-trimethylcyclopenta[f]indol-7-yl)methane,
(cyclopentadienyl)(5-R-7-methylcyclopenta[g]quinol-8-yl)methane,
(cyclopentadienyl)(2-R-5,7-dimethylcyclopenta[g]quinol-8-yl)methane,
(inden-1-yl)(4-R-2-methyl-5,6,7,8-tetrahydrocyclopenta[b]naphth-1-yl)methane,
(inden-1-yl)(5-R-2-methyl-6,7,8,9-tetrahydrocyclopenta[a]naphth-3-yl)methane,
(inden-1-yl)(4-R-2-methylcyclopenta[b]naphth-1-yl)methane,
(inden-1-yl)(7-R-2,4-dimethylcyclopenta[b]naphth-1-yl)methane,
(inden-1-yl)(8-R-6-methylindeno[5,6-d][1,3]dioxol-5-yl)methane,
(inden-1-yl)(4-R-2,3,6-trimethylindeno[5,6-b]thien-7-yl)methane,
(inden-1-yl)(2-R-4,6-dimethylindeno[5,6-b]thien-7-yl)methane,
(inden-1-yl)(4-R-1,2,3,6-tetramethylcyclopenta[f]indol-7-yl)methane,
(inden-1-yl)(4-R-1-phenyl-2,3,6-trimethylcyclopenta[f]indol-7-yl)methane,
(inden-2-yl)(4-R-cyclopenta[b]pyrid-7-yl)methane,
(inden-1-yl)(5-R-7-methylcyclopenta[g]quinol-8-yl)methane,
(inden-1-yl)(2-R-5,7-dimethylcyclopenta[g]quinol-8-yl)methane,
(inden-2-yl)(4-R-2-methyl-5,6,7,8-tetrahydrocyclopenta[b]naphth-1-yl)methane,
(inden-2-yl)(5-R-2-methyl-6,7,8,9-tetrahydrocyclopenta[a]naphth-3-yl)methane,
(inden-2-yl)(4-R-2-methylcyclopenta[b]naphth-1-yl)methane, (inden-2-yl)(7-R-2,4-dimethylcyclopenta[b]naphth-1-yl)methane,
(inden-2-yl)(8-R-6-methylindeno[5,6-d][1,3]dioxol-5-yl)methane,
(inden-2-yl)(4-R-2,3,6-trimethylindeno[5,6-b]thien-7-yl)methane,
(inden-2-yl)(2-R-4,6-dimethylindeno[5,6-b]thien-7-yl)methane,
(inden-2-yl)(4-R-1,2,3,6-tetramethylcyclopenta[f]indol-7-yl)methane,
(inden-2-yl)(4-R-1-phenyl-2,3,6-trimethylcyclopenta[/]indol-7-yl)methane,
(inden-2-yl)(5-R-7-methylcyclopenta[g]quinol-8-yl)methane,
(inden-2-yl)(2-R-5,7-dimethylcyclopenta[g]quinol-8-yl)methane,
(4-R-2-methylinden-1-yl)(4-R-2-methyl-5,6,7,8-tetrahydrocyclopenta[b]naphth-1-yl)methane,
(4-R-2-methylinden-1-yl)(5-R-2-methyl-6,7,8,9-tetrahydrocyclopenta[a]naphth-3-yl)methane,
(4-R-2-methylinden-1-yl)(4-R-2-methylcyclopenta[b]naphth-1-yl)methane,
(4-R-2-methylinden-1-yl)(7-R-2,4-dimethylcyclopenta[b]naphth-1-yl)methane,
(4-R-2-methylinden-1-yl)(8-R-6-methylindeno[5,6-d][1,3]dioxol-5-yl)methane,
(4-R-2-methylinden-1-yl)(4-R-2,3,6-trimethylindeno[5,6-b]thien-7-yl)methane,
(4-R-2-methylinden-1-yl)(2-R-4,6-dimethylindeno[5,6-b]thien-7-yl)methane,
(4-R-2-methylinden-1-yl)(4-R-1,2,3,6-tetramethylcyclopenta[/]indol-7-yl)methane,
(4-R-2-methylinden-1-yl)(4-R-1-phenyl-2,3,6-trimethylcyclopenta[/]indol-7-yl)methane,
(4-R-2-methylinden-1-yl)(5-R-7-methylcyclopenta[g]quinol-8-yl)methane,
(4-R-2-methylinden-1-yl)(2-R-5,7-dimethylcyclopenta[g]quinol-8-yl)methane,
(fluoren-9-yl)(4-R-2-methyl-5,6,7,8-tetrahydrocyclopenta[b]naphth-1-yl)methane,
(fluoren-9-yl)(5-R-2-methyl-6,7,8,9-tetrahydrocyclopenta[a]naphth-3-yl)methane,
(fluoren-9-yl)(4-R-2-methylcyclopenta[b]naphth-1-yl)methane,
(fluoren-9-yl)(7-R-2,4-dimethylcyclopenta[b]naphth-1-yl)methane,
(fluoren-9-yl)(8-R-6-methylindeno[5,6-d][1,3]dioxol-5-yl)methane,
(fluoren-9-yl)(4-R-2,3,6-trimethylindeno[5,6-b]thien-7-yl)methane,
(fluoren-9-yl)(2-R-4,6-dimethylindeno[5,6-b]thien-7-yl)methane,
(fluoren-9-yl)(4-R-1,2,3,6-tetramethylcyclopenta[/]indol-7-yl)methane,
(fluoren-9-yl)(4-R-1-phenyl-2,3,6-trimethylcyclopenta[f]indol-7-yl)methane,
(fluoren-9-yl)(4-R-cyclopenta[b]pyrid-7-yl)methane,
(fluoren-9-yl)(5-R-7-methylcyclopenta[g]quinol-8-yl)methane,
(fluoren-9-yl)(2-R-5,7-dimethylcyclopenta[g]quinol-8-yl)methane,
2,2'-bis(4-R-3-dimethylamino-1,3-benzothiaborollide)methane,
bis(4-R-3a,7a-azaborinden-1-yl)methane,
3,3'-bis(7-R-2-dimethylamino-1,2-benzothiaborollide)methane,
5,5'-bis(3-R-2-dimethylamino-1,2-thiaborollide)methane,
1,2'-(cyclopentadienyl)(4-R-3-dimethylamino-1,3-benzothiaborollide)methane,
(cyclopentadienyl)(4-R-3a,7a-azaborinden-1-yl)methane,
1,3'-(cyclopentadienyl)(7-R-2-dimethylamino-1,2-benzothiaborollide)methane,
1,5'-(cyclopentadienyl)(3-R-2-dimethylamino-1,2-thiaborollide)methane,
1,2'-(indenyl)(4-R-3-dimethylamino-1,3-benzothiaborollide)methane,
(inden-1-yl)(4-R-3a,7a-azaborinden-1-yl)methane,
1,3'-(indenyl)(7-R-2-dimethylamino-1,2-benzothiaborollide)methane,
1,5'-(indenyl)(3-R-2-dimethylamino-1,2-thiaborollide)methane,
2,2'-(indenyl)(4-R-3-dimethylamino-1,3-benzothiaborollide)methane,
(inden-2-yl)(4-R-3a,7a-azaborinden-1-yl)methane,
2,3'-(indenyl)(7-R-2-dimethylamino-1,2-benzothiaborollide)methane,
2,5'-(indenyl)(3-R-2-dimethylamino-1,2-thiaborollide)methane,
9,2'-(fluorenyl)(4-R-3-dimethylamino-1,3-benzothiaborollide)methane,
(fluoren-9-yl)(4-R-3a,7a-azaborinden-1-yl)methane,
9,3'-(fluorenyl)(7-R-2-dimethylamino-1,2-benzothiaborollide)methane,
9,5'-(fluorenyl)(3-R-2-dimethylamino-1,2-thiaborollide)methane,
2,2-bis(4-R-inden-1-yl)propane,
2,2-bis(4-R-inden-2-yl)propane,
2,2-(4-R-inden-1-yl)(4-R-inden-2-yl)propane,
2,2-bis(4,6-di-R-2-methylinden-1-yl)propane,
2,2-bis(4-R-2,6-dimethylinden-1-yl)propane,
2,2-bis(4-R-2-methyl-6-isopropylinden-1-yl)propane,
2,2-bis(4-R-2-methyl-6-fluoroinden-1-yl)propane,
2,2-bis(4-R-2-methyl-6-methoxyinden-1-yl)propane,
2,2-bis(4-R-2-methyl-6-dimethylaminoinden-1-yl)propane,
2,2-bis(4-R-2-methyl-6-diphenylphosphinoinden-1-yl)propane,
2,2-bis(4-R-2-methyl-6-methylsulfoinden-1-yl)propane,
2,2-bis(4-R-2-methyl-6-trimethylsilylinden-1-yl)propane,
2,2-bis(4-R-2-methyl-6-phenylinden-1-yl)propane,
2,2-bis(4-R-2-methyl-6-naphthylinden-1-yl)propane,
2,2-bis(4-R-2-methyl-6-N-indolylinden-1-yl)propane,
2,2-bis(4-R-2-methyl-6-trifluoromethylinden-1-yl)propane,
2,2-bis[4-R-2-methyl-6-(2-thienyl)inden-1-yl]propane,
2,2-bis[4-R-2-methyl-6-(4-pyridyl)inden-1-yl]propane,
2,2-bis(4-R-2-ethylinden-1-yl)propane,
2,2-bis(4-R-2-isopropylinden-1-yl)propane,
2,2-bis(4-R-2-phenylinden-1-yl)propane,
2-(4-R-2-methylinden-1-yl)-2-(4-fluoro-2-methylinden-1-yl)propane,
2-(4-R-2-methylinden-1-yl)-2-(2-methylinden-1-yl)propane,
2-(4-R-2-methylinden-1-yl)-2-(2-isopropylinden-1-yl)propane,
2-(4-R-2-methylinden-1-yl)-2-(inden-1-yl)propane,
2-(4-R-2-methylinden-1-yl)-2-(inden-2-yl)propane,
2-(4-R-2-methylinden-1-yl)-2-(2,4,6-trimethylinden-1-yl)propane,
2-(4-R-2-methylinden-1-yl)-2-(4-phenyl-2-methylinden-1-yl)propane,
2-(4-R-2-methylinden-1-yl)-2-(4-naphthyl-2-methylinden-1-yl)propane,
2-(4-R-2-methylinden-1-yl)-2-[4-(2,5-dimethylphenyl)-2-methylinden-1-yl]propane, 2-(4-R-2-methylinden-1-yl)-2-[4-(3,5-dimethylphenyl)-2-methylinden-1-yl]propane,
2-(4-R-2-methylinden-1-yl)-2-[4-(3,5-diisopropylphenyl)-2-methylinden-1-yl]propane,
2-(4-R-2-methylinden-1-yl)-2-[4-(3,5-di-tert-butylphenyl)-2-methylinden-1-yl]propane,
2-(4-R-2-methylinden-1-yl)-2-[4-(2-thienyl)-2-methylinden-1-yl]propane,
2-(4-R-2-methylinden-1-yl)-2-[4-(4-pyridyl)-2-methylinden-1-yl]propane,
2-(4-R-2-methylinden-1-yl)-2-(4-tert-butyl-2-methylinden-1-yl)propane,
2-(4-R-2-methylinden-1-yl)-2-(4-cyclohexyl-2-methylinden-1-yl)propane,
2-(4-R-2-methylinden-1-yl)-2-(4-isopropyl-2-methylinden-1-yl)propane,
2-(4-R-2-methylinden-1-yl)-2-(4-trimethysilyl-2-methylinden-1-yl)propane,
2-(4-R-2-methylinden-1-yl)-2-(4-trimethylgermyl-2-methylinden-1-yl)propane,
2-(4-R-2-methylinden-1-yl)-2-(4-methylthio-2-methylinden-1-yl)propane,
2-(4-R-2-methylinden-1-yl)-2-(4-diphenylphosphino-2-methylinden-1-yl)propane,
2-(4-R-2-methylinden-1-yl)-2-(4-trifluoromethyl-2-methylinden-1-yl)propane,
2-(4-R-2-methylinden-1-yl)-2-(cyclopentadienyl)propane,
2-(4-R-2-methylinden-1-yl)-2-(3-methylcyclopentadien-1-yl)propane,
2-(4-R-2-methylinden-1-yl)-2-(3-tert-butylcyclopentadien-1-yl)propane,
2-(4-R-2-methylinden-1-yl)-2-(3-trimethylsilylcyclopentadien-1-yl)propane,
2-(4-R-2-methylinden-1-yl)-2-(3-phenylcyclopentadien-1-yl)propane,
2-(4-R-2-methylinden-1-yl)-2-[3-(2-thienyl)cyclopentadien-1-yl]propane,
2-(4-R-2-methylinden-1-yl)-2-(3-diphenylphosphinocyclopentadien-1-yl)propane,
2-(4-R-2-methylinden-1-yl)-2-(2,3,4,5-tetramethylcyclopentadien-1-yl)propane,
2-(4-R-2-methylinden-1-yl)-2-(fluoren-9-yl)propane,
2-(4-R-2-methylinden-1-yl)-2-(3,6-dimethylfluoren-9-yl)propane,
2-(4-R-2-methylinden-1-yl)-2-(3,6-di-tert-butylfluoren-9-yl)propane,
2-(4-R-2-methylinden-1-yl)-2-(2,7-di-R-fluoren-9-yl)propane,
2-(2-methylinden-1-yl)-2-(2,7-di-R-fluoren-9-yl)propane,
2-(2-methyl-4-phenylinden-1-yl)-2-(2,7-di-R-fluoren-9-yl)propane,
2-(2,4-dimethylinden-1-yl)-2-(2,7-di-R-fluoren-9-yl)propane,
2-(2-methyl-4-trimethylsilylinden-1-yl)-2-(2,7-di-R-fluoren-9-yl)propane,
2-(2-methyl-4-tert-butylinden-1-yl)-2-(2,7-di-R-fluoren-9-yl)propane,
2-(2-methyl-4-methoxyinden-1-yl)-2-(2,7-di-R-fluoren-9-yl)propane,
2-(2-methyl-4-dimethylaminoinden-1-yl)-2-(2,7-di-R-fluoren-9-yl)propane,
2-(2-methyl-4-trifluoromethylinden-1-yl)-2-(2,7-di-R-fluoren-9-yl)propane,
2-(cyclopentadienyl)-2-(2,7-di-R-fluoren-9-yl)propane,
2-(3-methylcyclopentadien-1-yl)-2-(2,7-di-R-fluoren-9-yl)propane,
2-(3-tert-butylcyclopentadien-1-yl)-2-(2,7-di-R-fluoren-9-yl)propane,
2-(3-phenylcyclopentadien-1-yl)-2-(2,7-di-R-fluoren-9-yl)propane,
2-(3-trimethylsilylcyclopentadien-1-yl)-2-(2,7-di-R-fluoren-9-yl)propane,
2-(3,4-dimethylcyclopentadien-1-yl)-2-(2,7-di-R-fluoren-9-yl)propane,
2-[3-(2-thienyl)cyclopentadien-1-yl]-2-(2,7-di-R-fluoren-9-yl)propane,
2-(fluoren-9-yl)-2-(2,7-di-R-fluoren-9-yl)propane,
2-(3,6-dimethylfluoren-9-yl)-2-(2,7-di-R-fluoren-9-yl)propane,
2-(3,6-ditertbutylfluoren-9-yl)-2-(2,7-di-R-fluoren-9-yl)propane,
2-(3,6-diphenylfluoren-9-yl)-2-(2,7-di-R-fluoren-9-yl)propane,
2,2-bis(4-R-2-methyl-5,6,7,8-tetrahydrocyclopenta[b]naphth-1-yl)propane,
2,2-bis(5-R-2-methyl-6,7,8,9-tetrahydrocyclopenta[a]naphth-3-yl)propane,
2,2-bis(4-R-2-methylcyclopenta[b]naphth-1-yl)propane,
2,2-bis(7-R-2,4-dimethylcyclopenta[b]naphth-1-yl)propane,
2,2-bis(8-R-6-methylindeno[5,6-d][1,3]dioxol-5-yl)propane,
2,2-bis(4-R-2,3,6-trimethylindeno[5,6-b]thien-7-yl)propane,
2,2-bis(2-R-4,6-dimethylindeno[5,6-b]thien-7-yl)propane,
2,2-bis(4-R-1,2,3,6-tetramethylcyclopenta[/]indol-7-yl)propane,
2,2-bis(4-R-1-phenyl-2,3,6-trimethylcyclopenta[/]indol-7-yl)propane,
2,2-bis(5-R-7-methylcyclopenta[g]quinol-8-yl)propane,
2,2-bis(2-R-5,7-dimethylcyclopenta[g]quinol-8-yl)propane,
2-(cyclopentadienyl)-2-(4-R-2-methyl-5,6,7,8-tetrahydrocyclopenta[b]naphth-1-yl)propane,
2-(cyclopentadienyl)-2-(5-R-2-methyl-6,7,8,9-tetrahydrocyclopenta[a]naphth-3-yl)propane,
2-(cyclopentadienyl)-2-(4-R-2-methylcyclopenta[b]naphth-1-yl)propane,
2-(cyclopentadienyl)-2-(7-R-2,4-dimethylcyclopenta[b]naphth-1-yl)propane,
2-(cyclopentadienyl)-2-(8-R-6-methylindeno[5,6-d][1,3]dioxol-5-yl)propane,
2-(cyclopentadienyl)-2-(4-R-2,3,6-trimethylindeno[5,6-b]thien-7-yl)propane,
2-(cyclopentadienyl)-2-(2-R-4,6-dimethylindeno[5,6-b]thien-7-yl)propane,
2-(cyclopentadienyl)-2-(4-R-1,2,3,6-tetramethylcyclopenta[/]indol-7-yl)propane,
2-(cyclopentadienyl)-2-(4-R-1-phenyl-2,3,6-trimethylcyclopenta[f]indol-7-yl)propane,
2-(cyclopentadienyl)-2-(4-R-cyclopenta[b]pyrid-7-yl)propane,
2-(cyclopentadienyl)-2-(5-R-7-methylcyclopenta[g]quinol-8-yl)propane,
2-(cyclopentadienyl)-2-(2-R-5,7-dimethylcyclopenta[g]quinol-8-yl)propane,
2-(inden-1-yl)-2-(4-R-2-methyl-5,6,7,8-tetrahydrocyclopenta[b]naphth-1-yl)propane,
2-(inden-1-yl)-2-(5-R-2-methyl-6,7,8,9-tetrahydrocyclopenta[a]naphth-3-yl)propane,
2-(inden-1-yl)-2-(4-R-2-methylcyclopenta[b]naphth-1-yl)propane,
2-(inden-1-yl)-2-(7-R-2,4-dimethylcyclopenta[b]naphth-1-yl)propane, 2-(inden-1-yl)-2-(8-R-6-methylindeno[5,6-d][1,3]dioxol-5-yl)propane,
2-(inden-1-yl)-2-(4-R-2,3,6-trimethylindeno[5,6-b]thien-7-yl)propane,
2-(inden-1-yl)-2-(2-R-4,6-dimethylindeno[5,6-b]thien-7-yl)propane,
2-(inden-1-yl)-2-(4-R-1,2,3,6-tetramethylcyclopenta[/]indol-7-yl)propane,
2-(inden-1-yl)-2-(4-R-1-phenyl-2,3,6-trimethylcyclopenta[/]indol-7-yl)propane,
2-(inden-1-yl)-2-(5-R-7-methylcyclopenta[g]quinol-8-yl)propane,
2-(inden-1-yl)-2-(2-R-5,7-dimethylcyclopenta[g]quinol-8-yl)propane,
2-(inden-2-yl)-2-(4-R-2-methyl-5,6,7,8-tetrahydrocyclopenta[b]naphth-1-yl)propane,
2-(inden-2-yl)-2-(5-R-2-methyl-6,7,8,9-tetrahydrocyclopenta[a]naphth-3-yl)propane,
2-(inden-2-yl)-2-(4-R-2-methylcyclopenta[b]naphth-1-yl)propane,
2-(inden-2-yl)-2-(7-R-2,4-dimethylcyclopenta[b]naphth-1-yl)propane,
2-(inden-2-yl)-2-(8-R-6-methylindeno[5,6-d][1,3]dioxol-5-yl)propane,
2-(inden-2-yl)-2-(4-R-2,3,6-trimethylindeno[5,6-b]thien-7-yl)propane,
2-(inden-2-yl)-2-(2-R-4,6-dimethylindeno[5,6-b]thien-7-yl)propane,
2-(inden-2-yl)-2-(4-R-1,2,3,6-tetramethylcyclopenta[/]indol-7-yl)propane,
2-(inden-2-yl)-2-(4-R-1-phenyl-2,3,6-trimethylcyclopenta[f]indol-7-yl)propane,
2-(inden-2-yl)-2-(5-R-7-methylcyclopenta[g]quinol-8-yl)propane,
2-(inden-2-yl)-2-(2-R-5,7-dimethylcyclopenta[g]quinol-8-yl)propane,
2-(4-R-2-methylinden-1-yl)-2-(4-R-2-methyl-5,6,7,8-tetrahydrocyclopenta[b]naphth-1-yl)propane,
2-(4-R-2-methylinden-1-yl)-2-(5-R-2-methyl-6,7,8,9-tetrahydrocyclopenta[a]naphth-3-yl)propane,
2-(4-R-2-methylinden-1-yl)-2-(4-R-2-methylcyclopenta[b]naphth-1-yl)propane,
2-(4-R-2-methylinden-1-yl)-2-(7-R-2,4-dimethylcyclopenta[b]naphth-1-yl)propane,
2-(4-R-2-methylinden-1-yl)-2-(8-R-6-methylindeno[5,6-d][1,3]dioxol-5-yl)propane,
2-(4-R-2-methylinden-1-yl)-2-(4-R-2,3,6-trimethylindeno[5,6-b]thien-7-yl)propane,
2-(4-R-2-methylinden-1-yl)-2-(2-R-4,6-dimethylindeno[5,6-b]thien-7-yl)propane,
2-(4-R-2-methylinden-1-yl)-2-(4-R-1,2,3,6-tetramethylcyclopenta[/]indol-7-yl)propane,
2-(4-R-2-methylinden-1-yl)-2-(4-R-1-phenyl-2,3,6-trimethylcyclopenta[f]indol-7-yl)propane,
2-(4-R-2-methylinden-1-yl)-2-(4-R-cyclopenta[b]pyrid-7-yl)propane,
2-(4-R-2-methylinden-1-yl)-2-(5-R-7-methylcyclopenta[g]quinol-8-yl)propane,
2-(4-R-2-methylinden-1-yl)-2-(2-R-5,7-dimethylcyclopenta[g]quinol-8-yl)propane,
2-(fluoren-9-yl)-2-(4-R-2-methyl-5,6,7,8-tetrahydrocyclopenta[b]naphth-1-yl)propane,
2-(fluoren-9-yl)-2-(5-R-2-methyl-6,7,8,9-tetrahydrocyclopenta[a]naphth-3-yl)propane,
2-(fluoren-9-yl)-2-(4-R-2-methylcyclopenta[b]naphth-1-yl)propane,
2-(fluoren-9-yl)-2-(7-R-2,4-dimethylcyclopenta[b]naphth-1-yl)propane,
2-(fluoren-9-yl)-2-(8-R-6-methylindeno[5,6-d][1,3]dioxol-5-yl)propane,
2-(fluoren-9-yl)-2-(4-R-2,3,6-trimethylindeno[5,6-b]thien-7-yl)propane,
2-(fluoren-9-yl)-2-(2-R-4,6-dimethylindeno[5,6-b]thien-7-yl)propane,
2-(fluoren-9-yl)-2-(4-R-1,2,3,6-tetramethylcyclopenta[f]indol-7-yl)propane,
2-(fluoren-9-yl)-2-(4-R-1-phenyl-2,3,6-trimethylcyclopenta[f]indol-7-yl)propane,
2-(fluoren-9-yl)-2-(5-R-7-methylcyclopenta[g]quinol-8-yl)propane,
2-(fluoren-9-yl)-2-(2-R-5,7-dimethylcyclopenta[g]quinol-8-yl)propane,
1,2-bis(4-R-inden-1-yl)ethane,
1,2-bis(4-R-inden-2-yl)ethane,
1,2-(4-R-inden-1-yl)(4-R-inden-2-yl)ethane,
1,2-bis(4,6-di-R-2-methylinden-1-yl)ethane,
1,2-bis(4-R-2,6-dimethylinden-1-yl)ethane,
1,2-bis(4-R-2-methyl-6-isopropylinden-1-yl)ethane,
1,2-bis(4-R-2-methyl-6-fluoroinden-1-yl)ethane,
1,2-bis(4-R-2-methyl-6-methoxyinden-1-yl)ethane,
1,2-bis(4-R-2-methyl-6-dimethylaminoinden-1-yl)ethane,
1,2-bis(4-R-2-methyl-6-diphenylphosphinoinden-1-yl)ethane,
1,2-bis(4-R-2-methyl-6-methylsulfoinden-1-yl)ethane,
1,2-bis(4-R-2-methyl-6-trimethylsilylinden-1-yl)ethane,
1,2-bis(4-R-2-methyl-6-phenylinden-1-yl)ethane,
1,2-bis(4-R-2-methyl-6-naphthylinden-1-yl)ethane,
1,2-bis(4-R-2-methyl-6-N-indolylinden-1-yl)ethane,
1,2-bis(4-R-2-methyl-6-trifluoromethylinden-1-yl)ethane,
1,2-bis[4-R-2-methyl-6-(2-thienyl)inden-1-yl]ethane,
1,2-bis[4-R-2-methyl-6-(4-pyridyl)inden-1-yl]ethane,
1,2-bis(4-R-2-ethylinden-1-yl)ethane,
1,2-bis(4-R-2-isopropylinden-1-yl)ethane,
1,2-bis(4-R-2-phenylinden-1-yl)ethane,
1-(4-R-2-methylinden-1-yl)-2-(4-fluoro-2-methylinden-1-yl)ethane,
1-(4-R-2-methylinden-1-yl)-2-(2-methylinden-1-yl)ethane,
1-(4-R-2-methylinden-1-yl)-2-(2-isopropylinden-1-yl)ethane,
1-(4-R-2-methylinden-1-yl)-2-(inden-1-yl)ethane,
1-(4-R-2-methylinden-1-yl)-2-(inden-2-yl)ethane,
1-(4-R-2-methylinden-1-yl)-2-(2,4,6-trimethylinden-1-yl)ethane,
1-(4-R-2-methylinden-1-yl)-2-(4-phenyl-2-methylinden-1-yl)ethane,
1-(4-R-2-methylinden-1-yl)-2-(4-naphthyl-2-methylinden-1-yl)ethane,
1-(4-R-2-methylinden-1-yl)-2-[4-(2,5-dimethylphenyl)-2-methylinden-1-yl]ethane,
1-(4-R-2-methylinden-1-yl)-2-[4-(3,5-dimethylphenyl)-2-methylinden-1-yl]ethane,
1-(4-R-2-methylinden-1-yl)-2-[4-(3,5-diisopropylphenyl)-2-methylinden-1-yl]ethane,
1-(4-R-2-methylinden-1-yl)-2-[4-(3,5-di-tert-butylphenyl)-2-methylinden-1-yl]ethane,
1-(4-R-2-methylinden-1-yl)-2-[4-(2-thienyl)-2-methylinden-1-yl]ethane,
1-(4-R-2-methylinden-1-yl)-2-[4-(4-pyridyl)-2-methylinden-1-yl]ethane,
1-(4-R-2-methylinden-1-yl)-2-(4-tert-butyl-2-methylinden-1-yl)ethane,
1-(4-R-2-methylinden-1-yl)-2-(4-cyclohexyl-2-methylinden-1-yl)ethane, 1-(4-R-2-methylinden-1-yl)-2-(4-isopropyl-2-methylinden-1-yl)ethane,
1-(4-R-2-methylinden-1-yl)-2-(4-trimethysilyl-2-methylinden-1-yl)ethane,
1-(4-R-2-methylinden-1-yl)-2-(4-trimethylgermyl-2-methylinden-1-yl)ethane,
1-(4-R-2-methylinden-1-yl)-2-(4-methylthio-2-methylinden-1-yl)ethane,
1-(4-R-2-methylinden-1-yl)-2-(4-diphenylphosphino-2-methylinden-1-yl)ethane,
1-(4-R-2-methylinden-1-yl)-2-(4-trifluoromethyl-2-methylinden-1-yl)ethane,
1-(4-R-2-methylinden-1-yl)-2-(cyclopentadienyl)ethane,
1-(4-R-2-methylinden-1-yl)-2-(3-methylcyclopentadien-1-yl)ethane,
1-(4-R-2-methylinden-1-yl)-2-(3-tert-butylcyclopentadien-1-yl)ethane,
1-(4-R-2-methylinden-1-yl)-2-(3-trimethylsilylcyclopentadien-1-yl)ethane,
1-(4-R-2-methylinden-1-yl)-2-(3-phenylcyclopentadien-1-yl)ethane,
1-(4-R-2-methylinden-1-yl)-2-[3-(2-thienyl)cyclopentadien-1-yl]ethane,
1-(4-R-2-methylinden-1-yl)-2-(3-diphenylphosphinocyclopentadien-1-yl)ethane,
1-(4-R-2-methylinden-1-yl)-2-(2,3,4,5-tetramethylcyclopentadien-1-yl)ethane,
1-(4-R-2-methylinden-1-yl)-2-(fluoren-9-yl)ethane,
1-(4-R-2-methylinden-1-yl)-2-(3,6-dimethylfluoren-9-yl)ethane,
1-(4-R-2-methylinden-1-yl)-2-(3,6-di-tert-butylfluoren-9-yl)ethane,
1-(4-R-2-methylinden-1-yl)-2-(2,7-di-R-fluoren-9-yl)ethane,
1-(2-methylinden-1-yl)-2-(2,7-di-R-fluoren-9-yl)ethane,
1-(2-methyl-4-phenylinden-1-yl)-2-(2,7-di-R-fluoren-9-yl)ethane,
1-(2,4-dimethylinden-1-yl)-2-(2,7-di-R-fluoren-9-yl)ethane,
1-(2-methyl-4-trimethylsilylinden-1-yl)-2-(2,7-di-R-fluoren-9-yl)ethane,
1-(2-methyl-4-tert-butylinden-1-yl)-2-(2,7-di-R-fluoren-9-yl)ethane,
1-(2-methyl-4-methoxyinden-1-yl)-2-(2,7-di-R-fluoren-9-yl)ethane,
1-(2-methyl-4-dimethylaminoinden-1-yl)-2-(2,7-di-R-fluoren-9-yl)ethane,
1-(2-methyl-4-trifluoromethylinden-1-yl)-2-(2,7-di-R-fluoren-9-yl)ethane,
1-(cyclopentadienyl)-2-(2,7-di-R-fluoren-9-yl)ethane,
1-(3-methylcyclopentadien-1-yl)-2-(2,7-di-R-fluoren-9-yl)ethane,
1-(3-tert-butylcyclopentadien-1-yl)-2-(2,7-di-R-fluoren-9-yl)ethane,
1-(3-phenylcyclopentadien-1-yl)-2-(2,7-di-R-fluoren-9-yl)ethane,
1-(3-trimethylsilylcyclopentadien-1-yl)-2-(2,7-di-R-fluoren-9-yl)ethane,
1-(3,4-dimethylcyclopentadien-1-yl)-2-(2,7-di-R-fluoren-9-yl)ethane,
1-[3-(2-thienyl)cyclopentadien-1-yl]-2-(2,7-di-R-fluoren-9-yl)ethane,
1-(fluoren-9-yl)-2-(2,7-di-R-fluoren-9-yl)ethane,
1-(3,6-dimethylfluoren-9-yl)-2-(2,7-di-R-fluoren-9-yl)ethane,
1-(3,6-ditertbutylfluoren-9-yl)-2-(2,7-di-R-fluoren-9-yl)ethane,
1-(3,6-diphenylfluoren-9-yl)-2-(2,7-di-R-fluoren-9-yl)ethane,
1,2-bis(4-R-2-methyl-5,6,7,8-tetrahydrocyclopenta[b]naphth-1-yl)ethane,
1,2-bis(5-R-2-methyl-6,7,8,9-tetrahydrocyclopenta[a]naphth-3-yl)ethane,
1,2-bis(4-R-2-methylcyclopenta[b]naphth-1-yl)ethane,
1,2-bis(7-R-2,4-dimethylcyclopenta[b]naphth-1-yl)ethane,
1,2-bis(8-R-6-methylindeno[5,6-d][1,3]dioxol-5-yl)ethane,
1,2-bis(4-R-2,3,6-trimethylindeno[5,6-b]thien-7-yl)ethane,
1,2-bis(2-R-4,6-dimethylindeno[5,6-b]thien-7-yl)ethane,
1,2-bis(4-R-1,2,3,6-tetramethylcyclopenta[f]indol-7-yl)ethane,
1,2-bis(4-R-1-phenyl-2,3,6-trimethylcyclopenta[/]indol-7-yl)ethane,
1,2-bis(5-R-7-methylcyclopenta[g]quinol-8-yl)ethane,
1,2-bis(2-R-5,7-dimethylcyclopenta[g]quinol-8-yl)ethane,
1-(cyclopentadienyl)-2-(4-R-2-methyl-5,6,7,8-tetrahydrocyclopenta[b]naphth-1-yl)ethane,
1-(cyclopentadienyl)-2-(5-R-2-methyl-6,7,8,9-tetrahydrocyclopenta[a]naphth-3-yl)ethane,
1-(cyclopentadienyl)-2-(4-R-2-methylcyclopenta[b]naphth-1-yl)ethane,
1-(cyclopentadienyl)-2-(7-R-2,4-dimethylcyclopenta[b]naphth-1-yl)ethane,
1-(cyclopentadienyl)-2-(8-R-6-methylindeno[5,6-d][1,3]dioxol-5-yl)ethane,
1-(cyclopentadienyl)-2-(4-R-2,3,6-trimethylindeno[5,6-b]thien-7-yl)ethane,
1-(cyclopentadienyl)-2-(2-R-4,6-dimethylindeno[5,6-b]thien-7-yl)ethane,
1-(cyclopentadienyl)-2-(4-R-1,2,3,6-tetramethylcyclopenta[f]indol-7-yl)ethane,
1-(cyclopentadienyl)-2-(4-R-1-phenyl-2,3,6-trimethylcyclopenta[f]indol-7-yl)ethane,
1-(cyclopentadienyl)-2-(5-R-7-methylcyclopenta[g]quinol-8-yl)ethane,
1-(cyclopentadienyl)-2-(2-R-5,7-dimethylcyclopenta[g]quinol-8-yl)ethane,
1-(inden-1-yl)-2-(4-R-2-methyl-5,6,7,8-tetrahydrocyclopenta[b]naphth-1-yl)ethane,
1-(inden-1-yl)-2-(5-R-2-methyl-6,7,8,9-tetrahydrocyclopenta[a]naphth-3-yl)ethane,
1-(inden-1-yl)-2-(4-R-2-methylcyclopenta[b]naphth-1-yl)ethane,
1-(inden-1-yl)-2-(7-R-2,4-dimethylcyclopenta[b]naphth-1-yl)ethane,
1-(inden-1-yl)-2-(8-R-6-methylindeno[5,6-d][1,3]dioxol-5-yl)ethane,
1-(inden-1-yl)-2-(4-R-2,3,6-trimethylindeno[5,6-b]thien-7-yl)ethane,
1-(inden-1-yl)-2-(2-R-4,6-dimethylindeno[5,6-b]thien-7-yl)ethane,
1-(inden-1-yl)-2-(4-R-1,2,3,6-tetramethylcyclopenta[/]indol-7-yl)ethane,
1-(inden-1-yl)-2-(4-R-1-phenyl-2,3,6-trimethylcyclopenta[f]indol-7-yl)ethane,
1-(inden-1-yl)-2-(5-R-7-methylcyclopenta[g]quinol-8-yl)ethane,
1-(inden-1-yl)-2-(2-R-5,7-dimethylcyclopenta[g]quinol-8-yl)ethane,
1-(inden-2-yl)-2-(4-R-2-methyl-5,6,7,8-tetrahydrocyclopenta[b]naphth-1-yl)ethane,
1-(inden-2-yl)-2-(5-R-2-methyl-6,7,8,9-tetrahydrocyclopenta[a]naphth-3-yl)ethane,
1-(inden-2-yl)-2-(4-R-2-methylcyclopenta[b]naphth-1-yl)ethane, 1-(inden-2-yl)-2-(7-R—R-2,4-dimethylcyclopenta[b]
naphth-1-yl)ethane,
1-(inden-2-yl)-2-(8-R-6-methylindeno[5,6-d][1,3]dioxol-5-
yl)ethane,
1-(inden-2-yl)-2-(4-R-2,3,6-trimethylindeno[5,6-b]thien-7-
yl)ethane,
1-(inden-2-yl)-2-(2-R-4,6-dimethylindeno[5,6-b]thien-7-yl)
ethane,
1-(inden-2-yl)-2-(4-R-1,2,3,6-tetramethylcyclopenta[f]in-
dol-7-yl)ethane,
1-(inden-2-yl)-2-(4-R-1-phenyl-2,3,6-trimethylcyclo-
penta[/]indol-7-yl)ethane,
1-(inden-2-yl)-2-(5-R-7-methylcyclopenta[g]quinol-8-yl)
ethane,
1-(inden-2-yl)-2-(2-R-5,7-dimethylcyclopenta[g]quinol-8-
yl)ethane,
1-(4-R-2-methylinden-1-yl)-2-(4-R-2-methyl-5,6,7,8-tet-
rahydrocyclopenta[b]naphth-1-yl)ethane,
1-(4-R-2-methylinden-1-yl)-2-(5-R-2-methyl-6,7,8,9-tet-
rahydrocyclopenta[a]naphth-3-yl)ethane,
1-(4-R-2-methylinden-1-yl)-2-(4-R-2-methylcyclopenta[b]
naphth-1-yl)ethane,
1-(4-R-2-methylinden-1-yl)-2-(7-R-2,4-dimethylcyclopenta
[b]naphth-1-yl)ethane,
1-(4-R-2-methylinden-1-yl)-2-(8-R-6-methylindeno[5,6-d]
[1,3]dioxol-5-yl)ethane,
1-(4-R-2-methylinden-1-yl)-2-(4-R-2,3,6-trimethylindeno
[5,6-b]thien-7-yl)ethane,
1-(4-R-2-methylinden-1-yl)-2-(2-R-4,6-dimethylindeno[5,
6-b]thien-7-yl)ethane,
1-(4-R-2-methylinden-1-yl)-2-(4-R-1,2,3,6-tetramethylcy-
clopenta[/]indol-7-yl)ethane,
1-(4-R-2-methylinden-1-yl)-2-(4-R-1-phenyl-2,3,6-trimeth-
ylcyclopenta[/]indol-7-yl)ethane,
1-(4-R-2-methylinden-1-yl)-2-(5-R-7-methylcyclopenta[g]
quinol-8-yl)ethane,
1-(4-R-2-methylinden-1-yl)-2-(2-R-5,7-dimethylcyclopenta
[g]quinol-8-yl)ethane,
1-(fluoren-9-yl)-2-(4-R-2-methyl-5,6,7,8-tetrahydrocyclo-
penta[b]naphth-1-yl)ethane,
1-(fluoren-9-yl)-2-(5-R-2-methyl-6,7,8,9-tetrahydrocyclo-
penta[a]naphth-3-yl)ethane,
1-(fluoren-9-yl)-2-(4-R-2-methylcyclopenta[b]naphth-1-yl)
ethane,
1-(fluoren-9-yl)-2-(7-R-2,4-dimethylcyclopenta[b]naphth-
1-yl)ethane,
1-(fluoren-9-yl)-2-(8-R-6-methylindeno[5,6-d][1,3]dioxol-
5-yl)ethane,
1-(fluoren-9-yl)-2-(4-R-2,3,6-trimethylindeno[5,6-b]thien-
7-yl)ethane,
1-(fluoren-9-yl)-2-(2-R-4,6-dimethylindeno[5,6-b]thien-7-
yl)ethane,
1-(fluoren-9-yl)-2-(4-R-1,2,3,6-tetramethylcyclopenta[/]in-
dol-7-yl)ethane,
1-(fluoren-9-yl)-2-(4-R-1-phenyl-2,3,6-trimethylcyclo-
penta[/]indol-7-yl)ethane,
1-(fluoren-9-yl)-2-(4-R-cyclopenta[b]pyrid-7-yl)ethane,
1-(fluoren-9-yl)-2-(5-R-7-methylcyclopenta[g]quinol-8-yl)
ethane,
1-(fluoren-9-yl)-2-(2-R-5,7-dimethylcyclopenta[g]quinol-8-
yl)ethane,
1,2-bis[2-(4-R-3-dimethylamino-1,3-benzothiaborollide)]
ethane,
1,2-bis(4-R-3a,7a-azaborinden-1-yl)ethane,
1,2-bis[3-(7-R-2-dimethylamino-1,2-benzothiaborollide)]
ethane,
1,2-bis[5-(3-R-2-dimethylamino-1,2-thiaborollide)]ethane, 1-(cyclopentadienyl)-2-[2-(4-R-3-dimethylamino-1,3-ben-
zothiaborollide)]ethane,
1-(cyclopentadienyl)-2-(4-R-3a,7a-azaborinden-1-yl)
ethane,
1-(cyclopentadienyl)-2-[3-(7-R-2-dimethylamino-1,2-ben-
zothiaborollide)]ethane,
1-(cyclopentadienyl)-2-[5-(3-R-2-dimethylamino-1,2-thi-
aborollide)]ethane,
1-(inden-1-yl)-2-[2-(4-R-3-dimethylamino-1,3-benzothi-
aborollide)]ethane,
1-(inden-1-yl)-2-(4-R-3a,7a-azaborinden-1-yl)ethane,
1-(inden-1-yl)-2-[3-(7-R-2-dimethylamino-1,2-benzothi-
aborollide)]ethane,
1-(inden-1-yl)-2-[5-(3-R-2-dimethylamino-1,2-thiaborol-
lide)]ethane,
1-(inden-2-yl)-2-[2-(4-R-3-dimethylamino-1,3-benzothi-
aborollide)]ethane,
1-(inden-2-yl)-2-(4-R-3a,7a-azaborinden-1-yl)ethane,
1-(inden-2-yl)-2-[3-(7-R-2-dimethylamino-1,2-benzothi-
aborollide)]ethane,
1-(inden-2-yl)-2-[5-(3-R-2-dimethylamino-1,2-thiaborol-
lide)]ethane,
1-(fluoren-9-yl)-2-[2-(4-R-3-dimethylamino-1,3-benzothi-
aborollide)]ethane,
1-(fluoren-9-yl)-2-(4-R-3a,7a-azaborinden-1-yl)ethane,
1-(fluoren-9-yl)-2-[3-(7-R-2-dimethylamino-1,2-benzothi-
aborollide)]ethane, and
1-(fluoren-9-yl)-2-[5-(3-R-2-dimethylamino-1,2-thiaborol-
lide)]ethane.

Chelating ligands of the formula (II) that are substituted with hydrocarbyl, substituted hydrocarbyl, halocarbyl, or substituted halocarbyl groups in the six-membered ring of indenyl, heteroindenyl or related fluorenyl fragments, or in the five-membered heterocyclic ring of heterocyclopentalenyls, heterocyclopentapentalenyls, or related polycyclic fragments, can be obtained in high yields and/or high purity by the process of the present invention. A particular advantage of the present invention is that readily obtainable and inexpensive compounds of the formula (I) bearing chloroindenyl, bromoindenyl, chlorocyclopenta[b]thienyl, bromocyclopenta[b]thienyl fragments can be used as starting material, thus avoiding the necessity, as in the prior art, of first synthesizing the corresponding substituted indenes to then obtain the desired bridging ligands containing the respective hydrocarbyl, substituted hydrocarbyl, halocarbyl, or substituted halocarbyl substituted indenes and cyclopenta[b]thiophenes. The latter pathway is more time-consuming when the goal is to synthesize libraries of hydrocarbyl, substituted hydrocarbyl, halocarbyl, or substituted halocarbyl substituted bridging ligands of importance for the subsequent synthesis of metallocenes and related organometallic complexes.

The substituted chelating ligands of the formula (II) prepared according to the present invention can be used in all known applications of the chelating ligands, for example as intermediates for the preparation of transition metal complexes of importance for material chemistry, pharmacy, fine chemicals, organic light-emitting diodes (OLEDs), catalysis and the like.

The substituted chelating ligands of the formula (II) prepared according to the present invention can be advantageously used for the synthesis of metallocene complexes which are suitable for the polymerization of olefins, in particular α-olefins. These substituted chelating ligands of the formula (II) are preferably used for the synthesis of chiral ansa-bisindenyl metallocenes and related complexes.

The ansa-bisindenyl metallocenes and related complexes of the present invention contain a metal of Groups 4, 5 or 6, in particular Group 4, of the Periodic Table of the Elements, i.e. titanium, zirconium or hafnium. The metal is preferably zirconium or hafnium, most preferably zirconium.

The preparation of such ansa-metallocene complexes using the chelating ligands prepared according to the present invention or the chelating ligands of the present invention is carried out by known, customary synthetic methods, for example by the reaction of the chelating ligand (after deprotonation) with suitable transition metal chlorides, for example zirconium tetrachloride or the like. Such synthetic routes are known from the prior art (WO 01/48034).

In another embodiment this invention relates to:

1. A process for preparing a chelating ligand of the formula (II) from a chelating ligand of the formula (I) via an sp$^2$-sp$^2$ or sp$^2$-sp$^3$ coupling reaction comprising contacting, optionally in the presence of a coupling catalyst, a chelating ligand of the formula (I) with an organometallic compound of the formula (II):

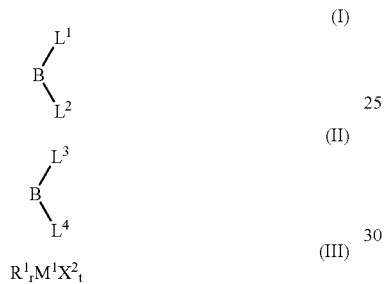

wherein
B is a bridging group that is bonded to L$^1$ and L$^2$ in formula (I) and to L$^3$ and L$^4$ in formula (II);
L$^1$ is a substituted monocyclic or polycyclic ligand that comprises at least one chlorine, bromine, iodine, or sulfonate substituent, directly bonded to an sp$^2$ carbon atom of the ring structure of the ligand;
L$^2$ is a monoanionic ligand; or L$^2$ may, independently, be defined as L$^1$;
L$^3$ is the same group as L$^1$, but said at least one chlorine, bromine, iodine, or sulfonate substituent is replaced with a hydrocarbyl, substituted hydrocarbyl, halocarbyl, or substituted halocarbyl fragment;
L$^4$ is the same group as L$^2$, though, when L$^2$ is defined as L$^1$, L$^4$ may be the same as L$^3$ or L$^1$;
R$^1$ is a hydrocarbyl, substituted hydrocarbyl, halocarbyl, or substituted halocarbyl;
M$^1$ is an element of group 1, 2, 12, 13 or 14 of the Periodic Table of the Elements; each X$^2$, if present, is selected independently from the group consisting of halogen atoms, the hydroxyl group, alkoxy groups, aryloxy groups, mesylate, tosylate and triflate;
r is 1, 2 or 3, and
t is 0, 1 or 2, where r+t corresponds to the oxidation number of M$^1$.

2. The process of paragraph 1 wherein L$^1$ comprises at least one chlorine, bromine, or triflate, preferably at least one bromine or triflate, directly bonded to an sp$^2$ carbon atom of the ring structure of the ligand.

3. The process of paragraph 1 or paragraph 2 wherein L$^1$ is a substituted indenyl, a substituted heteroindenyl, a substituted fluorenyl, or a substituted heterofluorenyl ligand.

4. The process of any preceding paragraph 1 to 3 wherein the coupling catalyst comprises poly(ethylene glycol)triphenylphosphin, polymer bound; dicyclohexylphenylphosphine, polymer-bound; (4-hydroxyphenyl)diphenylphosphine, polymer-bound; triphenylphosphine, polymer-supported; R-(+)-2,2'-bis(diphenylphosphino)-1,1'-binaphthalene, polymer-bound; or S-(−)-2,2'-bis(diphenylphosphino)-1,1'-binaphthalene, polymer bound.

5. The process of any preceding paragraph 1 to 4 wherein L$^2$ is a substituted or unsubstituted monocyclic or polycyclic ligand, preferably L$^2$ is a substituted or unsubstituted cyclopentadienyl ligand, a substituted or unsubstituted heterocyclopentadienyl ligand, a substituted or unsubstituted indenyl ligand, a substituted or unsubstituted heteroindenyl ligand, a substituted or unsubstituted fluorenyl ligand, a substituted or unsubstituted heterofluorenyl ligand.

6. A process for preparing a chelating ligand of the formula (IIa), (IIb), or (IIc) from a chelating ligand of the formula (Ia), (Ib), or (Ic), respectively, and a coupling component of the formula (III),

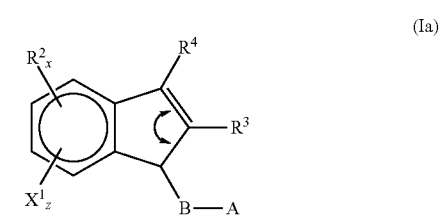

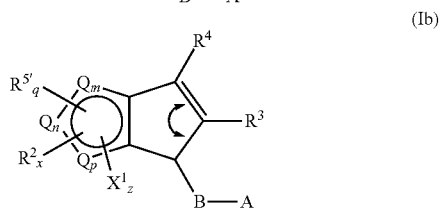

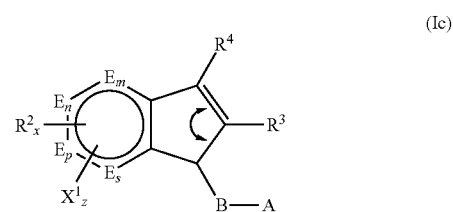

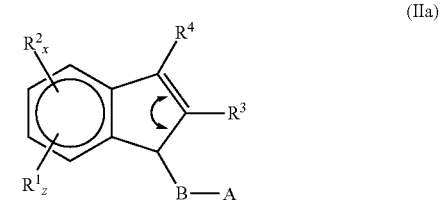

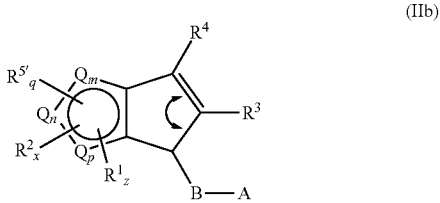

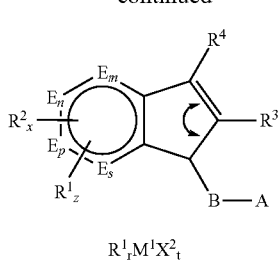

(IIc)

(III)

wherein:
M¹ is an element of group 1, 2, 12, 13 or 14 of the Periodic Table of the Elements; the or each X¹ is a chlorine, bromine, iodine, triflate, or sulfonate group, and the or each X¹ is directly bonded to an sp² carbon atom of the ring structure of the ligand;
each X², if present, is selected independently from the group consisting of halogen atoms, the hydroxyl groups, alkoxy groups and aryloxy groups.
R¹ is a hydrocarbyl, substituted hydrocarbyl, halocarbyl, or substituted halocarbyl;
R², R³, R⁴, and R⁵' are, independently, hydrogen, hydrocarbyl, substituted hydrocarbyl, halocarbyl, substituted halocarbyl, silylcarbyl, germylcarbyl radical or polar group as defined above; provided that all R² groups may be different and, optionally, adjacent R², R³, R⁴, and R⁵' groups may also together form a cyclic aliphatic or aromatic ring system which may in turn be substituted and may contain heteroatoms; and provided further that R², R³, and R⁴ groups are attached to ring carbons; R⁵' groups are attached to heteroatoms;
each Q, if present, is, independently, a Group 16 atom, a Group 15 atom, or boron, and preferably S, O, N, or P; when a Q is a Group 15 atom or boron, "q" is one, indicating the presence of one R⁵' bonded to Q, and when a Q is a Group 16 atom, "q" is zero, indicating the absence of R⁵'; m, n, and p are independently zero or one, and m+n+p=1; when m or n or p is one, Q is present in the ring as a Group 16 or Group 15 atom or as boron; when m or n or p is zero, Q is absent and is replaced by a ring carbon atom having either a substituent R² or a substituent X¹;
each E, if present, is, independently, a Group 15 atom, preferably N or P; when E is present, it does not have any substituents; m, n, p, and s are independently zero or one, and m+n+p+s=1; when m or n or p or s is one, E is present in the ring as a Group 15 atom; when m or n or p or s is zero, E is absent and is replaced by a ring carbon atom having either a substituent R² or a substituent X¹;
B is a bridging group that contains a Group 13, 14, 15, or 16 element;
A is a substituted or unsubstituted monocyclic or polycyclic ligand;
x represents the number of R² substituents bonded to the aryl fused to the cyclopentadienyl in structures (Ia) and (IIa), the number of R² substituents bonded to the 5-member heterocyclic fragment in the structures (Ib) and (IIb), or the number of R² substituents bonded to the 6-member heterocyclic fragment in the structures (Ic) and (IIc);
x is 0, 1, 2, or 3 in structures (Ia) and (IIa);
x is 0 or 1 in structures (Ib) and (IIb);
x is 0, 1, or 2 in structures (Ic and IIc);
z represents the number of X¹ substituents converted to R¹ substituents and is 1, 2, 3, or 4 in structures (Ia) and (IIa); 1 or 2 in structures (Ib) and (IIb); and 1, 2, or 3 in structures (Ic) and (IIc);

x+z is 4 in structures (Ia) and (IIa);
x+z is 2 in structures (Ib) and (IIb);
x+z is 3 in structures (Ic) and (IIc);
r is 1, 2 or 3, and
t is 0, 1 or 2, where r+t corresponds to the oxidation number of M¹.

7. A process for preparing a chelating ligand of the formula (IId), (IIe), or (IIf) from a chelating ligand of the formula (Id), (Ie), or (If), respectively, and a coupling component of the formula (III),

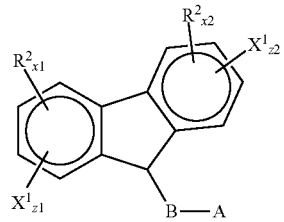

(Id)

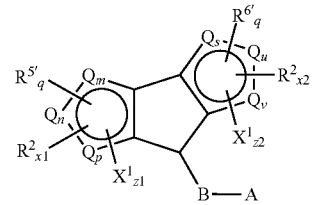

(Ie)

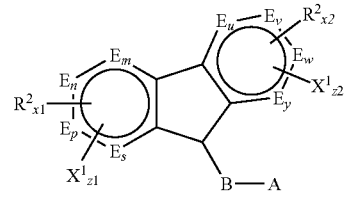

(If)

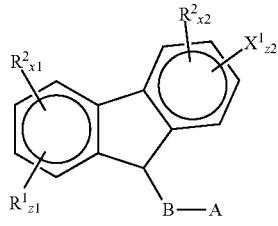

(IId)

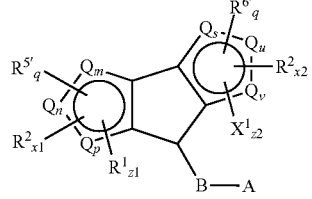

(IIe)

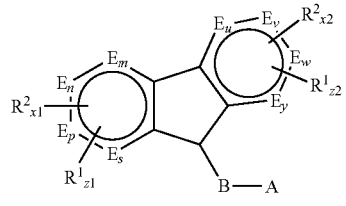

(IIf)

(III)

wherein:

$M^1$ is an element of Group 1, 2, 12, 13 or 14 of the Periodic Table of the Elements;

each $X^1$ is independently a chlorine, bromine, iodine, triflate, or sulfonate group, and each $X^1$ is directly bonded to an $sp^2$ carbon atom of the ring structure of the ligand;

each $X^2$, if present, is selected independently from the group consisting of halogen atoms, the hydroxyl groups, alkoxy groups and aryloxy groups;

$R^1$ is a hydrocarbyl, substituted hydrocarbyl, halocarbyl, or substituted halocarbyl;

$R^2$, $R5'$, and $R6'$ are, independently, hydrogen, hydrocarbyl, substituted hydrocarbyl, halocarbyl, substituted halocarbyl, silylcarbyl, germylcarbyl radical or polar group; provided that all $R^2$ groups may be different and, optionally, adjacent $R^2$, $R^{5'}$, and $R^{6'}$ groups may also together form a cyclic aliphatic or aromatic ring system which may in turn be substituted and may contain heteroatoms; and provided further that $R^2$ groups are attached to ring carbons; $R^{5'}$ and $R^{6'}$ groups are attached to heteroatoms;

B is a bridging group that contains a Group 13, 14, 15, or 16 element;

A is a substituted or unsubstituted monocyclic or polycyclic ligand;

each Q, if present, is independently, a Group 16 atom, a Group 15 atom, or boron, and preferably S, O, N, or P; when a Q is a Group 15 atom or boron, "q" is one, indicating the presence of one $R^{5'}$ or $R^{6'}$, as the case may be, bonded to Q, and when a Q is a Group 16 atom, "q" is zero, indicating the absence of $R^{5'}$ or $R^{6'}$, as the case may be; m, n, p, s, u, and v are independently zero or one, m+n+p=1, and s+u+v=1; when m or n or p or s or u or v is one, Q is present as a Group 16 or a Group 15 atom or as boron; when m or n or p or s or u or v is zero, Q is absent and is replaced by a ring carbon atom having either a substituent $R^1$ or a substituent $X^1$;

each E if present, is, independently, a Group 15 atom, preferably N or P; when E is present it does not have any substituents; m, n, p, s, u, v, w, and y are independently zero or one, m+n+p+s=1, and u+v+w+y=0 or 1; when m or n or p or s or u or v or w or y is present, E is present in the ring as a Group 15 atom; when m or n or p or s or u or v or w or y is zero, E is absent and is replaced by a ring carbon having either a substituent $R^2$ or a substituent $X^1$;

x1+x2 represents the total number of $R^2$ substituents bonded to the fluorenyl ligand in structures (Id) and (IId) or the total number of $R^2$ substituents bonded to the heterofluorenyl ligands in structures (Ie), (If), (IIe) and (IIf);

x1+x2 is 0, 1, 2, 3, 4, 5, 6, or 7 in structures (Id) and (IId);
x1+x2 is 0, 1, 2, or 3 in structures (Ie) and (IIe);
x1+x2 is 0, 1, 2, 3, 4, or 5 in structures (If) and (IIf); z1+z2 represents the total number of $X^1$ substituents converted to $R^1$ substituents and bonded to the fluorenyl ligand in structures (Id) and (IId), or the number of $X^1$ substituents converted to $R^1$ substituents and bonded to the heterofluorenyl ligand in structures (Ie), (If), (IIe), and (IIf);
z1+z2 is 1, 2, 3, 4, 5, 6, 7, or 8 in structures (Id) and (IId);
z1+z2 is 1, 2, 3 or 4 in structures (Ie) and (IIe);
z1+z2 is 1, 2, 3, 4, 5, 6, or 7 in structures (If) and (IIf);
x1+x2+z1+z2 is 8 in structures (Id) and (IId);
x1+x2+z1+z2 is 4 in structures (Ie) and (IIe);
x1+x2+z1+z2 is 6 in structures (If) and (IIf) when u+v+w+y=1;
x1+x2+z1+z2 is 7 in structures (If) and (IIf) when u+v+w+y=0;
r is 1, 2 or 3, and
t is 0, 1 or 2, where r+t corresponds to the oxidation number of $M^1$.

8. The process of paragraph 6 or paragraph 7 wherein the or each $X^1$ is chlorine, bromine, or triflate preferably bromine or triflate.

9. The process of any one of paragraphs 6 to 8 wherein A is a substituted or unsubstituted cyclopentadienyl, a substituted or unsubstituted heterocyclopentadienyl, a substituted or unsubstituted indenyl, a substituted or unsubstituted heteroindenyl, a substituted or unsubstituted fluorenyl, or a substituted or unsubstituted heterofluorenyl.

10. A process for preparing a chelating ligand of the formula (Va), (Vb), (Vc), (Vd), (Ve), (Vf), (Vg), (Vh), (Vi), (Vk), (Vm), (Vn), (Vo), (Vp), (Vq), (Vr), (Vs), (Vt), (Vu), (Vv), (Vw), (Vx), or (Vy) from a chelating ligand of the formula (IVa), (IVb), (IVc), (IVd), (IVe), (IVf), (IVg), (IVh), (IVi), (IVk), (IVm), (IVn), (IVo), (IVp), (IVq), (IVr), (IVs), (IVt), (IVu), (IVv), (IVw), (IVx), or (IVy), respectively, and a coupling component of the formula (III), $$R^1_r M^1 X^2_t \qquad (III)$$

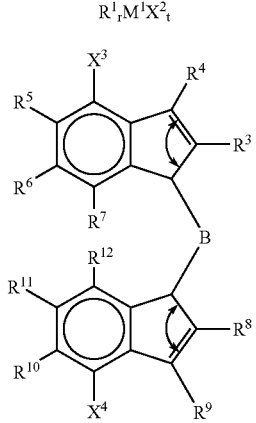

(IVa)

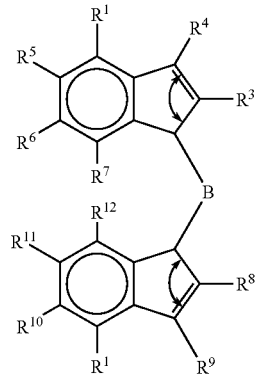

(Va)

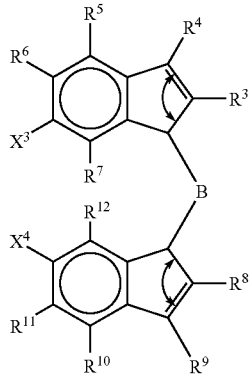

(IVb)

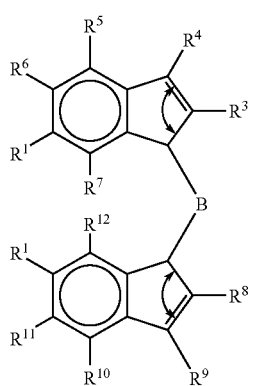 (Vb)
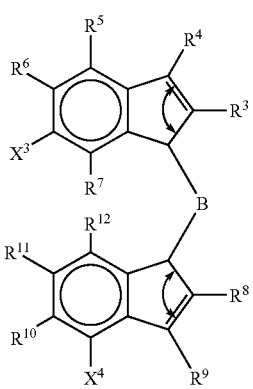 (IVc)
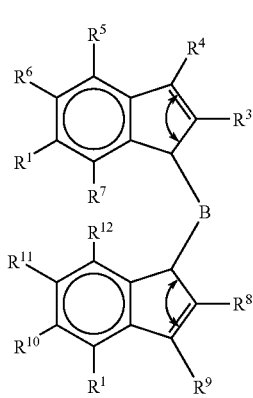 (Vc)
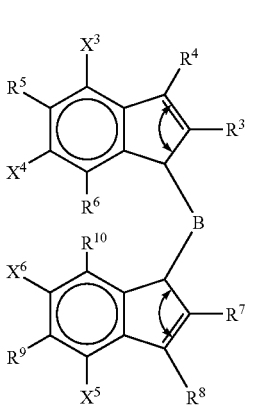 (IVd)
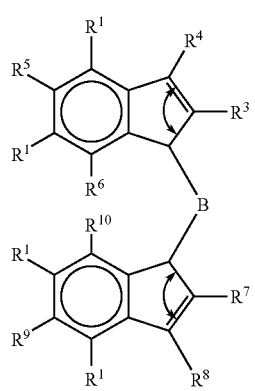 (Vd)
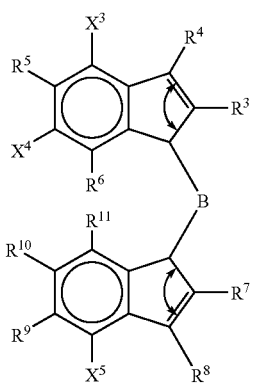 (IVe)
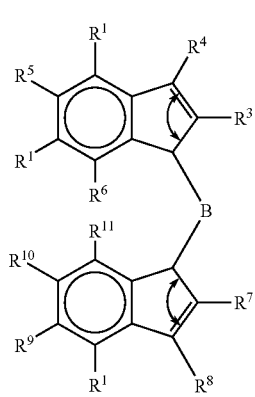 (Ve)
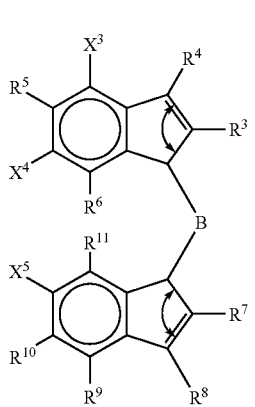 (IVf)

(Vf)
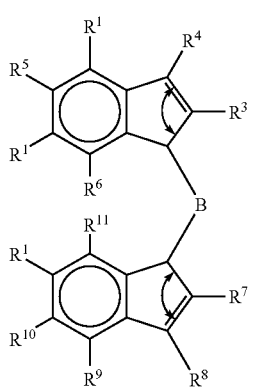
(IVg)
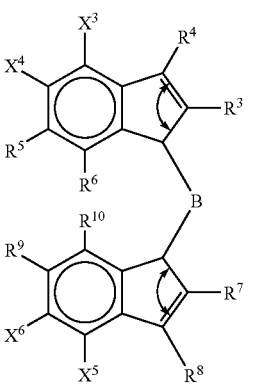
(Vg)
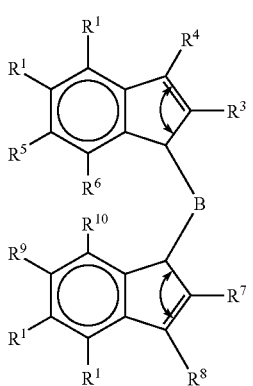
(IVh)
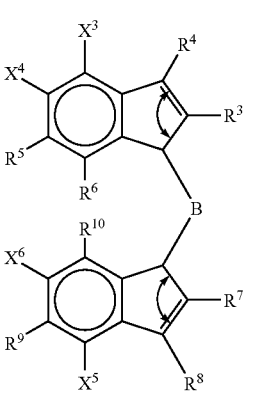
(Vh)
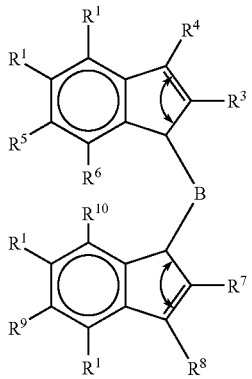
(IVi)
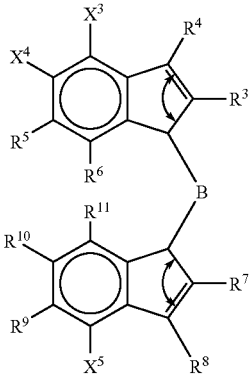
(Vi)
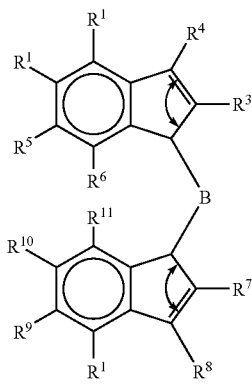
(IVk)
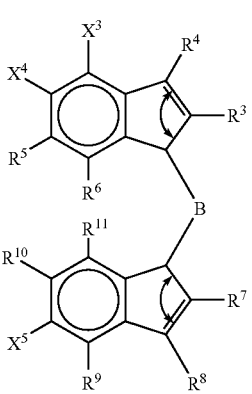

(Vk)
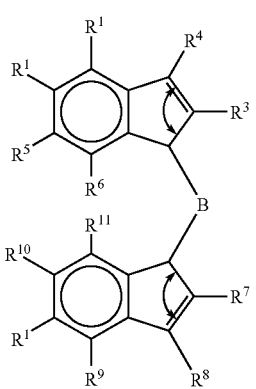
(IVm)
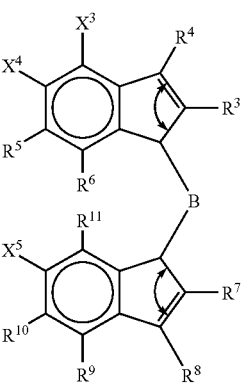
(Vm)
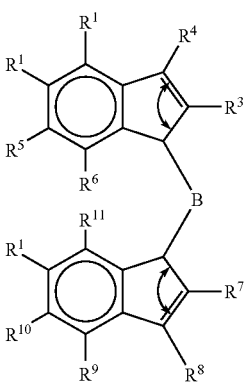
(IVn)
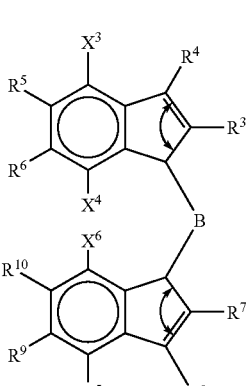
(Vn)
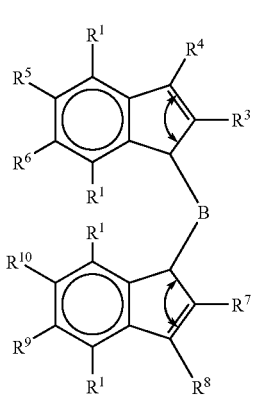
(IVo)
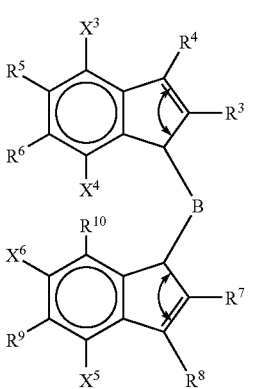
(Vo)
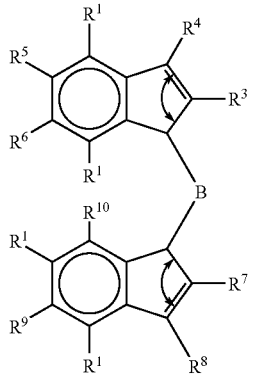
(IVp)
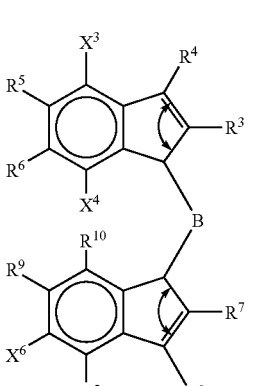

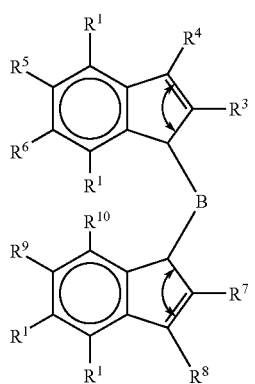
(Vp)
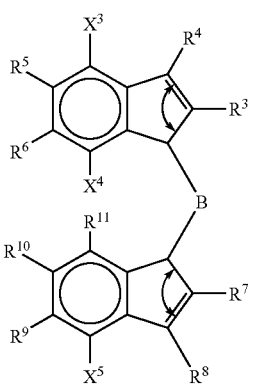
(IVq)
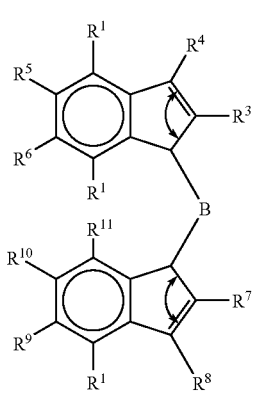
(Vq)
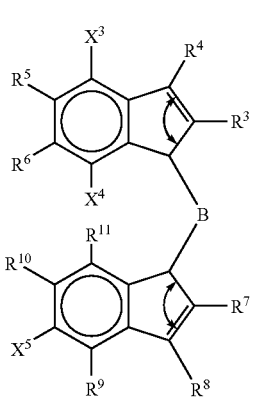
(IVr)
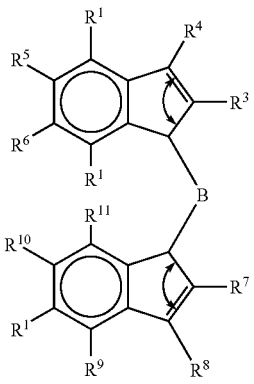
(Vr)
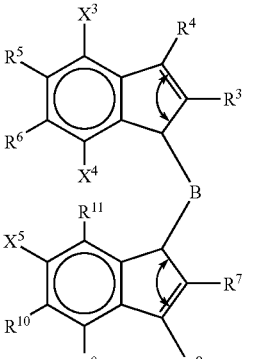
(IVs)
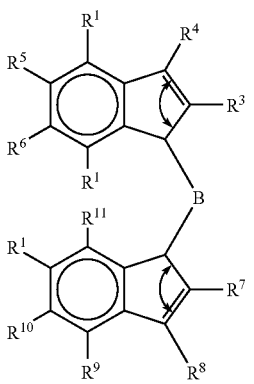
(Vs)
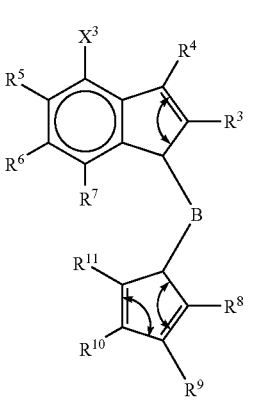
(IVt)

(Vt)
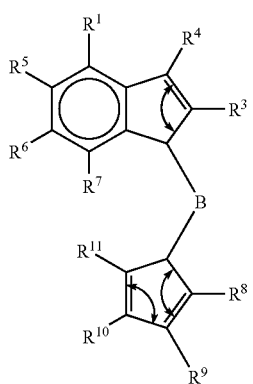
(Vv)
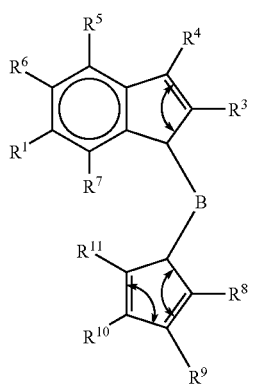
(IVu)
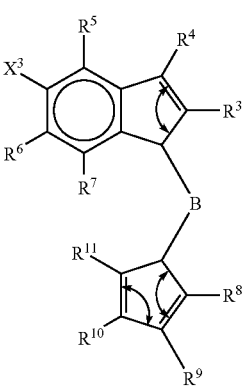
(IVw)
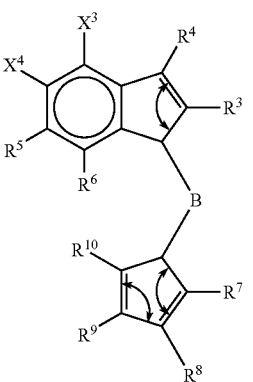
(Vu)
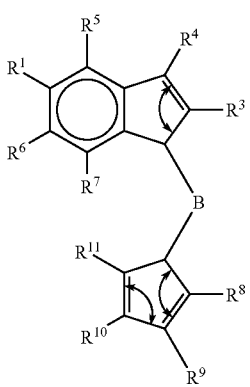
(Vw)
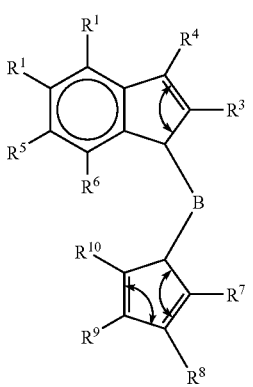
(IVv)
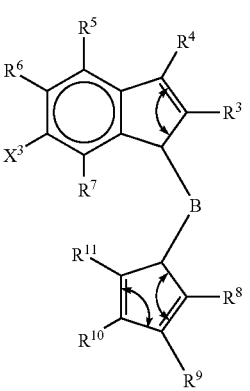
(IVx)
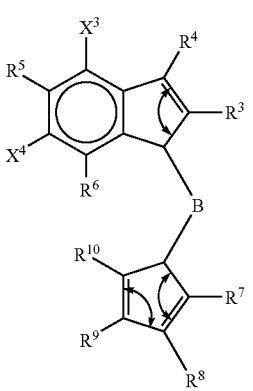

-continued

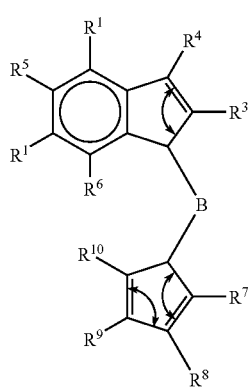

(Vx)

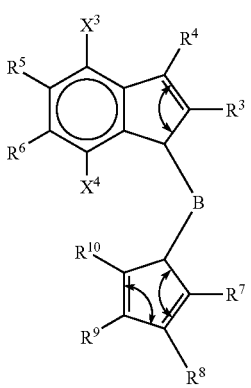

(IVy)

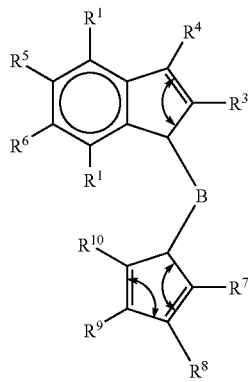

(Vy)

wherein:
$M^1$ is an element of group 1, 2, 12, 13 or 14 of the Periodic Table of the Elements;
$X^3$, $X^4$, $X^5$, and $X^6$ are independently selected from chlorine, bromine, iodine, triflate, and sulfonate groups;
each $X^2$, if present, is selected independently from the group consisting of halogen atoms, the hydroxyl groups, alkoxy groups and aryloxy groups;
$R^1$ is a hydrocarbyl, substituted hydrocarbyl, halocarbyl, or substituted halocarbyl;
$R^3$, $R^4$, $R^5$, $R^6$, $R^7$, $R^8$, $R^9$, $R^{10}$, $R^{11}$, and $R^{12}$ are, independently, hydrogen, hydrocarbyl, substituted hydrocarbyl, halocarbyl, substituted halocarbyl, silylcarbyl, germylcarbyl radical or polar group, where, optionally, adjacent $R^3$, $R^4$, $R^5$, $R^6$, $R^7$, $R^8$, $R^9$, $R^{10}$, $R^{11}$, $R^{12}$ groups may also together form a cyclic aliphatic or aromatic ring system which may in turn be substituted and may contain heteroatoms;
B is a bridging group that contains a Group 13, 14, 15, or 16 element;

r is 1, 2 or 3, and
t is 0, 1 or 2, where r+t corresponds to the oxidation number of $M^1$.

11. The process of paragraph 10 wherein $X^3$, $X^4$, $X^5$, and $X^6$ are independently selected from chlorine, bromine, and triflate, preferably from bromine and triflate.

12. A process for preparing a chelating ligand of the formula (VIIa), (VIIb), (VIIc), (VIId), (VIIe), (VIIf), (VIIg), (VIIh), (VIIi), (VIIk), (VIIm), (VIIn), (VIIo), (VIIp), (VIIq), (VIIr), or (VIIs) from a chelating ligand of the formula (VIa), (VIb), (VIc), (VId), (VIe), (VIf), (VIg), (VIh), (VIi), (VIk), (VIn), (VIn), (VIo), (VIp), (VIq), (VIr), or (VIs), respectively, and a coupling component of the formula (III), $$R^1_r M^1 X^2_t \quad (III)$$

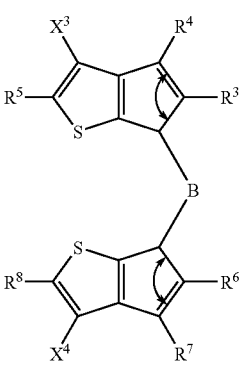

(VIa)

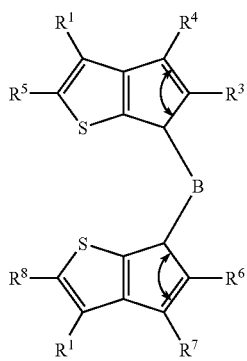

(VIIa)

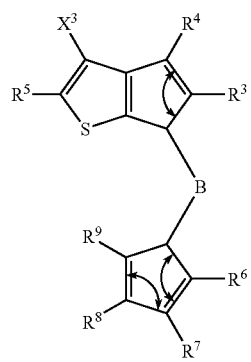

(VIb)

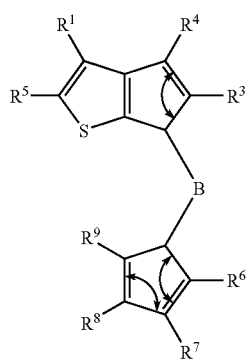
(VIIb)
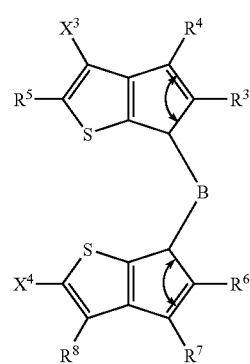
(VIc)
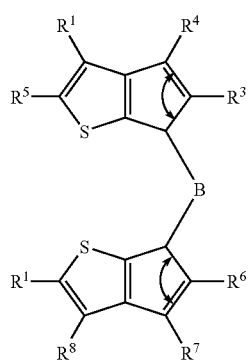
(VIIc)
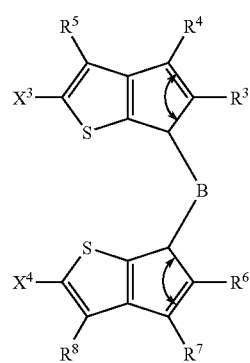
(VId)
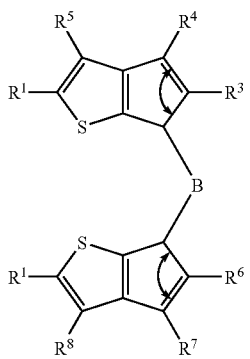
(VIId)
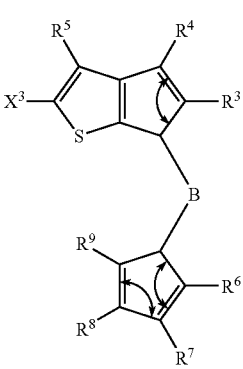
(VIe)
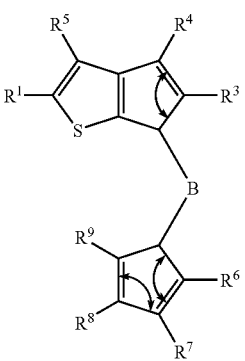
(VIIe)
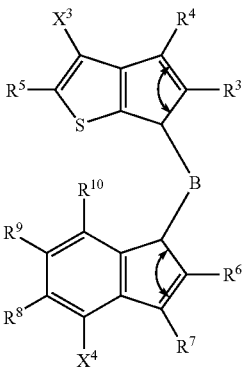
(VIf)

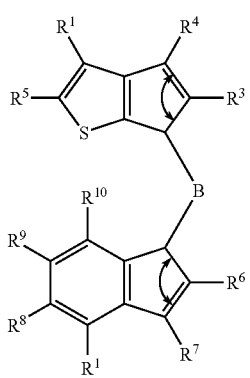
(VIIf)
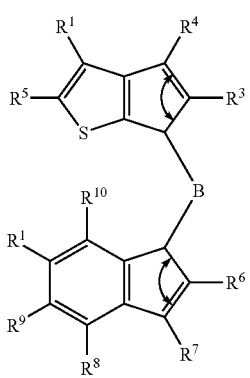
(VIIh)
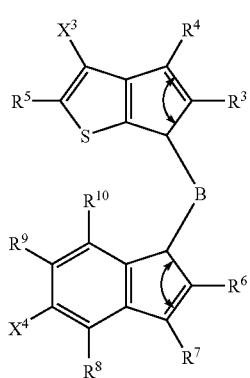
(VIg)
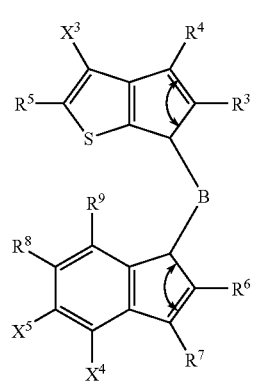
(VIi)
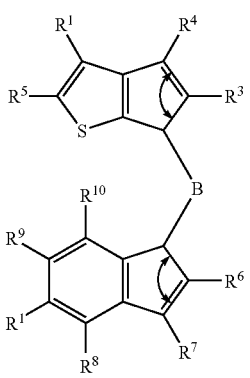
(VIIg)
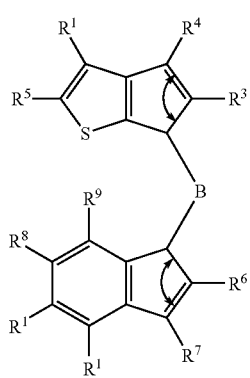
(VIIi)
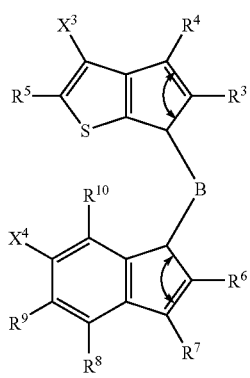
(VIh)
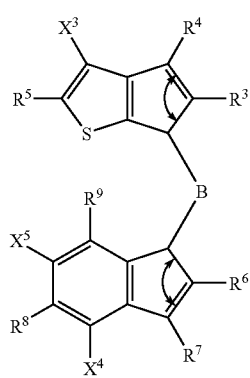
(VIk)

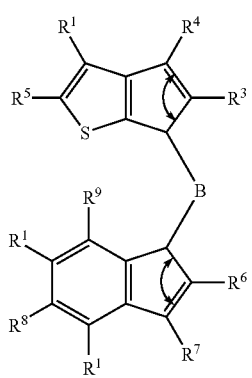
(VIIk)
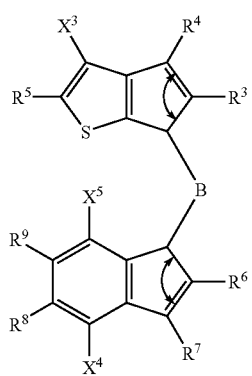
(VIm)
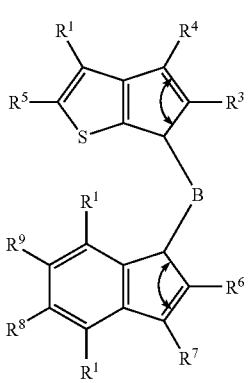
(VIIm)
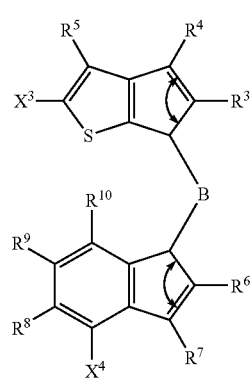
(VIn)
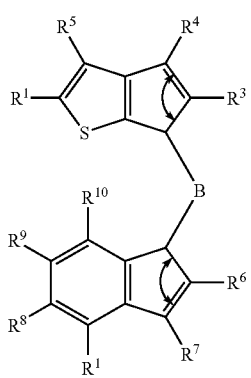
(VIIn)
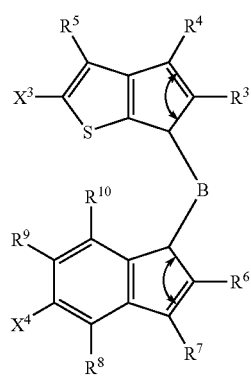
(VIo)
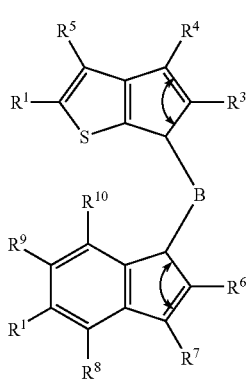
(VIIo)
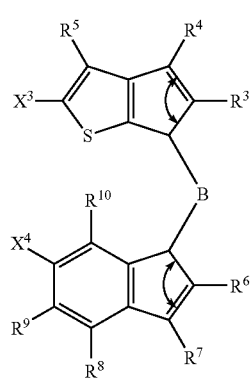
(VIp)

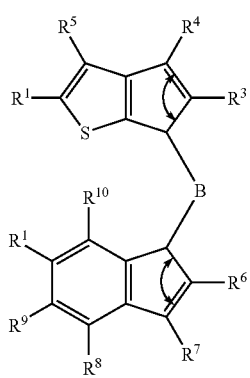
(VIIp)

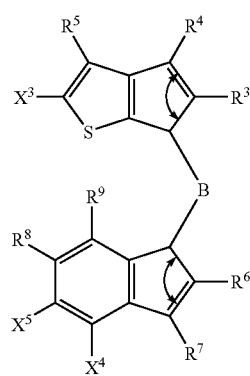
(VIq)

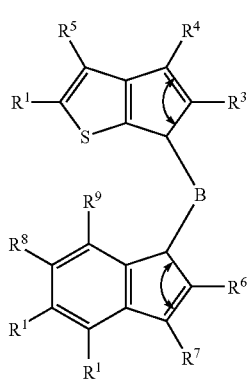
(VIIq)

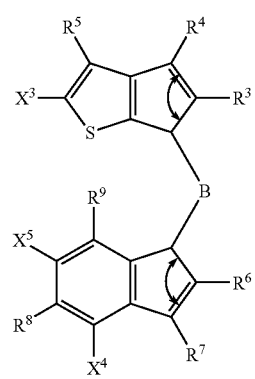
(VIr)

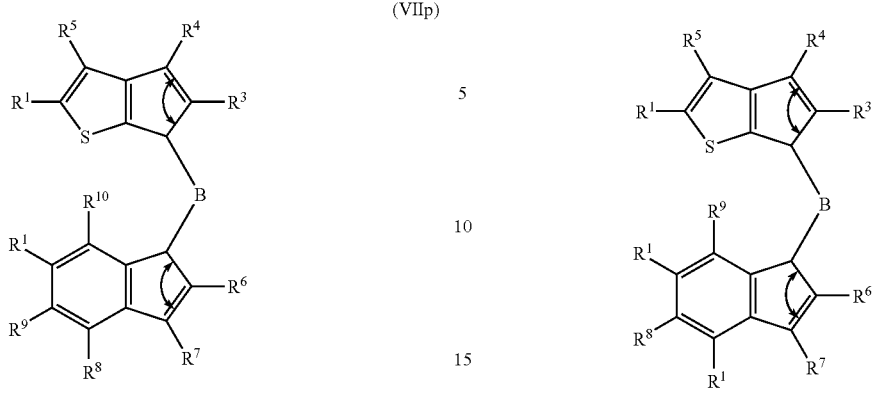
(VIIr)

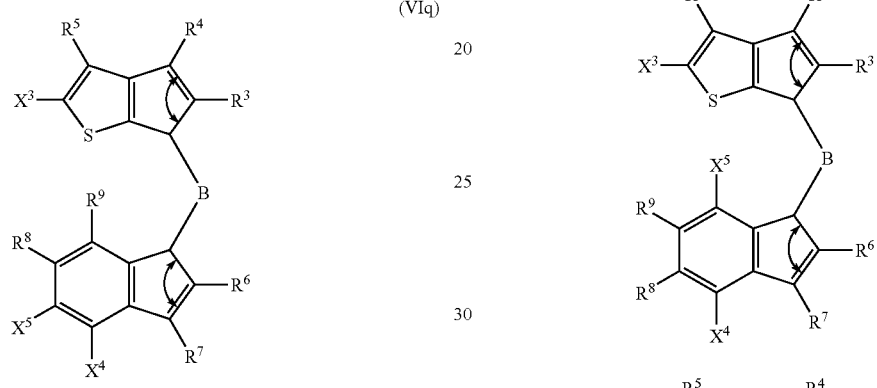
(VIs)

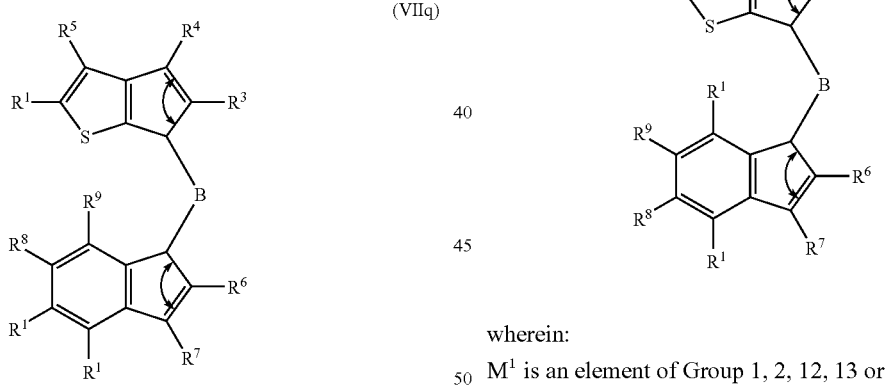
(VIIs)

wherein:

$M^1$ is an element of Group 1, 2, 12, 13 or 14 of the Periodic Table of the Elements;

$X^1, X^4, X^5$, and $X^6$ are independently selected from chlorine, bromine, iodine, triflate, and sulfonate groups;

each $X^2$, if present, is selected independently from the group consisting of halogen atoms, the hydroxyl groups, alkoxy groups and aryloxy groups;

$R^1$ is a hydrocarbyl, substituted hydrocarbyl, halocarbyl, or substituted halocarbyl;

$R^3, R^4, R^5, R^6, R^7, R^8, R^9$, and $R^{10}$ are, independently, hydrogen, hydrocarbyl, substituted hydrocarbyl, halocarbyl, substituted halocarbyl, silylcarbyl, germylcarbyl radical or polar group, where, optionally, adjacent $R^3, R^4, R^5, R^6, R^7, R^8, R^9$, and $R^{10}$ groups may also together form a cyclic aliphatic or aromatic ring system which may in turn be substituted and may contain heteroatoms;

B is a bridging group that contains a Group 13, 14, 15, or 16 element;
r is 1, 2 or 3; and
t is 0, 1 or 2, where r+t corresponds to the oxidation number of $M^1$.

13. The process of paragraph 12 wherein $X^3$, $X^4$, $X^5$, and $X^6$ are independently selected from chlorine, bromine, and triflate, preferably from bromine and triflate.

14. A process for preparing a chelating ligand of the formula (IXa), (IXb), (IXc), (IXd), (IXe), (IXf), (IXg), (IXh), (IXi), or (IXk) from a chelating ligand of the formula (VIIIa), (VIIIb), (VIIIc), (VIIId), (VIIIe), (VIIIf), (VIIIg), (VIIIh), (VIIIi), or (VIIk), respectively, and a coupling component of the formula (III), $$R^1{}_r M^1 X^2{}_t \quad \text{(III)}$$

(VIIIa)
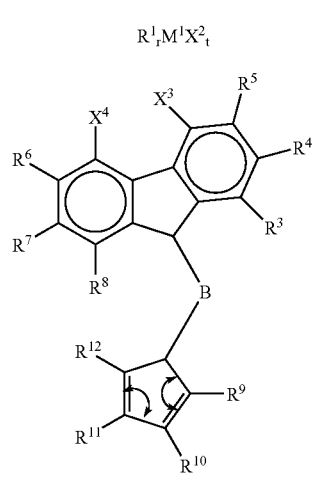

(IXa)
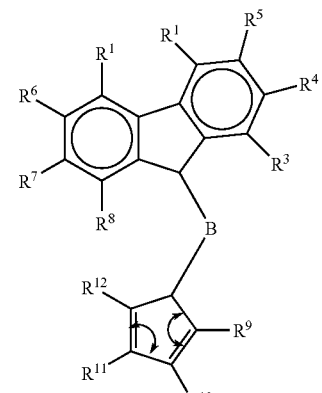

(VIIIb)
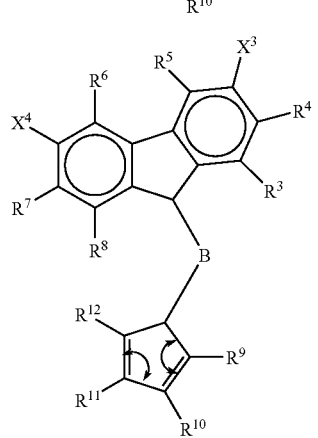

(IXb)
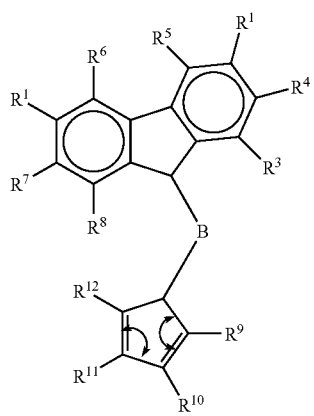

(VIIIc)
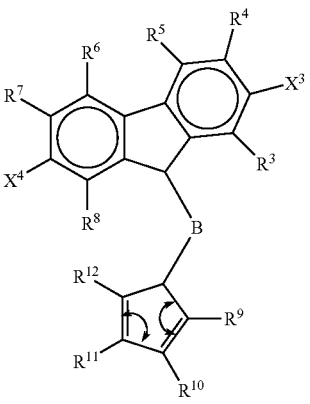

(IXc)
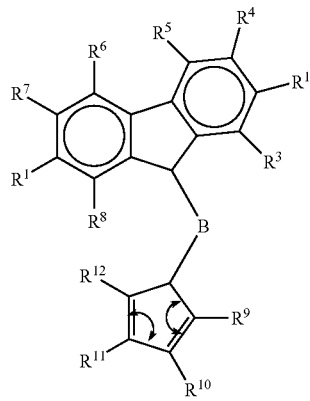

(VIIId)
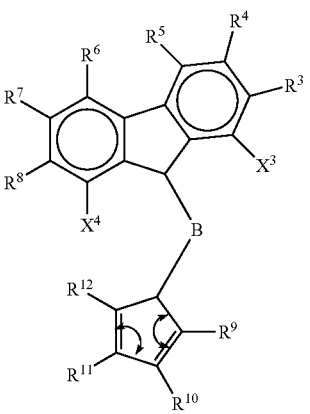

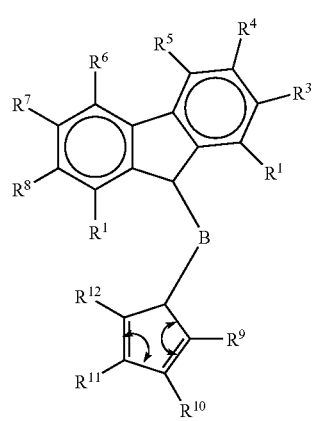
(IXd)
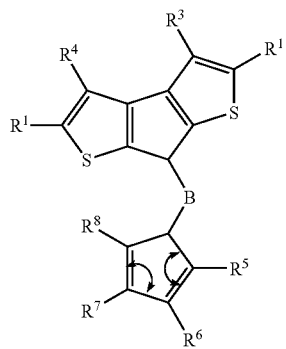
(IXf)
(VIIIe)
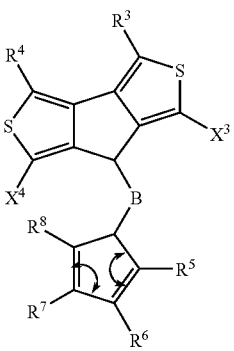
(VIIIg)
(IXe)
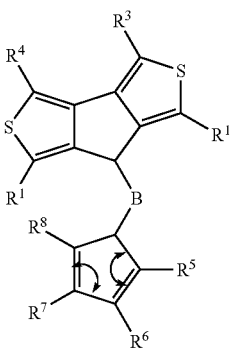
(IXg)
(VIIIf)
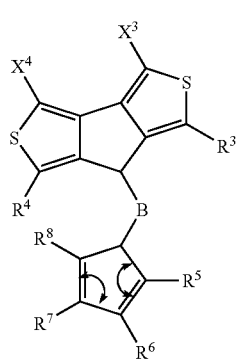
(VIIIh)

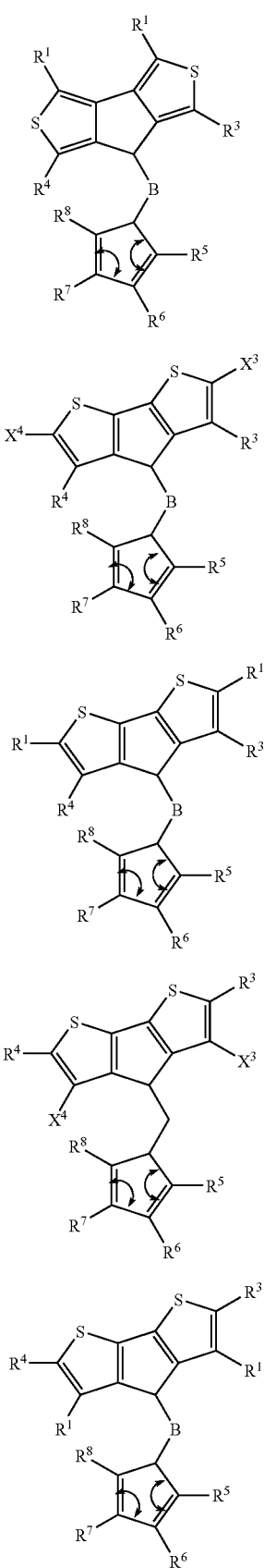

wherein:

M¹ is an element of Group 1, 2, 12, 13 or 14 of the Periodic Table of the Elements;

$X^3$ and $X^4$ are, independently, chlorine, bromine, iodine, triflate, or sulfonate groups;

each $X^2$, if present, is selected independently from the group consisting of halogen atoms, the hydroxyl groups, alkoxy groups and aryloxy groups;

$R^1$ is a hydrocarbyl, substituted hydrocarbyl, halocarbyl, or substituted halocarbyl;

$R^3$, $R^4$, $R^5$, $R^6$, $R^7$, $R^8$, $R^9$, $R^{10}$, $R^{11}$, $R^{12}$ are, independently, hydrogen, hydrocarbyl, substituted hydrocarbyl, halocarbyl, substituted halocarbyl, silylcarbyl, germylcarbyl radical or polar group, where, optionally, adjacent $R^3$, $R^4$, $R^5$, $R^6$, $R^7$, $R^8$, $R^9$, $R^{10}$, $R^{11}$, $R^{12}$ groups may also together form a cyclic aliphatic or aromatic ring system which may in turn be substituted and may contain heteroatoms;

B is a bridging group that contains a Group 13, 14, 15, or 16 element;

r is 1, 2 or 3, and t is 0, 1 or 2, where r+t corresponds to the oxidation number of $M^1$.

15. The process of paragraph 14 wherein $X^3$ and $X^4$ are, independently, chlorine, bromine, or triflate, preferably bromine or triflate.

16. The process of any preceding paragraph 1 to 15 wherein $M^1$ is Li, Na, K, Rb, Cs, Be, Mg, Ca, Sr, Ba, B, Si, Sn, Zn, Cd or Hg.

17. The process of any preceding paragraph 1 to 16 wherein $M^1$ is B, Si, Sn, Zn, Cd or Hg.

18. The process of any preceding paragraph 1 to 17 wherein $M^1$ is B, Sn or Zn.

19. The process of any preceding paragraph 1 to 18 wherein t is 1 or 2 and each $X^2$ is selected independently from the group consisting of halogen atoms, the hydroxyl group, alkoxy and aryloxy.

20. The process of any preceding paragraph 1 to 19 wherein B is a bridging group containing boron or a Group 14, 15 or 16 element.

21. The process of any preceding paragraph 1 to 20 wherein B selected from R'₂C, R'₂Si, R'₂Ge, R'₂CCR'₂, R'₂CCR'₂CR'₂, R'₂CCR'₂CR'₂CR'₂, R'C=CR', R'C=CR'CR'₂, R'₂CCR'=CR'CR'₂, R'C=CR'CR'=CR', R'C=CR'CR'₂CR'₂, R'₂CSiR'₂, R'₂SiSiR'₂, R'₂CSiR'₂CR'₂, R'₂SiCR'₂SiR'₂, R'C=CR'SiR'₂, R'₂CGeR'₂, R'₂GeGeR'₂, R'₂CGeR'₂CR'₂, R'₂GeCR'₂GeR'₂, R'₂SiGeR'₂, R'C=CR'GeR'₂, R'B, R'₂C—BR', R'₂C—BR'—CR'₂, R'₂CCR'₂, R'₂CR'₂C—O CR'₂CR'₂, R'₂CCR'₂CR'₂, R'₂C—OR'=CR', R'₂C—S—CR'₂, R'₂CR'₂C—S—CR'₂CR'₂, R'₂C—S—CR'₂CR'₂, R'₂C—S—CR'=CR', R'₂C—Se—CR'₂, R'₂CR'₂C—Se—CR'₂CR'₂, R'₂C—Se—CR'₂CR'₂, R'₂C—Se—CR'=CR', R'₂C—N=CR', R'₂C—NR'—CR'₂, R'₂C—NR'—CR'₂CR'₂, R'₂C—NR'—CR'=CR', R'₂CR'₂C—NR'—CR'₂CR'₂, R'₂C—P=CR', and R'₂C—PR'—CR₁₂ where R'is hydrogen or a $C_1$-$C_{20}$ containing hydrocarbyl, substituted hydrocarbyl, halocarbyl, substituted halocarbyl, silylcarbyl or germylcarbyl substituent and optionally two or more adjacent R' may join to form a substituted or unsubstituted, saturated, partially unsaturated or aromatic, cyclic or polycyclic substituent.

22. The process of any preceding paragraph 1 to 21 wherein B is selected from $CH_2$, $CH_2CH_2$, $CH(CH_3)_2$, $SiMe_2$, $SiPh_2$, SiMePh, $Si(CH_2)_3$, and $Si(CH_2)_4$.

23. The process of any preceding paragraph 1 to 22 wherein the reaction is conducted in the presence of a transition metal-containing catalyst.

24. The process of paragraph 23 wherein the transition metal is selected from Groups 8 to 10 of the Periodic Table of the Elements.

25. A method of synthesizing a metallocene complex, the method comprising using a chelating ligand prepared by the process of any preceding paragraph 1 to 24.

26. A process for polymerizing olefins comprising contacting a catalyst system comprising a metallocene complex synthesized by the method of paragraph 25 with at least one olefin.

EXPERIMENTAL

Synthesis of Pre-Catalysts

All manipulations with air and moisture sensitive compounds were performed either in an atmosphere of thoroughly purified argon using a standard Schlenk technique or in a controlled atmosphere Glove Box (Vacuum Atmospheres Co.). Tetrahydrofuran (THF, Merck=Merck KGaA, Darmstadt, Germany) and diethyl ether (Merck) for synthesis were purified by distillation over LiAlH$_4$, and stored over sodium benzophenone ketyl under an inert atmosphere; prior to use, the solvents were distilled from the benzophenone ketyl. Hydrocarbon solvents such as benzene (Merck), toluene (Merck) and hexanes (Merck) and including benzene-d$_6$ for NMR measurements were typically distilled over CaH$_2$, and were stored over Na/K alloy under an inert atmosphere; prior to use, the solvents were distilled from the Na/K alloy. Methylene chloride (Merck) and CCl$_2$D$_2$ (Cambridge Isotope) for NMR measurements were distilled and stored over CaH$_2$ under an inert atmosphere; prior to use, the solvents were distilled from the CaH$_2$. Benzothiophene (Aldrich), 2.5 M $^n$BuLi in hexanes (Acros=Acros Organics), 1.6 M MeLi in ether (Acros), 3.0 M methylzinc chloride in THF (Aldrich), 1.0 M phenylmagnesium bromide in THF (Aldrich), 1.0 M p-tolylmagnesium bromide in THF (Aldrich), 1.0 M mesityl bromide in THF (Aldrich), 0.5 M 4-N,N-dimethylaminophenylmagnesium bromide in THF (Aldrich), 2-bromobenzylbromide (Aldrich), 2-chlorobenzylchloride (Merck), diethyl methylmalonate (Acros), 2-bromobenzotrifluoride (Acros), 3-bromobenzotrifluoride (Acros), 1,3-bis(trifluoromethyl)-5-bromobenzene (Aldrich), 4-tert-butylbromobenzene (Acros), 2-bromo-4-isopropylaniline (Aldrich), 2-bromo-2-methylpropanoyl bromide (Aldrich), 1-bromonaphthalene (Acros), 0.5 M ZnCl$_2$ in THF (Aldrich), and Pd(P$^t$Bu$_3$)$_2$ (Strem=Strem Chemical Co.), 2-[di(tert-butyl)phosphino]-1,1'-biphenyl (Strem), ZrCl$_4$(THF)$_2$ (Aldrich), NaBH$_4$ (Acros), NaBPh$_4$ (Aldrich), anhydrous powdered AlCl$_3$ (Merck), and dichlorodimethylsilane (Merck) were used as obtained. Solutions of Grignard reagents (2-trifluoromethylphenylmagnesium bromide, 3-trifluoromethylphenylmagnesium bromide, 4-tert-butylphenylmagnesium bromide, 1,3-bis(trifluoromethyl)-5-bromobenzene, and 1-naphthylmagnesium bromide) in THF were obtained from magnesium turnings (Aldrich) and the respective arylbromides in THF at reflux. 5-Methyl-4,5-dihydro-6H-cyclopenta[b]-thiophen-6-one [Ryabov, A. N.; Gribkov, D. V.; Izmer, V. V.; Voskoboynikov, A. Z. *Organometallics* 2002, 21, 2842] was prepared according to the published method. 2-Bromo-1-(bromomethyl)-3-methylbenzene [Baker, R. W.; Foulkes, M. A.; Griggs, M.; Nguyen, B. N. *Tetrahedron Lett.* 2002, 43, 9319] was prepared from 2-bromo-m-xylene (Acros) according to the published procedure. Pd(dba)$_2$ was prepared from PdCl$_2$ (Aldrich) and dibenzolidenacetone (Acros) as described in literature [Coulson, D. R. *Inorg. Synth.* 1972, 13, 121].

$^1$H and $^{13}$C NMR spectra were recorded with a Varian VXR 400 or Brucker DPX-300 for 0.1-5% solutions in deuterated solvents. Chemical shifts for $^1$H and $^{13}$C were measured relative to TMS. In $^1$H NMR spectra, the assignment was made on the evidence of double resonance and NOE experiments. C, H microanalyses were done using CHN—O-Rapid analyzer (Heracus).

Example 1

Synthesis of bis(4-bromo-2-methyl-1H-inden-1-yl)(dimethyl)silane (1)

3-(2-Bromophenyl)-2-methylpropanoic acid. 3-(2-bromophenyl)-2-methylpropanoyl chloride, and 4-bromo-2-methyl-1-indanone

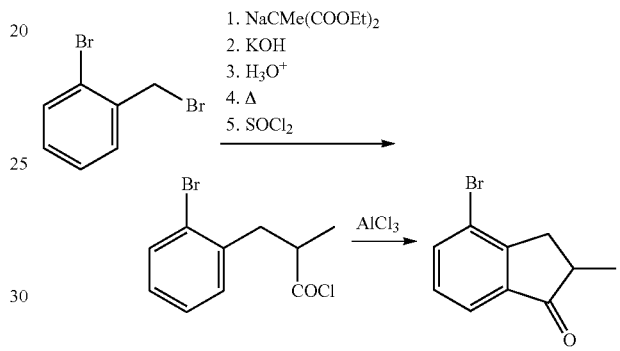

In a three-necked round-bottom 2000 ml flask equipped with a reflux condenser, dropping funnel with pressure-equalizing, and magnetic stirring bar 20.5 g (0.89 mol) of sodium metal were dissolved in 450 ml of dry ethanol. To the resulting solution 155 g (0.89 mol) of diethylmethylmalonate in 150 ml of dry ethanol were added dropwise within 15 min. This mixture was stirred for 15 min; then, 186 g (0.89 mol) of o-bromobenzyl bromide were added, while vigorously stirring, at a rate that allowed the reaction mixture to maintain a gentle reflux. This mixture was further refluxed for 4 hours and cooled to room temperature. A solution of 151 g of potassium hydroxide in 400 ml of water was added. The resulting mixture was refluxed for 3 hours to saponificate the ester formed. Ethanol and water were distilled off. To the residue 500 ml of water and, then, 12 M HCl (to pH 1) were added. The substituted methylmalonic acid precipitate was separated, washed with 2×200 ml of cold water, and dried overnight on a watch glass. Crude 3-(2-bromophenyl)-2-methylpropanoic acid was obtained after decarboxilation of this substituted methylmalonic acid by heating it at 160° C. for 2 hours. The product was used without further purification. Mixture of this acid and 160 ml of SOCl$_2$ was stirred for 24 hours at ambient temperature. Thionyl chloride was distilled off. The crude 3-(2-bromophenyl)-2-methylpropanoyl chloride was dissolved in 270 ml of CH$_2$Cl$_2$ and was added dropwise, while vigorously stirring, to a suspension of 136 g (1.02 mol) of AlCl$_3$ in 1350 ml of CH$_2$Cl$_2$ over a period of 1 hour at 0° C. Then, this mixture was refluxed for 3 hours, cooled to ambient temperature, and poured on 500 cm$^3$ of ice. The organic layer was separated. The aqueous layer was extracted with 3×300 ml of methyl-tert-butyl ether. The combined organic fractions were dried over K$_2$CO$_3$ and evaporated to dryness. Fractional distillation gave the title indanone, b.p. 131-134° C./2 mm Hg. Yield 125.5 g (75%) of colorless solid.

Anal. calc. for $C_{10}H_9BrO$: C, 53.36; H, 4.03. Found: C, 53.19; H, 3.98.

$^1$H NMR (CDCl$_3$): δ 7.76 (d, J=7.6 Hz, 1H, 7-H), 7.71 (d, J=7.6 Hz, 1H, 5-H), 7.28 (t, J=7.6 Hz, 1H, 6-H), 3.36 (dd, J=17.5 Hz, J=7.6 Hz, 1H, 3-H), 2.70-2.82 (m, 1H, 2-H), 2.67 (dd, J=17.5 Hz, J=3.8 Hz, 1H, 3'-H), 1.34 (d, J=7.3 Hz, 3H, 2-Me).

$^{13}$C{$^1$H} NMR (CDCl$_3$): δ 208.3, 152.9, 138.2, 137.2, 129.0, 122.6, 122.0, 41.8, 35.7, 16.0.

7-Bromo-2-methyl-1H-indene

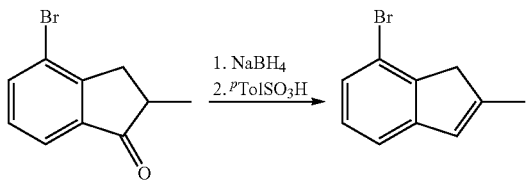

To a solution of 116 g (0.52 mol) of 4-bromo-6-chloro-2-methyl-1-indanone in 950 ml of THF-methanol (2:1, vol.) 38.3 g (1.02 mol) of NaBH$_4$ were added in small portions for 2 hours at −5° C. (Caution: temperature must be lower than 0° C.). The mixture was stirred overnight at ambient temperature. The resulting mixture was poured over 1000 cm$^3$ of ice and acidified with 10% HCl to pH=4. The organic layer was separated; the aqueous layer was extracted with 3×300 ml of methyl-tert-butyl ether. The combined organic fractions were dried over K$_2$CO$_3$ and evaporated to dryness. To the residue 1500 ml of toluene were added. This toluene solution was treated with a catalytic amount of $^p$TolSO$_3$H (ca. 2 g) for 2 hours at reflux. Then this mixture was cooled to room temperature and passed through a short Silica Gel 60 column (40-63 μm, d 60 mm, 140 mm). This column was additionally eluted with 250 ml of toluene. The chromatographed product was evaporated to dryness. Fractional distillation gave the title indene, b.p. 104-108° C./5 mm Hg. Yield 100 g (93%) of colorless solid.

Anal. calc. for $C_{10}H_9Br$: C, 57.44; H, 4.34. Found: C, 57.59; H, 4.40.

$^1$H NMR (CDCl$_3$): δ 7.23 (dd, J=7.9 Hz, J=1.0 Hz, 1H, 6-H), 7.18 (dd, J=7.4 Hz, J=1.0 Hz, 1H, 4-H), 7.10 (m, 1H, 5-H), 6.51 (m, 1H, 3-H), 3.28 (m, 2H, 1,1'-H), 2.17 (s, 3H, 2-Me).

$^{13}$C{$^1$H} NMR (CDCl$_3$): δ 147.3, 146.8, 143.3, 128.2, 127.1, 126.6, 118.7, 118.3, 44.2, 16.7.

Bis(4-bromo-2-methyl-1H-inden-1-yl)(dimethyl)silane (1)

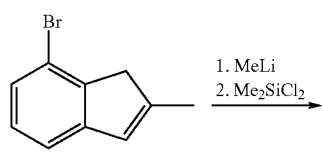

-continued

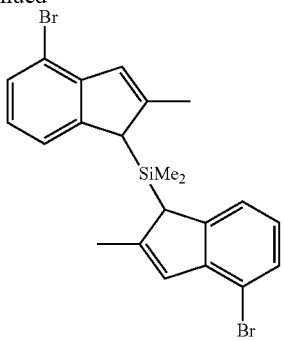

In an argon atmosphere, to a solution of 10.0 g (47.8 mmol) of 2-methyl-7-bromoindene in 250 ml of diethyl ether, 29.9 ml of 1.6 M MeLi (47.8 mmol) in ether was added at 10° C. This mixture was stirred for 1 hour at 20° C. and, then, cooled to 0° C. At this temperature, 2.89 ml (3.08 g, 23.9 mmol) of Me$_2$SiCl$_2$ was added. The resulting mixture was stirred for 2 hours at ambient temperature; then 100 ml of water was added. The organic layer was separated, dried over K$_2$CO$_3$, and evaporated to dryness. The residue was treated with 25 ml of hexanes. The white solid that precipitated was filtered off, washed with 3×30 ml of hexanes, and dried in vacuum. Yield 5.37 g (47%) of white solid of ca. 1 to 1 mixture of rac- and meso-compounds.

Anal. calc. for $C_{22}H_{22}Br_2Si$: C, 55.71; H, 4.68. Found: C, 56.02; H, 4.77.

$^1$H NMR (CDCl$_3$): δ 7.36 (d, J=8.5 Hz, 2H, 5,5'-H in rac- or meso-compound), 7.34 (d, J=8.5 Hz, 2H, 5,5'-H in meso- or rac-compound), 7.32 (d, J=7.6 Hz, 2H, 7,7'-H in rac- or meso-compound), 7.23 (d, J=7.6 Hz, 2H, 7,7'-H in meso- or rac-compound), 6.95 (t, J=8.1 Hz, 2H, 6,6'-H in rac- or meso-compound), 6.93 (t, J=8.1 Hz, 2H, 6,6'-H in meso- or rac-compound), 6.70 (br.s, 4H, 3,3'-H in rac- and meso-compounds), 3.74 (s, 2H, CHSi, CHSi' in rac- or meso-compound), 3.73 (s, 2H, CHSi, CHSi' in meso- or rac-compound) 2.23 (d, 6H, J=1.2 Hz, 2,2'-Me in rac- or meso-compound), 2.17 (d, 6H, J=1.2 Hz, 2,2'-Me in meso- or rac-compound), −0.19 (s, 3H, SiMe in meso-compound), −0.24 (s, 6H, SiMe$_2$ in rac-compound), −0.27 (s, 3H, SiMe' in meso-compound).

$^{13}$C{$^1$H} NMR (CDCl$_3$): δ 148.4, 148.3, 145.9*, 145.1, 145.0, 128.4*, 126.5*, 124.2, 124.1, 121.8*, 114.1*, 48.6, 48.5, 17.9*, −5.4*, −5.6 (* two resonance of rac- and meso-isomers).

Example 1-Cl

Synthesis of bis(4-chloro-2-methyl-1H-inden-1-yl)(dimethyl)silane (1-Cl)

4-chloro-2-methyl-1-indanone via 3-(2-chlorophenyl)-2-methylpropanoic acid via 3-(2-chlorophenyl)-2-methylpropanoyl chloride

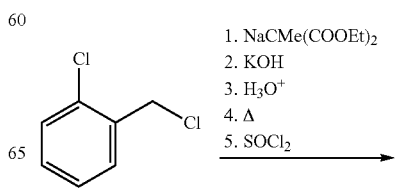

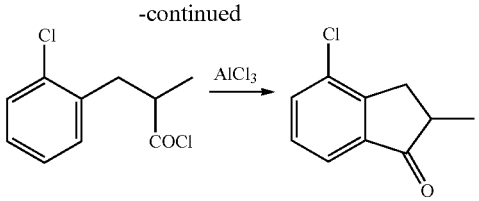

In a 2000 ml three-necked round-bottom flask equipped with a reflux condenser, dropping funnel with pressure-equalizing, and magnetic stirring bar, 19.5 g (0.87 mol) of sodium metal was dissolved in 480 ml of dry ethanol. To the resulting solution, 141 g (0.84 mol) of diethylmethylmalonate in 150 ml of dry ethanol was added dropwise within 15 min. This mixture was stirred for 15 min; then, 108 ml (138 g, 086 mol) of o-chlorobenzyl chloride was added, while vigorously stirring, at a rate that allowed the reaction mixture to maintain a gentle reflux. This mixture was further refluxed for 4 hours and, then, cooled to room temperature. A solution of 168 g of potassium hydroxide in 450 ml of water was added. The resulting mixture was refluxed for 3 hours to saponificate the ester formed. Ethanol and water were distilled off. To the residue, 500 ml of water and, then, 12 M HCl (to pH 1) were added. The substituted methylmalonic acid precipitate was separated, washed with 2×200 ml of cold water, and dried in vacuum. Crude 3-(2-chlorophenyl)-2-methylpropanoic acid was obtained after decarboxylation of the substituted methylmalonic acid by heating it at 180° C. for 2 hours. This product was used without further purification. A mixture of this acid with 210 ml of $SOCl_2$ was stirred for 24 hours at ambient temperature. Thionyl chloride was distilled off. Fractional distillation gave 147 g of a colorless oil, 3-(2-chlorophenyl)-2-methylpropanoyl chloride, b.p. 115-117° C./7 mm Hg. This acid chloride was dissolved in 300 ml of $CH_2Cl_2$ and was added dropwise, while vigorously stirring, to a suspension of 170 g (1.28 mol) of $AlCl_3$ in 1500 ml of $CH_2Cl_2$ over a period of 2 hours at 0° C. Then, this mixture was refluxed for 3 hours, cooled to ambient temperature, and poured over 500 $cm^3$ of ice. The organic layer was separated. The aqueous layer was extracted with 3×300 ml of methyl-tert-butyl ether. The combined organic fractions were dried over $K_2CO_3$ and evaporated to dryness. Fractional distillation gave 106 g (76%) of 4-chloro-2-methyl-1-indanone, b.p. 128° C./10 mm Hg.

Anal. calc. for $C_{10}H_9ClO$: C, 66.49; H, 5.02. Found: C, 66.32; H, 4.95.

$^1$H NMR ($CDCl_3$): δ 7.60 (m, 1H, 7-H), 7.52 (dd, J=7.8 Hz, J=0.9 Hz, 1H, 5-H), 7.29 (m, 1H, 6-H), 3.35 (m, 1H, 2-H), 2.69 (m, 2H, $CH_2$), 1.30 (d, 3H, Me).

$^{13}$C NMR ($CDCl_3$): δ 207.5, 150.4, 137.7, 133.6, 132.2, 128.4, 121.6, 41.3, 33.3, 15.5.

Mixture of 4-chloro-2-methyl-1H-indene and 7-chloro-2-methyl-1H-indene

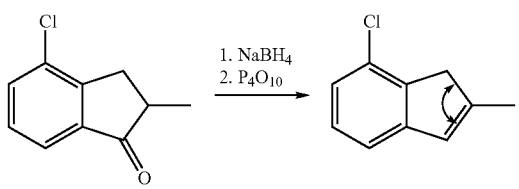

To a solution of 106 g (0.59 mol) of 4-chloro-2-methyl-1-indanone in 1000 ml of THF-methanol (2:1, vol.) 48.4 g (1.29 mol) of $NaBH_4$ were added in small portions over a period of 2 hours at −5° C. (Caution: temperature must be lower than 0° C.). The mixture was stirred for 12 hours at ambient temperature and, then, poured over 1000 $cm^3$ of ice, and acidified with 10% HCl to pH=4. The organic layer was separated. The aqueous layer was extracted with 3×300 ml of methyl-tert-butyl ether. The combined organic fractions were dried over $K_2CO_3$ and evaporated to dryness. To the yellowish oil obtained 1500 ml of toluene were added. This toluene solution was treated with a catalytic amount of $^pTolSO_3H$ (ca. 2 g) for 2 hours at reflux. Then, the mixture was cooled to room temperature and passed through a short Silica Gel 60 column (40-63 μm, d 80 mm, 150 mm). This column was additionally eluted with 500 ml of toluene. The chromatographed product was evaporated to dryness. Fractional distillation gave the chloro-substituted indenes, b.p. 120-125° C./10 mm Hg. Yield 89.9 g (97%) of colorless oil of ca. 1 to 9 mixture of 4-chloro-2-methylindene and 7-chloro-2-methylindene.

Anal. calc. for $C_{10}H_9Cl$: C, 72.96; H, 5.51. Found: C, 72.80; H, 5.47.

$^1$H NMR ($CDCl_3$): 4-chloro-2-methylindene, δ 7.14-7.31 (m, 3H, 5,6,7-H), 6.72 (m, 1H, 3-H), 3.38 (m, 2H, 1,1'-H), 2.23 (s, 3H, 2-Me); 7-chloro-2-methylindene, □ 7.14-7.31 (m, 3H, 4,5,6-H), 6.53 (m, 1H, 3-H), 3.36 (m, 2H, 1,1'-H), 2.23 (s, 3H, 2-Me).

$^{13}$C NMR ($CDCl_3$): 7-chloro-2-methylindene, δ 147.9, 147.2, 141.3, 129.7, 128.3, 127.4, 124.1, 118.5, 42.6, 17.0.

Bis(4-chloro-2-methyl-1H-inden-1-yl)(dimethyl) silane (1-Cl)

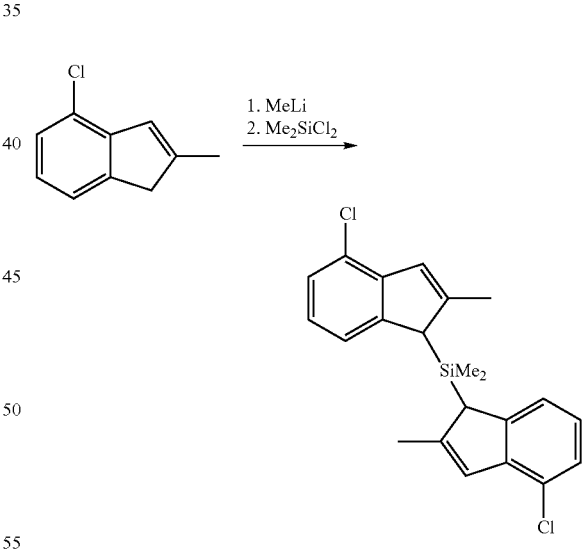

In argon atmosphere to a solution of 6.15 g (37.4 mmol) of 2-methyl-4/7-chloroindenes in 200 ml of diethyl ether, 23.4 ml of 1.6 M MeLi (37.4 mmol) in ether was added at 0° C. This mixture was stirred for 2 hour at 20° C. and, then, cooled to 0° C. At this temperature, 2.26 ml (2.41 g, 18.7 mmol) of $Me_2SiCl_2$ was added. The resulting mixture was stirred for 2 hours at ambient temperature; then 100 ml of water was added. The organic layer was separated, dried over $K_2CO_3$, and evaporated to dryness. The residue was re-crystallized from hexanes. Yield 5.37 g (69%) of white solid of ca. 1 to 1 mixture of rac- and meso-compounds.

Anal. calc. for $C_{22}H_{22}Cl_2Si$: C, 68.56; H, 5.75. Found: C, 68.70; H, 5.88.

$^1$H NMR (CDCl$_3$): δ 7.18 (m, 2H, 5,5'-H in rac- or meso-compound), 7.15 (m, 2H, 5,5'-H in meso- or rac-compound), 7.09 (d, J=7.9 Hz, 2H, 7,7'-H in rac- or meso-compound), 7.07 (d, J=7.9 Hz, 2H, 7,7'-H in meso- or rac-compound), 6.90 (m, 6,6'-H in rac- or meso-compound), 6.88 (m, 2H, 6,6'-H in meso- or rac-compound), 6.63 (m, 4H, 3,3'-H in rac- and meso-compounds), 3.59 (m, 2H, CHSi, CHSi' in rac- or meso-compound), 3.58 (m, 2H, CHSi, CHSi' in meso- or rac-compound), 2.11 (d, 6H, J=1.0 Hz, 2,2'-Me in rac- or meso-compound), 2.06 (d, 6H, J=1.0 Hz, 2,2'-Me in meso- or rac-compound), −0.33 (s, 3H, SiMe in meso-compound), −0.38 (s, 6H, SiMe$_2$ in rac-compound), −0.40 (s, 3H, SiMe' in meso-compound).

$^{13}$C{$^1$H} NMR (CDCl$_3$): δ 148.31, 148.24, 146.1*, 143.15, 143.05, 128.0, 126.3, 125.3*, 124.6*, 123.88, 123.82, 121.3, 48.3, 48.2, 17.9*, −5.52, −5.59, −5.8 (* two resonance of rac- and meso-isomers).

Example 1a

Synthesis of bis(4-phenyl-2-methyl-1H-inden-1-yl)(dimethyl)silane (1a)

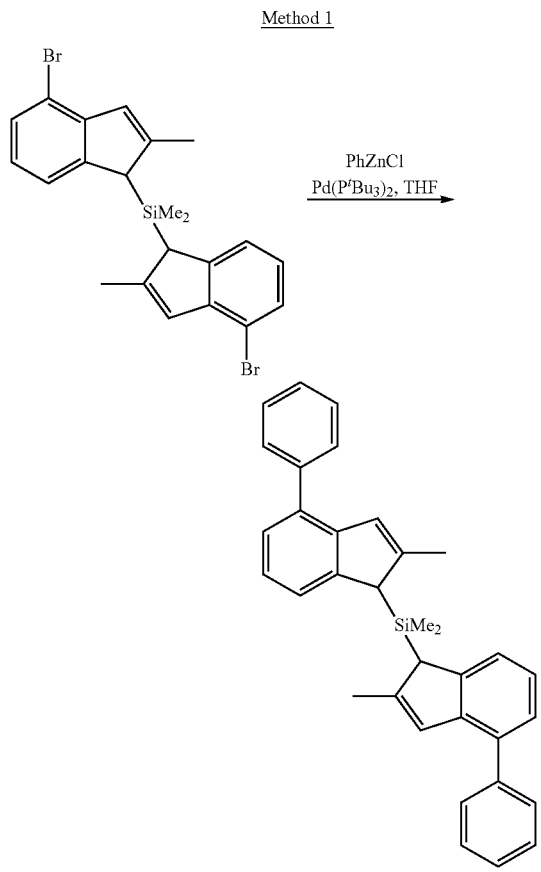

Method 1

In an argon atmosphere, to a solution of 15 mL of THF with 29.0 ml of 0.5 M ZnCl$_2$ (14.5 mmol) in THF 13.0 ml of 1.0 M phenylmagnesium bromide (13.0 mmol) in THF was added at ambient temperature. This mixture was stirred for 1 hour, and, then, 10.0 ml of 0.02 M Pd(P$^t$Bu$_3$)$_2$ (0.20 mmol, 4 mol. %) in THF and 2.37 g (5.0 mmol) of 1 were added. The resulting mixture was stirred for 5 hours at reflux. The product was isolated by flash chromatography on Silica Gel 60 (40-63 µm, d 30 mm, l 100 mm; eluent: hexanes). Yield 2.27 g (97%) of white solid of ca. 1 to 1 mixture of rac- and meso-compounds.

Anal. calc. for $C_{34}H_{32}Si$: C, 87.13; H, 6.88. Found: C, 87.30; H, 6.93.

$^1$H NMR (CDCl$_3$): δ 7.60-7.16 (m, 18H, 5,5',6,6',7,7'-H in indenyl and Ph in rac- and meso-compounds), 6.84 (m, 2H, 3,3'-H in indenyl of rac- or meso-compound), 6.82 (m, 2H, 3,3'-H in indenyl of meso- or rac-compound), 3.83 (s, 4H, 1,1'-H in indenyl of rac- and meso-compounds), 2.27 (d, J=0.9 Hz, 6H, 2,2'-Me in rac- or meso-compound), 2.19 (d, J=0.9 Hz, 6H, 2,2'-Me in meso- or rac-compound), −0.150 (s, 3H, SiMe in meso-compound), −0.152 (s, 6H, SiMe$_2$ in rac-compound), −0.17 (s, 3H, SiMe' in meso-compound).

$^{13}$C{$^1$H} NMR (CDCl$_3$): δ 147.7, 147.6, 145.52, 145.48, 143.0, 142.9, 141.40, 141.36, 134.2*, 128.9*, 128.4*, 126.7*, 126.05, 126.00, 125.60, 125.58, 123.11, 123.05, 122.19, 122.14, 47.7, 47.6, 18.0, 17.9, −5.57*, −5.60 (* two resonance of rac- and meso-isomers).

Method 2

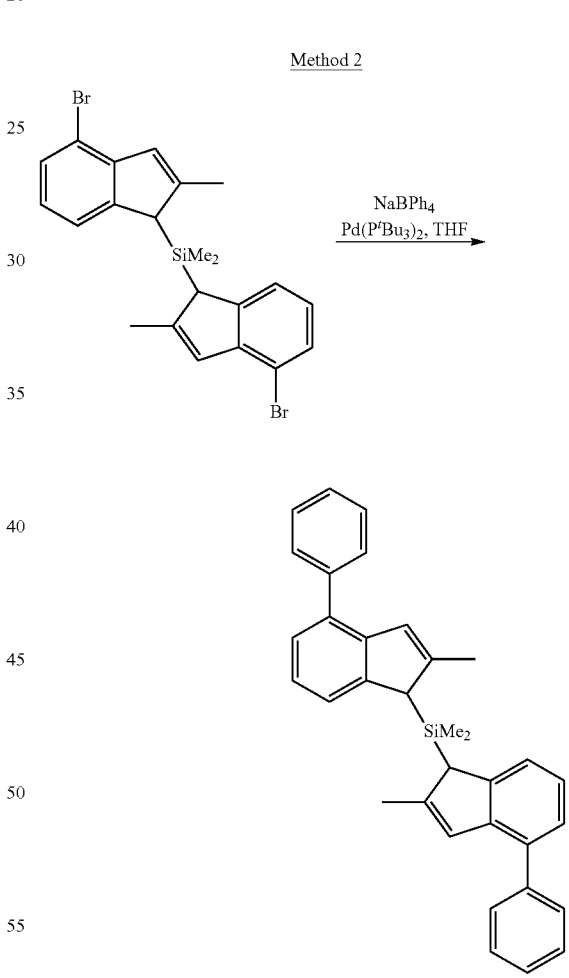

In an argon atmosphere, a mixture of 1.75 g (5.1 mmol) of NaBPh$_4$, 2.37 g (5.0 mmol) of 1, 10.0 ml of 0.02 M Pd(P$^t$Bu$_3$)$_2$ (0.20 mmol, 4 mol. %) in THF, and 50 ml of THF were stirred for 15 hours at reflux. The product was isolated by flash chromatography on Silica Gel 60 (40-63 µm, d 30 mm, l 100 mm; eluent: hexanes). Yield 2.30 g (98%) of white solid of ca. 1 to 1 mixture of rac- and meso-compounds.

Anal. calc. for $C_{34}H_{32}Si$: C, 87.13; H, 6.88. Found: C, 87.38; H, 6.80.

Example 1a@

Synthesis of rac-dimethylsilyl-bis(η⁵-2-methyl-4-phenylinden-1-yl)zirconium dichloride (1a@)

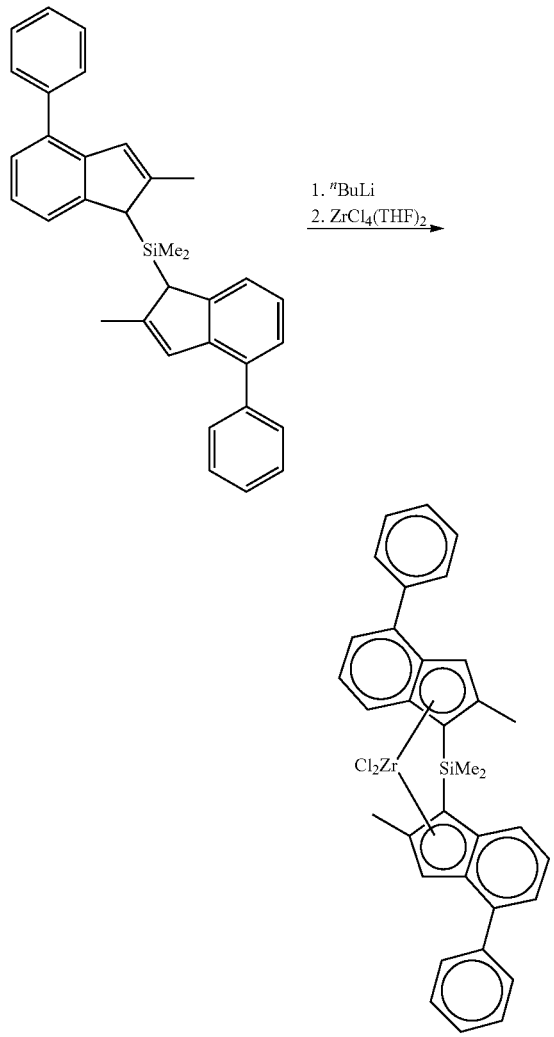

In the Glove Box, to a solution of 2.15 g (4.6 mmol) of 1a in 100 ml of ether, 3.7 ml of 2.5M ⁿBuLi (9.2 mmol) in hexanes was added at ambient temperature. This mixture was stirred for 24 hours and, then, cooled to −78° C.; 1.74 g (4.6 mmol) of $ZrCl_4(THF)_2$ was added. The resulting mixture was stirred for 24 hours at room temperature and, then, evaporated to dryness. To the residue 100 ml of toluene was added. This mixture was stirred for 8 hours at 90° C. The hot solution was filtered through a glass frit (G4). The residue was additionally washed with 5×70 ml of hot toluene. The filtrate was evaporated to dryness. The solid obtained was recrystallized from dichloromethane. Yield 1.04 g (36%) of orange crystalline solid.

Anal. calc. for $C_{34}H_{30}Cl_2SiZr$: C, 64.94; H, 4.81. Found: C, 65.11; H, 4.92.

¹H NMR ($CD_2Cl_2$): δ 7.66 (m, 2H, 7,7'-H of indenyl), 7.62 (m, 2H, 4,4'-H of Ph), 7.58 (dd, J=6.9 Hz, J=1.5 Hz, 2H, 5,5'-H of indenyl), 7.40 (m, 4H, 3,3',5,5'-H of Ph), 7.33 (m, 2H, 2,2',6,6'-H of Ph), 7.09 (dd, J=8.7 Hz, J=6.9 Hz, 2H, 6,6'-H of indenyl), 6.88 (m, 2H, 3,3'-H of indenyl), 2.21 (d, J=0.5 Hz, 6H, 2,2'-Me of indenyl), 1.32 (s, 6H, $SiMe_2$).

Example 1b

Synthesis of bis[4-(4-methylphenyl)-2-methyl-1H-inden-1-yl] (dimethyl)silane (1b)

Method A

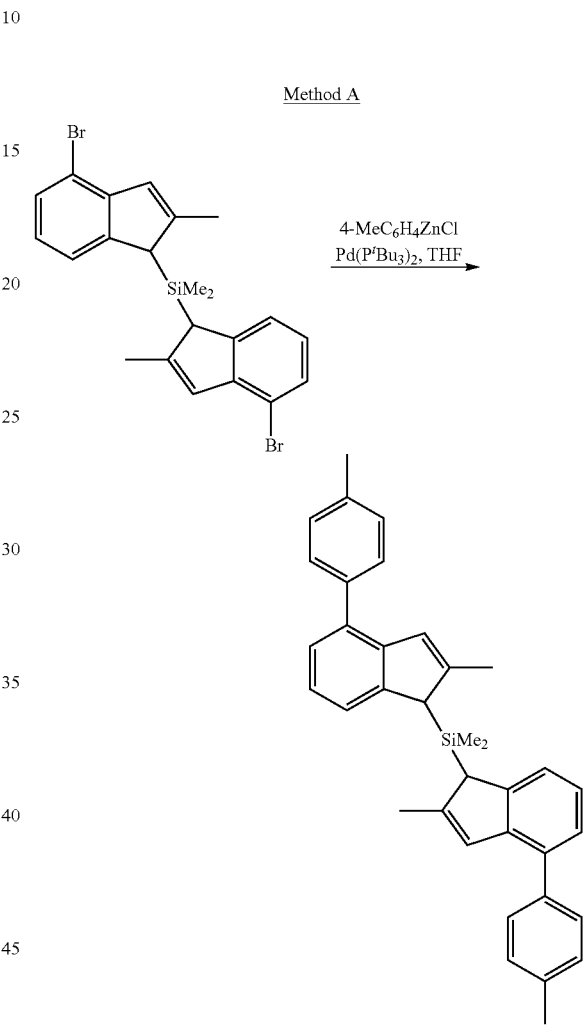

In an argon atmosphere, to a solution of 15 mL of THF with 34.0 ml of 0.5 M $ZnCl_2$ (17.0 mmol) in THF, 15.2 ml of 1.0 M p-tolylmagnesium bromide (15.2 mmol) in THF was added at ambient temperature. This mixture was stirred for 1 hour, and, then, 11.7 ml of 0.02 M $Pd(P^tBu_3)_2$ (0.23 mmol, 4 mol. %) in THF and 2.78 g (5.86 mmol) of 1 were added. The resulting mixture was stirred for 5 hours at reflux. The product was isolated by flash chromatography on Silica Gel 60 (40-63 µm, d 30 mm, 1 100 mm; eluent: hexanes). Yield 2.79 g (96%) of white solid of ca. 1 to 1 mixture of rac- and meso-compounds.

Anal. calc. for $C_{36}H_{36}Si$: C, 87.04; H, 7.30. Found: C, 87.22; H, 7.39.

¹H NMR ($CDCl_3$): δ 7.45-7.51 (m, 6H, 7,7'-H in indenyl of rac-compound and 3,3',5,5'-H in p-tolyl of rac- and meso-compounds), 7.38 (m, 2H, 7,7'-H in indenyl of meso-compound), 7.27-7.32 (m, 12H, 5,5'-H in indenyl and 2,2',6,6'-H in p-tolyl of rac- and meso-compounds), 7.16-7.22 (m, 4H, 6,6'-H in indenyl of rac- and meso-compounds), 6.84 (m, 2H, 3,3'-H in indenyl of meso-compound), 6.82 (m, 2H, 3,3'-H in indenyl of rac-compound), 3.82 (s, 4H, 1,1'-H in indenyl rac- and meso-compounds), 2.46 (s, 6H, 4,4'-Me in p-tolyl of rac-compound), 2.45 (s, 6H, 4,4'-Me in p-tolyl of meso-compound), 2.27 (d, J=0.9 Hz, 6H, 2,2'-Me in indenyl of meso-compound), 2.19 (d, J=0.9 Hz, 6H, 2,2'-Me in indenyl of rac-compound), −0.15 (s, 9H, SiMe$_2$ in rac-compound and SiMe in meso-compound), −0.17 (s, 3H, SiMe' in meso-compound).

$^{13}$C{$^1$H} NMR (CDCl$_3$): δ 147.6, 147.4, 145.47, 145.42, 143.0, 142.9, 136.46, 136.41, 136.39, 136.35, 134.1 (two resonances), 129.1 (two resonances), 128.8 (two resonances), 126.1, 126.0, 125.49, 125.46, 123.1, 123.0, 122.0, 121.9, 47.6, 47.5, 21.2 (two resonances), 18.0, 17.9, −5.7 (br.s, three resonances).

Method B

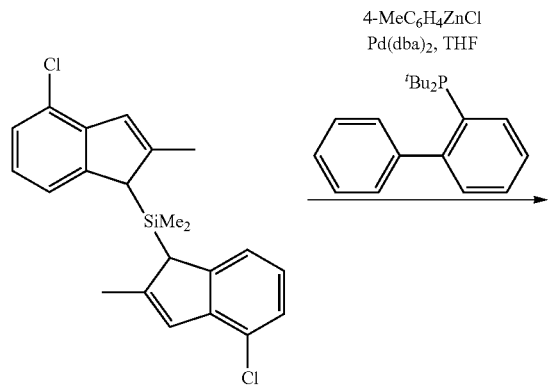

1100 mm; eluent: hexanes). Yield 1.59 g (82%) of white solid of ca. 1 to 1 mixture of rac- and meso-compounds.

Anal. calc. for C$_{36}$H$_{36}$Si: C, 87.04; H, 7.30. Found: C, 87.14; H, 7.25.

Example 1b@

Synthesis of rac-dimethylsilyl-bis(η$^5$-2-methyl-4-p-tolylinden-1-yl)zirconium dichloride (1b@)

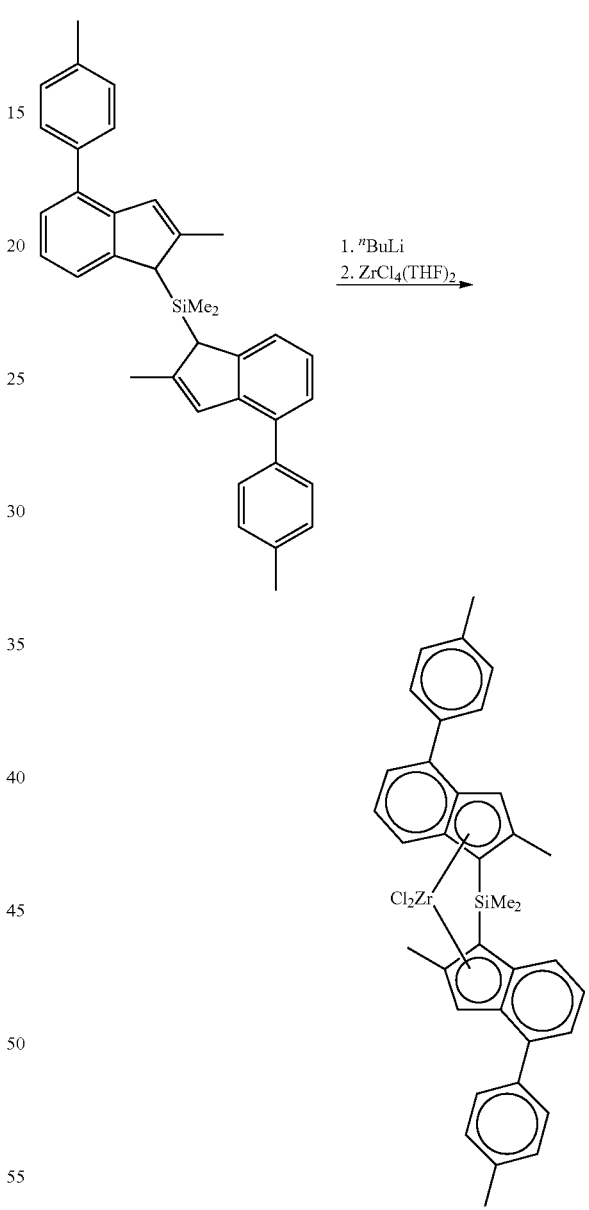

In an argon atmosphere, to a solution of 20 mL of THF with 22.7 ml of 0.5 M ZnCl$_2$ (11.3 mmol) in THF, 10.1 ml of 1.0 M p-tolylmagnesium bromide (10.1 mmol) in THF was added at ambient temperature. This mixture was stirred for 1 hour, and, then, 86.3 mg (0.15 mmol, 4 mol. %) of Pd(dba)$_2$, 89.5 mg (0.30 mmol) of 2-di-tert-butylphosphinobiphenyl, and 1.85 g (3.91 mmol) of 1-Cl were added. The resulting mixture was stirred for 15 hours at reflux. The product was isolated by flash chromatography on Silica Gel 60 (40-63 µm, d 30 mm, In the Glove Box, to a solution of 2.48 g (5.0 mmol) of 1b in 100 ml of ether, 4.0 ml of 2.5M $^n$BuLi (10.0 mmol) in hexanes was added at ambient temperature. This mixture was stirred for 24 hours and, then, cooled to −78° C.; 1.89 g (5.0 mmol) of ZrCl$_4$(THF)$_2$ was added. The resulting mixture was stirred for 24 hours at room temperature and, then, evaporated to dryness. To the residue 100 ml of toluene was added. This mixture was stirred for 8 hours at 90° C. The hot solution was filtered through a glass frit (G4). The residue was additionally washed with 3×50 ml of hot toluene. The filtrate was evaporated to dryness. The solid obtained was recrystallized from dichloromethane. Yield 0.92 g (28%) of orange crystalline solid.

Anal. calc. for $C_{36}H_{34}Cl_2SiZr$: C, 65.83; H, 5.22. Found: C, 65.97; H, 5.04.

$^1$H NMR ($CD_2Cl_2$): δ 7.63 (d, J=8.7 Hz, 2H, 7,7'-H of indenyl), 7.46 (m, 4H, 2,2',6,6'-H of p-tolyl), 7.30 (d, J=7.0 Hz, 2H, 5,5'-H of indenyl), 7.21 (m, 4H, 3,3',5,5'-H of p-tolyl), 7.06 (dd, J=8.7 Hz, J=7.0 Hz, 2H, 6,6'-H of indenyl), 6.86 (s, 2H, 3,3'-H of indenyl), 2.33 (s, 6H, 4,4'-Me of p-tolyl), 2.20 (s, 6H, 2,2'-Me of indenyl), 1.30 (s, 6H, $SiMe_2$).

Example 1c

Synthesis of bis[4-(2,4,6-trimethylphenyl)-2-methyl-1H-inden-1-yl](dimethyl)silane (1c)

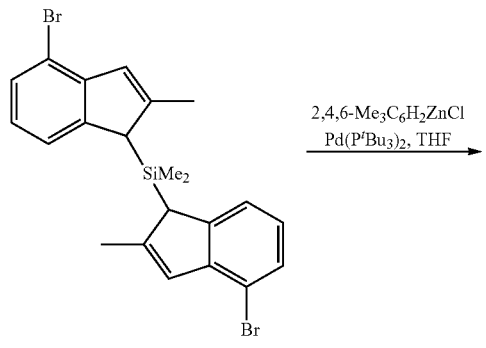

In an argon atmosphere, to a solution of 15 mL of THF with 29.0 ml of 0.5 M $ZnCl_2$ (14.5 mmol) in THF. 13.0 ml of 1.0 M mesitylmagnesium bromide (13.0 mmol) in THF was added at ambient temperature. This mixture was stirred for 1 hour, and, then, 10.0 ml of 0.02 M $Pd(P^tBu_3)_2$ (0.20 mmol, 4 mol. %) in THF and 2.51 g (5.0 mmol) of 1 were added. The resulting mixture was stirred for 5 hours at reflux. The product was isolated by flash chromatography on Silica Gel 60 (40-63 µm, d 30 mm, l 100 mm; eluent: hexanes). Yield 2.60 g (94%) of white solid of ca. 1 to 1 mixture of rac- and meso-compounds.

Anal. calc. for $C_{40}H_{44}Si$: C, 86.90; H, 8.02. Found: C, 87.17; H, 8.10.

$^1$H NMR ($CDCl_3$): δ 7.72 (d, J=7.5 Hz, 2H, 7,7'-H in indenyl of rac- or meso-compound), 7.49 (d, J=7.5 Hz, 2H, 7,7'-H in indenyl of meso- or rac-compound), 7.29 (t, J=7.5 Hz, 2H, 6,6'-H in indenyl of rac- or meso-compound), 7.24 (t, J=7.5 Hz, 2H, 6,6'-H in indenyl of meso- or rac-compound), 7.05-7.13 (m, 12H, 6,6'-H in indenyl and 3,3',5,5'-H in mesityl of rac- and meso-compounds), 6.31 (s, 4H, 3,3'-H in indenyl of rac- and meso-compounds), 4.03 (s, 2H, 1,1'-H in indenyl of rac- or meso-compound), 4.00 (s, 2H, 1,1'-H in indenyl of meso- or rac-compound), 2.45 (s, 12H, 2,6-Me in mesityl of rac- or meso-compound), 2.34 (d, J=0.9 Hz, 6H, 2,2'-Me in indenyl of rac- or meso-compound), 2.23 (d, J=0.9 Hz, 6H, 2,2'-Me in indenyl of meso- or rac-compound), 2.11 (s, 6H, 4,4'-H in mesityl of rac- or meso-compound), 2.10 (s, 6H, 4,4'-H in mesityl of meso- or rac-compound), 2.07 (s, 12H, 2,6-Me in mesityl of meso- or rac-compound), −0.22 (s, 3H, SiMe of meso-compound), −0.246 (s, 3H, SiMe' of meso-compound), −0.252 (s, 6H, $SiMe_2$ of rac-compound).

$^{13}C\{^1H\}$ NMR ($CDCl_3$): δ 147.01, 146.97, 144.75, 144.70, 144.0, 143.9, 137.5*, 136.28*, 136.23*, 132.9, 132.8, 127.93*, 127.89*, 126.0*, 123.0, 122.9, 121.6*, 47.63, 47.61, 21.1*, 20.5*, 18.0, 17.8, −6.3, −6.8* (* two resonance of rac- and meso-isomers).

Example 1c@

Synthesis of rac-dimethylsilyl-bis($\eta^5$-2-methyl-4-mesitylinden-1-yl)zirconium dichloride (1c@)

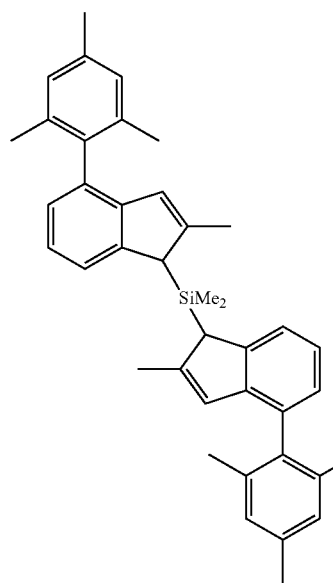

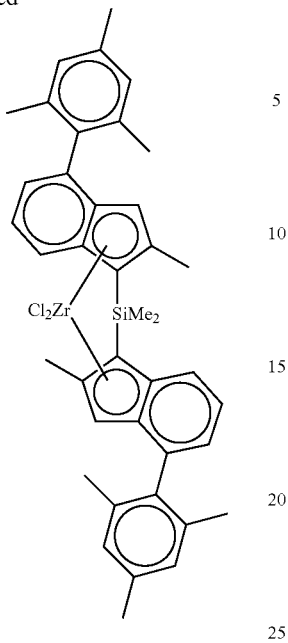

In the Glove Box, to a solution of 2.43 g (4.4 mmol) of 1c in 100 ml of ether, 3.5 ml of 2.5M "BuLi (8.8 mmol) in hexanes was added at ambient temperature. This mixture was stirred for 24 hours and, then, cooled to −78° C.; 1.66 g (4.4 mmol) of ZrCl$_4$(THF)$_2$ was added. The resulting mixture was stirred for 24 hours at room temperature and, then, evaporated to dryness. To the residue 100 ml of toluene was added. This mixture was stirred for 8 hours at 90° C. The hot solution was filtered through a glass frit (G4). The residue was additionally washed with 3×50 ml of hot toluene. The filtrate was evaporated to dryness. The solid obtained was recrystallized from dichloromethane. Yield 0.78 g (25%) of red crystalline solid.

Anal. calc. for $C_{40}H_{42}Cl_2SiZr$: C, 67.38; H, 5.94. Found: C, 67.45; H, 6.00.

$^1$H NMR (CD$_2$Cl$_2$): δ 7.63 (dt, J=8.6 Hz, J=0.9 Hz, 2H, 7,7'-H of indenyl), 7.10 (dd, J=6.9 Hz, J=0.9 Hz, 2H, 5,5'-H of indenyl), 7.02 (dd, J=8.6 Hz, J=6.9 Hz, 2H, 6,6'-H of indenyl), 6.89 (s, 2H, 3,3'-H of mesityl), 6.80 (s, 2H, 5,5'-H of mesityl), 6.35 (s, 2H, 3,3'-H of indenyl), 2.32 (s, 6H, 2,2'-Me of mesityl), 2.29 (s, 6H, 4,4'-Me of mesityl), 2.25 (s, 6H, 6,6'-Me of mesityl), 1.52 (s, 6H, 2,2'-Me), 1.28 (s, 6H, SiMe$_2$).

$^{13}$C{$^1$H} NMR (CD$_2$Cl$_2$): δ 139.3, 138.6, 138.5, 138.2, 137.5, 137.4, 137.1, 128.4, 72.5, 23.0, 22.2, 21.6, 20.2, 3.7.

Example 1d

Synthesis of bis[4-(3-trifluoromethylphenyl)-2-methyl-1H-inden-1-yl](dimethyl)silane (1d)

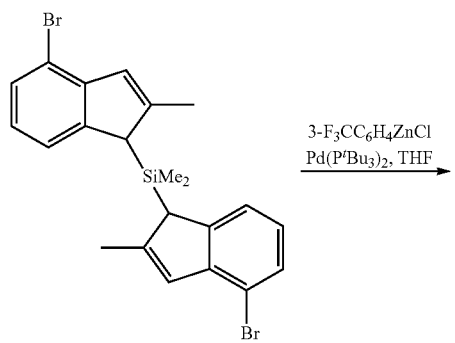

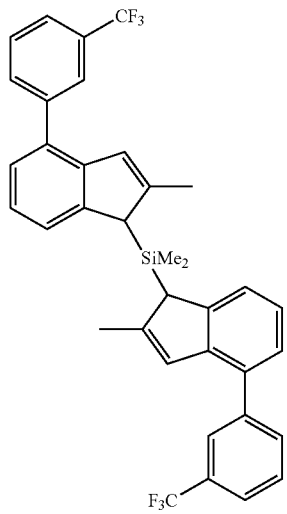

In an argon atmosphere, to a solution of 28.0 ml of 15 mL of THF with 0.5 M ZnCl$_2$ (14.0 mmol) in THF, 12.3 ml of 1.02 M 3-trifluoromethylphenylmagnesium bromide (12.6 mmol) in THF was added at ambient temperature. This mixture was stirred for 1 hour, and, then, 9.66 ml of 0.02 M Pd(P$^t$Bu$_3$)$_2$ (0.19 mmol, 4 mol. %) in THF and 2.42 g (4.83 mmol) of 1 were added. The resulting mixture was stirred for 5 hours at reflux. The product was isolated by flash chromatography on Silica Gel 60 (40-63 μm, d 30 mm, l 100 mm; eluent: hexanes). Yield 2.86 g (98%) of white solid of ca. 1 to 1 mixture of rac- and meso-compounds.

Anal. calc. for $C_{36}H_{30}F_6Si$: C, 71.50; H, 5.00. Found: C, 71.69; H, 5.13.

$^1$H NMR (CDCl$_3$): δ 7.39-7.84 (m, 24H, 5,5',7,7'-H in indenyl and CF$_3$C$_6$H$_4$ of rac- and meso-compound), 7.29 (m, 2H, 6,6'-H in indenyl of rac-compound), 7.23 (t, J=7.5 Hz, 2H, 6,6'-H in indenyl of meso-compound), 6.76 (s, 4H, 3,3'-H in indenyl of rac- and meso-compounds), 3.85 (s, 2H, 1,1'-H in indenyl of rac-compound), 3.82 (s, 2H, 1,1'-H in indenyl of meso-compound), 2.28 (s, 12H, 2,6-Me in mesityl of meso-compound), 2.23 (d, J=0.9 Hz, 6H, 2,2'-Me in indenyl of rac-compound), −0.11 (s, 3H, SiMe of meso-compound), −0.15 (s, 3H, SiMe' of meso-compound), −0.16 (s, 6H, SiMe$_2$ of rac-compound).

$^{13}$C{$^1$H} NMR (CDCl$_3$): δ 148.60, 148.55, 145.7*, 142.95, 142.88, 142.12, 142.10, 132.63, 132.57, 132.2*, 130.9* (q, $^1$J($^{13}$C—$^{19}$F)=32.2 Hz), 128.8*, 125.65, 125.62, 125.57, 125.53, 125.37, 125.34, 123.50, 123.47, 123.43, 122.9, 122.78, 122.75, 47.80, 47.74, 18.0*, −5.33, −5.39, −5.6 (* two resonance of rac- and meso-isomers).

Example 1d@

Synthesis of rac-dimethylsilyl-bis[η⁵-2-methyl-4-(3-trifluoromethylphenyl)inden-1-yl]zirconium dichloride (1d@)

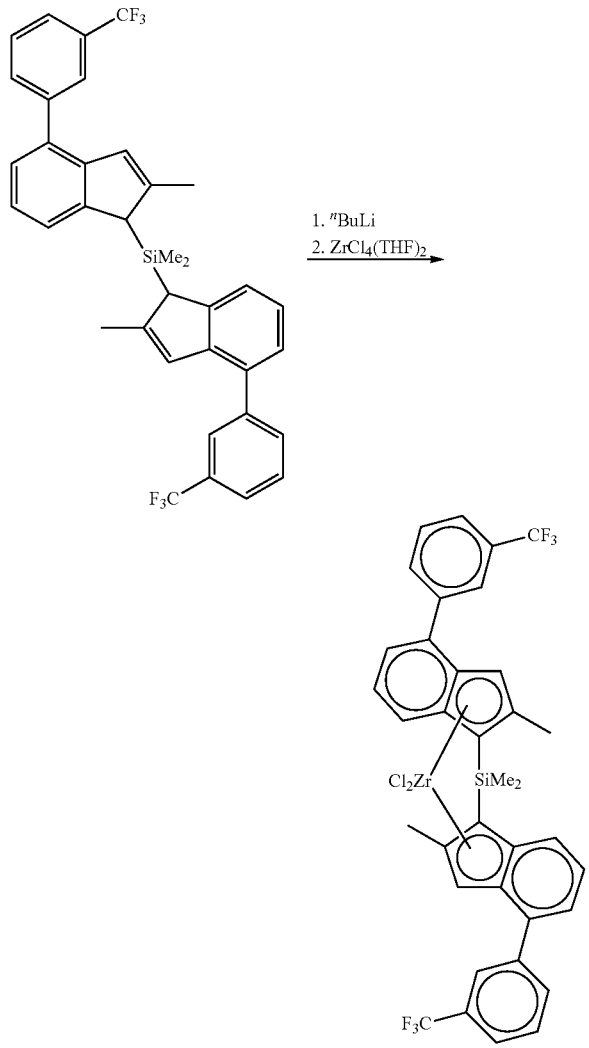

In the Glove Box, to a solution of 2.73 g (4.5 mmol) of 1d in 100 ml of ether, 3.6 ml of 2.5M $^n$BuLi (9.0 mmol) in hexanes was added at ambient temperature. This mixture was stirred for 24 hours and, then, cooled to −78° C.; 1.70 g (4.5 mmol) of ZrCl$_4$(THF)$_2$ was added. The resulting mixture was stirred for 24 hours at room temperature and, then, evaporated to dryness. To the residue 100 ml of toluene was added. This mixture was stirred for 8 hours at 90° C. The hot solution was filtered through a glass frit (G4). The residue was additionally washed with 3×50 ml of hot toluene. The filtrate was evaporated to dryness. The solid obtained was recrystallized from dichloromethane. Yield 0.76 g (22%) of orange crystalline solid.

Anal. calc. for C$_{36}$H$_{28}$Cl$_2$F$_6$SiZr: C, 56.53; H, 3.69. Found: C, 56.70; H, 3.75.

$^1$H NMR (CD$_2$Cl$_2$): δ 7.81-7.90 (m, 4H, 2,2',6,6'-H of C$_6$H$_4$), 7.69-7.74 (m, 2H, 7,7'-H of indenyl), 7.51-7.63 (m, 4H, 5,5',4,4'-H of C$_6$H$_4$), 7.37 (dd, J=7.0 Hz, J=0.6 Hz, 2H, 5,5'-H of indenyl), 7.12 (dd, J=8.7 Hz, J=7.0 Hz, 2H, 6,6'-H of indenyl), 6.84 (s, 2H, 3,3'-H of indenyl), 2.22 (s, 6H, 2,2'-Me of indenyl), 1.33 (s, 6H, SiMe$_2$).

Example 1e

Synthesis of bis[4-(4-N,N-dimethylaminophenyl)-2-methyl-1H-inden-1-yl](dimethyl)silane (1e)

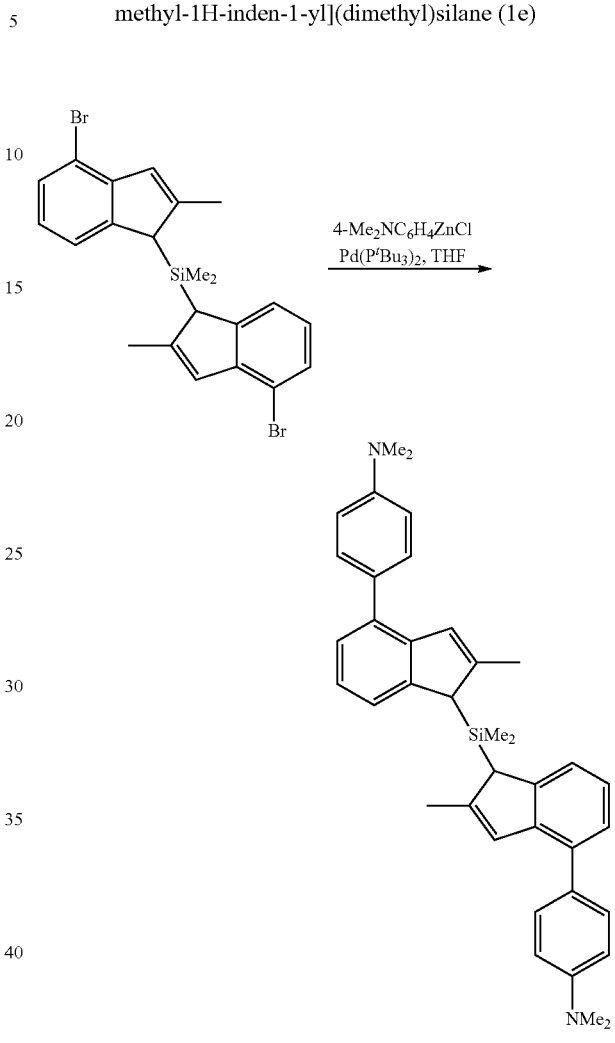

In an argon atmosphere, to a solution of 29.0 ml of 0.5 M ZnCl$_2$ (14.5 mmol) in THF, 26.0 ml of 0.5 M N,N-dimethylaminophenylmagnesium bromide (13.0 mmol) in THF was added at ambient temperature. This mixture was stirred for 1 hour, and, then, 10.0 ml of 0.02 M Pd(P$^t$Bu$_3$)$_2$ (0.20 mmol, 4 mol. %) in THF and 2.51 g (5.0 mmol) of 1 were added. The resulting mixture was stirred for 5 hours at reflux. The product was isolated by flash chromatography on Silica Gel 60 (40-63 μm, d 30 mm, l 100 mm; eluent: hexanes). Yield 2.55 g (92%) of white solid of ca. 1 to 1 mixture of rac- and meso-compounds.

Anal. calc. for C$_{38}$H$_{42}$N$_2$Si: C, 82.26; H, 7.63. Found: C, 82.41; H, 7.58.

$^1$H NMR (CDCl$_3$): δ 7.45-7.51 (m, 6H, 7,7'-H in indenyl of rac-compound and 3,3',5,5'-H in C$_6$H$_4$ of rac- and meso-compounds), 7.34 (d, J=7.5 Hz, 2H, 7,7'-H in indenyl of meso-compound), 7.29 (m, 2H, 6,6'-H in indenyl of rac-compound), 7.26 (m, 2H, 6,6'-H in indenyl of meso-compound), 7.18 (dd, J=7.5 Hz, J=5.9 Hz, 2H, 6,6'-H in indenyl of meso-compound), 7.16 (dd, J=7.5 Hz, J=5.9 Hz, 2H, 6,6'-H in indenyl of rac-compound), 6.85-6.90 (m, 12H, 3,3'-H in indenyl and 2,2',6,6'-H in C$_6$H$_4$ of rac- and meso-compounds), 3.82 (s, 4H, 1,1'-H in indenyl rac- and meso-compounds), 3.04 (s, 12H, 4,4'-NMe$_2$ of rac-compound), 3.03 (s, 12H, 4,4'-NMe$_2$ of meso-compound), 2.27 (d, J=0.9 Hz, 6H, 2,2'-Me in indenyl of meso-compound), 2.18 (d, J=0.9 Hz, 6H, 2,2'-Me in indenyl of rac-compound), −0.16 (s, 6H, SiMe$_2$ in rac-compound), −0.17 (s, 3H, SiMe in meso-compound), −0.19 (and SiMe' in meso-compound).

$^{13}$C{$^1$H} NMR (CDCl$_3$): δ 149.5*, 147.1, 146.9, 145.51, 145.46, 142.84, 142.76, 134.3*, 129.8*, 129.6*, 126.35, 126.30, 125.18, 125.14, 123.02, 122.97, 121.38, 121.32, 112.6*, 47.6, 47.5, 40.7*, 17.94, 17.85, −5.67 (three resonances) (* two resonance of rac- and meso-isomers).

Example 1e@

Synthesis of rac-dimethylsilyl-bis[η$^5$-2-methyl-4-(4-N,N-dimethylaminophenyl)inden-1-yl]zirconium dichloride (1e@)

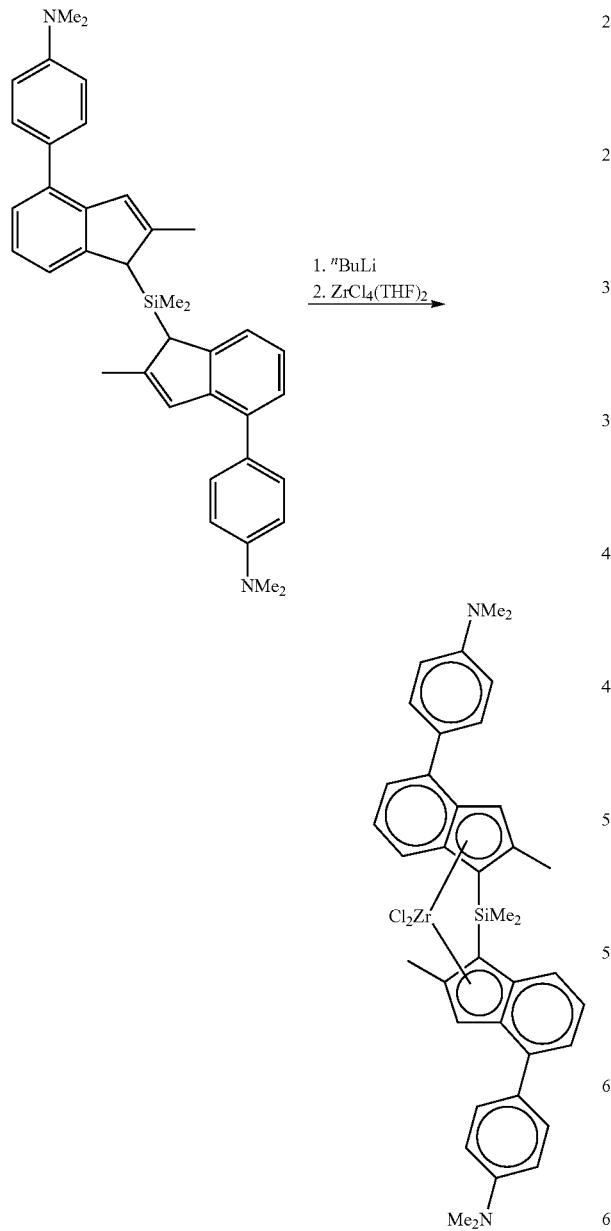

In the Glove Box, to a solution of 2.33 g (4.2 mmol) of 1e in 100 ml of ether, 3.4 ml of 2.5M $^n$BuLi (8.4 mmol) in hexanes was added at ambient temperature. This mixture was stirred for 24 hours and, then, cooled to −78° C.; 1.58 g (4.2 mmol) of ZrCl$_4$(THF)$_2$ was added. The resulting mixture was stirred for 24 hours at room temperature and, then, evaporated to dryness. To the residue 100 ml of toluene was added. This mixture was stirred for 8 hours at 90° C. The hot solution was filtered through a glass frit (G4). The residue was additionally washed with 3×50 ml of hot toluene. The filtrate was evaporated to dryness. The solid obtained was recrystallized from dichloromethane. Yield 0.69 g (23%) of orange crystalline solid.

Anal. calc. for C$_{38}$H$_{40}$Cl$_2$N$_2$SiZr: C, 63.84; H, 5.64. Found: C, 64.05; H, 5.77.

$^1$H NMR (CD$_2$Cl$_2$): δ 7.54-7.70 (m, 6H, 7,7'-H in indenyl and 2,2',6,6'-H in C$_6$H$_4$), 7.27-7.40 (m, 6H, 5,5'-H in indenyl and 3,3',5,5'-H in C$_6$H$_4$), 7.09 (dd, J=8.7 Hz, J=7.2 Hz, 2H, 6,6'-H in indenyl), 6.87 (s, 2H, 3,3'-H in indenyl), 3.15 (s, 12H, 4,4'-NMe$_2$ in C$_6$H$_4$), 2.20 (s, 6H, 2,2'-Me in indenyl), 1.32 (s, 6H, SiMe$_2$).

Example 1f

Synthesis of bis[4-(1-benzothien-2-yl)-2-methyl-1H-inden-1-yl](dimethyl)silane (1f)

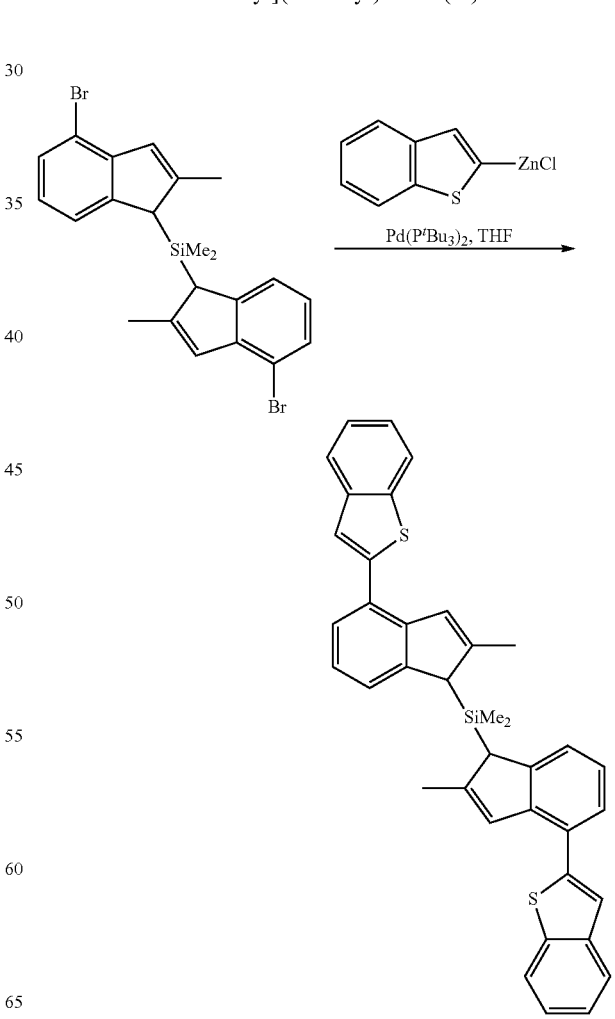

In an argon atmosphere, to a solution of 1.74 g (13.0 mmol) of benzothiophene in 30 ml of THF, 5.24 ml of 2.5 M ⁿBuLi (13.0 mmol) in hexanes was added at ambient temperature. This mixture was stirred for 2 hours, and, then, 29.0 ml of 0.5 M $ZnCl_2$ (14.5 mmol) in THF was added. The resulting mixture was stirred for 1 hour. Then, 10.0 ml of 0.02 M $Pd(P^tBu_3)_2$ (0.20 mmol, 4 mol. %) in THF and 2.37 g (5.0 mmol) of 1 were added. This mixture was stirred for 5 hours at reflux. The product was isolated by flash chromatography on Silica Gel 60 (40-63 μm, d 30 mm, l 100 mm; eluent: hexanes). Yield 2.76 g (95%) of white solid of ca. 1 to 1 mixture of rac- and meso-compounds.

Anal. calc. for $C_{38}H_{32}S_2Si$: C, 78.57; H, 5.55. Found: C, 78.70; H, 5.46.

$^1H$ NMR (CDCl₃): δ 6.96-7.82 (m, 36H, 3,3',5,5',6,6',7,7'-H in indenyls and benzothienyls of rac- and meso-compounds), 3.70 (s, 2H, 1,1'-H in indenyls of rac- or meso-compound), 3.66 (s, 2H, 1,1'-H in indenyls of meso- or rac-compound), 2.22 (m, 6H, 2,2'-Me in indenyls of rac- or meso-compound), 2.07 (m, 6H, 2,2'-Me in indenyls of meso- or rac-compound), −0.11 (s, 3H, SiMe₂ of rac-compound), −0.14 (s, 3H, SiMe of meso-compound), −0.18 (s, 6H, SiMe' of meso-compound).

$^{13}C\{^1H\}$ NMR (CDCl₃): δ 148.7, 148.5, 145.8*, 143.83, 143.81, 143.0, 142.8, 140.5*, 139.77, 149.76, 126.57, 126.55, 126.2, 126.1, 126.0, 125.9, 124.3*, 123.9*, 123.39, 123.35, 123.07, 123.04, 122.9, 122.05, 122.03, 121.5, 47.8, 47.7, 18.0, 17.8, −4.9, −5.1, −5.2 (* two resonance of rac- and meso-isomers).

Example 1f@

Synthesis of rac-dimethylsilyl-bis[η⁵-2-methyl-4-(1-benzothien-2-yl)inden-1-yl]zirconium dichloride (1f@)

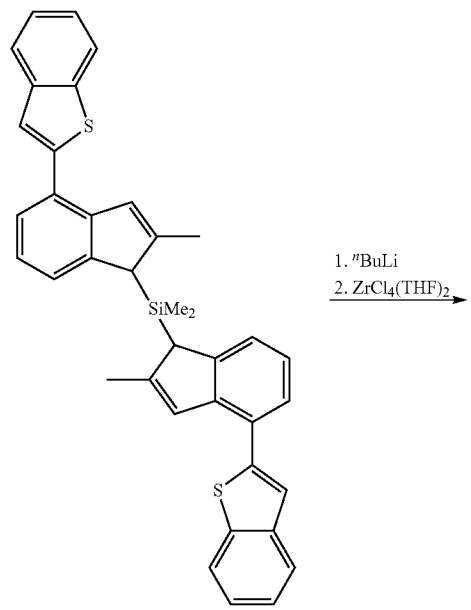

1. ⁿBuLi
2. ZrCl₄(THF)₂

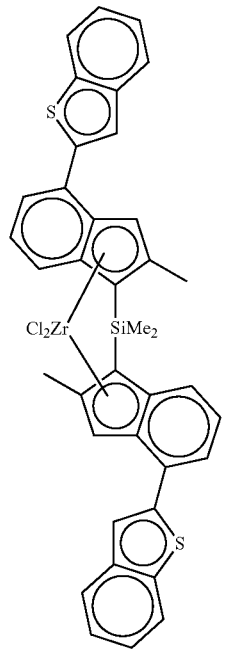

In the Glove Box, to a solution of 2.50 g (4.3 mmol) of 1f in 100 ml of ether, 3.45 ml of 2.5M ⁿBuLi (8.6 mmol) in hexanes was added at ambient temperature. This mixture was stirred for 24 hours and, then, cooled to −78° C.; 1.62 g (4.3 mmol) of ZrCl₄(THF)₂ was added. The resulting mixture was stirred for 24 hours at room temperature and, then, evaporated to dryness. To the residue 100 ml of toluene was added. This mixture was stirred for 8 hours at 90° C. The hot solution was filtered through a glass frit (G4). The residue was additionally washed with 5×70 ml of hot toluene. The filtrate was evaporated to dryness. The solid obtained was recrystallized from dichloromethane. Yield 1.12 g (35%) of orange crystalline solid.

Anal. calc. for $C_{38}H_{30}Cl_2S_2SiZr$: C, 61.59; H, 4.08. Found: C, 61.74; H, 4.17.

$^1H$ NMR (CD₂Cl₂): δ 7.77 (m, 4H, 4,4',7,7'-H of benzothienyl), 7.71 (d, J=8.7 Hz, 2H, 7,7'-H of indenyl), 7.60 (s, 2H, 3,3'-H of benzothienyl), 7.57 (d, J=7.1 Hz, 2H, 5,5'-H of indenyl), 7.29 (m, 4H, 5,5',6,6'-H of benzothienyl), 7.21 (s, 2H, 3,3'-H of indenyl), 7.11 (dd, J=8.7 Hz, J=7.1 Hz, 2H, 6,6'-H of indenyl), 2.26 (s, 6H, 2,2'-Me of indenyl), 1.34 (s, 6H, SiMe₂).

$^{13}C\{^1H\}$ NMR (CD₂Cl₂): δ 144.7, 138.3, 138.1, 137.6, 135.6, 133.3, 130.2, 130.1, 128.3, 128.1 (two resonances), 127.4 (three resonances), 121.8, 120.6, 72.4, 20.7, 0.7.

Example 1g

Synthesis of bis(4,2-dimethyl-1H-inden-1-yl)(dimethyl)silane (1g)

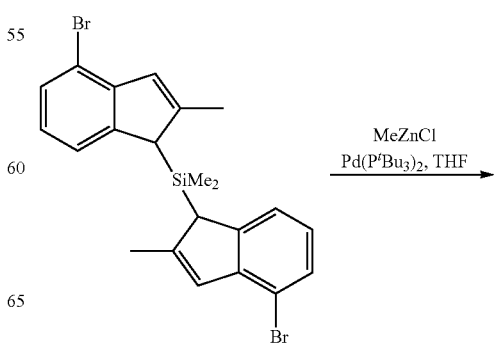

MeZnCl
Pd(P^tBu_3)_2, THF

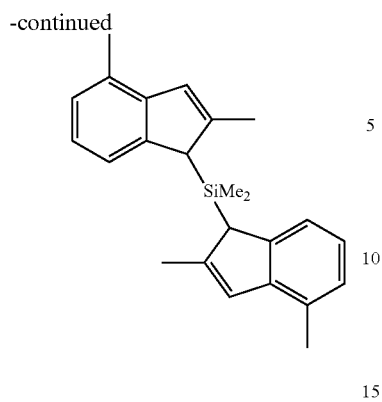

In an argon atmosphere, to a solution of 50 mL of THF with 58.0 ml of 0.5 M ZnCl$_2$ (29.0 mmol) in THF, 8.7 ml of 3.0 M methylmagnesium chloride (26.0 mmol) in THF was added at ambient temperature. This mixture was stirred for 1 hour, and, then, 20.0 ml of 0.02 M Pd(P$^t$Bu$_3$)$_2$ (0.40 mmol, 4 mol. %) in THF and 5.02 g (10.0 mmol) of 1 were added. The resulting mixture was stirred for 5 hours at reflux. The product was isolated by flash chromatography on Silica Gel 60 (40-63 μm, d 50 mm, l 100 mm; eluent: hexanes). Yield 3.34 g (97%) of white solid of ca. 1 to 1 mixture of rac- and meso-compounds.

Anal. calc. for C$_{24}$H$_{28}$Si: C, 83.66; H, 8.19. Found: C, 83.70; H, 8.26.

$^1$H NMR (CDCl$_3$): δ 7.32-7.38 (m, 4H, 7,7'-H in rac- and meso-compounds), 7.19-7.25 (m, 4H, 5,5'-H in rac- and meso-compounds), 6.96-7.06 (m, 4H, 6,6'-H in rac- and meso-compounds), 6.71 (m, 4H, 3,3'-H in rac- and meso-compounds), 3.75 (s, 2H, 1,1'-H in rac-compound), 3.72 (s, 2H, 1,1'-H in meso-compound), 2.45 (s, 6H, 4,4'-Me in rac-compound), 2.44 (s, 6H, 4,4'-Me in meso-compound), 2.26 (d, J=1.0 Hz, 6H, 2,2'-Me in rac-compound), 2.21 (d, J=1.0 Hz, 6H, 2,2'-Me in meso-compound), −0.28 (s, 3H, SiMe in meso-compound), −0.325 (s, 6H, SiMe$_2$ in rac-compound), −0.334 (s, 3H, SiMe' in meso-compound).

$^{13}$C{$^1$H} NMR (CD$_2$Cl$_2$): δ 146.6, 146.5, 144.61, 144.55, 144.26, 144.20, 129.04, 129.01, 126.0 (two resonances), 124.98, 124.95, 122.81, 122.74, 120.71, 120.67, 47.49, 47.42, 18.8 (two resonances), 18.0 (two resonances), −5.7, −5.9, −6.1.

Example 1g@

Synthesis of rac-dimethylsilyl-bis(η$^5$-2,4-dimethyl-inden-1-yl)zirconium dichloride (1g@)

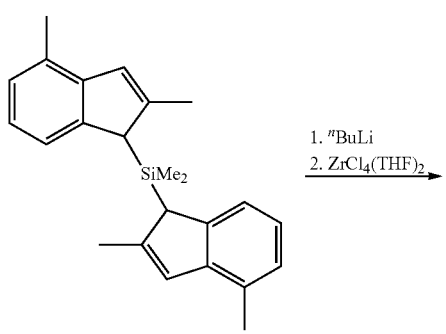

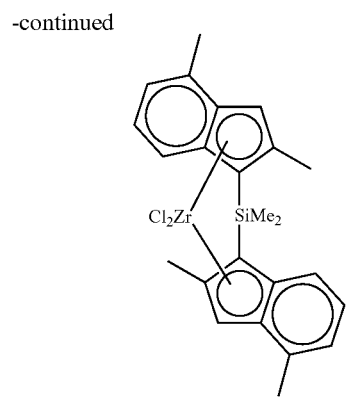

In the Glove Box, to a solution of 3.04 g (5.3 mmol) of 1 g in 100 ml of ether, 4.25 ml of 2.5M $^n$BuLi (10.6 mmol) in hexanes was added at ambient temperature. This mixture was stirred for 24 hours and, then, cooled to −78° C.; 2.00 g (5.3 mmol) of ZrCl$_4$(THF)$_2$ was added. The resulting mixture was stirred for 24 hours at room temperature and, then, evaporated to dryness. To the residue 100 ml of toluene was added. This mixture was stirred for 8 hours at 90° C. The hot solution was filtered through a glass frit (G4). The residue was additionally washed with 3×50 ml of hot toluene. The filtrate was evaporated to dryness. The solid obtained was recrystallized from dichloromethane. Yield 0.80 g (30%) of yellow crystalline solid.

Anal. calc. for C$_{24}$H$_{26}$Cl$_2$SiZr: C, 57.12; H, 5.19. Found: C, 57.22; H, 5.24.

$^1$H NMR (CD$_2$Cl$_2$): δ 7.35-7.41 (m, 2H, 7,7'-H), 6.99-7.04 (m, 2H, 5,5'-H), 6.80-6.87 (m, 2H, 6,6'-H), 6.73 (s, 2H, 3,3'-H), 2.31 (s, 6H, 4,4'-Me), 2.11 (s, 6H, 2,2'-Me), 0.92 (s, 6H, SiMe$_2$).

Example 1i

Synthesis of bis[2-methyl-4-(2-trifluoromethylphenyl)-1H-inden-1-yl](dimethyl)silane (1i)

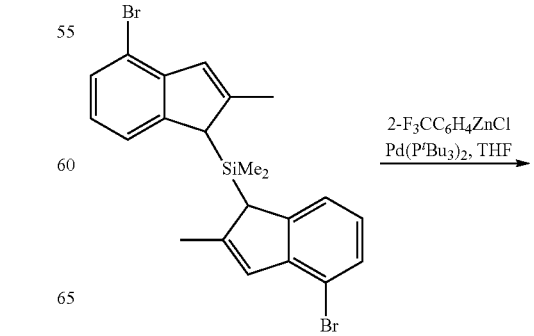

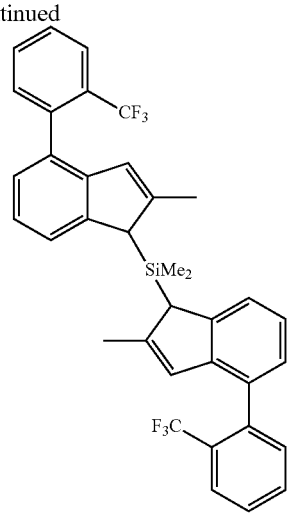

In an argon atmosphere, to a solution of 15 mL of THF with 29.0 ml of 0.5 M ZnCl$_2$ (14.5 mmol) in THF, 13.0 ml of 1.0 M 2-(trifluoromethyl)phenyl magnesium bromide (13.0 mmol) in THF was added at ambient temperature. This mixture was stirred for 1 hour, and, then, 10.0 ml of 0.02 M Pd(P$^t$Bu$_3$)$_2$ (0.20 mmol, 4 mol. %) in THF and 2.37 g (5.0 mmol) of 1 were added. The resulting mixture was stirred for 5 hours at reflux. The product was isolated by flash chromatography on Silica Gel 60 (40-63 μm, d 30 mm, l 100 mm; eluent: hexanes). Yield 2.93 g (97%) of white solid of ca. 1 to 1 mixture of rac- and meso-compounds.

Anal. calc. for C$_{36}$H$_{30}$F$_6$Si: C, 71.50; H, 5.00. Found: C, 71.66; H, 5.12.

$^1$H NMR (CDCl$_3$): δ 7.21-7.94 (m, 28H, 5,5',6,6',7,7'-H in indenyl and 3,3',4,4',5,5',6,6'-H in C$_6$H$_4$ of rac- and meso-isomers), 6.40 (m, 4H, 3,3'-H in indenyl of rac- and meso-isomers), 3.92-4.07 (m, 4H, 1,1'-H in indenyl of rac- and meso-isomers), 2.21-2.39 (m, 12H, 2,2'-Me in indenyl of rac- and meso-isomers), −0.04-0.24 (m, 12H, Me$_2$Si in indenyl of rac- and meso-isomers).

Example 1i@

Synthesis of rac-dimethylsilyl-bis[η$^5$-2-methyl-4-(2-trifluoromethylphenyl)inden-1-yl]zirconium dichloride (1i@)

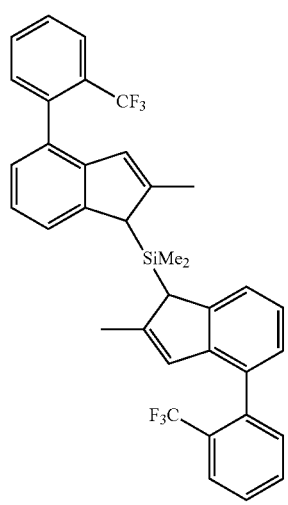

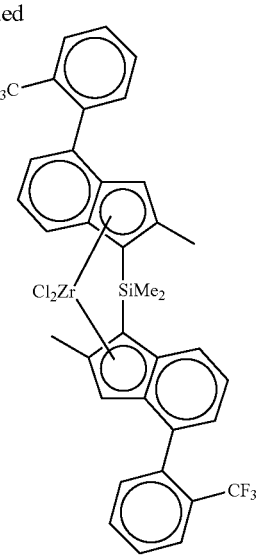

To a solution of 4.84 g (8.0 mmol) of 1i in 150 ml of ether, 6.50 ml 2.5 M (16.3 mmol) of $^n$BuLi in hexanes was added dropwise over 15 min at 0° C. This mixture was stirred for 5 h at room temperature and then cooled to −78° C. Next, 3.02 g (8.0 mmol) of ZrCl$_4$(THF)$_2$ was added. The resulting mixture was slowly (ca. 2 h) warmed to ambient temperature with vigorous stirring and then stirred for 24 h. The organic solvents were distilled off under reduced pressure, and 200 ml of toluene was added. This mixture was stirred for 1 h at 80° C. and then filtered through a glass frit (G4) at this temperature. The filtrate was evaporated to ca. 80 ml. The orange crystals precipitated at −30° C. were collected, washed with 2×5 ml of cold toluene and 3×30 ml of hexanes, and dried in vacuum. This procedure gave 1.71 g (28%) of pure rac-1i@.

Anal. calc. for C$_{36}$H$_{28}$Cl$_2$F$_6$SiZr: C, 56.53; H, 3.69. Found: C, 56.60; H, 3.77.

$^1$H NMR (CD$_2$Cl$_2$): δ 7.85 (m, 2H, 6,6'-H in C$_6$H$_4$), 7.77 (m, 2H, 3,3'-H in C$_6$H$_4$), 7.73 (m, 5,5'-H in indenyl), 7.65 (m, 4,4'-H in C$_6$H$_4$), 7.53 (m, 5,5'-H in C$_6$H$_4$), 7.26 (m, 7,7'-H in indenyl), 7.09 (dd, J=8.8 Hz, J=7.0 Hz, 2H, 6,6'-H in indenyl), 6.41 (s, 2H, 3,3'-H in indenyl), 2.23 (s, 6H, 2,2'-Me in indenyl), 1.34 (s, 6H, SiMe$_2$).

Example 1k

Synthesis of bis[4-(4-tert-butylphenyl)-2-methyl-1H-inden-1-yl](dimethyl)silane (1k)

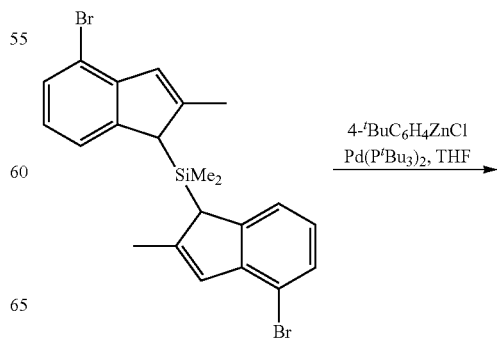

-continued

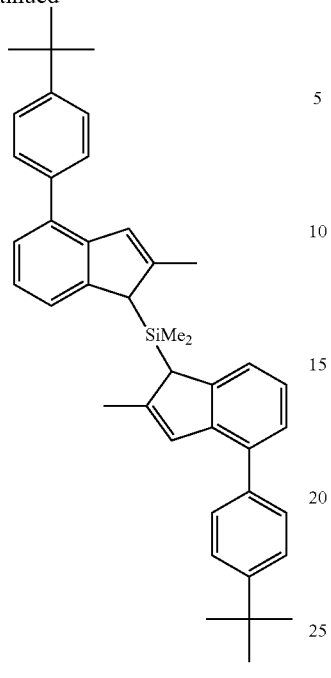

In an argon atmosphere, to a solution of 15 mL of THF with 29.0 ml of 0.5 M ZnCl$_2$ (14.5 mmol) in THF, 13.0 ml of 1.0 M 4-(tert-butyl) phenylmagnesium bromide (13.0 mmol) in THF was added at ambient temperature. This mixture was stirred for 1 hour, and, then, 10.0 ml of 0.02 M Pd(P$^t$Bu$_3$)$_2$ (0.20 mmol, 4 mol. %) in THF and 2.37 g (5.0 mmol) of 1 were added. The resulting mixture was stirred for 5 hours at reflux. The product was isolated by flash chromatography on Silica Gel 60 (40-63 µm, d 30 mm, 1 100 mm; eluent: hexanes). Yield 2.85 g (98%) of white solid of ca. 1 to 1 mixture of rac- and meso-compounds.

Anal. calc. for C$_{42}$H$_{48}$Si: C, 86.84; H, 8.33. Found: C, 86.90; H, 8.39.

$^1$H NMR (CDCl$_3$): δ 7.52-7.57 (m, 18H, 7,7'-H in indenyl of rac- or meso-isomers and 2,2',3,3',5,5',6,6'-H in C$_6$H$_4$ of rac- and meso-isomers), 7.39-7.43 (m, 2H, 7,7'-H in indenyl of meso- or rac-isomers), 7.31-7.36 (m, 4H, 5,5'-H in indenyl of rac- and meso-isomers), 7.19-7.26 (m, 4H, 6,6'-H in indenyl of rac- and meso-isomers), 6.92 (m, 4H, 3,3'-H in indenyl of rac- and meso-isomers), 3.88 (m, 2H, 1,1'-H in indenyl of rac- or meso-isomer), 3.85 (m, 2H, 1,1'-H in indenyl of meso- or rac-isomer), 2.30 (m, 6H, 2,2'-Me in indenyl of rac- or meso-isomer), 2.24 (m, 6H, 2,2'-Me in indenyl of meso- or rac-isomer), 1.46 (s, 18H, $^t$Bu of rac- or meso-isomer), 1.45 (s, 18H, $^t$Bu of meso- or rac-isomer), −0.13 (s, 3H, MeMe'Si of meso-isomer), −0.15 (s, 3H, MeMe'Si of meso-isomer), −0.16 (s, 6H, Me$_2$Si of rac-isomer).

$^{13}$C{$^1$H} NMR (CDCl$_3$): δ 149.6, 147.5, 147.4, 145.52, 145.50, 143.00, 142.95, 138.49, 138.45, 134.09, 134.04, 128.6, 126.3, 126.2, 125.63, 125.58, 125.3, 123.14, 123.06, 122.05, 122.00, 47.7, 47.6, 34.6, 31.5, 18.03, 18.01, −5.58, −5.59, −5.8.

Example 1k@

Synthesis of rac-dimethylsilyl-bis[η5-2-methyl-4-(4-tert-butylphenyl)inden-1-yl]zirconium dichloride (1k@)

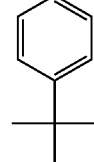

1. $^n$BuLi
2. ZrCl$_4$(THF)$_2$

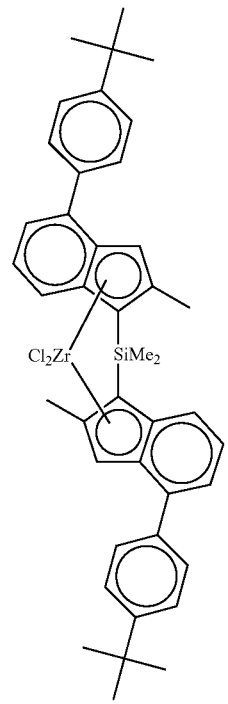

To a solution of 2.91 g (5.0 mmol) of 1k in 100 ml of ether, 4.10 ml 2.5 M (10.3 mmol) of n BuLi in hexanes was added dropwise over 15 min at 0° C. This mixture was stirred for 12 h at room temperature and then cooled to −78° C. Next, 1.89 g (5.0 mmol) of ZrCl$_4$(THF)$_2$ was added. The resulting mixture was slowly (ca. 1.5 h) warmed to ambient temperature with vigorous stirring and then stirred for 12 h. The organic solvents were distilled off under reduced pressure, and 100 ml of toluene was added. This mixture was stirred for 1 h at 80° C. and then filtered through a glass frit (G4) at this temperature. The filtrate was evaporated to ca. 30 ml. The yellow crystals precipitated at −30° C. were collected, washed with 2×5 ml of cold toluene and 3×30 ml of hexanes, and dried in vacuum. This procedure gave 0.67 g (18%) of pure rac-1k@.

Anal. calc. for $C_{42}H_{46}Cl_2SiZr$: C, 68.07; H, 6.26. Found: C, 68.22; H, 6.05.

$^1$H NMR ($CD_2Cl_2$): δ 7.64 (m, 2H, 7,7'-H of indenyl), 7.50-7.56 (m, 4H, 2,2',6,6'-H of $C_6H_4$), 7.41-7.47 (m, 4H, 3,3',5,5'-H of $C_6H_4$) 7.33 (dd, J=7.0 Hz, J=0.8 Hz, 2H, 5,5'-H of indenyl), 7.08 (dd, J=8.7 Hz, J=7.0 Hz, 2H, 6,6'-H of indenyl), 6.91 (m, 2H, 3,3'-H of indenyl), 2.21 (d, J=0.4 Hz, 6H, 2,2'-Me of indenyl), 1.31 (s, 6H, $SiMe_2$), 1.30 (s, 18H, $^tBu$).

Example 2

Synthesis of bis(4-bromo-2,5-dimethyl-1H-inden-1-yl)(dimethyl)silane (2)

3-(2-Bromo-3-methylphenyl)-2-methylpropanoic acid, 3-(2-bromo-3-methylphenyl)-2-methylpropanoyl chloride, and 4-bromo-2,5-dimethyl-1-indanone

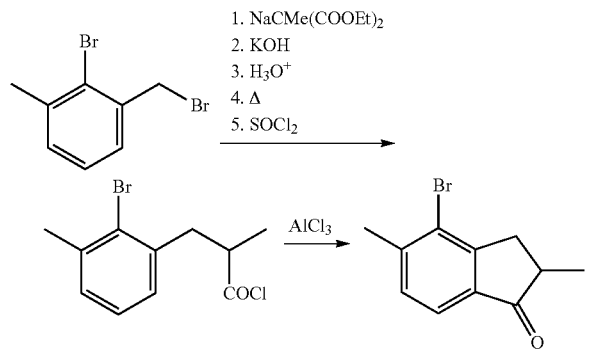

In a three-necked round-bottom 500 ml flask equipped with a reflux condenser, dropping funnel with pressure-equalizing, and magnetic stirring bar 5.95 g (0.26 mol) of sodium metal were dissolved in 200 ml of dry ethanol. To the resulting solution 45.1 g (0.26 mol) of diethylmethylmalonate were added dropwise within 15 min. This mixture was stirred for 15 min; then, 62.1 g (0.24 mol) of 2-bromo-1-(bromomethyl)-3-methylbenzene in 50 ml of ethanol were added, while vigorously stirring, at a rate that allowed the reaction mixture to maintain a gentle reflux. This mixture was further refluxed for 4 h and cooled to room temperature. A solution of 51.8 g of KOH in 150 ml of water was added. This mixture was refluxed for 3 h to saponificate the ester formed. Ethanol and water were distilled off. To the residue 200 ml of water and, then, 12 M HCl (to pH 1) were added. The substituted methylmalonic acid precipitate was separated, washed with 2×60 ml of cold water, and dried overnight on a watch glass. Crude 3-(2-bromo-3-methylphenyl)-2-methylpropanoic acid was obtained after decarboxilation of this substituted methylmalonic acid by heating it at 160° C. for 2 hours. The product was used without further purification. Mixture of this acid and 60 ml of $SOCl_2$ was stirred for 24 h at ambient temperature. Thionyl chloride was distilled off. The crude 3-(2-bromo-3-methylphenyl)-2-methylpropanoyl chloride was dissolved in 200 ml of $CH_2Cl_2$ and was added dropwise, while vigorously stirring, to a suspension of 37.7 g (0.28 mol) of $AlCl_3$ in 800 ml of $CH_2Cl_2$ over a period of 1 h at 0° C. Then, this mixture was refluxed for 3 h, cooled to ambient temperature, and poured over 300 $cm^3$ of ice. The organic layer was separated. The aqueous layer was extracted with 3×100 ml of methyl-tert-butyl ether. The combined organic fractions were dried over $K_2CO_3$ and evaporated to dryness. Fractional distillation gave the title indanone, b.p. 120-121° C./1 mm Hg. Yield 47.6 g (85%) of colorless solid.

Anal. calc. for $C_{11}H_{11}BrO$: C, 55.25; H, 4.64. Found: C, 55.35; H, 4.66.

$^1$H NMR ($CDCl_3$): δ 7.64 (d, J=7.8 Hz, 1H, 7-H), 7.22 (d, J=7.8 Hz, 1H, 6-H), 3.29 (dd, J=17.6 Hz, J=7.9 Hz, 1H, 3-H), 2.70 (m, 1H, 2-H), 2.59 (dd, J=17.6 Hz, J=3.9 Hz, 1H, 3'-H), 2.45 (s, 3H, 5-Me), 1.28 (d, J=7.6 Hz, 2-Me).

$^{13}C\{^1H\}$ NMR ($CDCl_3$): δ 208.1, 153.8, 145.1, 136.1, 130.3, 124.1, 122.3, 42.2, 36.5, 23.1, 16.2.

A mixture of 4-bromo-2,5-dimethyl-1H- and 7-bromo-2,6-dimethyl-1H-indenes

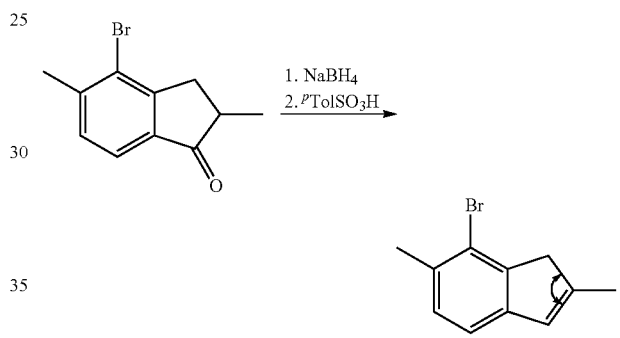

To a solution of 47.6 g (199 mmol) of 4-bromo-2,5-dimethyl-1-indanone in 270 ml of THF-methanol (2:1, vol.), 11.3 g (299 mmol) of $NaBH_4$ were added for 1 h at −5° C. (Caution: temperature must be lower than 0° C.). The mixture was stirred overnight at ambient temperature, then diluted with 300 ml of water, and acidified with 10% HCl to pH=1. The crude product was extracted with 3×200 ml of $CH_2Cl_2$. This extract was evaporated to dryness. To the white solid obtained 500 ml of toluene was added. This toluene solution was treated with a catalytic amount of $^PTolSO_3H$ (ca. 2 g) for 2 hours at reflux using a Dean-Stark head. The reaction was cooled to room temperature, washed with aqueous $NaHCO_3$, dried over $Na_2SO_4$, and evaporated to dryness. The product was isolated by flash chromatography on Silica Gel 60 (40-63 μm, d 30 mm, l 300 mm; eluent: hexanes). Yield 38.7 g (87%) of white crystalline product.

Anal. calc. for $C_{11}H_{11}Br$: C, 59.22; H, 4.97. Found: C, 59.40; H, 5.04.

$^1$H NMR ($CDCl_3$) of 4-bromo-2,5-dimethyl-1H-indene: δ 7.03 (m, 1H, 7-H in indenyl), 6.97 (d, J=7.4 Hz, 1H, 6-H on indenyl), 6.36 (m, 1H, 3-H in indenyl), 3.22 (m, 2H, $CH_2$), 2.35 (s, 3H, 5-Me in indenyl), 2.09 (m, 3H, 2-Me in indenyl); 7-bromo-2,6-dimethyl-1H-indene: δ 7.03 (m, 1H, 4-H in indenyl), 7.00 (d, J=7.5 Hz, 1H, 5-H on indenyl), 6.40 (m, 1H, 3-H in indenyl), 3.20 (m, 2H, $CH_2$), 2.38 (s, 3H, 6-Me in indenyl), 2.09 (m, 3H, 2-Me in indenyl).

$^{13}C\{^1H\}$ NMR ($CDCl_3$) of 7-bromo-2,6-dimethyl-1H-indene: δ 145.6, 144.6, 144.0, 132.5, 128.7, 126.9, 121.0, 118.3, 44.8, 22.3, 16.6.

Bis(4-bromo-2,5-dimethyl-1H-inden-1-yl)(dimethyl)silane (2)

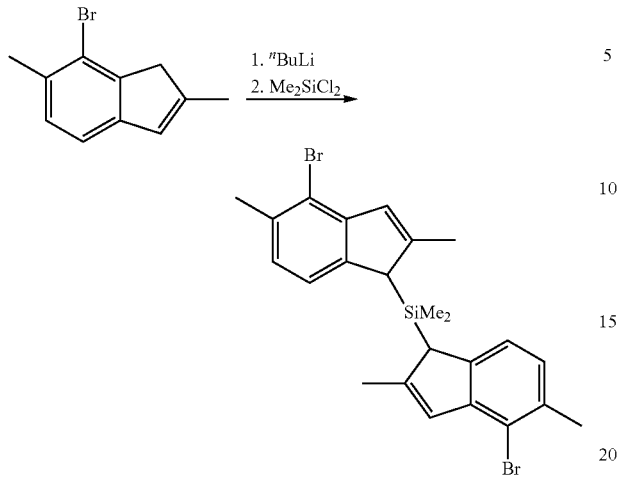

In an argon atmosphere, to a solution of 10.0 g (44.8 mmol) of a mixture of 4-bromo-2,5-dimethyl-1H- and 7-bromo-2,6-dimethyl-1H-indenes in 400 ml of diethyl ether, 17.9 ml of 2.5 M $^n$BuLi (44.8 mmol) in hexanes was added at ambient temperature. This mixture was stirred overnight at room temperature, and, then, 2.72 ml (2.89 g, 22.4 mmol) of Me$_2$SiCl$_2$ was added. The resulting mixture was stirred for 24 hours at ambient temperature; then 50 ml of water was added. The organic layer was separated, dried over Na$_2$SO$_4$, and evaporated to dryness. The residue was washed with 3×30 ml of hexanes and dried in vacuum. Yield 7.02 g (61%) of white solid of ca. 1 to 1 mixture of rac- and meso-compounds.

Anal. calc. for C$_{24}$H$_{26}$Br$_2$Si: C, 57.38; H, 5.22. Found: C, 57.55; H, 5.34.

$^1$H NMR (CDCl$_3$): δ 7.53 (d, J=7.5 Hz, 2H, 7,7'-H in rac-compound), 7.41 (d, J=7.5 Hz, 2H, 7,7'-H in meso-compound), 7.25 (d, J=7.5 Hz, 2H, 6,6'-H in rac-compound), 7.22 (d, J=7.5 Hz, 2H, 6,6'-H in meso-compound), 7.02 (m, 4H, 3,3'-H in rac- and meso-compounds), 4.02 (s, 2H, 1,1'-H in rac-compound), 3.99 (s, 2H, 1,1'-H in meso-compound), 2.74 (s, 6H, 5,5'-Me in rac-compound), 2.72 (s, 6H, 5,5'-Me in meso-compound), 2.51 (m, 6H, 2,2'-Me in meso-compound), 2.46 (m, 6H, 2,2'-Me in rac-compound), 0.08 (s, 3H, SiMe in meso-compound), 0.015 (s, 3H, SiMe' in meso-compound), 0.006 (s, 6H, SiMe$_2$ in rac-compound).

Example 2a

Synthesis of bis(4-phenyl-2,5-dimethyl-1H-inden-1-yl)(dimethyl)silane (2a)

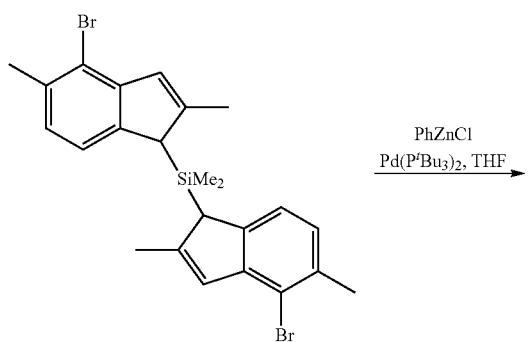

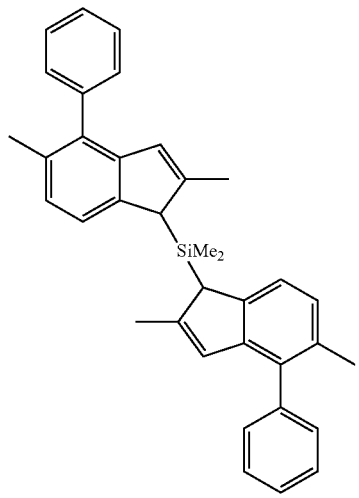

In an argon atmosphere, to a solution of 15 mL of THF with 29.0 ml of 0.5 M ZnCl$_2$ (14.5 mmol) in THF, 13.0 ml of 1.0 M phenylmagnesium bromide (13.0 mmol) in THF was added at ambient temperature. This mixture was stirred for 1 hour, and, then, 10.0 ml of 0.02 M Pd(P$^t$Bu$_3$)$_2$ (0.20 mmol, 4 mol. %) in THF and 2.51 g (5.0 mmol) of 2 were added. The resulting mixture was stirred for 5 hours at reflux. The product was isolated by flash chromatography on Silica Gel 60 (40-63 μm, d 30 mm, l 100 mm; eluent: hexanes). Yield 2.36 g (95%) of white solid of ca. 1 to 1 mixture of rac- and meso-compounds.

Anal. calc. for C$_{36}$H$_{36}$Si: C, 87.04; H, 7.30. Found: C, 87.91; H, 7.38.

$^1$H NMR (CDCl$_3$): δ 7.28-7.50 (m, 24H, 7,7'-H and 4,4'-Ph in indenyl of rac- and meso-compounds), 7.07 (d, J=7.5 Hz, 2H, 6,6'-H in indenyl of rac- or meso-compound), 7.04 (d, J=7.5 Hz, 2H, 6,6'-H in indenyl of meso- or rac-compound), 6.34 (m, 4H, 3,3'-H in rac- and meso-compounds), 3.80 (s, 2H, 1,1'-H in indenyl of rac- or meso-compound), 3.79 (s, 2H, 1,1'-H in indenyl of meso- or rac-compound), 2.254 (s, 6H, 5,5'-Me in indenyl of rac- or meso-compound), 2.246 (s, 6H, 5,5'-Me in indenyl of meso- or rac-compound), 2.21 (d, J=0.9 Hz, 6H, 2,2'-Me in indenyl of rac- or meso-compound), 2.14 (d, J=0.9 Hz, 6H, 2,2'-Me in indenyl of meso- or rac-compound), −0.21 (s, 3H, SiMe of meso-compound), −0.22 (s, 9H, SiMe' of meso-compound and SiMe$_2$ of rac-compound).

$^{13}$C{$^1$H} NMR (CDCl$_3$): δ 147.17, 147.05, 144.58, 144.53, 142.27, 142.23, 140.4 (two resonances), 133.89, 133.84, 132.05, 132.01, 129.9 (br), 129.7 (br), 128.0 (two resonances), 126.6 (two resonances), 126.38, 126.33, 124.88, 124.81, 122.04, 122.01, 47.32, 47.26, 20.1 (two resonances), 17.89, 17.85, −5.9, −6.0, −6.1.

Example 2a@

Synthesis of rac-dimethylsilyl-bis(η⁵-2,5-dimethyl-4-phenylinden-1-yl)zirconium dichloride (2a@)

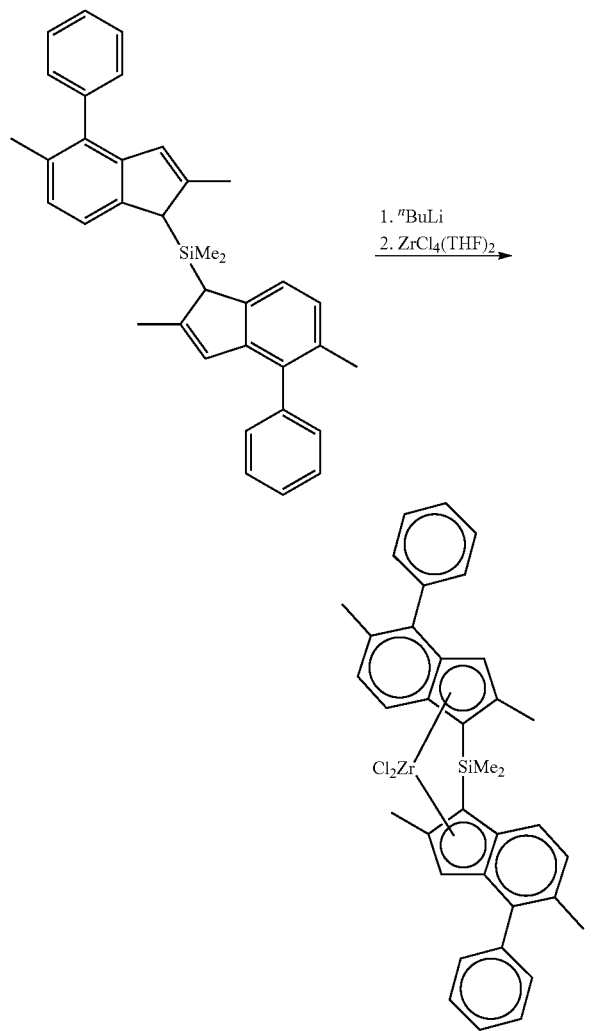

In the Glove Box, to a solution of 2.18 g (4.4 mmol) of 2a in 100 ml of ether, 3.5 ml of 2.5M ⁿBuLi (8.8 mmol) in hexanes was added at ambient temperature. This mixture was stirred for 24 hours and, then, cooled to −78° C.; 1.66 g (4.4 mmol) of ZrCl$_4$(THF)$_2$ was added. The resulting mixture was stirred for 24 hours at room temperature and, then, evaporated to dryness. To the residue 100 ml of toluene was added. This mixture was stirred for 8 hours at 90° C. The hot solution was filtered through a glass frit (G4). The residue was additionally washed with 3×50 ml of hot toluene. The filtrate was evaporated to dryness. The solid obtained was recrystallized from dichloromethane. Yield 0.84 g (29%) of orange crystalline solid.

Anal. calc. for $C_{36}H_{34}Cl_2SiZr$: C, 65.83; H, 5.22. Found: C, 65.95; H, 5.31.

$^1$H NMR (CD$_2$Cl$_2$): δ 7.51 (d, J=8.9 Hz, 2H, 7,7'-H in indenyl), 7.40 (m, 4H, 2,2',6,6'-H in Ph), 7.35 (m, 4H, 3,3',5,5'-H in Ph), 7.20 (m, 2H, 4,4'-H in Ph), 6.95 (d, J=8.9 Hz, 2H, 6,6'-H in indenyl), 6.35 (m, 2H, 3,3'-H in indenyl), 2.23 (s, 6H, 5,5'-Me), 2.14 (s, 6H, 2,2'-Me), 1.26 (s, 6H, SiMe$_2$).

Example 2b

Synthesis of bis{4-[3,5-bis-(trifluoromethyl)phenyl]-2,5-dimethyl-1H-inden-1-yl}(dimethyl)silane (2b)

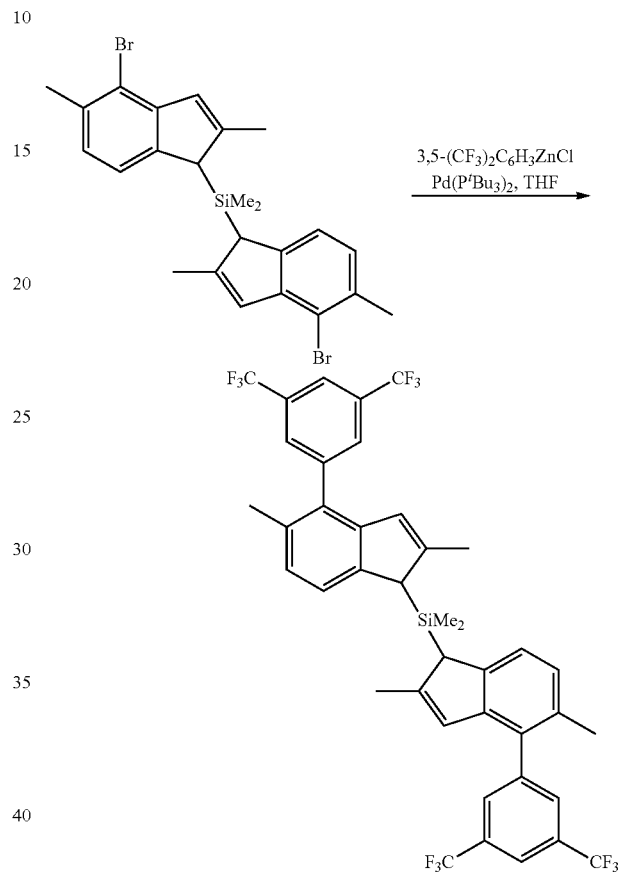

In an argon atmosphere, to a solution of 15 mL of THF with 29.0 ml of 0.5 M ZnCl$_2$ (14.5 mmol) in THF, 13.0 ml of 1.0 M 3,5-bis(trifluoromethyl) phenylmagnesium bromide (13.0 mmol) in THF was added at ambient temperature. This mixture was stirred for 1 hour, and, then, 10.0 ml of 0.02 M Pd(P$^t$Bu$_3$)$_2$ (0.20 mmol, 4 mol. %) in THF and 2.51 g (5.0 mmol) of 2 were added. The resulting mixture was stirred for 5 hours at reflux. The product was isolated by flash chromatography on Silica Gel 60 (40-63 μm, d 30 mm, 1 100 mm; eluent: hexanes). Yield 3.65 g (95%) of white solid of ca. 1 to 1 mixture of rac- and meso-compounds.

Anal. calc. for $C_{40}H_{32}F_{12}Si$: C, 62.49; H, 4.20. Found: C, 62.55; H, 4.28.

$^1$H NMR (CDCl$_3$): δ 8.02 (m, 4H, 4,4'-H in aryl of rac- and meso-isomers), 7.93 (m, 4H, 2,2',6,6'-H in aryl of rac- or meso-isomer), 7.89 (m, 4H, 2,2',6,6'-H in aryl of meso- or rac-isomer), 7.57 (m, 2H, 7,7'-H in indenyl of rac- or meso-isomer), 7.46 (m, 2H, 7,7'-H in indenyl of meso- or rac-isomer), 7.20 (m, 2H, 6,6'-H in indenyl of rac- or meso-isomer), 7.17 (m, 2H, 6,6'-H in indenyl of meso- or rac-isomer), 6.36 (m, 4H, 3,3'-H in indenyl of rac- and meso-isomers), 3.92 (m, 2H, 1,1'-H in indenyl of rac- or meso-isomer), 3.91 (m, 2H, 1,1'-H in indenyl of meso- or rac-isomer), 2.34 (m, 6H, 2,2'-Me of rac- or meso-isomer), 2.33 (s, 6H, 5,5'-Me of rac- or meso-isomer), 2.32 (s, 6H, 5,5'-Me of meso- or rac-isomer), 2.28 (m, 6H, 2,2'-Me of meso- or rac-isomer), −0.05 (s, 3H, SiMeMe' of meso-isomer), −0.08 (s, 3H, SiMeMe' of meso-isomer), −0.09 (s, 6H, SiMe$_2$ of rac-isomer).

Example 2b@

Synthesis of rac-dimethylsilyl-bis{η$^5$-2,5-dimethyl-4-[3,5-bis(trifluoromethyl)phenyl]inden-1-yl}zirconium dichloride (2b@)

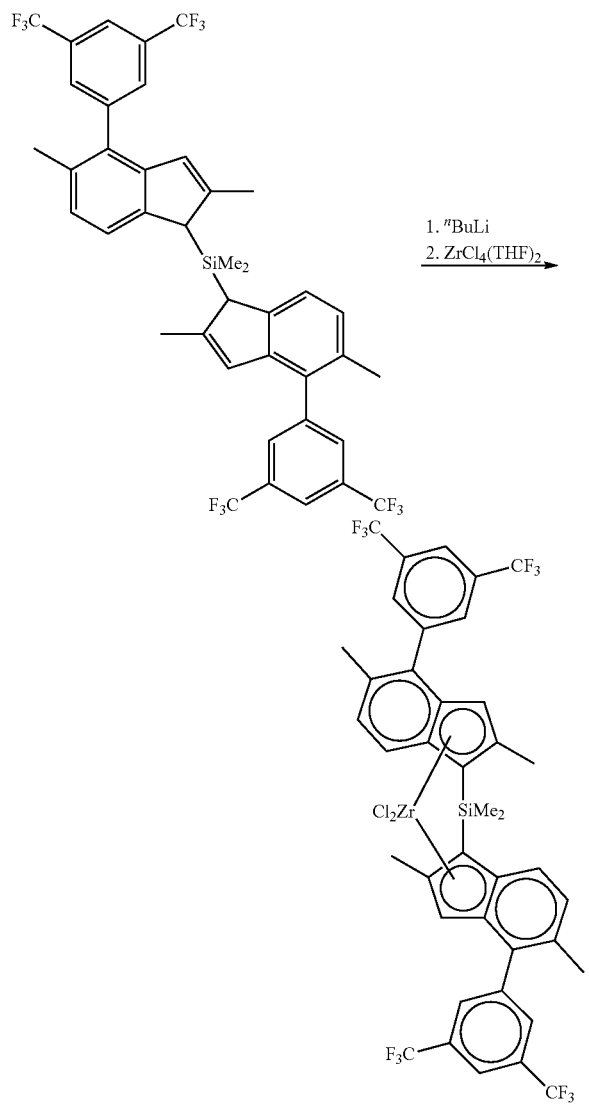

To a solution of 6.15 g (8.0 mmol) of 2b in 100 ml of ether, 6.50 ml 2.5 M (16.3 mmol) of $^n$BuLi in hexanes was added dropwise over 15 min at 0° C. This mixture was stirred for 12 h at room temperature and then cooled to −78° C. Next, 3.02 g (8.0 mmol) of ZrCl$_4$(THF)$_2$ was added. The resulting mixture was slowly (ca. 1.5 h) warmed to ambient temperature with vigorous stirring and then stirred for 20 h. The organic solvents were distilled off under reduced pressure, and 100 ml of dichloromethane was added. This mixture was filtered through a glass frit (G4). The precipitate was washed by 4×20 ml of dichloromethane and dried in vacuum. This procedure gave 1.41 g (19%) of pure rac-2b@ as orange-red powder.

Anal. calc. for C$_{40}$H$_{30}$Cl$_2$F$_{12}$SiZr: C, 51.72; H, 3.26. Found: C, 51.60; H, 3.14.

$^1$H NMR (CD$_2$Cl$_2$): δ 7.47-7.57 (m, 6H, 2,2',4,4',6,6'-H in aryl), 6.95-6.99 (m, 4H, 6,6',7,7'-H in indenyl), 6.43 (s, 2H, 3,3'-H in indenyl), 2.29 (s, 6H, 5,5'-Me in indenyl), 2.19 (s, 6H, 2,2'-Me in indenyl), 1.29 (s, 6H, SiMe$_2$).

Example 3

Synthesis of bis(3-bromo-5-methyl-6H-cyclopenta[b]thien-6-yl)(dimethyl)silanes (3)

3-Bromo-5-methyl-4,5-dihydro-6H-cyclopenta[b]thiophen-6-one

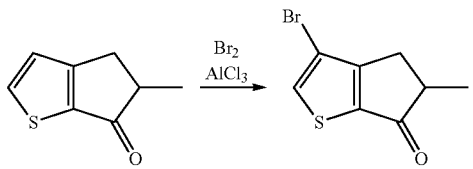

To a suspension of 250 g (1.89 mol) of AlCl$_3$ (anhydrous powder) in 350 ml of CHCl$_3$, 129 g (0.85 mol) of 5-methyl-4,5-dihydro-6H-cyclopenta[b]thiophen-6-one in 130 ml of CHCl$_3$ was added at 0° C. over a period of 0.5 hours. The reaction mixture was stirred for 10 min at this temperature; then a solution of 46.7 ml of Br$_2$ (0.91 mol) in 90 ml of CHCl$_3$ was added dropwise over a period of 1 hour. The resulting mixture was stirred for 1 hour at room temperature and, then, poured over 2000 cm$^3$ of ice. The organic layer was separated. The aqueous layer was extracted with 4×200 ml of CH$_2$Cl$_2$. The combined organic fractions were washed with 1000 ml of the saturated aqueous Na$_2$CO$_3$, dried over K$_2$CO$_3$, passed through short column with Silica Gel 60 (40-63 μm, d 40 mm, l 50 mm), and evaporated to dryness. Fractional distillation gave white crystalline product, b.p. 128° C./0.8 mm Hg. Yield 185 g (94%).

Anal. calc. for C$_8$H$_7$BrOS: C, 41.58; H, 3.05. Found: C, 41.78; H, 3.16.

$^1$H NMR (CDCl$_3$): δ 7.77 (s, 1H, 2-H), 3.15 (dd, J=17.2 Hz, J=7.0 Hz, 1H, 4-H), 3.04 (m, 1H, 5-H), 2.50 (dd, J=17.2 Hz, J=2.9 Hz, 1H, 4'-H), 1.34 (d, J=7.5 Hz, 3H, 5-Me).

$^{13}$C{$^1$H} NMR (CDCl$_3$): δ 199.3, 165.6, 140.2, 136.7, 108.4, 47.4, 32.3, 16.7.

3-Bromo-5-methyl-4H-cyclopentanta[b]thiophene

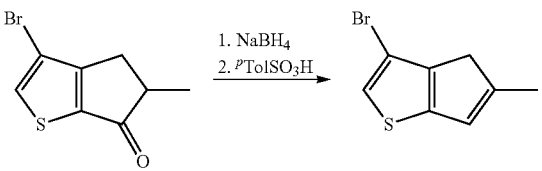

To a solution of 5.0 g (21.5 mmol) of 3-bromo-5-methyl-4,5-dihydro-6H-cyclopenta[b]thiophen-6-one in 60 ml of THF-methanol (2:1, vol.), 1.30 g (34.4 mmol) of NaBH$_4$ was added over a period of 1 hour at −5° C. (Caution: temperature must be lower than 0° C.). The mixture was stirred for 10 hours at ambient temperature, then diluted with 20 ml of water, and acidified with 10% HCl to pH=1. The crude product was extracted with 3×100 ml of $CH_2Cl_2$. This extract was washed with the saturated aqueous $Na_2CO_3$, dried over $K_2CO_3$, and evaporated to dryness. To the yellow oil obtained, 150 ml of toluene was added. This toluene solution was treated with a catalytic amount of $^pTolSO_3H$ (ca. 0.2 g) for 10 min at reflux, cooled to room temperature, and, then, passed through a short Silica Gel 60 column (40-63 µm, d 20 mm, 150 mm). This column was additionally eluted with 300 ml of hexanes-methyl-tert-butyl ether mixture (10:1, vol.). The chromatographed product was evaporated to dryness. This procedure gave 4.61 g (99%) of beige crystalline product of 3-bromo-5-methyl-4H-cyclopenta[b]thiophene (containing 3-5% of 3-bromo-5-methyl-6H-cyclopenta[b]thiophene).

Anal. calc. for $C_8H_7BrS$: C, 44.67; H, 3.28. Found: C, 44.80; H, 3.34.

$^1H$ NMR ($CDCl_3$): δ 6.94 (s, 1H, 2-H), 6.43 (m, 1H, 6-H), 3.10 (d, J=1.3 Hz, 2H, $CH_2$), 2.16 (d, J=1.5 Hz, 3H, Me).

$^{13}C\{^1H\}$ NMR ($CDCl_3$): δ 129.0, 127.6, 127.5, 122.6, 120.2, 106.5, 40.0, 17.4.

Bis(3-bromo-5-methyl-6H-cyclopenta[b]thien-6-yl) (dimethyl)silanes (3)

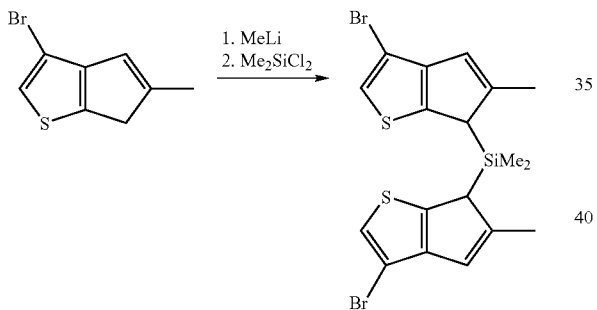

In an argon atmosphere, to a solution of 5.50 g (25.6 mmol) of 3-bromo-5-methyl-4H-cyclopenta[b]thiophene in 250 ml of diethyl ether, 16.0 ml of 1.6 M MeLi (25.6 mmol) in ether was added at −60° C. This mixture was stirred for 1 hour at room temperature and, then, cooled to 0° C. To this mixture, 1.55 ml (12.8 mmol) of $Me_2SiCl_2$ was added at this temperature. The resulting mixture was stirred for 12 hours at ambient temperature. Then, 50 ml of water was added. The organic layer was separated, dried over $K_2CO_3$, and evaporated to dryness in vacuum. The crude product was purified using flash chromatography on Silica Gel 60 (40-63 µm, d 40 mm, 1500 mm, eluent hexanes). This procedure gave 2.61 g (42%) the title product of ca. 60% purity (i.e. up to 40% of 4,4'- and 4,6'-substituted isomers). Analytically pure 3 was obtained by crystallization of crude product from hexanes-ether (3:1, vol.).

Anal. calc. for $C_{18}H_{18}Br_2S_2Si$: C, 44.45; H, 3.73. Found: C, 44.90; H, 3.87.

$^1H$ NMR ($CDCl_3$): rac-isomer, δ 7.11 (s, 2H, 2,2'-H), 6.52 (m, 2H, 4,4'-H), 3.84 (s, 2H, 6,6'-H), 2.25 (s, 6H, 5,5'-Me), −0.25 (s, 6H, $SiMe_2$); meso-isomer, δ 7.09 (s, 2H, 2,2'-H), 6.52 (m, 2H, 4,4'-H), 3.76 (s, 2H, 6,6'-H), 2.26 (s, 6H, 5,5'-Me), −0.21 (s, 3H, SiMe), −0.26 (s, 3H, SiMe').

Example 3a

Synthesis of bis(3-phenyl-5-methyl-6H-cyclopenta [b]thien-6-yl)(dimethyl)silanes (3a)

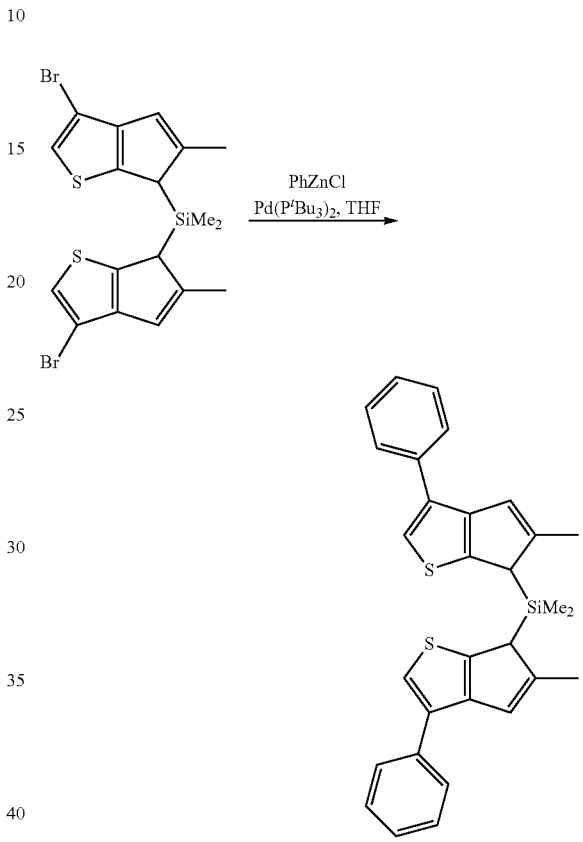

In an argon atmosphere, to a solution of 15 mL of THF with 25.4 ml of 0.5 M $ZnCl_2$ (12.7 mmol) in THF, 11.4 ml of 1.0 M phenylmagnesium bromide (11.4 mmol) in THF was added at ambient temperature. This mixture was stirred for 1 hour, and, then, 8.8 ml of 0.02 M $Pd(P^tBu_3)_2$ (0.18 mmol, 4 mol. %) in THF and 2.14 g (4.40 mmol) of 3 were added. The resulting mixture was stirred for 5 hours at reflux. The product was isolated by flash chromatography on Silica Gel 60 (40-63 µm, d 30 mm, 1 100 mm; eluent: hexanes). Yield 2.03 g (96%) of white solid of ca. 1 to 2 mixture of rac- and meso-compounds.

Anal. calc. for $C_{30}H_{28}S_2Si$: C, 74.95; H, 5.87. Found: C, 75.20; H, 5.99.

$^1H$ NMR ($CDCl_3$), rac-3b: δ 7.63-7.67 (m, 4H, 2,2',6,6'-H in $C_6H_4$), 7.39-7.46 (m, 4H, 3,3',5,5'-H in $C_6H_4$), 7.30-7.34 (m, 2H, 4,4'-H in $C_6H_4$), 7.29 (d, J=0.6 Hz, 2H, 5-H in cyclopenta[b]thienyl), 6.80 (m, 2H, 3,3'-H in cyclopenta[b]thienyl), 3.94 (m, 2H, 1,1'-H in cyclopenta[b]thienyl), 2.19 (d, J=1.4 Hz, 6H, 2,2'-Me in cyclopenta[b]thienyl), −0.23 (s, 6H, $SiMe_2$); meso-3b: δ 7.62-7.66 (m, 4H, 2,2',6,6'-H in $C_6H_4$), 7.39-7.46 (m, 4H, 3,3',5,5'-H in $C_6H_4$), 7.30-7.34 (m, 2H, 4,4'-H in $C_6H_4$), 7.26 (d, J=0.6 Hz, 2H, 5-H in cyclopenta[b]thienyl), 6.81 (m, 2H, 3,3'-H in cyclopenta[b]thienyl), 3.83

(m, 2H, 1,1'-H in cyclopenta[b]thienyl), 2.32 (d, J=1.4 Hz, 6H, 2,2'-Me in cyclopenta[b]thienyl), −0.20 (s, 3H, SiMe), −0.21 (s, 3H, SiMe').

Example 3a@

Synthesis of rac-dimethylsilyl-bis($\eta^5$-3-phenyl-5-methylcyclopenta[b]thien-6-yl)zirconium dichloride (3a@)

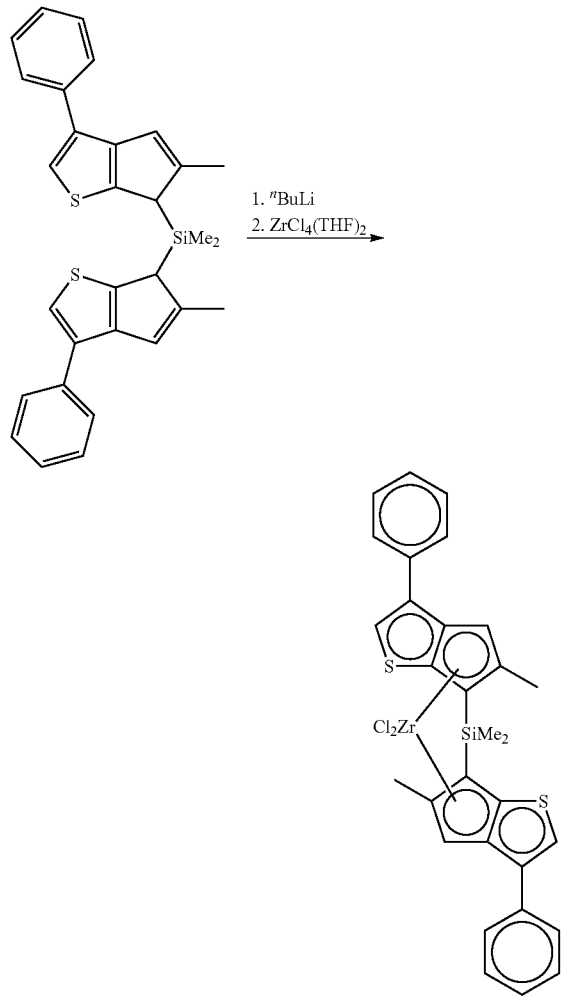

In the Glove Box, to a solution of 1.92 g (4.0 mmol) of 3a in 100 ml of ether, 3.2 ml of 2.5M $^n$BuLi (8.0 mmol) in hexanes was added at ambient temperature. This mixture was stirred for 24 hours and, then, cooled to −78° C.; 1.51 g (4.0 mmol) of ZrCl$_4$(THF)$_2$ was added. The resulting mixture was stirred for 24 hours at room temperature and, then, evaporated to dryness. To the residue 100 ml of toluene was added. This mixture was stirred for 8 hours at 90° C. The hot solution was filtered through a glass frit (G4). The residue was additionally washed with 3×50 ml of hot toluene. The filtrate was evaporated to dryness. The solid obtained was recrystallized from dichloromethane. Yield 0.64 g (25%) of orange crystalline solid.

Anal. calc. for C$_{30}$H$_{26}$Cl$_2$S$_2$SiZr: C, 56.22; H, 4.09. Found: C, 56.41; H, 4.15.

$^1$H NMR (CD$_2$Cl$_2$): δ 7.54-7.62 (m, 4H, 2,2',6,6'-H of Ph), 7.49 (s, 2H, 3,3'-H of cyclopentathienyl), 7.34-7.43 (m, 4H, 3,3',5,5'-H of Ph), 7.25-7.34 (m, 2H, 4,4'-H of Ph), 6.86 (s, 2H, 3,3'-H of cyclopentathienyl), 2.32 (s, 6H, 2,2'-Me of cyclopentathienyl), 1.09 (s, 6H, SiMe$_2$).

$^{13}$C{$^1$H} NMR (CD$_2$Cl$_2$): δ 144.7, 137.7, 136.2, 135.7, 130.8, 130.4, 129.4, 128.6, 121.4, 120.4, 72.5, 20.7, 0.7.

Example 3b

Synthesis of bis{3-(4-tert-butylphenyl)-5-methyl-6H-cyclopenta[b]thien-6-yl}(dimethyl)silanes (3b)

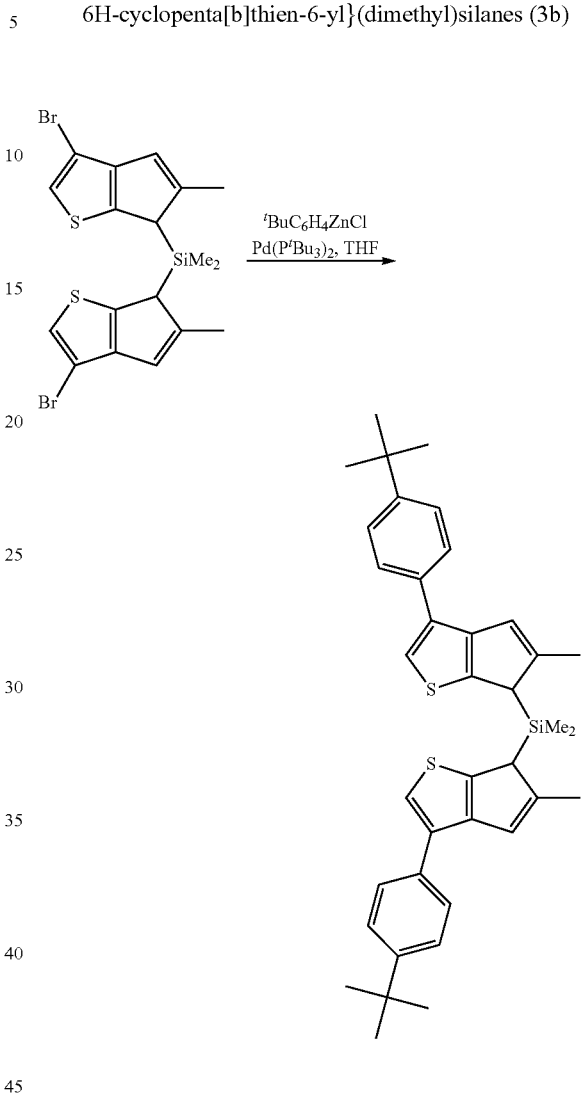

In an argon atmosphere, to a solution of 15 mL of THF with 29.0 ml of 0.5 M ZnCl$_2$ (14.5 mmol) in THF, 10.7 ml of 1.22 M 4-tert-butylphenylmagnesium bromide (13.0 mmol) in THF was added at ambient temperature. This mixture was stirred for 1 hour, and, then, 10.0 ml of 0.02 M Pd(P$^t$Bu$_3$)$_2$ (0.20 mmol, 4 mol. %) in THF and 2.43 g (5.0 mmol) of 3 were added. The resulting mixture was stirred for 5 hours at reflux. The product was isolated by flash chromatography on Silica Gel 60 (40-63 μm, d 30 mm, l 100 mm; eluent: hexanes). Yield 2.76 g (93%) of white solid of ca. 1 to 3 mixture of rac- and meso-compounds.

Anal. calc. for C$_{38}$H$_{44}$S$_2$Si: C, 76.97; H, 7.48. Found: C, 77.21; H, 7.56.

$^1$H NMR (CDCl$_3$), rac-3b: δ 7.57-7.61 (m, 4H, 3,3',5,5'-H in C$_6$H$_4$), 7.42-7.46 (m, 4H, 2,2',6,6'-H in C$_6$H$_4$), 7.26 (m, 2H, 5-H in cyclopenta[b]thienyl), 6.81 (m, 2H, 3,3'-H in cyclopenta[b]thienyl), 3.93 (m, 2H, 1,1'-H in cyclopenta[b]thienyl), 2.19 (d, J=1.3 Hz, 6H, 2,2'-Me in cyclopenta[b]thienyl), 1.367 (s, 18H, $^t$Bu), −0.26 (s, 6H, SiMe$_2$); meso-3b: δ 7.55-7.59 (m, 4H, 3,3',5,5'-H in C$_6$H$_4$), 7.43-7.47 (m, 4H, 2,2',6,6'-H in C$_6$H$_4$), 7.23 (m, 2H, 5-H in cyclopenta[b]thienyl), 6.81 (m, 2H, 3,3'-H in cyclopenta[b]thienyl), 3.82 (m, 2H, 1,1'-H in cyclopenta[b]thienyl), 2.31 (d, J=1.3 Hz, 6H, 2,2'-Me in cyclopenta[b]thienyl), 1.363 (s, 18H, $^t$Bu), −0.23 (s, 3H, SiMe), −0.24 (s, 3H, SiMe').

Example 3b@

Synthesis of rac-dimethylsilyl-bis[η$^5$-3-(4-tert-butylphenyl)-5-methylcyclopenta[b]thien-6-yl]zirconium dichloride (3b@)

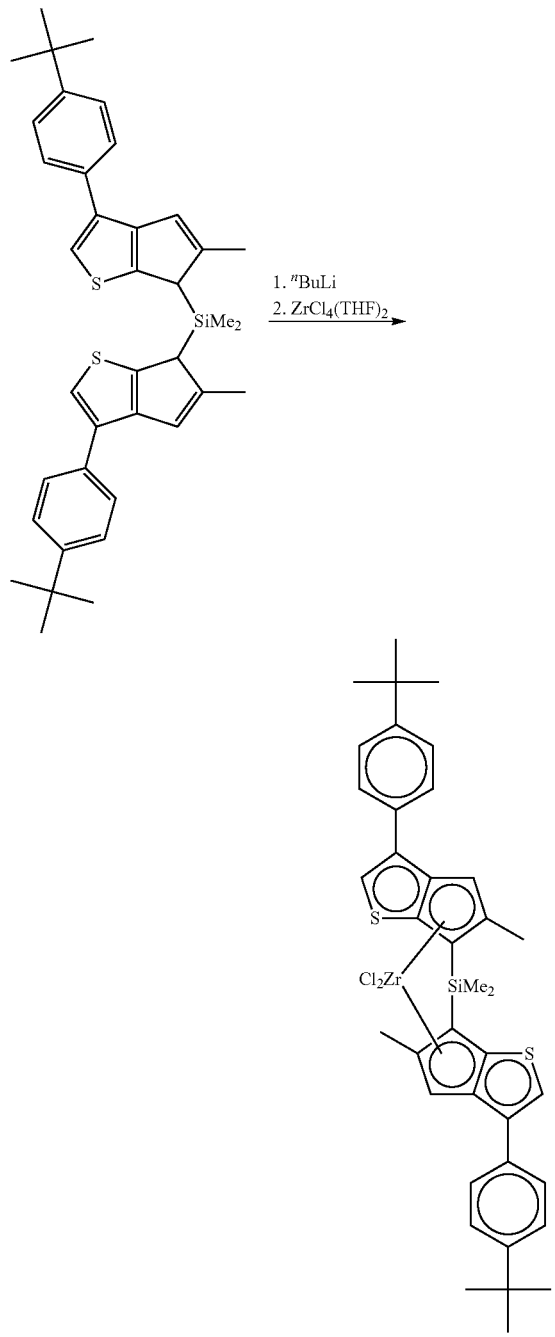

In the Glove Box, to a solution of 2.49 g (4.2 mmol) of 3b in 100 ml of ether, 3.35 ml of 2.5M $^n$BuLi (8.4 mmol) in hexanes was added at ambient temperature. This mixture was stirred for 24 hours and, then, cooled to −78° C.; 1.58 g (4.2 mmol) of ZrCl$_4$(THF)$_2$ was added. The resulting mixture was stirred for 24 hours at room temperature and, then, evaporated to dryness. To the residue 100 ml of toluene was added. This mixture was stirred for 8 hours at 90° C. The hot solution was filtered through a glass frit (G4). The residue was additionally washed with 3×50 ml of hot toluene. The filtrate was evaporated to dryness. The solid obtained was recrystallized from dichloromethane. Yield 0.60 g (19%) of orange crystalline solid.

Anal. calc. for C$_{38}$H$_{42}$Cl$_2$S$_2$SiZr: C, 60.60; H, 5.62. Found: C, 60.79; H, 5.69.

$^1$H NMR (CD$_2$Cl$_2$): δ 7.37-7.61 (m, 10H, 5,5'-H of cyclopentathienyl and 2,2',3,3',5,5',6,6'-H of C$_6$H$_4$), 6.85 (s, 2H, 3,3'-H of cyclopentathienyl), 2.31 (s, 6H, 2,2'-Me of cyclopentathienyl), 1.29 (s, 18H, $^t$Bu), 1.09 (s, 6H, SiMe$_2$).

$^{13}$C{$^1$H} NMR (CD$_2$Cl$_2$): δ 138.3, 138.1, 137.6, 135.6, 133.3, 130.1, 128.1, 127.4, 121.5, 120.6, 72.5, 36.1, 32.6, 20.7, 0.7.

Example 3c

Synthesis of bis{3-(1-naphthyl)-5-methyl-6H-cyclopenta[b]thien-6-yl}(dimethyl)silanes (3c)

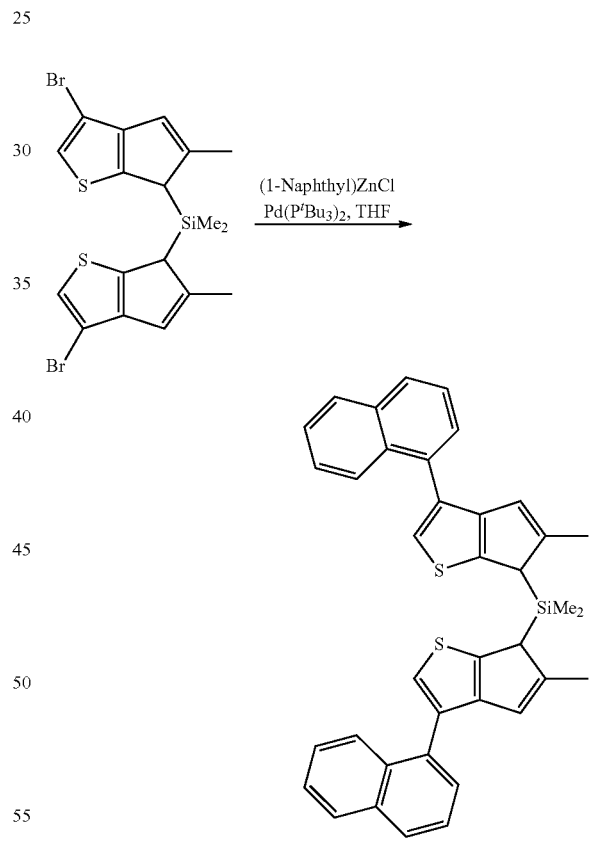

In an argon atmosphere, to 29.0 ml of 0.5 M ZnCl$_2$ (14.5 mmol) in THF, 52.0 ml of 0.25 M naphthylmagnesium bromide (13.0 mmol) in THF was added at ambient temperature. This mixture was stirred for 1 hour, and, then, 10.0 ml of 0.02 M Pd(P$^t$Bu$_3$)$_2$ (0.20 mmol, 4 mol. %) in THF and 2.43 g (5.0 mmol) of 3 were added. The resulting mixture was stirred for 5 hours at reflux. The product was isolated by flash chromatography on Silica Gel 60 (40-63 μm, d 30 mm, l 100 mm; eluent: hexanes). Yield 2.56 g (88%) of white solid of ca. 1 to 2 mixture of rac- and meso-compounds.

Anal. calc. for $C_{38}H_{32}S_2Si$: C, 78.57; H, 5.55. Found: C, 78.79; H, 5.66.

$^1$H NMR (CDCl$_3$), rac-3c: δ 7.25-7.96 (m, 14H, naphthyl), 7.20 (s, 2H, 5,5'-H in cyclopenta[b]thienyl), 6.26 (s, 2H, 3,3'-H in cyclopenta[b]thienyl), 3.96 (s, 2H, 1,1'-H in cyclopenta[b]thienyl), 2.06 (s, 6H, 2-Me in cyclopenta[b]thienyl), −0.22 (s, 6H, SiMe$_2$); meso-3c: δ 7.25-7.96 (m, 14H, naphthyl), 7.17 (s, 2H, 5,5'-H in cyclopenta[b]thienyl), 6.26 (s, 2H, 3,3'-H in cyclopenta[b]thienyl), 3.84 (s, 2H, 1,1'-H in cyclopenta[b]thienyl), 2.19 (s, 6H, 2-Me in cyclopenta[b]thienyl), −0.18 (s, 3H, SiMe), −0.22 (s, 3H, SiMe').

Example 3c@

Synthesis of rac-dimethylsilyl-bis[η$^5$-3-(1-naphthyl)-5-methylcyclopenta[b]thien-6-yl]zirconium dichloride (3c@)

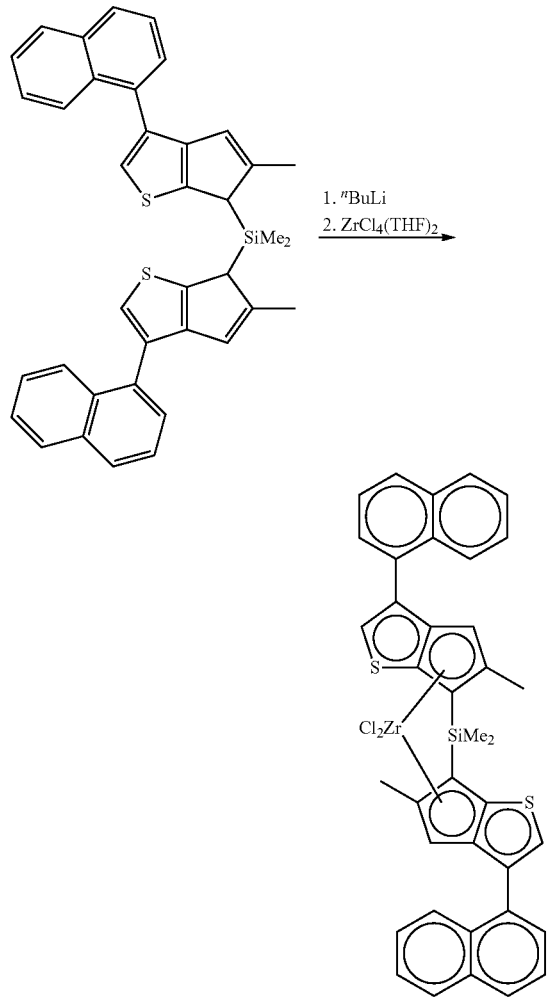

In the Glove Box, to a solution of 2.38 g (4.1 mmol) of 3c in 100 ml of ether, 3.3 ml of 2.5M $^n$BuLi (8.2 mmol) in hexanes was added at ambient temperature. This mixture was stirred for 24 hours and, then, cooled to −78° C.; 1.55 g (4.1 mmol) of ZrCl$_4$(THF)$_2$ was added. The resulting mixture was stirred for 24 hours at room temperature and, then, evaporated to dryness. To the residue 100 ml of toluene was added. This mixture was stirred for 8 hours at 90° C. The hot solution was filtered through a glass frit (G4). The residue was additionally washed with 3×50 ml of hot toluene. The filtrate was evaporated to dryness. The solid obtained was recrystallized from toluene. Yield 0.67 g (22%) of red crystalline solid.

Anal. calc. for $C_{38}H_{30}Cl_2S_2SiZr$: C, 61.59; H, 4.08. Found: C, 61.68; H, 4.15.

$^1$H NMR (CD$_2$Cl$_2$): δ 8.06 (d, J=8.4 Hz, 2H, 4,4'-H in naphthyl), 7.87 (m, 2H, 8,8'-H in naphthyl), 7.83 (d, J=8.4 Hz, 2H, 2,2'-H in naphthyl), 7.72 (dd, J=7.2 Hz, J=0.9 Hz, 2H, 5,5'-H in naphthyl), 7.53 (s, 2H, 5,5'-H in cyclopenta[b]thienyl), 7.37-7.52 (m, 6H, 3,3',6,6',7,7'-H in naphthyl), 6.58 (s, 2H, 3,3'-H in cyclopenta[b]thienyl), 2.34 (s, 6H, 2,2'-Me in cyclopenta[b]thienyl), 1.14 (s, 6H, SiMe$_2$).

Example 4

Synthesis of bis(4-bromo-6-isopropyl-2-methyl-1H-inden-1-yl)(dimethyl)silane (4)

1-Bromo-3-isopropylbenzene

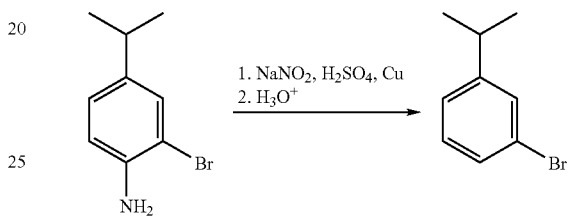

To a mixture of 1000 ml of 96% ethanol and 94 ml of 98% H$_2$SO$_4$, 117 g (0.55 mol) of 2-bromo-4-isopropylaniline was added over 15 min. with vigorous stirring at −5° C. Then, a solution of 63 g of NaNO$_2$ in 125 ml of water was added at this temperature over 1 h, and the resulting mixture was stirred for about 30 min longer. Then, 12 g of copper powder was added. The reaction mixture was refluxed for 4 h and filtered through a glass frit (G3). The filtrate was poured into 2500 cm$^3$ of cold water. The organic product was extracted with 4×400 ml of dichloromethane. The combined extract was dried over K$_2$CO$_3$ and evaporated to dryness. Fractional distillation gave the title product, b.p. 64-67° C./3 mm Hg. Yield 117.4 g (75%) of yellowish oil.

Anal. calc. for $C_9H_{11}Br$: C, 54.30; H, 5.57. Found: C, 54.44; H, 5.49.

$^1$H NMR (CDCl$_3$): δ 7.37 (m, 1H, 2-H), 7.28-7.34 (m, 1H, 5-H), 7.15-7.16 (m, 1H, 6-H), 7.14 (d, J=1.0 Hz, 1H, 2-H), 2.87 (sept, J=6.9 Hz, 1H, CHMe$_2$), 1.24 (d, J=6.9 Hz, 6H, CHMe$_2$).

7-Bromo-5-isopropyl-2-methyl-1-indanone

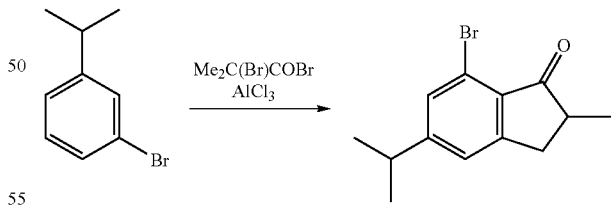

To a mixture of 34.9 g (0.26 mol) of AlCl$_3$ and 350 ml of dichloromethane, a solution of 50.9 g (0.22 mol) of 2-bromo-2-methylpropanoyl bromide in 120 ml of dichloromethane was added dropwise with vigorous stirring at −10° C. Then, a solution of 40.0 g (0.20 mol) of 1-bromo-3-isopropylbenzene in 70 ml of dichloromethane was added dropwise at this temperature. The resulting mixture was refluxed for 12 h and then poured onto 2000 cm$^3$ of ice. The organic product was extracted with 4×300 ml of dichloromethane. The combined extract was dried over K$_2$CO$_3$ and evaporated to dryness. Fractional distillation gave the title product, b.p. 130-135° C./1.5 mm Hg. Yield 36.2 g (67%).

Anal. calc. for C$_{13}$H$_{15}$BrO: C, 58.44; H, 5.66. Found: C, 58.40; H, 5.67.

$^1$H NMR (CDCl$_3$): δ 7.37 (s, 1H, 6-H), 7.23 (s, 1H, 4-H), 3.31 (dd, J=16.7 Hz, J=8.0 Hz, 1H, 3-H), 2.94 (sept, J=6.8 Hz, 1H, CHMe$_2$), 2.71 (m, 1H, 2-H), 2.65 (m, 1H, 3'-H), 1.30 (d, J=7.4 Hz, 3H, 2-Me), 1.27 (d, J=6.8 Hz, 6H, CHMe$_2$).

4-Bromo-6-isopropyl-2-methyl-1H-indene

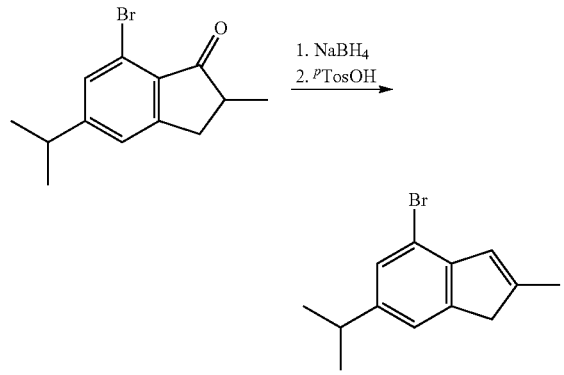

To a solution of 22.2 g (83.2 mmol) of 7-bromo-5-isopropyl-2-methyl-1-indanone in 120 ml of THF-methanol (2:1, vol.), 5.06 g (133 mmol) of NaBH$_4$ was added with vigorous stirring over 3 h at 0° C. This mixture was stirred overnight at room temperature; then, 300 ml of cold water was added, and the resulting mixture was acidified with 1 M HCl to pH 1. The organic layer was separated, and the aqueous layer was extracted with 3×150 ml of dichloromethane. The combined organic fractions were dried over K$_2$CO$_3$ and evaporated to dryness, and 200 ml of toluene was added to the yellowish oil obtained. This toluene solution was treated with a catalytic amount of $^P$TolSO$_3$H (ca. 0.2 g) for 1 h at reflux, cooled to room temperature, and evaporated to dryness. The crude product was purified using flash chromatography on Silica Gel 60 (40-63 μm, d 40 mm, 1400 mm; eluent: hexanes). Yield 19.6 g (94%) of 4-bromo-6-isopropyl-2-methyl-1H-indene.

Anal. calc. for C$_{13}$H$_{15}$Br: C, 62.17; H, 6.02. Found: C, 61.99; H, 6.08.

$^1$H NMR (CDCl$_3$): δ 7.20 (s, 1H, 5-H), 7.13 (s, 1H, 7-H), 6.52 (m, 1H, 3-H), 3.32 (s, 2H, 1,1'-H), 2.86 (sept, J=6.9 Hz, 1H, CHMe$_2$), 2.12 (m, 3H, 2-Me), 1.23 (d, J=6.9 Hz, 6H, CHMe$_2$).

$^{13}$C{$^1$H} NMR (CDCl$_3$): δ 146.5, 146.4, 144.9, 143.6, 127.4, 126.5, 120.6, 113.4, 43.7, 33.9, 24.2, 16.8.

Bis(4-bromo-6-isopropyl-2-methyl-1H-inden-1-yl)(dimethyl)silane (4)

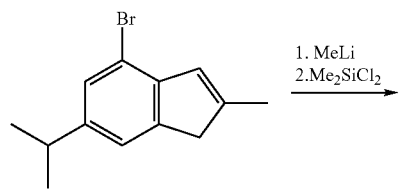

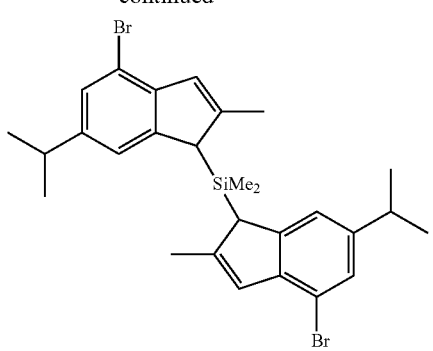

In an argon atmosphere, to a solution of 10.0 g (47.8 mmol) of 4-bromo-6-isopropyl-2-methyl-1H-indene in 250 ml of diethyl ether, 29.9 ml of 1.6 M MeLi (47.8 mmol) in ether was added at 10° C. This mixture was stirred for 12 hours at 20° C. and, then, cooled to 0° C. At this temperature, 2.89 ml (3.08 g, 23.9 mmol) of Me$_2$SiCl$_2$ was added. The resulting mixture was stirred for 24 hours at ambient temperature; then 100 ml of water was added. The organic layer was separated, dried over K$_2$CO$_3$, and evaporated to dryness. The residue was treated with 25 ml of hexanes. The white solid that precipitated was filtered off, washed with 3×30 ml of hexanes, and dried in vacuum. Yield 5.47 g (41%) of white solid of ca. 1 to 1 mixture of rac- and meso-compounds.

Anal. calc. for C$_{38}$H$_{42}$N$_2$Si: C, 82.26; H, 7.63. Found: C, 82.41; H, 7.58.

$^1$H NMR (CDCl$_3$): δ 7.21-7.24 (m, 4H, 5,5'-H in indenyl of rac- and meso-compounds), 7.13 (m, 2H, 7,7'-H in indenyl of rac-compound), 7.09 (m, 2H, 7,7'-H in indenyl of meso-compound), 6.66 (m, 2H, 3,3'-H in indenyl of meso-compound), 6.63 (m, 2H, 3,3'-H in indenyl of rac-compound), 2.80-2.93 (m, 4H, CHMe$_2$ of rac- and meso-compounds), 2.19 (m, 6H, 2,2'-Me of meso-compound), 2.17 (m, 6H, 2,2'-Me of rac-compound), 1.19-1.25 (m, 24H, CHMe$_2$ of rac- and meso-compounds), −0.15 (s, 3H, SiMeMe' of meso-compound), −0.21 (s, 6H, SiMe$_2$ of rac-compound), −0.29 (s, 3H, SiMeMe' of meso-compound).

Example 4a

Synthesis of bis(2-methyl-6-isopropyl-4-phenyl-1H-inden-1-yl)(dimethyl)silane (4a)

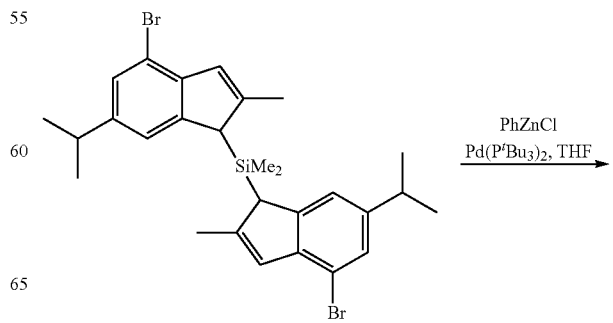

-continued

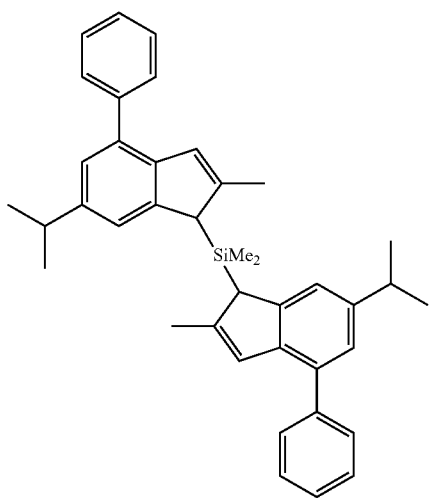

In an argon atmosphere, to a solution of 15 mL of THF with 29.0 ml of 0.5 M $ZnCl_2$ (14.5 mmol) in THF, 13.0 ml of 1.0 M phenylmagnesium bromide (13.0 mmol) in THF was added at ambient temperature. This mixture was stirred for 1 hour, and, then, 10.0 ml of 0.02 M $Pd(P^tBu_3)_2$ (0.20 mmol, 4 mol. %) in THF and 2.79 g (5.0 mmol) of 4 were added. The resulting mixture was stirred for 5 hours at reflux. The product was isolated by flash chromatography on Silica Gel 60 (40-63 μm, d 30 mm, l 100 mm; eluent: hexanes). Yield 2.71 g (98%) of white solid of ca. 1 to 1 mixture of rac- and meso-compounds.

Anal. calc. for $C_{40}H_{44}Si$: C, 86.90; H, 8.02. Found: C, 87.11; H, 8.10.

$^1H$ NMR ($CDCl_3$): δ 7.57-7.61 (m, 8H, 2,2',6,6'-H in Ph of rac- and meso-isomers), 7.46-7.52 (m, 8H, 3,3',5,5'-H in Ph of rac- and meso-isomers), 7.35-7.42 (m, 8H, 5,5'-H in indenyl and 4,4'-H in Ph of rac- and meso-isomers), 7.16-7.19 (m, 4H, 7,7'-H in indenyl of rac- and meso-isomers), 6.81 (m, 2H, 3,3'-H in indenyl of rac- or meso-isomer), 6.77 (m, 2H, 3,3'-H in indenyl of meso- or rac-isomer), 3.76 (s, 2H, 1,1'-H in indenyl of rac- or meso-isomer), 3.75 (s, 2H, 1,1'-H in indenyl of meso- or rac-isomer), 3.01 (sept, J=Hz, 4H, $CHMe_2$ of rac- and meso-isomers), 2.25 (s, 6H, 2,2'-Me in indenyl of rac- or meso-isomer), 2.18 (s, 6H, 2,2'-Me in indenyl of meso- or rac-isomer), 1.30-1.35 (m, 24H, $CHMe_2$ of rac- and meso-isomers), −0.09 (s, 3H, SiMeMe' of meso-isomer), −0.10 (s, 6H, $SiMe_2$ of rac-isomer), −0.16 (s, 3H, SiMeMe' of meso-isomer).

$^{13}C\{H\}$ NMR ($CDCl_3$): δ 147.0, 146.8, 145.92, 145.86, 143.95, 143.93, 141.71, 141.65, 140.9, 140.8, 133.73, 133.70, 128.9, 128.4, 126.67, 126.65, 125.73, 125.66, 124.13, 124.06, 120.45, 120.42, 47.5, 47.4, 34.21, 34.20, 24.6, 24.5, 24.4, 24.3, 18.0, 17.9, −5.13 (two resonances), −5.24.

Example 4a@

Synthesis of rac-dimethylsilyl-bis[$η^5$-2-methyl-6-isopropyl-4-phenylinden-1-yl]zirconium dichloride (4a@)

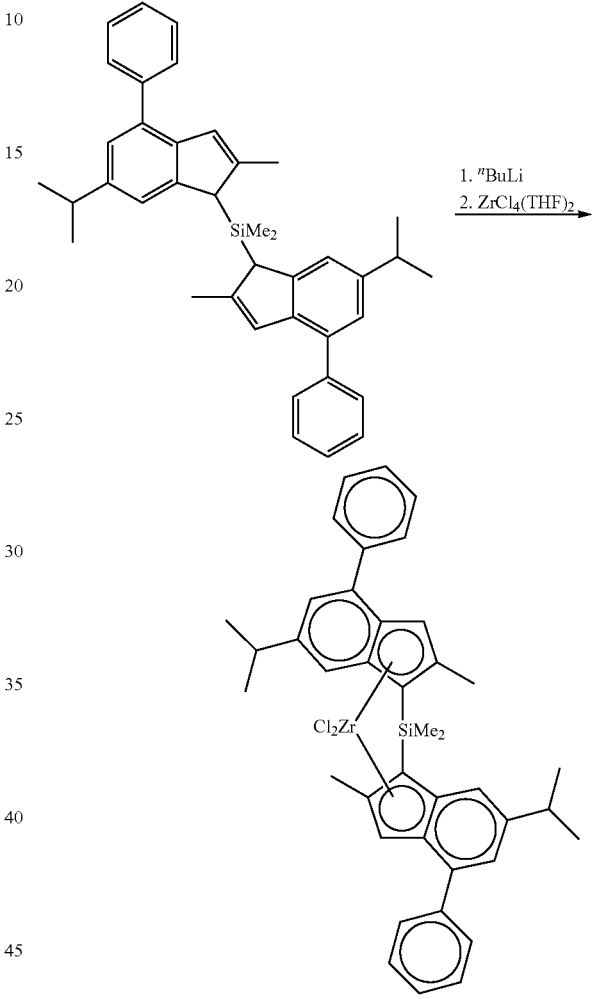

To a solution of 5.53 g (10.0 mmol) of 4a in 150 ml of ether, 8.10 ml of 2.5 M of $^nBuLi$ (20.3 mmol) in hexanes was added dropwise over 15 min at 0° C. This mixture was stirred for 12 h at room temperature and then cooled to −78° C. Next, 3.77 g (10.0 mmol) of $ZrCl_4(THF)_2$ was added. The resulting mixture was slowly (ca. 1.5 h) warmed to ambient temperature with vigorous stirring and then stirred for 24 h. The organic solvents were distilled off under reduced pressure, and 100 ml of dichloromethane was added. This mixture was filtered through a glass frit (G4). The precipitate was washed with 4×20 ml of dichloromethane and dried in vacuum. The crude product was recrystallized from toluene. This procedure gave 1.00 g (14%) of pure rac-4a@ as orange crystalline solid.

Anal. calc. for $C_{40}H_{42}Cl_2SiZr$: C, 67.38; H, 5.94. Found: C, 67.47; H, 6.00.

$^1$H NMR (CD$_2$Cl$_2$): δ 7.60-7.65 (m, 4H, 2,2',6,6'-H in Ph), 7.47 (m, 2H, 5,5'-H in indenyl), 7.41-7.46 (m, 3,3',5,5'-H in Ph), 7.34-7.39 (m, 4,4'-H in Ph), 7.29 (d, J=1.2 Hz, 2H, 7,7'-H in indenyl), 6.87 (s, 2H, 3,3'-H in indenyl), 2.93 (sept, J=6.9 Hz, 2H, CHMe$_2$), 2.26 (s, 6H, 2,2'-Me), 1.36 (s, 6H, SiMe$_2$), 1.26 (d, J=6.9 Hz, CHMe$_2$).

All documents described herein are incorporated by reference herein, including any priority documents and/or testing procedures to the extent they are not inconsistent with this text. While there have been described what are presently believed to be the preferred embodiments of the present invention, those skilled in the art will realize that other and further embodiments can be made without departing from the spirit of the invention, and is intended to include all such further modifications and changes as come within the true scope of the claims set forth herein. Likewise, the term "comprising" is considered synonymous with the term "including" for purposes of Australian law.

We claim:

1. A process for preparing a chelating ligand of the formula (II) from a chelating ligand of the formula (I) via an sp$^2$-sp$^2$ or sp$^2$-sp$^3$ coupling reaction comprising contacting, optionally in the presence of a coupling catalyst, a chelating ligand of the formula (I) with an organometallic compound of the formula (III):

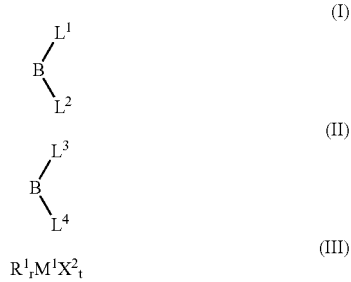

wherein

B is a bridging group that is bonded to L$^1$ and L$^2$ in formula (I) and to L$^3$ and L$^4$ in formula (II);

L$^1$ is a substituted monocyclic or polycyclic ligand that comprises at least one chlorine, bromine, iodine, or sulfonate substituent, directly bonded to an sp$^2$ carbon atom of the ring structure of the ligand;

L$^2$ is a monoanionic ligand; or L$^2$ may, independently, be defined as L$^1$;

L$^3$ is the same group as L$^1$, but said at least one chlorine, bromine, iodine, or sulfonate substituent is replaced with a hydrocarbyl, substituted hydrocarbyl, halocarbyl, or substituted halocarbyl fragment;

L$^4$ is the same group as L$^2$, though, when L$^2$ is defined as L$^1$, L$^4$ may be the same as L$^3$ or L$^1$;

R$^1$ is a hydrocarbyl, substituted hydrocarbyl, halocarbyl, or substituted halocarbyl;

M$^1$ is an element of group 1, 2, 12, 13 or 14 of the Periodic Table of the Elements;

each X$^2$, if present, is selected independently from the group consisting of halogen atoms, the hydroxyl group, alkoxy groups, aryloxy groups, mesylate, tosylate and triflate;

r is 1, 2 or 3, and t is 0, 1 or 2, where r+t corresponds to the oxidation number of M$^1$.

2. The process of claim 1 wherein L$^1$ comprises at least one chlorine, bromine, or triflate directly bonded to an sp$^2$ carbon atom of the ring structure of the ligand.

3. The process of claim 1 wherein L$^1$ comprises at least one bromine or triflate directly bonded to an sp$^2$ carbon atom of the ring structure of the ligand.

4. The process of claim 1 wherein L$^1$ is a substituted indenyl, a substituted heteroindenyl, a substituted fluorenyl, or a substituted heterofluorenyl ligand.

5. The process of claim 1 wherein the coupling catalyst comprises poly(ethylene glycol)triphenylphosphine, polymer bound; dicyclohexylphenylphosphine, polymer-bound; (4-hydroxyphenyl)diphenylphosphine, polymer-bound; triphenylphosphine, polymer-supported; R-(+)-2,2'-bis(diphenylphosphino)-1,1'-binaphthalene, polymer-bound; or S-(−)-2,2'-bis(diphenylphosphino)-1,1'-binaphthalene, polymer bound.

6. The process of claim 1 wherein L$^2$ is a substituted or unsubstituted cyclopentadienyl ligand, a substituted or unsubstituted heterocyclopentadienyl ligand, a substituted or unsubstituted indenyl ligand, a substituted or unsubstituted heteroindenyl ligand, a substituted or unsubstituted fluorenyl ligand, a substituted or unsubstituted heterofluorenyl ligand.

7. The process of claim 1 wherein M$^1$ is Li, Na, K, Rb, Cs, Be, Mg, Ca, Sr, Ba, boron, Si, Sn, Zn, Cd or Hg.

8. The process of claim 1 wherein M$^1$ is boron, Si, Sn, Zn, Cd or Hg.

9. The process of claim 1 wherein M$^1$ is boron, Sn or Zn.

10. The process of claim 1 wherein t is 1 or 2 and each X$^2$ is selected independently from the group consisting of halogen atoms, the hydroxyl group, alkoxy and aryloxy.

11. The process of claim 1 wherein the reaction is conducted in the presence of a transition metal-containing catalyst.

12. The process of claim 11 wherein the transition metal is selected from Groups 8 to 10 of the Periodic Table of the Elements.

13. The process of claim 11 wherein the transition metal is selected from Group 10 of the Periodic Table of the Elements.

14. A process for preparing a chelating ligand of the formula (IIa), (IIb), or (IIc) from a chelating ligand of the formula (Ia), (Ib), or (Ic), respectively, and a coupling component of the formula (III),

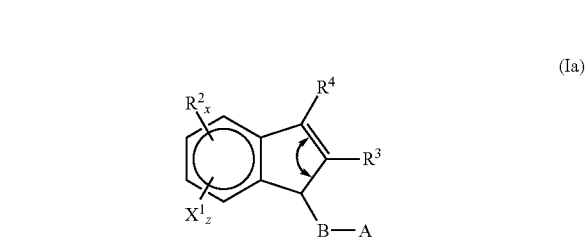

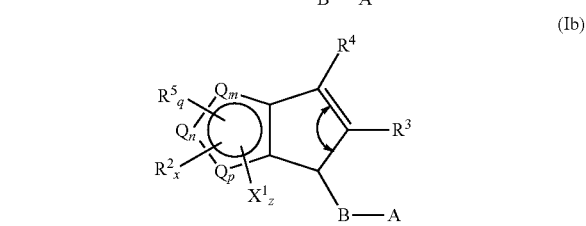

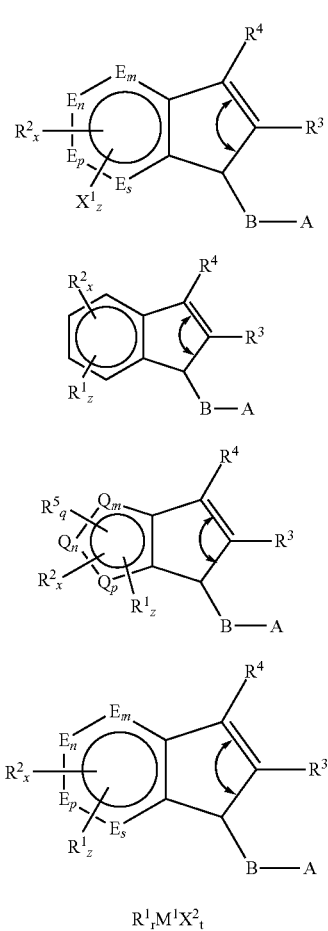

wherein:

M¹ is an element of group 1, 2, 12, 13 or 14 of the Periodic Table of the Elements;

the or each X¹ is a chlorine, bromine, iodine, triflate, or sulfonate group, and the or each X¹ is directly bonded to an sp² carbon atom of the ring structure of the ligand;

each X², if present, is selected independently from the group consisting of halogen atoms, the hydroxyl groups, alkoxy groups and aryloxy groups;

R¹ is a hydrocarbyl, substituted hydrocarbyl, halocarbyl, or substituted halocarbyl;

R², R³, R⁴, and R⁵' are, independently, hydrogen, hydrocarbyl, substituted hydrocarbyl, halocarbyl, substituted halocarbyl, silylcarbyl, germylcarbyl radical or polar group as defined above; provided that all R² groups may be different and, optionally, adjacent R², R³, R⁴, and R⁵' groups may also together form a cyclic aliphatic or aromatic ring system which may in turn be substituted and may contain heteroatoms; and provided further that R², R³, and R⁴ groups are attached to ring carbons; R⁵' groups are attached to heteroatoms;

each Q, if present, is, independently, a Group 16 atom, a Group 15 atom, or boron, and preferably S, O, N, or P; when a Q is a Group 15 atom or boron, "q" is one, indicating the presence of one R⁵' bonded to Q, and when a Q is a Group 16 atom, "q" is zero, indicating the absence of R⁵'; m, n, and p are independently zero or one, and m+n+p=1; when m or n or p is one, Q is present in the ring as a Group 16 or Group 15 atom or as boron; when m or n or p is zero, Q is absent and is replaced by a ring carbon atom having either a substituent R² or a substituent X¹;

each E, if present, is, independently, a Group 15 atom, preferably N or P; when E is present, it does not have any substituents; m, n, p, and s are independently zero or one, and m+n+p+s=1; when m or n or p or s is one, E is present in the ring as a Group 15 atom; when m or n or p or s is zero, E is absent and is replaced by a ring carbon atom having either a substituent R² or a substituent X¹;

B is a bridging group that contains a Group 13, 14, 15, or 16 element;

A is a substituted or unsubstituted monocyclic or polycyclic ligand;

x represents the number of R² substituents bonded to the aryl fused to the cyclopentadienyl in structures (Ia) and (IIa), the number of R² substituents bonded to the 5-member heterocyclic fragment in the structures (Ib) and (IIb), or the number of R² substituents bonded to the 6-member heterocyclic fragment in the structures (Ic) and (IIc);

x is 0, 1, 2, or 3 in structures (Ia) and (IIa);

x is 0 or 1 in structures (Ib) and (IIb);

x is 0, 1, or 2 in structures (Ic and IIc);

z represents the number of X¹ substituents converted to R¹ substituents and is 1, 2, 3, or 4 in structures (Ia) and (IIa); 1 or 2 in structures (Ib) and (IIb); and 1, 2, or 3 in structures (Ic) and (IIc);

x+z is 4 in structures (Ia) and (IIa);

x+z is 2 in structures (Ib) and (IIb);

x+z is 3 in structures (Ic) and (IIc);

r is 1, 2 or 3, and t is 0, 1 or 2, where r+t corresponds to the oxidation number of M¹.

15. The process of claim 14 wherein the or each X¹ is chlorine, bromine, or triflate.

16. The process of claim 14 wherein the or each X¹ is bromine or triflate.

17. The process of claim 14 wherein A is a substituted or unsubstituted cyclopentadienyl, a substituted or unsubstituted heterocyclopentadienyl, a substituted or unsubstituted indenyl, a substituted or unsubstituted heteroindenyl, a substituted or unsubstituted fluorenyl, or a substituted or unsubstituted heterofluorenyl.

18. The process of claim 14 wherein M¹ is Li, Na, K, Rb, Cs, Be, Mg, Ca, Sr, Ba, boron, Si, Sn, Zn, Cd or Hg.

19. The process of claim 14 wherein M¹ is boron, Si, Sn, Zn, Cd or Hg.

20. The process of claim 14 wherein M¹ is boron, Sn or Zn.

21. The process of claim 14 wherein B is a bridging group containing boron or a Group 14, 15 or 16 element.

22. The process of claim 14 wherein B selected from R'₂C, R'₂Si, R'₂Ge, R'₂CCR'₂, R'₂CCR'₂CR'₂, R'₂CCR'₂CR'₂CR'₂, R'C=CR', R'C=CR'CR'₂, R'₂CCR'=CR'CR'₂, R'C=CR'CR'=CR', R'C=CR'CR'₂CR'₂, R'₂CSiR'₂, R'₂SiSiR'₂, R'₂CSiR'₂CR'₂, R'₂SiCR'₂SiR'₂, R'C=CR'SiR'₂, R'₂CGeR'₂, R'₂GeGeR'₂, R'₂CGeR'₂CR'₂, R'₂GeCR'₂GeR'₂, R'₂SiGeR'₂, R'C=CR'GeR'₂, R'B*, R'₂C—B*R', R'₂C—B*R'—CR'₂ (where B* is boron), R'₂C—O—CR'₂, R'₂CR'₂C—O—CR'₂CR'₂, R'₂C—O—CR'₂CR'₂, R'₂C—O—CR'=CR', R'₂C—S—CR'₂, R'₂CR'₂C—S—CR'₂CR'₂, R'₂C—S—CR'₂CR'₂, R'₂C—S—CR'=CR', R'₂C—Se—CR'₂, R'₂CR'₂C—Se—CR'₂CR'₂, R'₂C—Se—CR'₂CR'₂, R'₂C—Se—CR'=CR', R'₂C—N=CR', R'₂C—NR'—CR'₂, R'₂C—NR'—CR'₂CR'₂, R'₂C—NR'—CR'=CR', R'₂CR'₂C—NR'—CR'₂CR'₂, R'₂C—P=CR', and R'₂C—PR'—CR'₂ where R' is hydrogen or a C₁-C₂₀ containing hydrocarbyl, substituted hydrocarbyl, halocarbyl, substituted halocarbyl, silylcarbyl or germylcarbyl substituent and optionally two or more adjacent R' may join to form a substituted or unsubstituted, saturated, partially unsaturated or aromatic, cyclic or polycyclic substituent.

23. The process of claim 14 wherein B is selected from $CH_2$, $CH_2CH_2$, $CH(CH_3)_2$, $SiMe_2$, $SiPh_2$, $SiMePh$, $Si(CH_2)_3$, and $Si(CH_2)_4$.

24. The process of claim 14 wherein t is 1 or 2 and each $X^2$ is selected independently from the group consisting of halogen atoms, the hydroxyl group, alkoxy and aryloxy.

25. The process of claim 14 and conducted in the presence of a transition metal-containing catalyst.

26. A process for preparing a chelating ligand of the formula (Va), (Vb), (Vc), (Vd), (Ve), (Vf), (Vg), (Vh), (Vi), (Vk), (Vm), (Vn), (Vo), (Vp), (Vq), (Vr), (Vs), (Vt), (Vu), (Vv), (Vw), (Vx), or (Vy) from a chelating ligand of the formula (IVa), (IVb), (IVc), (IVd), (IVe), (IVf), (IVg), (IVh), (IVi), (IVk), (IVm), (IVn), (IVo), (IVp), (IVq), (IVr), (IVs), (IVt), (IVu), (IVv), (IVw), (IVx), or (IVy), respectively, and a coupling component of the formula (III), $$R^1_r M^1 X^2_t \quad (III)$$

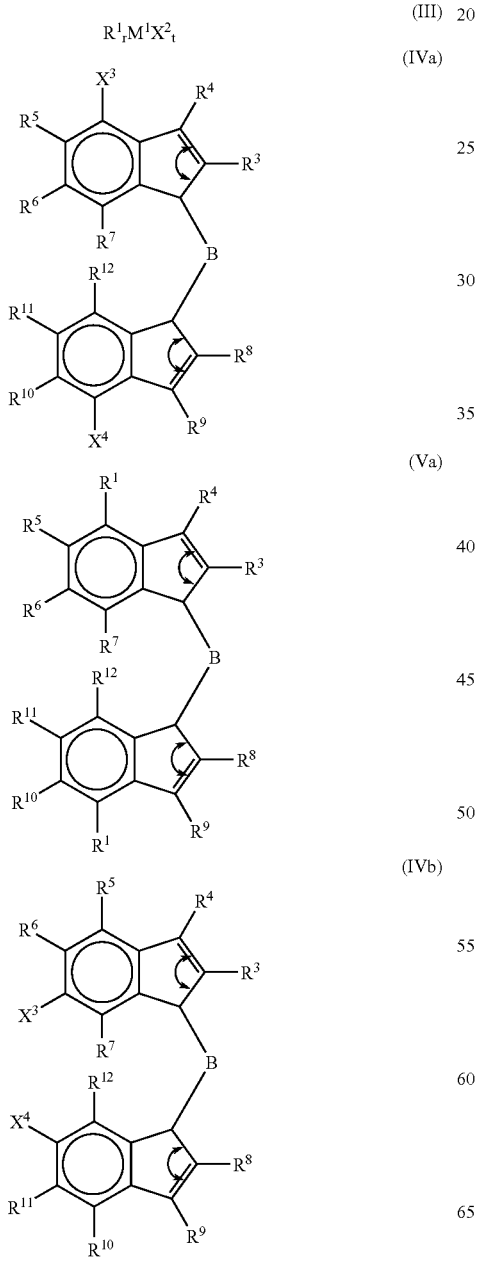

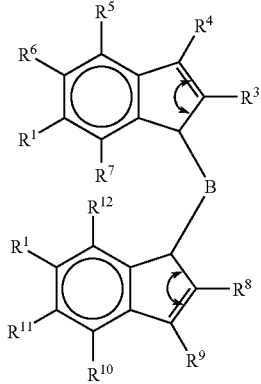

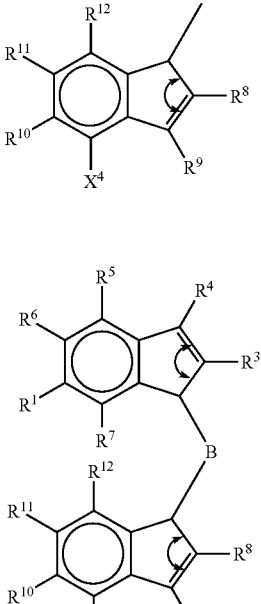

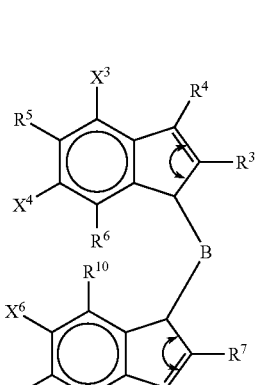

(Vd)
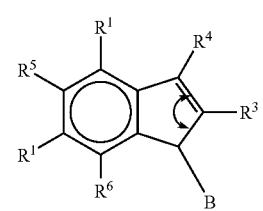
(IVe)
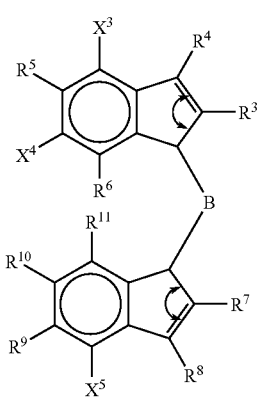
(Ve)
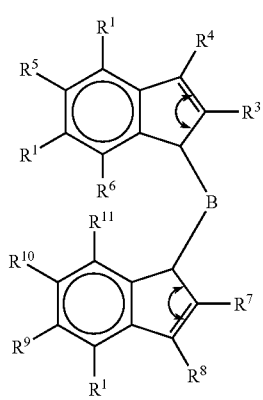
(IVf)
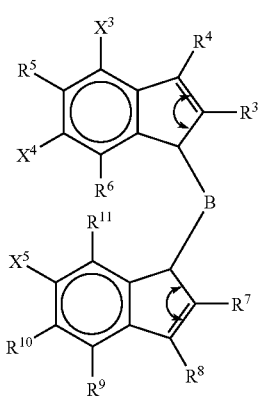
(Vf)
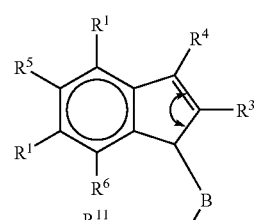
(IVg)
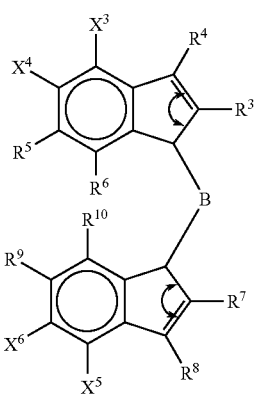
(Vg)
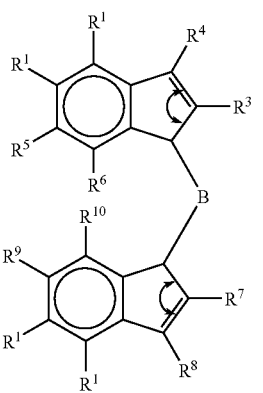
(IVh)
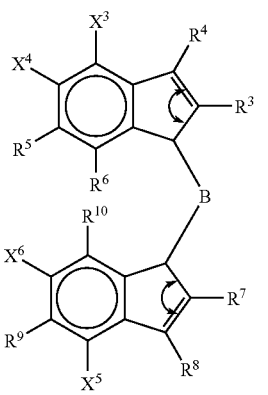

(Vh)
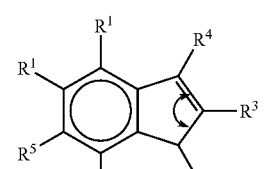
(IVi)
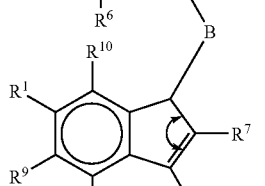
(Vi)
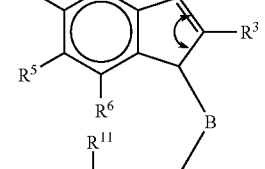
(IVk)
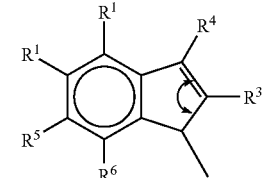
(Vk)
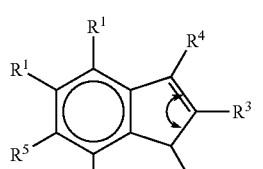
(IVm)
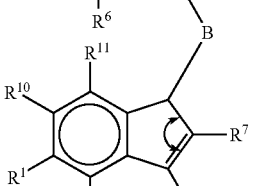
(Vm)
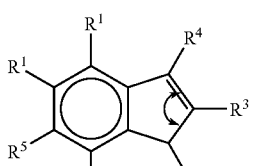
(IVn)
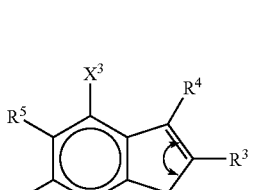

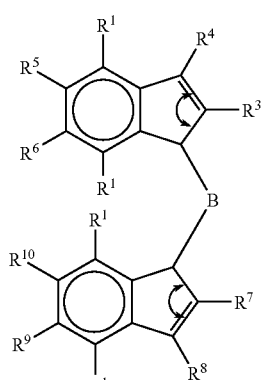 (Vn)
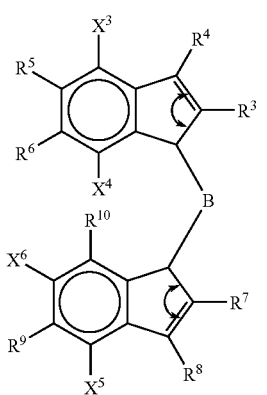 (IVo)
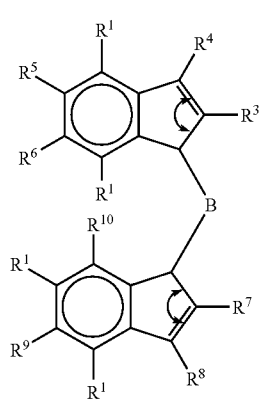 (Vo)
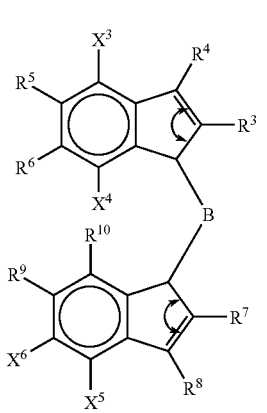 (IVp)
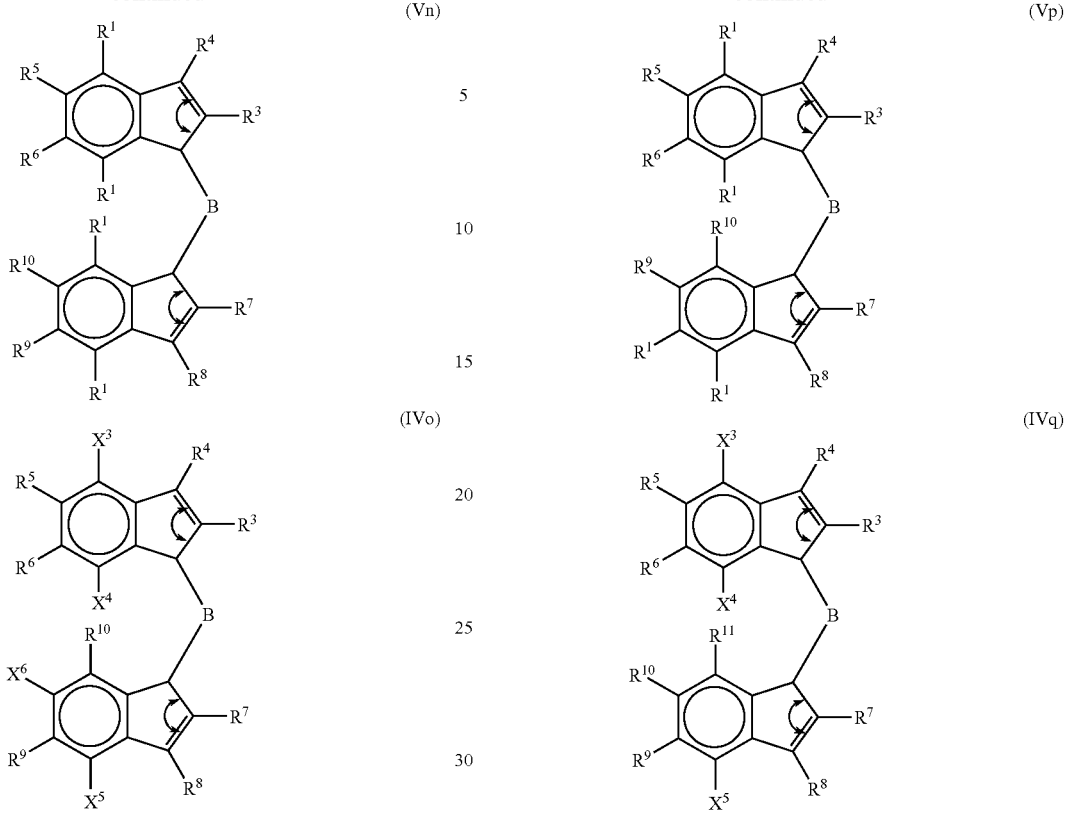
(Vp)
(IVq)
(Vq)
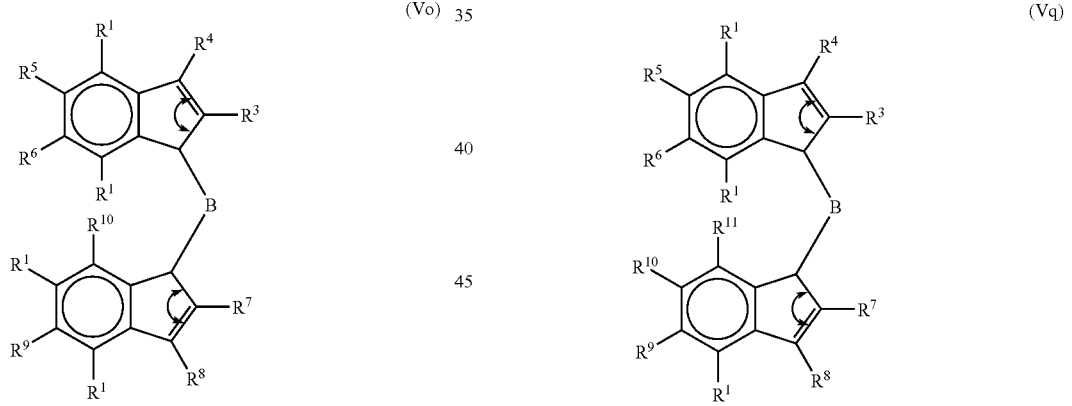 (IVr)

-continued
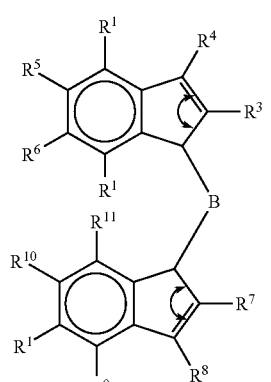 (Vr)
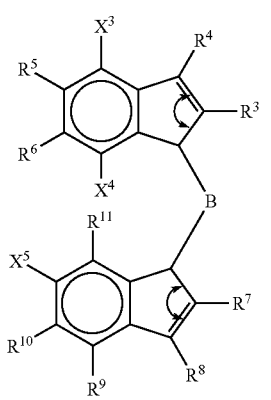 (IVs)
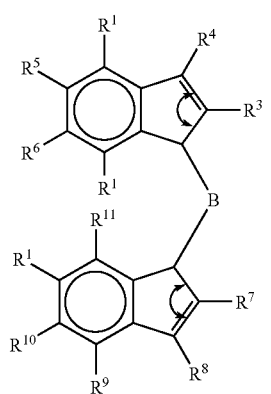 (Vs)
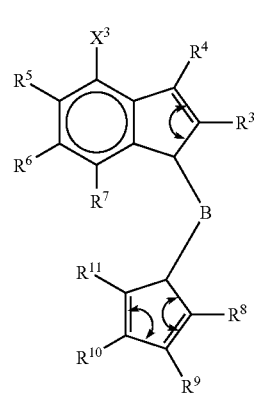 (IVt)
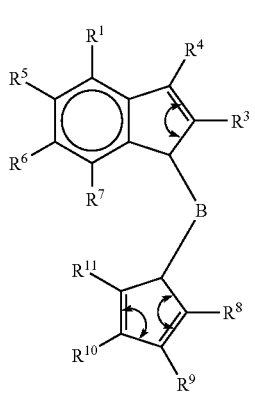 (Vt)
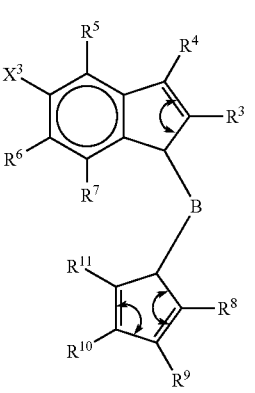 (IVu)
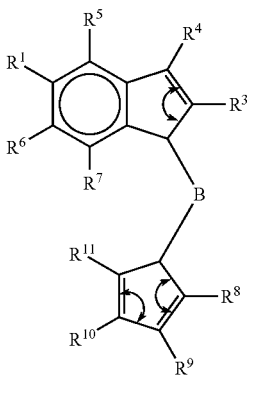 (Vu)
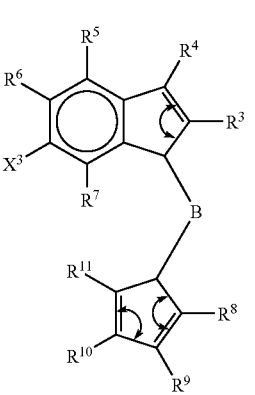 (IVv)

(Vv)
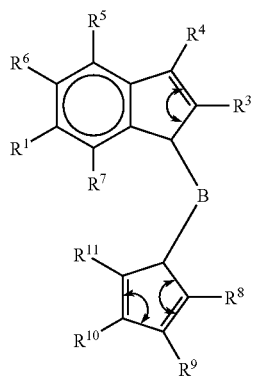

(IVw)
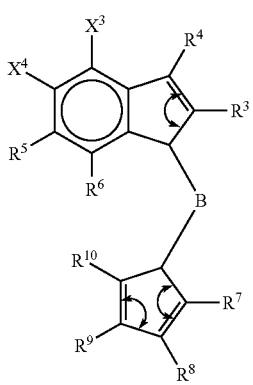

(Vw)
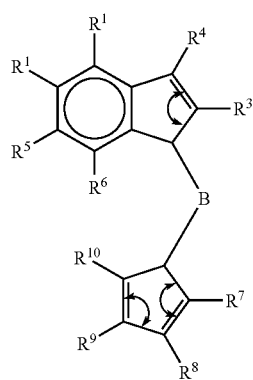

(IVx)
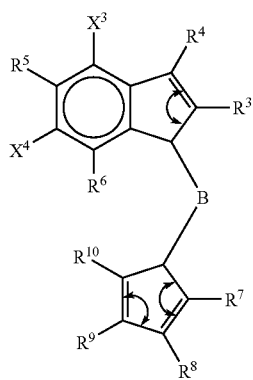

(Vx)
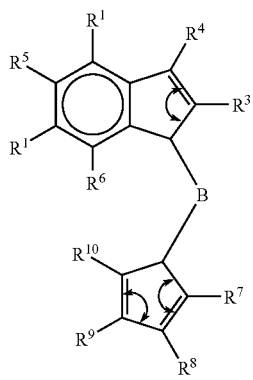

(IVy)
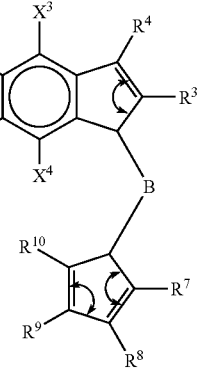

(Vy)
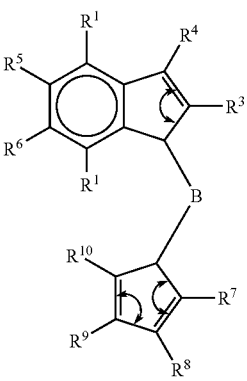

wherein:

$M^1$ is an element of group 1, 2, 12, 13 or 14 of the Periodic Table of the Elements;

$X^3$, $X^4$, $X^5$, and $X^6$ are independently selected from chlorine, bromine, iodine, triflate, and sulfonate groups;

each $X^2$, if present, is selected independently from the group consisting of halogen atoms, the hydroxyl groups, alkoxy groups and aryloxy groups;

$R^1$ is a hydrocarbyl, substituted hydrocarbyl, halocarbyl, or substituted halocarbyl;

R³, R⁴, R⁵, R⁶, R⁷, R⁸, R⁹, R¹⁰, R¹¹, and R¹² are independently, hydrogen, hydrocarbyl, substituted hydrocarbyl, halocarbyl, substituted halocarbyl, silylcarbyl, germylcarbyl radical or polar group, where, optionally, adjacent R³, R⁴, R⁵, R⁶, R⁷, R⁸, R⁹, R¹⁰, R¹¹, R¹² groups may also together form a cyclic aliphatic or aromatic ring system which may in turn be substituted and may contain heteroatoms;

B is a bridging group that contains a Group 13, 14, 15, or 16 element;

r is 1, 2, or 3, and t is 0, 1 or 2, where r+t corresponds to the oxidation number of $M^1$.

27. The process of claim 26 wherein $X^3$, $X^4$, $X^5$, and $X^6$ are independently selected from chlorine, bromine, and triflate.

28. The process of claim 26 wherein $X^3$, $X^4$, $X^5$, and $X^6$ are independently selected from bromine and triflate.

29. The process of claim 26 wherein $M^1$ is Li, Na, K, Rb, Cs, Be, Mg, Ca, Sr, Ba, boron, Si, Sn, Zn, Cd or Hg.

30. The process of claim 26 wherein $M^1$ is boron, Si, Sn, Zn, Cd or Hg.

31. The process of claim 26 wherein $M^1$ is boron, Sn or Zn.

32. The process of claim 26 wherein B is a bridging group containing boron or a Group 14, 15 or 16 element.

33. The process of claim 26 wherein B is selected from R'₂C, R'₂Si, R'₂Ge, R'₂CCR'₂, R'₂CCR'₂CR'₂, R'₂CCR'₂CR'₂CR'₂, R'C=CR', R'C=CR'CR'₂, R'₂CCR'=CR'CR'₂, R'C=CR'CR'=CR', R'C=CR'CR'₂CR'₂, R'₂CSiR'₂, R'₂SiSiR'₂, R'₂CSiR'₂CR'₂, R'₂SiCR'₂SiR'₂, R'C=CR'SiR'₂, R'₂CGeR'₂, R'₂GeGeR'₂, R'₂CGeR'₂CR'₂, R'₂GeCR'₂GeR'₂, R'₂SiGeR'₂, R'C=CR'GeR'₂, R'B*, R'₂C—B*R', R'₂C—B*R'—CR'₂ (where B* is boron), R'₂C—O—CR'₂, R'₂CR'₂C—O—CR'₂CR'₂, R'₂C—O—CR'₂CR'₂, R'₂C—O—CR'=CR', R'₂C—S—CR'₂, R'₂CR'₂C—S—CR'₂CR'₂, R'₂C—S—CR'₂CR'₂, R'₂C—S—CR'=CR', R'₂C—Se—CR'₂, R'₂CR'₂C—Se—CR'₂CR'₂, R'₂C—Se—CR'₂CR'₂, R'₂C—Se—CR'=CR', R'₂C—N=CR', R'₂C—NR'—CR'₂, R'₂C—NR'—CR'₂CR'₂, R'₂C—NR'—CR'=CR', R'₂CR'₂C—NR'—CR'₂CR'₂, R'₂C—P=CR', and R'₂C—PR'—CR'₂ where R' is hydrogen or a $C_1$-$C_{20}$ containing hydrocarbyl, substituted hydrocarbyl, halocarbyl, substituted halocarbyl, silylcarbyl or germylcarbyl substituent and optionally two or more adjacent R' may join to form a substituted or unsubstituted, saturated, partially unsaturated or aromatic, cyclic or polycyclic substituent.

34. The process of claim 26 wherein B is selected from $CH_2$, $CH_2CH_2$, $CH(CH_3)_2$, $SiMe_2$, $SiPh_2$, $SiMePh$, $Si(CH_2)_3$, and $Si(CH_2)_4$.

35. The process of claim 26 wherein t is 1 or 2 and each $X^2$ is selected independently from the group consisting of halogen atoms, the hydroxyl group, alkoxy and aryloxy.

36. The process of claim 26 and conducted in the presence of a transition metal-containing catalyst.

37. A process for preparing a chelating ligand of the formula (VIIa), (VIIb), (VIIc), (VIId), (VIIe), (VIIf), (VIIg), (VIIh), (VIIi), (VIIk), (VIIm), (VIIn), (VIIo), (VIIp), (VIIq), (VIIr), or (VIIs) from a chelating ligand of the formula (VIa), (VIb), (VIc), (VId), (VIe), (VIf), (VIg), (VIh), (VIi), (VIk), (VIm), (VIn), (VIo), (VIp), (VIq), (VIr), or (VIs), respectively, and a coupling component of the formula (III), $R^1{}_rM^1X^2{}_t$ (III)

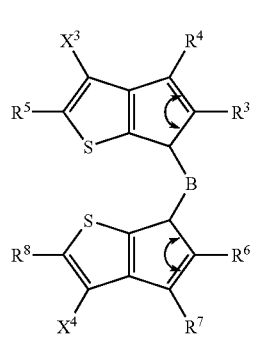
(VIa)

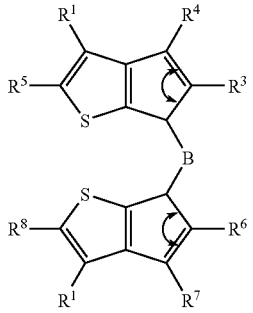
(VIIa)

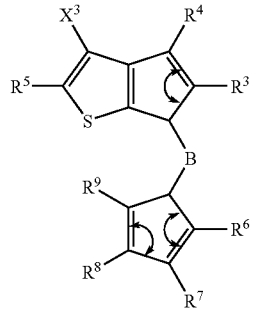
(VIb)

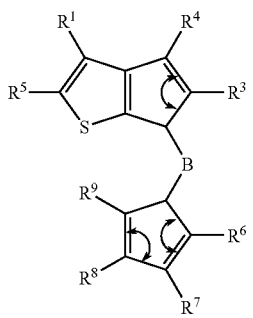
(VIIb)

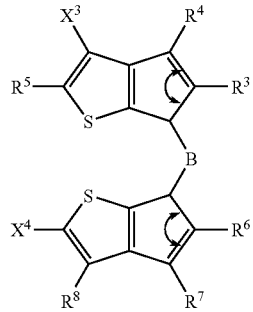
(VIc)

-continued
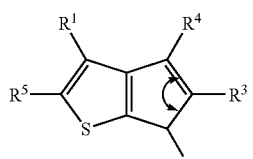
(VIIc)
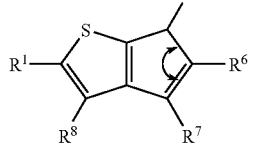
(VId)
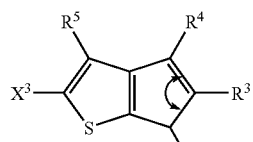
(VIId)
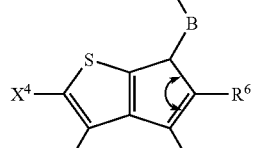
(VIe)
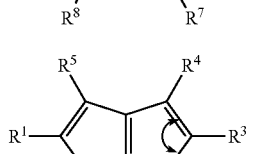
(VIIe)
-continued
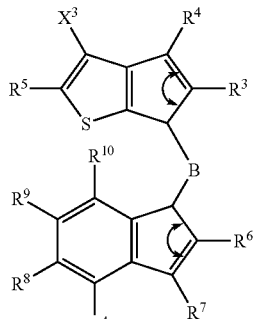
(VIf)
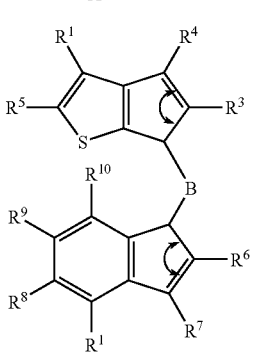
(VIIf)
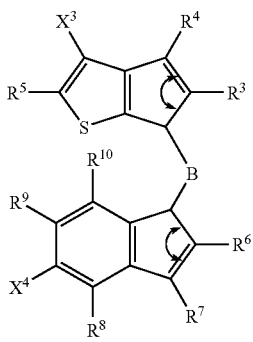
(VIg)
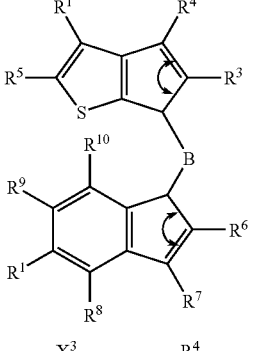
(VIIg)
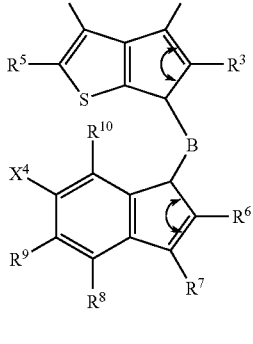
(VIh)

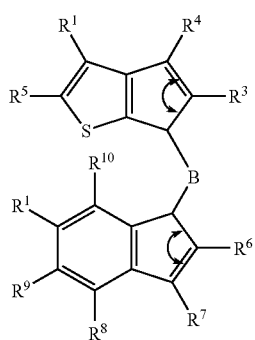
(VIIh)
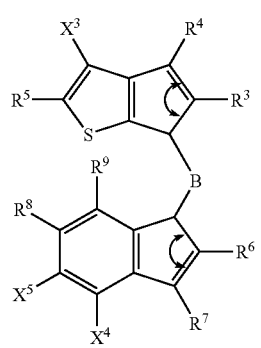
(VIi)
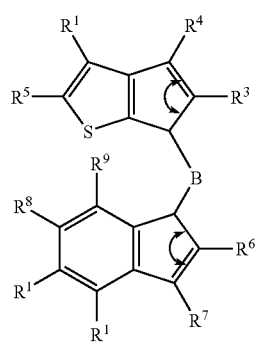
(VIIi)
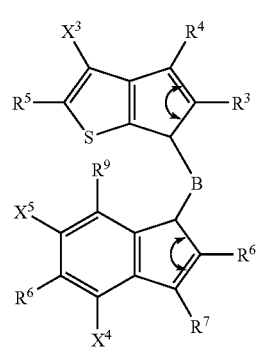
(VIk)
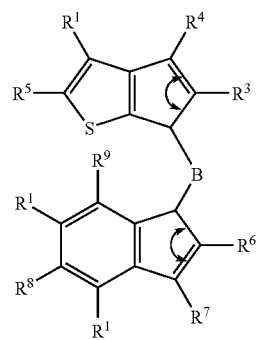
(VIIk)
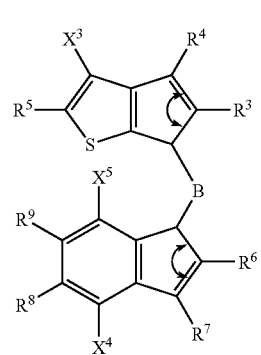
(VIm)
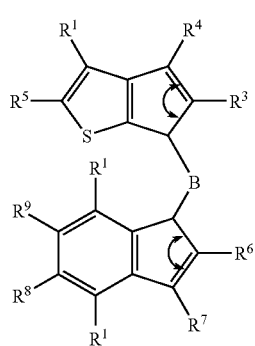
(VIIm)
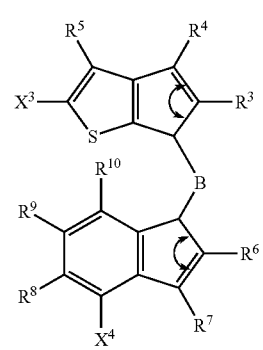
(VIn)

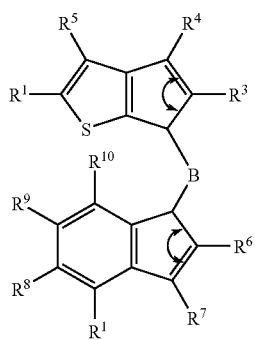
(VIIn)
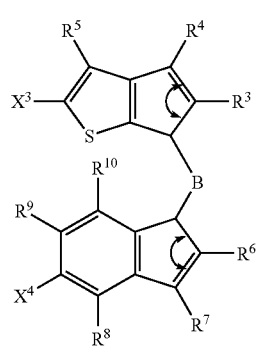
(VIo)
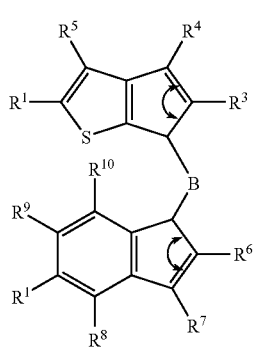
(VIIo)
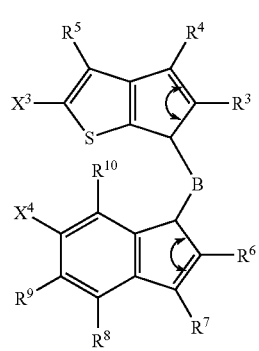
(VIp)
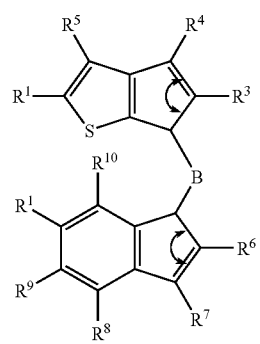
(VIIp)
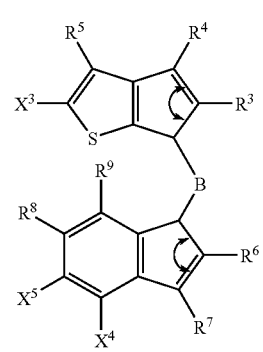
(VIq)
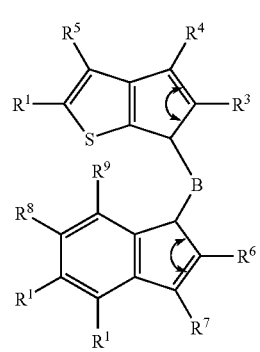
(VIIq)
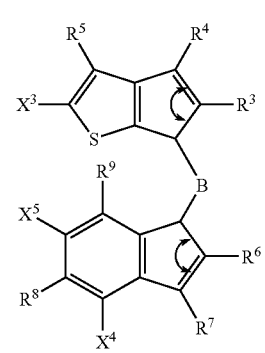
(VIr)

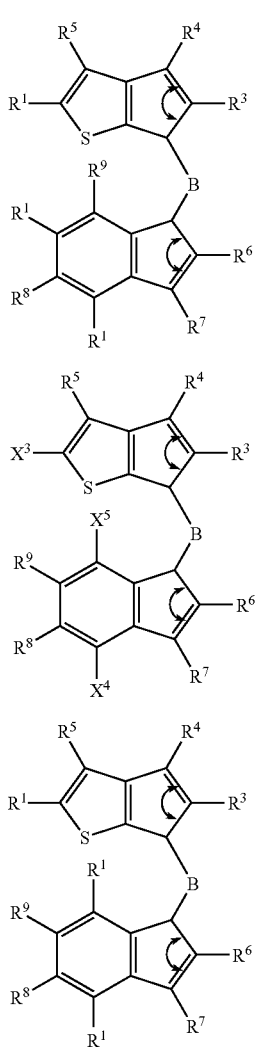

(VIIr)

(VIs)

(VIIs)

wherein:
$M^1$ is an element of Group 1, 2, 12, 13 or 14 of the Periodic Table of the Elements;
$X^3$, $X^4$, $X^5$, and $X^6$ are independently selected from chlorine, bromine, iodine, triflate, and sulfonate groups;
each $X^2$, if present, is selected independently from the group consisting of halogen atoms, the hydroxyl groups, alkoxy groups and aryloxy groups;
$R^1$ is a hydrocarbyl, substituted hydrocarbyl, halocarbyl, or substituted halocarbyl;
$R^3$, $R^4$, $R^5$, $R^6$, $R^7$, $R^8$, $R^9$, and $R^{10}$ are, independently, hydrogen, hydrocarbyl, substituted hydrocarbyl, halocarbyl, substituted halocarbyl, silylcarbyl, germylcarbyl radical or polar group, where, optionally, adjacent $R^3$, $R^4$, $R^5$, $R^6$, $R^7$, $R^8$, $R^9$, and $R^{10}$ groups may also together form a cyclic aliphatic or aromatic ring system which may in turn be substituted and may contain heteroatoms;
B is a bridging group that contains a Group 13, 14, 15, or 16 element;
r is 1, 2 or 3; and
t is 0, 1 or 2, where r+t corresponds to the oxidation number of $M^1$.

38. The process of claim 37 wherein $X^3$, $X^4$, $X^5$, and $X^6$ are independently selected from chlorine, bromine, and triflate.

39. The process of claim 37 wherein $X^3$, $X^4$, $X^5$, and $X^6$ are independently selected from bromine and triflate.

40. The process of claim 37 wherein $M^1$ is Li, Na, K, Rb, Cs, Be, Mg, Ca, Sr, Ba, boron, Si, Sn, Zn, Cd or Hg.

41. The process of claim 37 wherein $M^1$ is boron, Si, Sn, Zn, Cd or Hg.

42. The process of claim 37 wherein $M^1$ is boron, Sn or Zn.

43. The process of claim 37 wherein B is a bridging group containing boron or a Group 14, 15 or 16 element.

44. The process of claim 37 wherein B is selected from $R'_2C$, $R'_2Si$, $R'_2Ge$, $R'_2CCR'_2$, $R'_2CCR'_2CR'_2$, $R'_2CCR'_2CR'_2CR'_2$, $R'C=CR'$, $R'C=CR'CR'_2$, $R'_2CCR'=CR'CR'_2$, $R'C=CR'CR'=CR'$, $R'C=CR'CR'_2CR'_2$, $R'_2CSiR'_2$, $R'_2SiSiR'_2$, $R'_2CSiR'_2CR'_2$, $R'_2SiCR'_2SiR'_2$, $R'C=CR'SiR'_2$, $R'_2CGeR'_2$, $R'_2GeGeR'_2$, $R'_2CGeR'_2CR'_2$, $R'_2GeCR'_2GeR'_2$, $R'_2SiGeR'_2$, $R'C=CR'GeR'_2$, $R'B*R'_2C-B*R'$, $R'_2C-B*R'-CR'_2$ (where B* is boron), $R'_2C-O-CR'_2$, $R'_2CR'_2C-O-CR'_2CR'_2$, $R'_2C-O-CR'_2CR'_2$, $R'_2C-O-CR'=CR'$, $R'_2C-S-CR'_2$, $R'_2CR'_2C-S-CR'_2CR'_2$, $R'_2C-S-CR'_2CR'_2$, $R'_2C-S-CR'=CR'$, $R'_2C-Se-CR'_2$, $R'_2CR'_2C-Se-CR'_2CR'_2$, $R'_2C-Se-CR'_2CR'_2$, $R'_2C-Se-CR'=CR'$, $R'_2C-N=CR'$, $R'_2C-NR'-CR'_2$, $R'_2C-NR'-CR'_2CR'_2$, $R'_2C-NR'-CR'=CR'$, $R'_2CR'_2C-NR'-CR'_2CR'_2$, $R'_2C-P=CR'$, and $R'_2C-PR'-CR'_2$ where R' is hydrogen or a $C_1$-$C_{20}$ containing hydrocarbyl, substituted hydrocarbyl, halocarbyl, substituted halocarbyl, silylcarbyl or germylcarbyl substituent and optionally two or more adjacent R' may join to form a substituted or unsubstituted, saturated, partially unsaturated or aromatic, cyclic or polycyclic substituent.

45. The process of claim 37 wherein B is selected from $CH_2$, $CH_2CH_2$, $CH(CH_3)_2$, $SiMe_2$, $SiPh_2$, $SiMePh$, $Si(CH_2)_3$, and $Si(CH_2)_4$.

46. The process of claim 37 wherein t is 1 or 2 and each $X^2$ is selected independently from the group consisting of halogen atoms, the hydroxyl group, alkoxy and aryloxy.

47. The process of claim 37 and conducted in the presence of a transition metal-containing catalyst.

48. The process for preparing a chelating ligand of the formula (IId), (IIe), or (IIf) from a chelating ligand of the formula (Id), (Ie), or (If), respectively, and a coupling component of the formula (III),

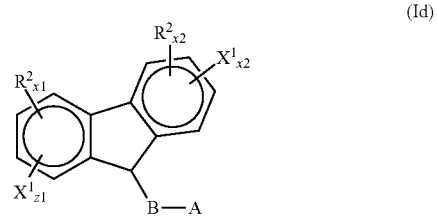

(Id)

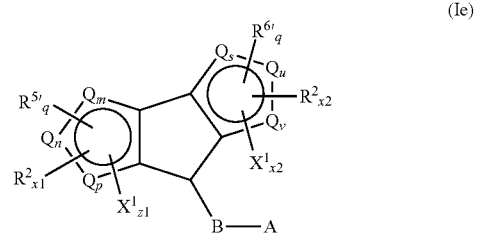

(Ie)

-continued

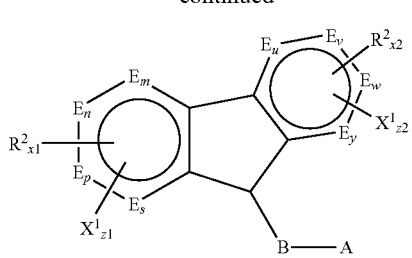
(If)

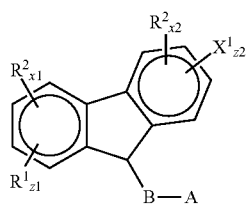
(IId)

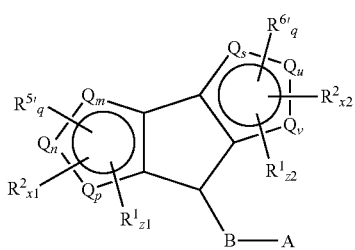
(IIe)

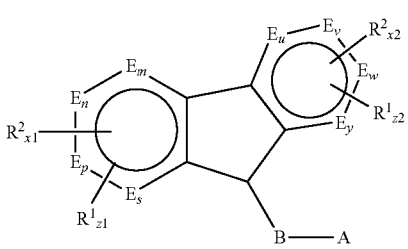
(IIf)

(III)

wherein:
$M^1$ is an element of Group 1, 2, 12, 13 or 14 of the Periodic Table of the Elements;
each $X^1$ is independently a chlorine, bromine, iodine, triflate, or sulfonate group, and each $X^1$ is directly bonded to an $sp^2$ carbon atom of the ring structure of the ligand;
each $X^2$, if present, is selected independently from the group consisting of halogen atoms, the hydroxyl groups, alkoxy groups and aryloxy groups;
$R^1$ is a hydrocarbyl, substituted hydrocarbyl, halocarbyl, or substituted halocarbyl;
$R^2$, $R^{5'}$, and $R^{6'}$ are, independently, hydrogen, hydrocarbyl, substituted hydrocarbyl, halocarbyl, substituted halocarbyl, silylcarbyl, germylcarbyl radical or polar group; provided that all $R^2$ groups may be different and, optionally, adjacent $R^2$, $R^{5'}$, and $R^{6'}$ groups may also together form a cyclic aliphatic or aromatic ring system which may in turn be substituted and may contain heteroatoms; and provided further that $R^2$ groups are attached to ring carbons; $R^{5'}$ and $R^{6'}$ groups are attached to heteroatoms;
B is a bridging group that contains a Group 13, 14, 15, or 16 element;
A is a substituted or unsubstituted monocyclic or polycyclic ligand;

each Q, if present, is independently, a Group 16 atom, a Group 15 atom, or boron, and preferably S, O, N, or P; when a Q is a Group 15 atom or boron, "q" is one, indicating the presence of one $R^{5'}$ or $R^{6'}$, as the case may be, bonded to Q, and when a Q is a Group 16 atom, "q" is zero, indicating the absence of $R^{5'}$ or $R^{6'}$, as the case may be; m, n, p, s, u, and v are independently zero or one, m+n+p=1, and s+u+v=1; when m or n or p or s or u or v is one, Q is present as a Group 16 or a Group 15 atom or as boron; when m or n or p or s or u or v is zero, Q is absent and is replaced by a ring carbon atom having either a substituent $R^2$ or a substituent $X^1$;
each E if present, is, independently, a Group 15 atom, preferably N or P; when E is present it does not have any substituents; m, n, p, s, u, v, w, and y are independently zero or one, m+n+p+s=1, and u+v+w+y=0 or 1; when m or n or p or s or u or v or w or y is present, E is present in the ring as a Group 15 atom; when m or n or p or s or u or v or w or y is zero, E is absent and is replaced by a ring carbon having either a substituent $R^2$ or a substituent $X^1$;
x1+x2 represents the total number of $R^2$ substituents bonded to the fluorenyl ligand in structures (Id) and (IId) or the total number of $R^2$ substituents bonded to the heterofluorenyl ligands in structures (Ie), (If), (IIe) and (IIf);
x1+x2 is 0, 1, 2, 3, 4, 5, 6, or 7 in structures (Id) and (IId);
x1+x2 is 0, 1, 2, or 3 in structures (Ie) and (IIe);
x1+x2 is 0, 1, 2, 3, 4, or 5 in structures (If) and (IIf); z1+z2 represents the total number of $X^1$ substituents converted to $R^1$ substituents and bonded to the fluorenyl ligand in structures (Id) and (IId), or the number of $X^1$ substituents converted to $R^1$ substituents and bonded to the heterofluorenyl ligand in structures (Ie), (If), (IIe), and (IIf);
z1+z2 is 1, 2, 3, 4, 5, 6, 7, or 8 in structures (Id) and (IId);
z1+z2 is 1, 2, 3 or 4 in structures (Ie) and (IIe);
z1+z2 is 1, 2, 3, 4, 5, 6, or 7 in structures (If) and (IIf);
x1+x2+z1+z2 is 8 in structures (Id) and (IId);
x1+x2+z1+z2 is 4 in structures (Ie) and (IIe);
x1+x2+z1+z2 is 6 in structures (If) and (IIf) when u+v+w+y=1;
x1+x2+z1+z2 is 7 in structures (If) and (IIf) when u+v+w+y=0;
r is 1, 2 or 3, and
t is 0, 1 or 2, where r+t corresponds to the oxidation number of $M^1$.

49. The process of claim 48 wherein each $X^1$ is independently chlorine, bromine, or triflate.

50. The process of claim 48 wherein each $X^1$ is independently bromine or triflate.

51. The process of claim 48 wherein A is a substituted or unsubstituted cyclopentadienyl, a substituted or unsubstituted heterocyclopentadienyl, a substituted or unsubstituted indenyl, a substituted or unsubstituted heteroindenyl, a substituted or unsubstituted fluorenyl, or a substituted or unsubstituted heterofluorenyl.

52. The process of claim 48 wherein $M^1$ is Li, Na, K, Rb, Cs, Be, Mg, Ca, Sr, Ba, boron, Si, Sn, Zn, Cd or Hg.

53. The process of claim 48 wherein $M^1$ is boron, Si, Sn, Zn, Cd or Hg.

54. The process of claim 48 wherein $M^1$ is boron, Sn or Zn.

55. The process of claim 48 wherein B is a bridging group containing boron or a Group 14, 15 or 16 element.

56. The process of claim 48 wherein B is selected from R'$_2$C, R'$_2$Si, R'$_2$Ge, R'$_2$CCR'$_2$, R'$_2$CCR'$_2$CR'$_2$, R'$_2$CCR'$_2$CR'$_2$CR'$_2$, R'C=CR', R'C=CR'CR'$_2$, R'$_2$CCR'=CR'CR'$_2$, R'C=CR'CR'=CR', R'C=CR'CR'$_2$CR'$_2$, R'$_2$CSiR'$_2$, R'$_2$SiSiR'$_2$, R'$_2$CSiR'$_2$CR'$_2$, R'₂SiCR'₂SiR'₂, R'C=CR'SiR'₂, R'₂CGeR'₂, R'₂GeGeR'₂, R'₂CGeR'₂CR'₂, R'₂GeCR'₂GeR'₂, R'₂SiGeR'₂, R'C=CR'GeR'₂, R'B*, R'₂C—B*R', R'₂C—B*R'—CR'₂ (where B* is boron), R'₂C—O—CR'₂, R'₂CR'₂C—O—CR'₂CR'₂, R'₂C—O—CR'₂CR'₂, R'₂C—O—CR'=CR', R'₂C—S—CR'₂, R'₂CR'₂C—S—CR'₂CR'₂, R'₂C—S—CR'₂CR'₂, R'₂C—S—CR'=CR', R'₂C—Se—CR'₂, R'₂CR'₂C—Se—CR'₂CR'₂, R'₂C—Se—CR'₂CR'₂, R'₂C—Se—CR'=CR', R'₂C—N=CR', R'₂C—NR'—CR'₂, R'₂C—NR'—CR'₂CR'₂, R'₂C—NR'—CR'=CR', R'₂CR'₂C—NR'—CR'₂CR'₂, R'₂C—P=CR', and R'₂C—PR'—CR'₂ where R' is hydrogen or a $C_1$-$C_{20}$ containing hydrocarbyl, substituted hydrocarbyl, halocarbyl, substituted halocarbyl, silylcarbyl or germylcarbyl substituent and optionally two or more adjacent R' may join to form a substituted or unsubstituted, saturated, partially unsaturated or aromatic, cyclic or polycyclic substituent.

57. The process of claim 48 wherein B is present and is selected from $CH_2$, $CH_2CH_2$, $CH(CH_3)_2$, $SiMe_2$, $SiPh_2$, SiMePh, $Si(CH_2)_3$, and $Si(CH_2)_4$.

58. The process of claim 48 wherein t is 1 or 2 and each $X^2$ is selected independently from the group consisting of halogen atoms, the hydroxyl group, alkoxy and aryloxy.

59. The process of claim 48 and conducted in the presence of a transition metal-containing catalyst.

60. A process for preparing a chelating ligand of the formula (IXa), (IXb), (IXc), (IXd), (IXe), (IXf), (IXg), (IXh), (IXi), or (IXk) from a chelating ligand of the formula (VIIIa), (VIIIb), (VIIIc), (VIIId), (VIIIe), (VIIIf), (VIIIg), (VIIIh), (VIIIi), or (VIIIk), respectively, and a coupling component of the formula (III), $$R^1{}_r M^1 X^2{}_t \qquad (III)$$

(VIIIa)

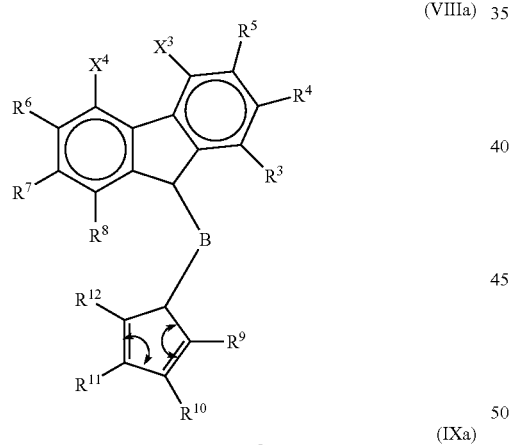

(IXa)

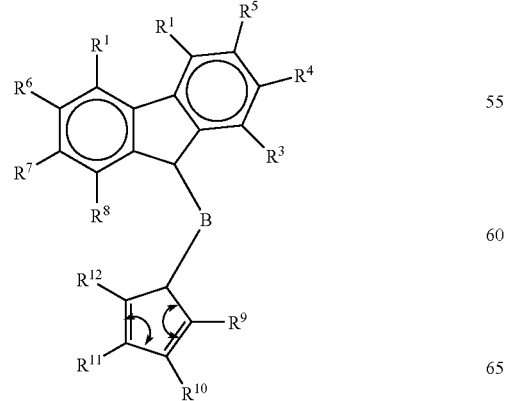

(VIIIb)

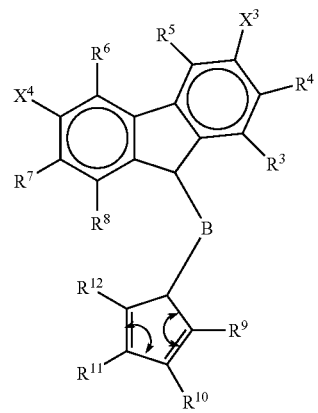

(IXb)

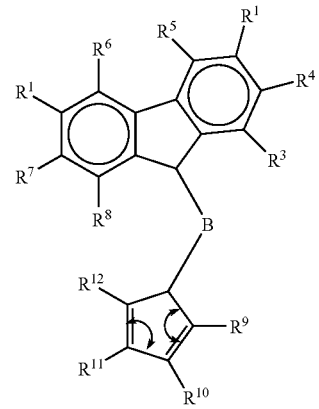

(VIIIc)

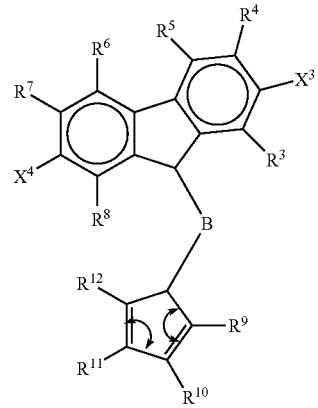

(IXc)

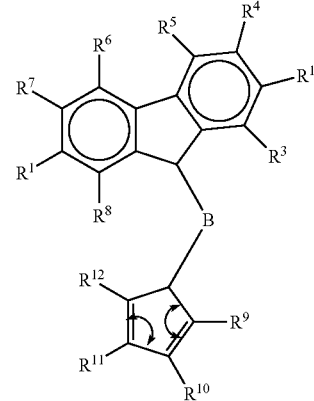

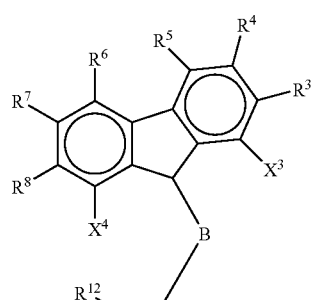
(VIIId)
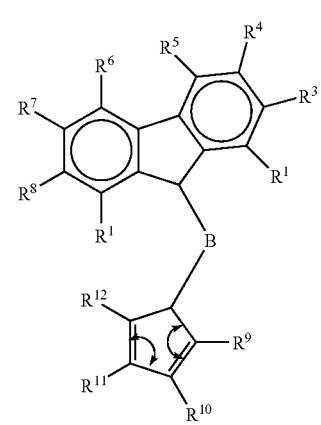
(IXd)
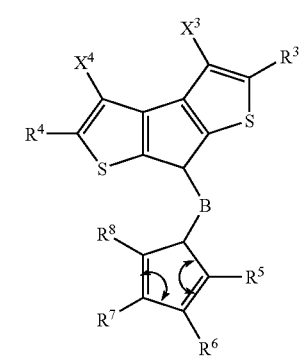
(VIIIe)
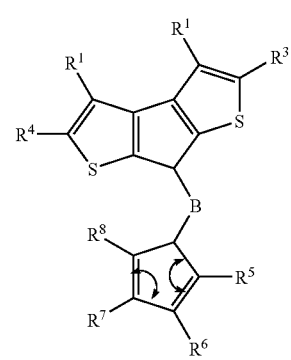
(IXe)
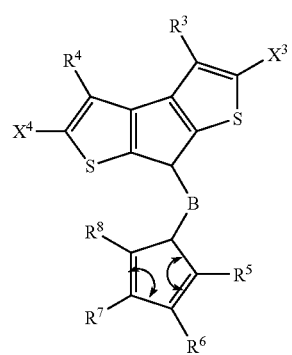
(VIIIf)
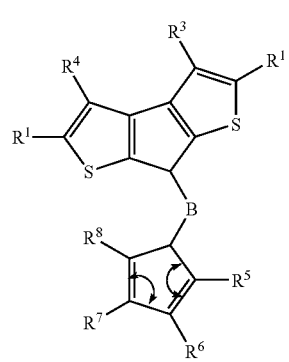
(IXf)
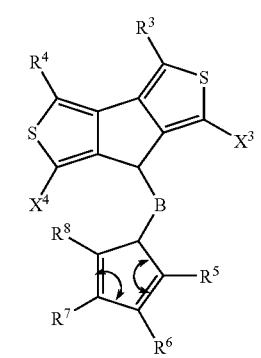
(VIIIg)
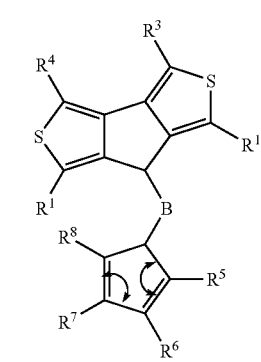
(IXg)

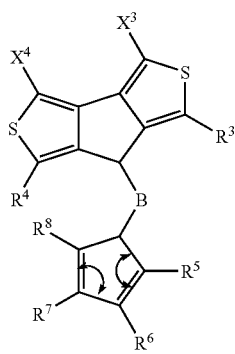
(VIIIh)

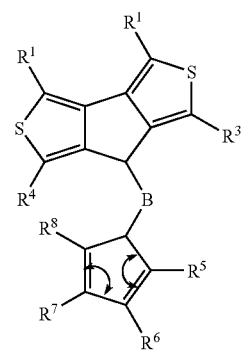
(IXh)

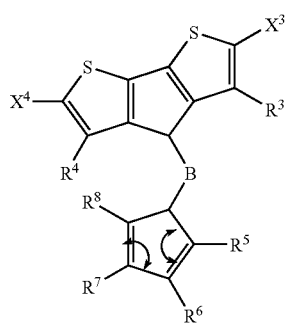
(VIIIi)

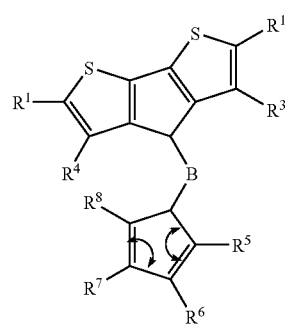
(IXi)

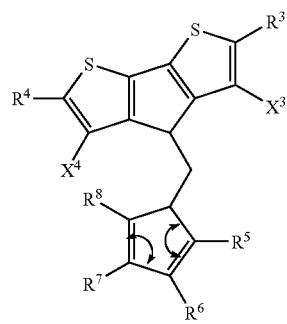
(VIIIk)

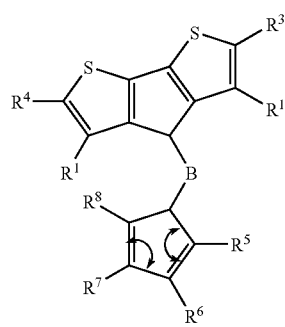
(IXk)

wherein
M¹ is an element of Group 1, 2, 12, 13 or 14 of the Periodic Table of the Elements;
X³ and X⁴ are, independently, chlorine, bromine, iodine, triflate, or sulfonate groups;
each X², if present, is selected independently from the group consisting of halogen atoms, the hydroxyl groups, alkoxy groups and aryloxy groups;
R¹ is a hydrocarbyl, substituted hydrocarbyl, halocarbyl, or substituted halocarbyl;
R³, R⁴, R⁵, R⁶, R⁷, R⁸, R⁹, R¹⁰, R¹¹, R¹² are, independently, hydrogen, hydrocarbyl, substituted hydrocarbyl, halocarbyl, substituted halocarbyl, silylcarbyl, germylcarbyl radical or polar group, where, optionally, adjacent R³, R⁴, R⁵, R⁶, R⁷, R⁸, R⁹, R¹⁰, R¹¹, R¹² groups may also together form a cyclic aliphatic or aromatic ring system which may in turn be substituted and may contain heteroatoms;
B is a bridging group that contains a Group 13, 14, 15, or 16 element;
r is 1, 2 or 3, and
t is 0, 1 or 2, where r+t corresponds to the oxidation number of M¹.

61. The process of claim 60 wherein X³ and X⁴ are, independently, chlorine, bromine, or triflate.

62. The process of claim 60 wherein X³ and X⁴ are, independently, bromine or triflate.

63. The process of claim 60 wherein M¹ is Li, Na, K, Rb, Cs, Be, Mg, Ca, Sr, Ba, boron, Si, Sn, Zn, Cd or Hg.

64. The process of claim 60 wherein M¹ is boron, Si, Sn, Zn, Cd or Hg.

65. The process of claim 60 wherein M¹ is boron, Sn or Zn.

66. The process of claim 60 wherein B is a bridging group containing boron or a Group 14, 15 or 16 element.

67. The process of claim 60 wherein B is selected from R′₂C, R′₂Si, R′₂Ge, R′₂CCR′₂, R′₂CCR′₂CR′₂, R′₂CCR′₂CR′₂CR′₂, R′C=CR′, R′C=CR′CR′₂, R′₂CCR′=CR′CR′₂, R′C=CR′CR′=CR′, R′C=CR′CR′₂CR′₂, R′₂CSiR′₂, R′₂SiSiR′₂, R′₂CSiR′₂CR′₂, $R'_2SiCR'_2SiR'_2$, $R'C=CR'SiR'_2$, $R'_2CGeR'_2$, $R'_2GeGeR'_2$, $R'_2CGeR'_2CR'_2$, $R'_2GeCR'_2GeR'_2$, $R'_2SiGeR'_2$, $R'C=CR'GeR'_2$, $R'B^*$, $R'_2C-B^*R'$, $R'_2C-B^*R'-CR'_2$ (where $B^*$ is boron), $R'_2C-O-CR'_2$, $R'_2CR'_2C-O-CR'_2CR'_2$, $R'_2C-O-CR'_2CR'_2$, $R'_2C-O-CR'=CR'$, $R'_2C-S-CR'_2$, $R'_2CR'_2C-S-CR'_2CR'_2$, $R'_2C-S-CR'_2CR'_2$, $R'_2C-S-CR'=CR'$, $R'_2C-Se-CR'_2$, $R'_2CR'_2C-Se-CR'_2CR'_2$, $R'_2C-Se-CR'_2CR'_2$, $R'_2C-Se-CR'=CR'$, $R'_2C-N=CR'$, $R'_2C-NR'-CR'_2$, $R'_2C-NR'-CR'_2CR'_2$, $R'_2C-NR'-CR'=CR'$, $R'_2CR'_2C-NR'-CR'_2CR'_2$, $R'_2C-P=CR'$, and $R'_2C-PR'-CR'_2$ where R' is hydrogen or a $C_1$-$C_{20}$ containing hydrocarbyl, substituted hydrocarbyl, halocarbyl, substituted halocarbyl, silylcarbyl or germylcarbyl substituent and optionally two or more adjacent R' may join to form a substituted or unsubstituted, saturated, partially unsaturated or aromatic, cyclic or polycyclic substituent.

68. The process of claim 60 wherein B is present and is selected from $CH_2$, $CH_2CH_2$, $CH(CH_3)_2$, $SiMe_2$, $SiPh_2$, SiMePh, $Si(CH_2)_3$, and $Si(CH_2)_4$.

69. The process of claim 60 wherein t is 1 or 2 and each $X^2$ is selected independently from the group consisting of halogen atoms, the hydroxyl group, alkoxy and aryloxy.

70. The process of claim 60 and conducted in the presence of a transition metal-containing catalyst.

71. The process of claim 1 wherein B is selected from $R'_2Si$, $R'_2Ge$, $R'_2CSiR'_2$, $R'_2SiSiR'_2$, $R'_2CSiR'_2CR'_2$, $R'_2SiCR'_2SiR'_2$, $R'C=CR'SiR'_2$, $R'_2CGeR'_2$, $R'_2GeGeR'_2$, $R'_2CGeR'_2CR'_2$, $R'_2GeCR'_2GeR'_2$, $R'_2SiGeR'_2$, $R'C=CR'GeR'_2$, $R'B^*$, $R'_2C-B^*R'$, $R'_2C-B^*R'-CR'_2$ (where $B^*$ is boron), $R'_2C-O-CR'_2$, $R'_2CR'_2C-O-CR'_2CR'_2$, $R'_2C-O-CR'_2CR'_2$, $R'_2C-O-CR'=CR'$, $R'_2C-S-CR'_2$, $R'_2CR'_2C-S-CR'_2CR'_2$, $R'_2C-S-CR'_2CR'_2$, $R'_2C-S-CR'=CR'$, $R'_2C-Se-CR'_2$, $R'_2CR'_2C-Se-CR'_2CR'_2$, $R'_2C-Se-CR'_2CR'_2$, $R'_2C-Se-CR'=CR'$, $R'_2C-N=CR'$, $R'_2C-NR'-CR'_2$, $R'_2C-NR'-CR'_2CR'_2$, $R'_2C-NR'-CR'=CR'$, $R'_2CR'_2C-NR'-CR'_2CR'_2$, $R'_2C-P=CR'$, and $R'_2C-PR'-CR'_2$ where R' is hydrogen or a $C_1$-$C_{20}$ containing hydrocarbyl, substituted hydrocarbyl, halocarbyl, substituted halocarbyl, silylcarbyl or germylcarbyl substituent and optionally two or more adjacent R' may join to form a substituted or unsubstituted, saturated, partially unsaturated or aromatic, cyclic or polycyclic substituent.

72. The process of claim 1 wherein B is selected from $R'_2Si$, $R'_2Ge$, $R'_2GeGeR'_2$, $R'_2SiGeR'_2$, and $R'B^*$, where $B^*$ is boron, and where R' is hydrogen or a $C_1$-$C_{20}$ containing hydrocarbyl, substituted hydrocarbyl, halocarbyl, substituted halocarbyl, silylcarbyl or germylcarbyl substituent and optionally two or more adjacent R' may join to form a substituted or unsubstituted, saturated, partially unsaturated or aromatic, cyclic or polycyclic substituent.

73. The process of claim 1 wherein B is selected from $R'_2Si$ and $R'_2Ge$ where R' is hydrogen or a $C_1$-$C_{20}$ containing hydrocarbyl, substituted hydrocarbyl, halocarbyl, substituted halocarbyl, silylcarbyl or germylcarbyl substituent and optionally two or more adjacent R' may join to form a substituted or unsubstituted, saturated, partially unsaturated or aromatic, cyclic or polycyclic substituent.

74. The process of claim 1 wherein B is selected from $SiMe_2$, $SiPh_2$, SiMePh, $Si(CH_2)_3$, and $Si(CH_2)_4$.

75. The process of claim 14 wherein B is selected from $R'_2Si$, $R'_2Ge$, $R'_2CSiR'_2$, $R'_2CSiR'_2CR'_2$, $R'_2SiCR'_2SiR'_2$, $R'C=CR'SiR'_2$, $R'_2CGeR'_2$, $R'_2GeGeR'_2$, $R'_2CGeR'_2CR'_2$, $R'_2GeCR'_2GeR'_2$, $R'_2SiGeR'_2$, $R'C=CR'GeR'_2$, $R'B^*$, $R'_2C-B^*R'$, $R'_2C-B^*R'-CR'_2$ (where $B^*$ is boron), $R'_2C-O-CR'_2$, $R'_2CR'_2C-O-CR'_2CR'_2$, $R'_2C-O-CR'_2CR'_2$, $R'_2C-O-CR'=CR'$, $R'_2CR'_2C-S-CR'_2CR'_2$, $R'_2C-S-CR'_2CR'_2$, $R'_2C-S-CR'=CR'$, $R'_2C-Se-CR'_2$, $R'_2CR'_2C-Se-CR'_2CR'_2$, $R'_2C-Se-CR'_2CR'_2$, $R'_2C-Se-CR'=CR'$, $R'_2C-N=CR'$, $R'_2C-NR'-CR'_2CR'_2$, $R'_2CR'_2C-NR'-CR'_2CR'_2$, $R'_2C-P=CR'$, and $R'_2C-PR'-CR'_2$ where R' is hydrogen or a $C_1$-$C_{20}$ containing hydrocarbyl, substituted hydrocarbyl, halocarbyl, substituted halocarbyl, silylcarbyl or germylcarbyl substituent and optionally two or more adjacent R' may join to form a substituted or unsubstituted, saturated, partially unsaturated or aromatic, cyclic or polycyclic substituent.

76. The process of claim 14 wherein B is selected from $R'_2Si$, $R'_2Ge$, $R'_2GeGeR'_2$, $R'_2SiGeR'_2$, and $R'B^*$, where $B^*$ is boron and where R' is hydrogen or a $C_1$-$C_{20}$ containing hydrocarbyl, substituted hydrocarbyl, halocarbyl, substituted halocarbyl, silylcarbyl or germylcarbyl substituent and optionally two or more adjacent R' may join to form a substituted or unsubstituted, saturated, partially unsaturated or aromatic, cyclic or polycyclic substituent.

77. The process of claim 14 wherein B is selected from $R'_2Si$ and $R'_2Ge$ where R' is hydrogen or a $C_1$-$C_{20}$ containing hydrocarbyl, substituted hydrocarbyl, halocarbyl, substituted halocarbyl, silylcarbyl or germylcarbyl substituent and optionally two or more adjacent R' may join to form a substituted or unsubstituted, saturated, partially unsaturated or aromatic, cyclic or polycyclic substituent.

78. The process of claim 14 wherein B is selected from $SiMe_2$, $SiPh_2$, SiMePh, $Si(CH_2)_3$, and $Si(CH_2)_4$.

79. The process of claim 26 wherein B is selected from $R'_2Si$, $R'_2Ge$, $R'_2CSiR'_2$, $R'_2CSiR'_2CR'_2$, $R'_2SiCR'_2SiR'_2$, $R'C=CR'SiR'_2$, $R'_2CGeR'_2$, $R'_2GeGeR'_2$, $R'_2CGeR'_2CR'_2$, $R'_2GeCR'_2GeR'_2$, $R'_2SiGeR'_2$, $R'C=CR'GeR'_2$, $R'B^*$, $R'_2C-B^*R'$, $R'_2C-B^*R'-CR'_2$ (where $B^*$ is boron), $R'_2C-O-CR'_2$, $R'_2CR'_2C-O-CR'_2CR'_2$, $R'_2C-O-CR'_2CR'_2$, $R'_2C-O-CR'=CR'$, $R'_2CR'_2C-S-CR'_2CR'_2$, $R'_2C-S-CR'_2CR'_2$, $R'_2C-S-CR'=CR'$, $R'_2C-Se-CR'_2$, $R'_2CR'_2C-Se-CR'_2CR'_2$, $R'_2C-Se-CR'_2CR'_2$, $R'_2C-Se-CR'=CR'$, $R'_2C-N=CR'$, $R'_2C-NR'-CR'_2CR'_2$, $R'_2CR'_2C-NR'-CR'_2CR'_2$, $R'_2C-P=CR'$, and $R'_2C-PR'-CR'_2$ where R' is hydrogen or a $C_1$-$C_{20}$ containing hydrocarbyl, substituted hydrocarbyl, halocarbyl, substituted halocarbyl, silylcarbyl or germylcarbyl substituent and optionally two or more adjacent R' may join to form a substituted or unsubstituted, saturated, partially unsaturated or aromatic, cyclic or polycyclic substituent.

80. The process of claim 26 wherein B is selected from $R'_2Si$, $R'_2Ge$, $R'_2GeGeR'_2$, $R'_2SiGeR'_2$, and $R'B^*$, where $B^*$ is boron and where R' is hydrogen or a $C_1$-$C_{20}$ containing hydrocarbyl, substituted hydrocarbyl, halocarbyl, substituted halocarbyl, silylcarbyl or germylcarbyl substituent and optionally two or more adjacent R' may join to form a substituted or unsubstituted, saturated, partially unsaturated or aromatic, cyclic or polycyclic substituent.

81. The process of claim 26 wherein B is selected from $R'_2Si$ and $R'_2Ge$ where R' is hydrogen or a $C_1$-$C_{20}$ containing hydrocarbyl, substituted hydrocarbyl, halocarbyl, substituted halocarbyl, silylcarbyl or germylcarbyl substituent and optionally two or more adjacent R' may join to form a substituted or unsubstituted, saturated, partially unsaturated or aromatic, cyclic or polycyclic substituent.

82. The process of claim 26 wherein B is selected from $SiMe_2$, $SiPh_2$, SiMePh, $Si(CH_2)_3$, and $Si(CH_2)_4$.

83. The process of claim 37 wherein B is selected from $R'_2Si$, $R'_2Ge$, $R'_2CSiR'_2$, $R'_2CSiR'_2CR'_2$, $R'_2SiCR'_2SiR'_2$, $R'C=CR'SiR'_2$, $R'_2CGeR'_2$, $R'_2GeGeR'_2$, $R'_2CGeR'_2CR'_2$, $R'_2GeCR'_2GeR'_2$, $R'_2SiGeR'_2$, $R'C=CR'GeR'_2$, $R'B^*$, $R'_2C-B^*R'$, $R'_2C-B^*R'-CR'_2$ (where $B^*$ is boron), $R'_2C$—O—$CR'_2$, $R'_2CR'_2C$—O—$CR'_2CR'_2$, $R'_2C$—O—$CR'_2CR'_2$, $R'_2C$—O—$CR'$=$CR'$, $R'_2CR'_2C$—S—$CR'_2CR'_2$, $R'_2C$—S—$CR'_2CR'_2$, $R'_2C$—S—$CR'$=$CR'$, $R'_2C$—Se—$CR'_2$, $R'_2CR'_2C$—Se—$CR'_2CR'_2$, $R'_2C$—Se—$CR'_2CR'_2$, $R'_2C$—Se—$CR'$=$CR'$, $R'_2C$—N=$CR'$, $R'_2C$—NR'—$CR'_2CR'_2$, $R'_2CR'_2C$—NR'—$CR'_2CR'_2$, $R'_2C$—P=$CR'$, and $R'_2C$—PR'—$CR'_2$ where R' is hydrogen or a $C_1$-$C_{20}$ containing hydrocarbyl, substituted hydrocarbyl, halocarbyl, substituted halocarbyl, silylcarbyl or germylcarbyl substituent and optionally two or more adjacent R' may join to form a substituted or unsubstituted, saturated, partially unsaturated or aromatic, cyclic or polycyclic substituent.

84. The process of claim 37 wherein B is selected from $R'_2Si$, $R'_2Ge$, $R'_2GeGeR'_2$, $R'_2SiGeR'_2$, and R'B*, where B* is boron and where R' is hydrogen or a $C_1$-$C_{20}$ containing hydrocarbyl, substituted hydrocarbyl, halocarbyl, substituted halocarbyl, silylcarbyl or germylcarbyl substituent and optionally two or more adjacent R' may join to form a substituted or unsubstituted, saturated, partially unsaturated or aromatic, cyclic or polycyclic substituent.

85. The process of claim 37 wherein B is selected from $R'_2Si$ and $R'_2Ge$ where R' is hydrogen or a $C_1$-$C_{20}$ containing hydrocarbyl, substituted hydrocarbyl, halocarbyl, substituted halocarbyl, silylcarbyl or germylcarbyl substituent and optionally two or more adjacent R' may join to form a substituted or unsubstituted, saturated, partially unsaturated or aromatic, cyclic or polycyclic substituent.

86. The process of claim 37 wherein B is selected from $SiMe_2$, $SiPh_2$, SiMePh, $Si(CH_2)_3$, and $Si(CH_2)_4$.

87. The process of claim 48 wherein B is selected from $R'_2Si$, $R'_2Ge$, $R'_2CSiR'_2$, $R'_2CSiR'_2CR'_2$, $R'_2SiCR'_2SiR'_2$, R'C=$CR'SiR'_2$, $R'_2CGeR'_2$, $R'_2GeGeR'_2$, $R'_2CGeR'_2CR'_2$, $R'_2GeCR'_2GeR'_2$, $R'_2SiGeR'_2$, R'C=$CR'GeR'_2$, R'B*, $R'_2C$—B*R', $R'_2C$—B*R'—$CR'_2$ (where B* is boron), $R'_2C$—O—$CR'_2$, $R'_2CR'_2C$—O—$CR'_2CR'_2$, $R'_2C$—O—$CR'_2CR'_2$, $R'_2C$—O—$CR'$=$CR'$, $R'_2CR'_2C$—S—$CR'_2CR'_2$, $R'_2C$—S—$CR'_2CR'_2$, $R'_2C$—S—$CR'$=$CR'$, $R'_2C$—Se—$CR'_2$, $R'_2CR'_2C$—Se—$CR'_2CR'_2$, $R'_2C$—Se—$CR'_2CR'_2$, $R'_2C$—Se—$CR'$=$CR'$, $R'_2C$—N=$CR'$, $R'_2C$—NR'—$CR'_2CR'_2$, $R'_2CR'_2C$—NR'—$CR'_2CR'_2$, $R'_2C$—P=$CR'$, and $R'_2C$—PR'—$CR'_2$ where R' is hydrogen or a $C_1$-$C_{20}$ containing hydrocarbyl, substituted hydrocarbyl, halocarbyl, substituted halocarbyl, silylcarbyl or germylcarbyl substituent and optionally two or more adjacent R' may join to form a substituted or unsubstituted, saturated, partially unsaturated or aromatic, cyclic or polycyclic substituent.

88. The process of claim 48 wherein B is selected from $R'_2Si$, $R'_2Ge$, $R'_2GeGeR'_2$, $R'_2SiGeR'_2$, and R'B*, where B* is boron and where R' is hydrogen or a $C_1$-$C_{20}$ containing hydrocarbyl, substituted hydrocarbyl, halocarbyl, substituted halocarbyl, silylcarbyl or germylcarbyl substituent and optionally two or more adjacent R' may join to form a substituted or unsubstituted, saturated, partially unsaturated or aromatic, cyclic or polycyclic substituent.

89. The process of claim 48 wherein B is selected from $R'_2Si$ and $R'_2Ge$ where R' is hydrogen or a $C_1$-$C_{20}$ containing hydrocarbyl, substituted hydrocarbyl, halocarbyl, substituted halocarbyl, silylcarbyl or germylcarbyl substituent and optionally two or more adjacent R' may join to form a substituted or unsubstituted, saturated, partially unsaturated or aromatic, cyclic or polycyclic substituent.

90. The process of claim 48 wherein B is selected from $SiMe_2$, $SiPh_2$, SiMePh, $Si(CH_2)_3$, and $Si(CH_2)_4$.

91. The process of claim 60 wherein B is selected from $R'_2Si$, $R'_2Ge$, $R'_2CSiR'_2$, $R'_2CSiR'_2CR'_2$, $R'_2SiCR'_2SiR'_2$, R'C=$CR'SiR'_2$, $R'_2CGeR'_2$, $R'_2GeGeR'_2$, $R'_2CGeR'_2CR'_2$, $R'_2GeCR'_2GeR'_2$, $R'_2SiGeR'_2$, R'C=$CR'GeR'_2$, R'B*, $R'_2C$—B*R', $R'_2C$—B*R'—$CR'_2$ (where B* is boron), $R'_2C$—O—$CR'_2$, $R'_2CR'_2C$—O—$CR'_2CR'_2$, $R'_2C$—O—$CR'_2CR'_2$, $R'_2C$—O—$CR'$=$CR'$, $R'_2CR'_2C$—S—$CR'_2CR'_2$, $R'_2C$—S—$CR'_2CR'_2$, $R'_2C$—S—$CR'$=$CR'$, $R'_2C$—Se—$CR'_2$, $R'_2CR'_2C$—Se—$CR'_2CR'_2$, $R'_2C$—Se—$CR'_2CR'_2$, $R'_2C$—Se—$CR'$=$CR'$, $R'_2C$—N=$CR'$, $R'_2C$—NR'—$CR'_2CR'_2$, $R'_2CR'_2C$—NR'—$CR'_2CR'_2$, $R'_2C$—P=$CR'$, and $R'_2C$—PR'—$CR'_2$ where R' is hydrogen or a $C_1$-$C_{20}$ containing hydrocarbyl, substituted hydrocarbyl, halocarbyl, substituted halocarbyl, silylcarbyl or germylcarbyl substituent and optionally two or more adjacent R' may join to form a substituted or unsubstituted, saturated, partially unsaturated or aromatic, cyclic or polycyclic substituent.

92. The process of claim 60 wherein B is selected from $R'_2Si$, $R'_2Ge$, $R'_2SiSiR'_2$, $R'_2GeGeR'_2$, $R'_2SiGeR'_2$, and R'B*, where B* is boron and where R' is hydrogen or a $C_1$-$C_{20}$ containing hydrocarbyl, substituted hydrocarbyl, halocarbyl, substituted halocarbyl, silylcarbyl or germylcarbyl substituent and optionally two or more adjacent R' may join to form a substituted or unsubstituted, saturated, partially unsaturated or aromatic, cyclic or polycyclic substituent.

93. The process of claim 60 wherein B is selected from $R'_2Si$ and $R'_2Ge$ where R' is hydrogen or a $C_1$-$C_{20}$ containing hydrocarbyl, substituted hydrocarbyl, halocarbyl, substituted halocarbyl, silylcarbyl or germylcarbyl substituent and optionally two or more adjacent R' may join to form a substituted or unsubstituted, saturated, partially unsaturated or aromatic, cyclic or polycyclic substituent.

94. The process of claim 60 wherein B is selected from $SiMe_2$, $SiPh_2$, SiMePh, $Si(CH_2)_3$, and $Si(CH_2)_4$.

95. A process for preparing a chelating ligand of the formula (II) from a chelating ligand of the formula (I) via an $sp^2$-$sp^2$ or $sp^2$-$sp^3$ coupling reaction comprising contacting, optionally in the presence of a coupling catalyst, a chelating ligand of the formula (I) with an organometallic compound of the formula (III):

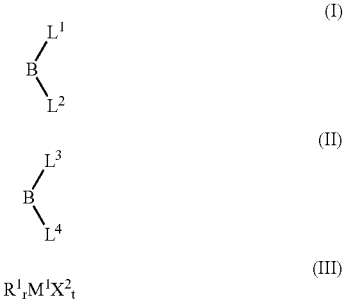

wherein

B is a bridging group that is bonded to $L^1$ and $L^2$ in formula (I) and to $L^3$ and $L^4$ in formula (II) selected from the group consisting of $SiMe_2$, $SiPh_2$, $Si(CH_2)_3$, and $Si(CH_2)_4$;

$L^1$ is a substituted monocyclic or polycyclic ligand that comprises at least one chlorine, bromine, iodine, or sulfonate substituent, directly bonded to an $sp^2$ carbon atom of the ring structure of the ligand;

$L^2$ is a monoanionic ligand; or $L^2$ may, independently, be defined as $L^1$;

$L^3$ is the same group as $L^1$, but said at least one chlorine, bromine, iodine, or sulfonate substituent is replaced with a hydrocarbyl, substituted hydrocarbyl, halocarbyl, or substituted halocarbyl fragment;

$L^4$ is the same group as $L^2$, though, when $L^2$ is defined as $L^1$, $L^4$ may be the same as $L^3$ or $L^1$;

$R^1$ is a hydrocarbyl, substituted hydrocarbyl, halocarbyl, or substituted halocarbyl;

$M^1$ is an element of group 1, 2, 12, 13 or 14 of the Periodic Table of the Elements;

each $X^2$, if present, is selected independently from the group consisting of halogen atoms, the hydroxyl group, alkoxy groups, aryloxy groups, mesylate, tosylate and triflate;

r is 1, 2 or 3, and t is 0, 1 or 2, where r+t corresponds to the oxidation number of $M^1$.

* * * * *